US010662464B2

(12) United States Patent
Broadt et al.

(10) Patent No.: US 10,662,464 B2
(45) Date of Patent: May 26, 2020

(54) METHODS OF ANALYZING VIRUS-DERIVED THERAPEUTICS

(71) Applicants: The United States of America, as represented by the Secretary, Department of Health and Human Services, Bethesda, MD (US); American International Biotechnology, LLC, Richmond, VA (US)

(72) Inventors: Trevor Lane Broadt, Frederick, MD (US); Michael D. Harwich, Richmond, VA (US); William T. Budd, Louisa, VA (US); Gregory A. Meyers, Midlothian, VA (US)

(73) Assignees: The United States of America, as represented by the Secretary, Department of Health and Human Serv, Bethesda, MD (US); American International Biotechnology, LLC, Richmond, VA (US)

( * ) Notice: Subject to any disclaimer, the term of this patent is extended or adjusted under 35 U.S.C. 154(b) by 113 days.

(21) Appl. No.: 15/580,299

(22) PCT Filed: Jul. 29, 2016

(86) PCT No.: PCT/US2016/044788
§ 371 (c)(1),
(2) Date: Dec. 7, 2017

(87) PCT Pub. No.: WO2017/023782
PCT Pub. Date: Feb. 9, 2017

(65) Prior Publication Data
US 2018/0237835 A1 Aug. 23, 2018

Related U.S. Application Data

(60) Provisional application No. 62/199,663, filed on Jul. 31, 2015.

(51) Int. Cl.
| | | |
|---|---|---|
| *C12Q 1/68* | (2018.01) | |
| *C12Q 1/70* | (2006.01) | |
| *C12N 15/10* | (2006.01) | |
| *C12N 15/70* | (2006.01) | |
| *C12N 15/86* | (2006.01) | |
| *C40B 40/06* | (2006.01) | |
| *C12Q 1/6827* | (2018.01) | |
| *C12Q 1/6806* | (2018.01) | |

(52) U.S. Cl.
CPC ....... *C12Q 1/6827* (2013.01); *C12N 15/1096* (2013.01); *C12N 15/70* (2013.01); *C12N 15/86* (2013.01); *C12Q 1/6806* (2013.01); *C12Q 1/701* (2013.01); *C40B 40/06* (2013.01); *C12Q 2521/301* (2013.01); *C12Q 2521/319* (2013.01); *C12Q 2535/122* (2013.01); *C12Q 2600/156* (2013.01)

(58) Field of Classification Search
CPC .. C12Q 1/6827; C12Q 1/70; C12Q 2521/301; C12Q 2535/122; C12Q 2600/156
See application file for complete search history.

(56) References Cited

U.S. PATENT DOCUMENTS

2017/0362605 A1* 12/2017 Chakraborty .......... C12N 15/85

FOREIGN PATENT DOCUMENTS

| WO | WO 2009/091934 A1 | 7/2009 |
|---|---|---|
| WO | WO 2014/020356 A1 | 2/2014 |
| WO | WO 2016/201224 A1 | 12/2016 |

OTHER PUBLICATIONS

Ambion, Inc., "Technical Bulletin # 176—Avoiding DNA Contamination in RT-PCR," 2007, retrieved from the Internet: URL:https://www.tamu.edu/faculty/riggs/BIOT602/ambion_dna_contamination.pdf [retrieved on Sep. 27, 2016].
Barzon et al., "Applications of next-generation sequencing technologies to diagnostic virology," *Int J Mol Sci* 12:7861-7884, 2011.
Clontech Laboratories, Inc., "SMART-Seq® v4 Ultra® Low Input RNA Kit for Sequencing User Manual," 2016. 21 pages.
Djikeng et al., "Viral genome sequencing by random priming methods," *BMC Genomics* 9:5, 2008.
Goetz and Gromeier, "Preparing an oncolytic poliovirus recombinant for clinical application against glioblastoma multiforme," *Cytokine Growth Factor Rev.* 21:197-203, 2010.
Gombold et al., "Lot Release and Characterization Testing of Live-Virus-Based Vaccines and Gene Therapy Products, Part 1," *BioProcess International*, pp. 46-54, 2006, Retrieved from the Internet: URL:http://www.bioprocessintl.com/wp-content/uploads/bpi-content/4-4_Schenerman_CMCp_103112a.pdf [retrieved on Sep. 29, 2016].
Greninger et al., "A metagenomic analysis of pandemic influenza A (2009 H1N1) infection in patients from North America," *PloS One* 5:e13381, 2010.

(Continued)

*Primary Examiner* — David C Thomas
(74) *Attorney, Agent, or Firm* — Klarquist Sparkman, LLP

(57) ABSTRACT

Described herein are massively parallel sequencing methods for virus-derived therapeutics such as viral vaccines, including the PVS-RIPO vaccine. The methods allow for the determination of micro-heterogeneity and quantitation of low frequency sequence variants and in the case of PVS-RIPO, are expected to replace the monkey neurovirulence safety test (MNVT) and the mutant analysis by PCR and restriction enzyme cleavage (MAPREC) methods that are currently used to screen lots of RNA virus-derived therapeutics.

17 Claims, 51 Drawing Sheets
Specification includes a Sequence Listing.

(56) References Cited

OTHER PUBLICATIONS

Hall et al., "Evaluation of rapid and simple techniques for the enrichment of viruses prior to metagenomic virus discovery," *J Virol. Methods* 195:194-204, 2014.

Life Technologies Corporation, "TURBO DNA-free™ Kit TURBO™ DNase Treatment and Removal Reagents," User Guide, Catalog No. AM1907, Publication No. 1907M, Revision G, 2012. 10 pages.

Life Technologies Corporation, "DNA-free™ Kit—DNase Treatment and Removal Reagents," User Guide, Catalog No. AM1906, Publication No. 1906M, Revision E, 2012, Retrieved from the Internet: URL:https://tools.thermofisher.com/content/sfs/manuals/cms_055739.pdf [retrieved on Sep. 28, 2016].

Martin et al., "WHO Working Group discussion on revision of the WHO recommendations for the production and control of poliomyelitis vaccines (oral): TRS Nos. 904 and 910. Report of Meeting held on Jul. 20-22, 2010, Geneva, Switzerland," *Vaccine* 29:6432-6436, 2011.

Neverov and Chumakov, "Massively parallel sequencing for monitoring genetic consistency and quality control of live viral vaccines," *Proc Natl Acad Sci U.S.A.* 107:20063-20068, 2010.

Qiagen, "QIAamp® Viral RNA Mini Handbook," Fourth Edition, Dec. 2014, retrieved from the Internet: URL:https://www.qiagen.com/us/resources/download.aspx?id=c80685c0-4103-49ea-aa72-8989420e3018&lang=en [retrieved on Sep. 28, 2016].

Rosseel et al., "Identification and complete genome sequencing of paramyxoviruses in mallard ducks (*Anas platyrhynchos*) using random access amplification and next generation sequencing technologies," *Virology J.* 8:463, 2011.

Rubin, "Toward replacement of the monkey neurovirulence test in vaccine safety testing," *Procedia Vaccinol.* 5:261-265, 2011.

Victoria et al., "Viral nucleic acids in live-attenuated vaccines: detection of minority variants and an adventitious virus," *J Virol.* 84:6033-6040, 2010.

World Health Organization, "Standard Operating Procedure—Mutant Analysis by PCR and Restriction Enzyme Cleavage (MAPREC) for Oral Poliovirus (SABIN) Vaccine Types 1, 2 or 3," Version 5, 2012. (34 pages).

PCT/US2016/044788 Written Opinion and International Search Report dated Oct. 11, 2016 (16 pages).

\* cited by examiner

FIG. 5A

| Position | Coverage | Reference | A count | T count | C count | G count | N count | Percent Specificity |
|---|---|---|---|---|---|---|---|---|
| 2 | 2 | T | 0 | 0 | 0 | 2 | 0 | 0 |
| 3 | 3 | A | 3 | 0 | 0 | 0 | 0 | 100 |
| 4 | 5 | A | 4 | 0 | 0 | 0 | 1 | 80 |
| 5 | 5 | A | 4 | 0 | 0 | 1 | 0 | 80 |
| 6 | 6 | A | 5 | 0 | 0 | 1 | 0 | 83.33 |
| 7 | 8 | C | 0 | 0 | 7 | 1 | 0 | 87.5 |
| 9 | 61 | G | 0 | 0 | 0 | 57 | 4 | 93.44 |
| 10 | 79 | C | 0 | 0 | 78 | 0 | 1 | 98.73 |
| 11 | 80 | T | 0 | 79 | 0 | 1 | 0 | 98.75 |
| 12 | 84 | C | 0 | 0 | 82 | 2 | 0 | 97.62 |
| 13 | 85 | T | 0 | 84 | 0 | 1 | 0 | 98.82 |
| 14 | 99 | G | 0 | 0 | 0 | 98 | 1 | 98.99 |
| 15 | 124 | G | 0 | 0 | 0 | 121 | 3 | 97.58 |
| 18 | 147 | T | 0 | 140 | 0 | 7 | 0 | 95.24 |
| 19 | 147 | T | 0 | 140 | 0 | 7 | 0 | 95.24 |
| 20 | 170 | G | 1 | 0 | 0 | 168 | 1 | 98.82 |
| 22 | 189 | A | 187 | 0 | 0 | 0 | 2 | 98.94 |
| 23 | 196 | C | 0 | 0 | 194 | 2 | 0 | 98.98 |
| 24 | 197 | C | 0 | 0 | 195 | 2 | 0 | 98.98 |
| 25 | 212 | C | 4 | 0 | 208 | 0 | 0 | 98.11 |
| 26 | 218 | A | 215 | 1 | 0 | 1 | 1 | 98.62 |
| 27 | 301 | C | 1 | 2 | 285 | 2 | 11 | 94.68 |
| 29 | 345 | C | 0 | 0 | 335 | 6 | 4 | 97.1 |
| 34 | 399 | G | 4 | 1 | 0 | 393 | 1 | 98.5 |
| 35 | 410 | G | 2 | 0 | 4 | 404 | 0 | 98.54 |
| 39 | 437 | A | 427 | 1 | 0 | 9 | 0 | 97.71 |
| 40 | 453 | C | 0 | 1 | 442 | 10 | 0 | 97.57 |
| 41 | 466 | G | 4 | 1 | 0 | 461 | 0 | 98.93 |
| 42 | 467 | T | 2 | 460 | 0 | 5 | 0 | 98.5 |
| 45 | 514 | C | 0 | 1 | 505 | 8 | 0 | 98.25 |
| 46 | 593 | G | 1 | 1 | 0 | 587 | 4 | 98.99 |
| 48 | 661 | C | 0 | 0 | 652 | 7 | 2 | 98.64 |
| 49 | 683 | T | 0 | 669 | 0 | 12 | 2 | 97.95 |
| 50 | 687 | A | 679 | 0 | 0 | 8 | 0 | 98.84 |
| 54 | 907 | C | 1 | 0 | 897 | 3 | 6 | 98.9 |
| 59 | 1134 | G | 1 | 1 | 0 | 1119 | 11 | 98.68 |
| 60 | 1131 | T | 5 | 1114 | 4 | 8 | 0 | 98.5 |
| 62 | 1191 | T | 1 | 1174 | 1 | 9 | 6 | 98.57 |
| 65 | 1356 | C | 0 | 2 | 1338 | 12 | 4 | 98.67 |
| 70 | 1820 | C | 1 | 3 | 1799 | 4 | 13 | 98.85 |
| 73 | 2080 | T | 6 | 2049 | 2 | 14 | 9 | 98.51 |
| 86 | 2881 | T | 2 | 2852 | 0 | 17 | 10 | 98.99 |
| 651 | 137246 | T | 1248 | 132985 | 1041 | 1964 | 8 | 97.29 |
| 834 | 164370 | T | 1339 | 157620 | 1229 | 4027 | 155 | 95.89 |
| 867 | 177895 | T | 999 | 173658 | 860 | 1990 | 318 | 97.64 |
| 1061 | 265209 | T | 2008 | 259719 | 2162 | 4271 | 49 | 96.83 |
| 1123 | 360642 | A | 356174 | 1478 | 75 | 1609 | 1606 | 98.68 |
| 1143 | 382247 | T | 1252 | 377721 | 1205 | 1876 | 193 | 98.82 |

FIG. 5B

| | | | | | | | | |
|---|---|---|---|---|---|---|---|---|
| 1152 | 446042 | T | 379 | 441363 | 567 | 1726 | 2005 | 98.95 |
| 1160 | 482910 | C | 349 | 577 | 478186 | 187 | 3591 | 99.02 |
| 1200 | 406594 | T | 1684 | 398198 | 2273 | 3420 | 19 | 97.94 |
| 1233 | 357036 | A | 351080 | 276 | 358 | 5212 | 110 | 98.33 |
| 1306 | 339635 | T | 1645 | 333668 | 1742 | 2255 | 125 | 98.24 |
| 1365 | 352479 | A | 347620 | 2322 | 74 | 2206 | 57 | 98.62 |
| 1383 | 444638 | T | 312 | 439191 | 366 | 1182 | 3607 | 98.77 |
| 1393 | 478224 | G | 825 | 261 | 79 | 474090 | 2979 | 99.13 |
| 1435 | 585445 | T | 1142 | 581317 | 1129 | 1837 | 20 | 99.29 |
| 1489 | 580125 | T | 1230 | 575073 | 1364 | 1799 | 739 | 99.13 |
| 1494 | 570329 | T | 1132 | 565745 | 1041 | 1345 | 866 | 99.2 |
| 1513 | 533453 | A | 528920 | 190 | 139 | 3901 | 322 | 99.15 |
| 1577 | 489806 | A | 482345 | 3293 | 111 | 3630 | 427 | 98.48 |
| 1628 | 402170 | A | 393379 | 4437 | 46 | 4054 | 224 | 97.81 |
| 1664 | 412703 | A | 406215 | 2847 | 185 | 3452 | 4 | 98.43 |
| 1821 | 51445 | C | 2560 | 2140 | 45997 | 561 | 187 | 89.41 |
| 2611 | 341779 | T | 1418 | 335828 | 1683 | 2833 | 15 | 98.26 |
| 3428 | 398718 | T | 1732 | 391777 | 1816 | 3390 | 3 | 98.26 |
| 3447 | 465302 | T | 2065 | 460498 | 2133 | 3762 | 21 | 98.29 |
| 3477 | 489262 | A | 483900 | 1926 | 83 | 1982 | 1371 | 98.9 |
| 3512 | 522336 | A | 517637 | 1192 | 1374 | 1922 | 111 | 99.12 |
| 3531 | 553448 | A | 548422 | 2184 | 69 | 2467 | 306 | 99.09 |
| 3542 | 596262 | T | 1624 | 590092 | 2005 | 2073 | 466 | 98.97 |
| 3554 | 566701 | A | 560999 | 963 | 463 | 3899 | 433 | 98.99 |
| 3588 | 540617 | A | 534535 | 522 | 510 | 4848 | 102 | 98.87 |
| 3592 | 545560 | T | 829 | 541370 | 1035 | 2117 | 189 | 99.23 |
| 3595 | 535524 | T | 1354 | 532441 | 1565 | 3069 | 95 | 98.87 |
| 3601 | 545392 | T | 3395 | 531029 | 4338 | 6402 | 168 | 97.37 |
| 3643 | 512224 | T | 1449 | 505991 | 1773 | 3267 | 44 | 98.78 |
| 3653 | 483115 | T | 1307 | 478237 | 1322 | 2096 | 353 | 98.99 |
| 3678 | 532253 | A | 527386 | 629 | 329 | 1315 | 2094 | 99.18 |
| 3737 | 491826 | T | 1651 | 487774 | 1594 | 2549 | 76 | 98.75 |
| 3807 | 556214 | T | 1464 | 550784 | 1375 | 2558 | 13 | 99.09 |
| 3892 | 682235 | C | 396 | 704 | 675687 | 247 | 3201 | 99.04 |
| 3893 | 682816 | A | 678370 | 1564 | 162 | 2394 | 26 | 99.35 |
| 3894 | 728310 | C | 372 | 915 | 723877 | 224 | 2922 | 99.39 |
| 3900 | 702930 | C | 533 | 661 | 697625 | 320 | 3851 | 99.23 |
| 3911 | 621323 | A | 613235 | 3405 | 175 | 3556 | 952 | 98.7 |
| 3929 | 603750 | T | 1947 | 596682 | 2330 | 4728 | 43 | 98.5 |
| 3950 | 615177 | T | 1216 | 609585 | 1440 | 2921 | 15 | 99.09 |
| 3983 | 597093 | A | 590727 | 2162 | 174 | 2478 | 1152 | 98.93 |
| 4006 | 504739 | T | 3014 | 493251 | 2901 | 5455 | 118 | 97.72 |
| 4061 | 429898 | T | 1215 | 424701 | 1387 | 2430 | 175 | 98.79 |
| 4063 | 428494 | T | 1573 | 421163 | 1907 | 3319 | 328 | 98.29 |
| 4187 | 650142 | A | 639812 | 659 | 98 | 1001 | 8572 | 98.41 |
| 4194 | 691603 | A | 687270 | 1838 | 142 | 2339 | 14 | 99.37 |
| 4195 | 687891 | C | 597 | 921 | 682963 | 256 | 3134 | 99.29 |
| 4198 | 655336 | A | 654069 | 208 | 136 | 537 | 3316 | 99.39 |
| 4242 | 867695 | T | 838 | 863411 | 1032 | 1773 | 641 | 99.51 |
| 4250 | 894752 | T | 1083 | 890445 | 1108 | 1985 | 131 | 99.52 |
| 4361 | 968067 | G | 817 | 676 | 298 | 962110 | 4168 | 99.38 |
| 4369 | 1022577 | G | 624 | 961 | 253 | 1017226 | 3569 | 99.48 |
| 4371 | 974354 | T | 3115 | 963433 | 3435 | 4246 | 125 | 98.88 |

FIG. 5C

| | | | | | | | | |
|---|---|---|---|---|---|---|---|---|
| 4279 | 1074295 | T | 450 | 1046122 | 186 | 1168 | 3969 | 99.43 |
| 4287 | 1010660 | C | 769 | 934 | 1003341 | 451 | 3145 | 99.46 |
| 4290 | 1009006 | T | 1007 | 1003985 | 1236 | 2731 | 47 | 99.5 |
| 4297 | 973186 | C | 2117 | 616 | 968296 | 363 | 1794 | 99.5 |
| 4301 | 930691 | A | 925910 | 204 | 338 | 4040 | 199 | 99.49 |
| 4319 | 971263 | C | 608 | 1183 | 967031 | 374 | 1983 | 99.56 |
| 4321 | 944670 | A | 939864 | 2049 | 228 | 2022 | 509 | 99.49 |
| 4323 | 980267 | C | 596 | 1263 | 977453 | 341 | 2594 | 99.51 |
| 4332 | 1137888 | A | 1121106 | 839 | 198 | 1272 | 12473 | 98.7 |
| 4340 | 1126023 | C | 806 | 1235 | 1116367 | 313 | 7302 | 99.14 |
| 4343 | 1026546 | T | 1025 | 1022333 | 1148 | 1702 | 338 | 99.59 |
| 4350 | 1028938 | G | 1443 | 966 | 544 | 1024085 | 1930 | 99.53 |
| 4359 | 1020164 | G | 1576 | 602 | 214 | 1015802 | 1970 | 99.57 |
| 4360 | 1028399 | T | 2004 | 1021141 | 1822 | 2856 | 576 | 99.29 |
| 4367 | 990411 | C | 741 | 998 | 986262 | 342 | 2068 | 99.38 |
| 4371 | 943331 | T | 2095 | 936542 | 2183 | 2303 | 6 | 99.28 |
| 4378 | 975725 | G | 851 | 1503 | 661 | 971437 | 1273 | 99.56 |
| 4382 | 942743 | G | 993 | 1108 | 365 | 937884 | 2393 | 99.46 |
| 4383 | 946323 | T | 2655 | 938205 | 2275 | 3294 | 94 | 99.12 |
| 4385 | 954147 | C | 610 | 1432 | 949216 | 290 | 2399 | 99.48 |
| 4390 | 887632 | C | 505 | 1137 | 880987 | 718 | 2283 | 99.48 |
| 4392 | 851705 | G | 1423 | 880 | 3031 | 846061 | 310 | 99.34 |
| 4405 | 882498 | T | 7259 | 859839 | 6926 | 8381 | 93 | 97.43 |
| 4460 | 692009 | T | 1065 | 686753 | 1042 | 2020 | 1129 | 99.24 |
| 4466 | 723028 | T | 1241 | 718754 | 1185 | 1523 | 345 | 99.41 |
| 4474 | 721380 | A | 713353 | 3797 | 328 | 3672 | 430 | 98.86 |
| 4491 | 781387 | A | 776115 | 2215 | 335 | 2708 | 14 | 99.33 |
| 4508 | 925878 | C | 703 | 628 | 920748 | 394 | 3402 | 99.43 |
| 4516 | 936240 | A | 931442 | 587 | 937 | 2049 | 625 | 99.49 |
| 4518 | 917765 | T | 3080 | 907251 | 3274 | 5817 | 343 | 98.64 |
| 4521 | 927508 | T | 2573 | 915038 | 3441 | 6045 | 109 | 98.66 |
| 4523 | 962014 | A | 956850 | 601 | 620 | 1257 | 2682 | 99.46 |
| 4530 | 938481 | A | 934128 | 620 | 413 | 1657 | 1823 | 99.51 |
| 4533 | 924833 | A | 917471 | 2106 | 362 | 2940 | 1954 | 99.2 |
| 4545 | 932652 | A | 923251 | 2189 | 872 | 3390 | 550 | 99.21 |
| 4554 | 967957 | G | 1024 | 739 | 288 | 962873 | 3035 | 99.47 |
| 4555 | 955382 | T | 2582 | 945182 | 2574 | 5336 | 8 | 98.91 |
| 4582 | 964891 | G | 914 | 892 | 237 | 958601 | 4247 | 99.35 |
| 4583 | 983449 | G | 1160 | 1511 | 194 | 977444 | 3140 | 99.39 |
| 4584 | 966748 | T | 3936 | 953074 | 3342 | 6018 | 178 | 98.59 |
| 4590 | 976291 | C | 710 | 996 | 968242 | 330 | 6013 | 99.18 |
| 4593 | 896743 | T | 1440 | 890833 | 1628 | 2747 | 90 | 99.34 |
| 4596 | 959395 | A | 953795 | 542 | 708 | 1536 | 2814 | 99.42 |
| 4597 | 992927 | G | 673 | 1216 | 144 | 987369 | 3125 | 99.44 |
| 4598 | 956118 | T | 1170 | 950880 | 1420 | 2408 | 240 | 99.47 |
| 4604 | 1004778 | C | 1058 | 1531 | 997313 | 343 | 4531 | 99.26 |
| 4606 | 963828 | A | 956224 | 2130 | 438 | 2816 | 2220 | 99.21 |
| 4643 | 981494 | A | 975943 | 3048 | 454 | 3865 | 184 | 99.43 |
| 4653 | 1003055 | A | 998364 | 1964 | 174 | 1631 | 922 | 99.53 |
| 4656 | 992216 | T | 977 | 987393 | 1247 | 1760 | 839 | 99.51 |
| 4685 | 996048 | T | 955 | 986102 | 6349 | 2011 | 731 | 99 |
| 4686 | 1013381 | C | 604 | 7634 | 1005569 | 392 | 973 | 99.03 |
| 4693 | 1008630 | C | 3806 | 702 | 1001255 | 266 | 601 | 99.27 |

FIG. 5D

| | | | | | | | |
|---|---|---|---|---|---|---|---|
| 4694 | 999368 | A | 986780 | 1375 | 6926 | 3027 | 360 | 98.74 |
| 4695 | 983147 | C | 4514 | 1285 | 972123 | 416 | 4804 | 98.88 |
| 4697 | 1043714 | G | 1695 | 1253 | 279 | 1035229 | 4935 | 99.23 |
| 4698 | 1063595 | T | 1103 | 1059048 | 1370 | 3618 | 456 | 99.39 |
| 4699 | 1091394 | G | 1018 | 1141 | 322 | 1086620 | 2193 | 99.56 |
| 4700 | 1090194 | G | 3086 | 1373 | 357 | 1084766 | 1400 | 99.5 |
| 4702 | 1071017 | A | 1066193 | 1112 | 910 | 1903 | 339 | 99.58 |
| 4703 | 1088528 | C | 1025 | 1062 | 1085916 | 368 | 2157 | 99.58 |
| 4705 | 1103133 | C | 987 | 1604 | 1094645 | 645 | 5232 | 99.23 |
| 4707 | 1183369 | G | 1023 | 1022 | 264 | 1173124 | 8934 | 98.97 |
| 4708 | 1185346 | T | 1683 | 1178974 | 2126 | 4912 | 631 | 99.21 |
| 4709 | 1206644 | G | 1052 | 566 | 210 | 1200480 | 2036 | 99.66 |
| 4712 | 1257389 | G | 2074 | 961 | 305 | 1250227 | 4022 | 99.41 |
| 4713 | 1260628 | C | 830 | 1907 | 1255245 | 621 | 2023 | 99.57 |
| 4715 | 1263772 | T | 410 | 1257774 | 452 | 518 | 4578 | 99.53 |
| 4718 | 1215626 | G | 1765 | 1308 | 613 | 1211225 | 713 | 99.64 |
| 4720 | 1209392 | C | 1071 | 846 | 1204528 | 583 | 2364 | 99.6 |
| 4733 | 1173524 | T | 850 | 1169355 | 1069 | 2063 | 154 | 99.65 |
| 4743 | 1244639 | A | 1237738 | 1271 | 1744 | 3002 | 884 | 99.45 |
| 4744 | 1346313 | C | 1041 | 1336 | 1342061 | 478 | 1367 | 99.66 |
| 4750 | 1271831 | G | 839 | 1108 | 244 | 1266459 | 3181 | 99.58 |
| 4752 | 1273681 | T | 2071 | 1259383 | 3717 | 4723 | 1385 | 98.89 |
| 4758 | 1401366 | A | 1393468 | 576 | 323 | 3122 | 3277 | 99.44 |
| 4761 | 1355018 | A | 1349371 | 900 | 1527 | 3136 | 84 | 99.58 |
| 4762 | 1404451 | G | 1561 | 1122 | 231 | 1398372 | 3145 | 99.57 |
| 4763 | 1402936 | T | 4442 | 1388723 | 3159 | 6138 | 464 | 98.99 |
| 4764 | 1489035 | A | 1481246 | 474 | 282 | 2456 | 4580 | 99.48 |
| 4765 | 1527761 | T | 423 | 1522608 | 485 | 1200 | 3045 | 99.66 |
| 4767 | 1531107 | C | 1132 | 1845 | 1526995 | 681 | 454 | 99.73 |
| 4770 | 1533130 | G | 680 | 922 | 187 | 1527388 | 3953 | 99.63 |
| 4771 | 1516747 | A | 1512548 | 824 | 1066 | 2252 | 57 | 99.72 |
| 4772 | 1518956 | G | 1508 | 1012 | 212 | 1512385 | 3739 | 99.57 |
| 4773 | 1458886 | A | 1449442 | 1063 | 1373 | 3783 | 3225 | 99.35 |
| 4783 | 1450502 | G | 1203 | 1019 | 425 | 1446250 | 1605 | 99.71 |
| 4786 | 1430138 | C | 937 | 1761 | 1425833 | 655 | 910 | 99.7 |
| 4789 | 1433891 | G | 1058 | 1215 | 539 | 1429784 | 1305 | 99.71 |
| 4790 | 1451411 | G | 1972 | 1606 | 730 | 1445601 | 1502 | 99.6 |
| 4791 | 1452188 | C | 1109 | 1809 | 1447745 | 914 | 611 | 99.69 |
| 4793 | 1452312 | G | 1533 | 1745 | 812 | 1446832 | 1400 | 99.62 |
| 4796 | 1410821 | G | 1416 | 1384 | 628 | 1406014 | 879 | 99.69 |
| 4797 | 1391634 | C | 1297 | 1873 | 1384012 | 1083 | 3389 | 99.43 |
| 4799 | 1377272 | A | 1370935 | 1417 | 259 | 1412 | 1249 | 99.68 |
| 4805 | 1346294 | A | 1341090 | 385 | 373 | 1345 | 3101 | 99.61 |
| 4807 | 1373245 | G | 1550 | 1065 | 143 | 1365505 | 4982 | 99.44 |
| 4808 | 1276125 | T | 1947 | 1266945 | 2018 | 4575 | 646 | 99.28 |
| 4810 | 1267827 | T | 1151 | 1263170 | 1135 | 1786 | 585 | 99.63 |
| 4813 | 1288645 | A | 1282764 | 1375 | 227 | 1804 | 2473 | 99.54 |
| 4816 | 1342010 | C | 912 | 903 | 1337317 | 676 | 2002 | 99.67 |
| 4818 | 1333940 | G | 1450 | 857 | 244 | 1329718 | 1671 | 99.68 |
| 4819 | 1335775 | T | 1007 | 1331292 | 938 | 2363 | 155 | 99.66 |
| 4821 | 1356364 | A | 1348340 | 3271 | 434 | 4313 | 166 | 99.39 |
| 4833 | 1485624 | A | 1478876 | 2822 | 256 | 3119 | 331 | 99.55 |
| 4834 | 1348800 | C | 907 | 1116 | 1338290 | 4275 | 4212 | 99.32 |

FIG. 5E

| | | | | | | | | |
|---|---|---|---|---|---|---|---|---|
| 4833 | 1543665 | T | 536 | 1539541 | 700 | 4697 | 191 | 99.6 |
| 4842 | 1548179 | G | 1075 | 891 | 225 | 1543099 | 2388 | 99.67 |
| 4846 | 1469713 | C | 1000 | 1853 | 1465243 | 761 | 854 | 99.7 |
| 4848 | 1534093 | G | 1582 | 936 | 234 | 1576750 | 3491 | 99.48 |
| 4849 | 1587309 | T | 1171 | 1581622 | 1161 | 3325 | 30 | 99.64 |
| 4850 | 1667253 | C | 953 | 1615 | 1659689 | 843 | 4121 | 99.35 |
| 4851 | 1667609 | C | 1460 | 3394 | 1661129 | 545 | 961 | 99.61 |
| 4856 | 1661370 | G | 1390 | 1108 | 223 | 1658206 | 10443 | 99.22 |
| 4857 | 1542855 | T | 2068 | 1534265 | 2068 | 4371 | 43 | 99.44 |
| 4858 | 1552008 | G | 1919 | 914 | 216 | 1543122 | 5797 | 99.43 |
| 4859 | 1478612 | T | 1623 | 1471072 | 1846 | 3971 | 140 | 99.49 |
| 4860 | 1534957 | G | 1361 | 935 | 139 | 1523859 | 3663 | 99.6 |
| 4861 | 1565241 | T | 1618 | 1555314 | 1783 | 4403 | 2079 | 99.37 |
| 4864 | 1546457 | T | 4041 | 1532192 | 3738 | 5392 | 3094 | 99.08 |
| 4869 | 1434107 | C | 1220 | 1371 | 1423959 | 926 | 4631 | 99.43 |
| 4896 | 1427743 | G | 664 | 863 | 232 | 1422853 | 3132 | 99.66 |
| 4898 | 1457949 | G | 816 | 1119 | 206 | 1451355 | 4450 | 99.35 |
| 4899 | 1454823 | T | 1069 | 1450080 | 1217 | 2257 | 262 | 99.67 |
| 4903 | 1551041 | A | 1544334 | 501 | 264 | 1225 | 4724 | 99.57 |
| 4904 | 1554143 | T | 408 | 1549625 | 330 | 888 | 2951 | 99.71 |
| 4906 | 1513749 | C | 1038 | 2418 | 1507477 | 385 | 4308 | 99.45 |
| 4908 | 1572271 | G | 1837 | 1111 | 278 | 1559560 | 10485 | 99.13 |
| 4909 | 1663100 | T | 1114 | 1662772 | 1090 | 2075 | 1049 | 99.68 |
| 4911 | 1703969 | T | 466 | 1702751 | 326 | 763 | 5663 | 99.58 |
| 4913 | 1667732 | G | 1378 | 1196 | 274 | 1662569 | 2315 | 99.69 |
| 4914 | 1664093 | A | 1618869 | 1640 | 378 | 2869 | 137 | 99.69 |
| 4915 | 1661580 | C | 3906 | 1767 | 1653368 | 621 | 1018 | 99.63 |
| 4916 | 1647682 | C | 1361 | 1655 | 1633820 | 685 | 10161 | 99.16 |
| 4918 | 1577185 | G | 1347 | 1102 | 263 | 1568482 | 6041 | 99.45 |
| 4920 | 1598818 | T | 811 | 1594755 | 466 | 1419 | 1407 | 99.74 |
| 4921 | 1603745 | C | 987 | 1304 | 1595741 | 471 | 2242 | 99.69 |
| 4922 | 1572996 | A | 1570665 | 2271 | 386 | 2679 | 93 | 99.66 |
| 4923 | 1681676 | C | 795 | 1626 | 1671852 | 587 | 6816 | 99.42 |
| 4926 | 1689762 | C | 1063 | 1581 | 1680903 | 463 | 5752 | 99.48 |
| 4931 | 1636695 | A | 1627128 | 707 | 637 | 1578 | 6647 | 99.42 |
| 4936 | 1517356 | C | 1026 | 1546 | 1513077 | 633 | 1054 | 99.72 |
| 4938 | 1512710 | A | 1506430 | 582 | 606 | 1144 | 1948 | 99.72 |
| 4942 | 1469909 | G | 1308 | 1163 | 396 | 1465650 | 1472 | 99.71 |
| 4948 | 1448996 | C | 1466 | 1598 | 1444658 | 646 | 688 | 99.7 |
| 4953 | 1469457 | G | 1621 | 1379 | 308 | 1464816 | 1133 | 99.69 |
| 4968 | 1474347 | C | 1291 | 1745 | 1469321 | 1390 | 600 | 99.66 |
| 4968 | 1469859 | A | 1465329 | 718 | 496 | 1113 | 2003 | 99.71 |
| 4971 | 1563369 | G | 1926 | 1201 | 267 | 1557171 | 2824 | 99.6 |
| 4972 | 1553853 | T | 2523 | 1545235 | 2330 | 3362 | 403 | 99.45 |
| 4976 | 1541079 | G | 1025 | 1003 | 435 | 1536501 | 2115 | 99.7 |
| 4979 | 1514911 | G | 1396 | 1036 | 348 | 1509881 | 2050 | 99.67 |
| 4980 | 1497349 | C | 1068 | 1564 | 1492700 | 967 | 1030 | 99.69 |
| 4983 | 1528333 | T | 1113 | 1523636 | 1212 | 2278 | 96 | 99.69 |
| 4986 | 1550794 | T | 697 | 1546514 | 708 | 1327 | 1548 | 99.72 |
| 4987 | 1574962 | C | 847 | 1373 | 1570207 | 564 | 1969 | 99.7 |
| 4992 | 1565663 | G | 1417 | 1361 | 634 | 1563370 | 2879 | 99.6 |
| 4993 | 1548168 | A | 1541192 | 2176 | 347 | 4172 | 81 | 99.55 |
| 4996 | 1561555 | A | 1554281 | 2972 | 343 | 3477 | 282 | 99.53 |

| | | | | | | | | |
|---|---|---|---|---|---|---|---|---|
| 5147 | 1344445 | G | 841 | 817 | 187 | 1339811 | 2789 | 99.66 |
| 5152 | 1376520 | G | 945 | 912 | 246 | 1370469 | 3758 | 99.57 |
| 5154 | 1396252 | A | 1391851 | 1455 | 228 | 2490 | 238 | 99.68 |
| 5155 | 1419228 | C | 988 | 2017 | 1413472 | 618 | 2093 | 99.59 |
| 5158 | 1436460 | C | 1230 | 1645 | 1431033 | 651 | 1871 | 99.62 |
| 5161 | 1484550 | C | 1234 | 1449 | 1426062 | 1978 | 3827 | 99.41 |
| 5163 | 1381020 | G | 718 | 852 | 232 | 1376614 | 2574 | 99.68 |
| 5166 | 1504754 | C | 1312 | 1953 | 1499011 | 1075 | 1403 | 99.62 |
| 5171 | 1515972 | A | 1510677 | 1688 | 242 | 2638 | 727 | 99.63 |
| 5172 | 1526043 | C | 1507 | 1381 | 1519793 | 709 | 2853 | 99.18 |
| 5175 | 1561103 | T | 826 | 1556254 | 293 | 1147 | 2581 | 99.69 |
| 5177 | 1532256 | C | 1003 | 1210 | 1531100 | 601 | 1342 | 99.73 |
| 5180 | 1510498 | C | 1101 | 1554 | 1506348 | 457 | 908 | 99.71 |
| 5183 | 1491350 | G | 1102 | 1061 | 323 | 1490083 | 1959 | 99.7 |
| 5186 | 1503733 | G | 1174 | 669 | 268 | 1499238 | 2364 | 99.7 |
| 5187 | 1473638 | T | 3833 | 1457648 | 4475 | 7669 | 33 | 98.91 |
| 5189 | 1474221 | A | 1469853 | 1235 | 662 | 2432 | 19 | 99.7 |
| 5192 | 1471552 | A | 1462042 | 3756 | 218 | 4406 | 1130 | 99.33 |
| 5193 | 1455599 | C | 1546 | 1190 | 1451489 | 542 | 822 | 99.72 |
| 5194 | 1448029 | C | 1269 | 1103 | 1443157 | 631 | 1869 | 99.66 |
| 5204 | 1422418 | G | 1653 | 978 | 683 | 1417892 | 1212 | 99.68 |
| 5205 | 1321880 | T | 2003 | 1312725 | 2162 | 4727 | 263 | 99.4 |
| 5206 | 1569278 | G | 1203 | 1635 | 735 | 1562588 | 3117 | 99.37 |
| 5207 | 1570147 | G | 2177 | 1556 | 453 | 1565646 | 285 | 99.71 |
| 5212 | 1573374 | A | 1566639 | 1008 | 1395 | 4271 | 61 | 99.57 |
| 5213 | 1571163 | G | 1827 | 1163 | 403 | 1566081 | 1695 | 99.68 |
| 5214 | 1565578 | T | 2813 | 1548302 | 2926 | 7440 | 4097 | 95.9 |
| 5215 | 1582313 | T | 318 | 1576267 | 613 | 1363 | 3732 | 99.62 |
| 5216 | 1683674 | G | 1236 | 2813 | 384 | 1673070 | 6109 | 99.37 |
| 5217 | 1687939 | T | 1765 | 1678578 | 1982 | 5368 | 246 | 99.45 |
| 5218 | 1685885 | C | 2357 | 2389 | 1678999 | 1220 | 721 | 99.59 |
| 5219 | 1689621 | T | 336 | 1684495 | 948 | 953 | 2186 | 99.73 |
| 5220 | 1695298 | A | 1690995 | 1544 | 677 | 1316 | 766 | 99.75 |
| 5221 | 1710422 | G | 2278 | 1946 | 361 | 1703013 | 2822 | 99.57 |
| 5223 | 1696833 | T | 1366 | 1685661 | 1676 | 3734 | 6376 | 99.22 |
| 5224 | 1606365 | C | 1996 | 2194 | 1593754 | 841 | 7578 | 99.21 |
| 5225 | 1520075 | A | 1515038 | 631 | 1349 | 1284 | 1773 | 99.67 |
| 5226 | 1603030 | T | 723 | 1593898 | 739 | 1606 | 6064 | 99.43 |
| 5227 | 1677327 | G | 2570 | 2985 | 418 | 1666767 | 4489 | 99.37 |
| 5228 | 1684866 | T | 1823 | 1675362 | 1860 | 4600 | 1221 | 99.44 |
| 5230 | 1670336 | T | 640 | 1665422 | 383 | 613 | 3078 | 99.71 |
| 5233 | 1663534 | A | 1666498 | 1860 | 339 | 2435 | 402 | 99.7 |
| 5234 | 1660800 | C | 1451 | 1206 | 1651889 | 481 | 5763 | 99.46 |
| 5236 | 1583482 | G | 1342 | 1339 | 245 | 1576271 | 4285 | 99.54 |
| 5237 | 1557471 | T | 1381 | 1551341 | 1338 | 3341 | 70 | 99.61 |
| 5240 | 1593330 | G | 1626 | 1442 | 448 | 1590842 | 972 | 99.72 |
| 5241 | 1596898 | C | 957 | 2062 | 1592163 | 1019 | 657 | 99.7 |
| 5245 | 1630279 | A | 1625603 | 1004 | 929 | 2779 | 1964 | 99.59 |
| 5246 | 1639111 | C | 1067 | 1728 | 1634049 | 550 | 1517 | 99.7 |
| 5247 | 1638070 | A | 1629583 | 3196 | 645 | 4454 | 192 | 99.48 |
| 5248 | 1660434 | C | 1147 | 2211 | 1653283 | 607 | 3184 | 99.57 |
| 5249 | 1652748 | C | 1509 | 1682 | 1648226 | 709 | 422 | 99.73 |
| 5250 | 1658781 | A | 1654269 | 738 | 957 | 2050 | 747 | 99.73 |

FIG. 5H

| | | | | | | | | |
|---|---|---|---|---|---|---|---|---|
| 5251 | 1676782 | G | 1420 | 2006 | 489 | 1671086 | 1781 | 99.66 |
| 5252 | 1736615 | G | 1350 | 1606 | 375 | 1732490 | 794 | 99.76 |
| 5253 | 1748415 | G | 1219 | 1414 | 438 | 1740223 | 3131 | 99.53 |
| 5254 | 1748041 | A | 1735614 | 1404 | 2001 | 6438 | 3384 | 99.23 |
| 5255 | 1782999 | G | 2515 | 2078 | 1029 | 1774050 | 3297 | 99.5 |
| 5256 | 1790006 | C | 1774 | 3732 | 1781399 | 1455 | 1446 | 99.53 |
| 5257 | 1793434 | A | 1790615 | 739 | 814 | 1590 | 1676 | 99.73 |
| 5259 | 1738146 | A | 1733248 | 2172 | 453 | 2579 | 694 | 99.67 |
| 5260 | 1786696 | C | 1362 | 2905 | 1789736 | 594 | 2049 | 99.62 |
| 5261 | 1779435 | A | 1773913 | 1804 | 837 | 2656 | 225 | 99.69 |
| 5262 | 1767429 | C | 1569 | 2087 | 1757019 | 781 | 3433 | 99.41 |
| 5263 | 1690019 | T | 671 | 1683922 | 1169 | 2128 | 2138 | 99.64 |
| 5264 | 1706678 | G | 1361 | 1576 | 303 | 1700219 | 3219 | 99.62 |
| 5265 | 1706490 | G | 1278 | 1928 | 417 | 1702736 | 2131 | 99.66 |
| 5266 | 1677864 | T | 2603 | 1665720 | 3667 | 5339 | 315 | 99.23 |
| 5269 | 1688688 | A | 1684141 | 1790 | 429 | 2147 | 181 | 99.73 |
| 5270 | 1685583 | C | 1545 | 1812 | 1683579 | 631 | 1016 | 99.7 |
| 5271 | 1677844 | C | 2110 | 1413 | 1672591 | 569 | 1161 | 99.69 |
| 5273 | 1608722 | C | 4438 | 1305 | 1613224 | 473 | 1242 | 99.54 |
| 5281 | 1673957 | A | 1667612 | 1823 | 1369 | 2927 | 226 | 99.62 |
| 5282 | 1674084 | C | 4973 | 922 | 1667315 | 382 | 492 | 99.6 |
| 5288 | 1681330 | G | 2269 | 1393 | 695 | 1685704 | 969 | 99.67 |
| 5289 | 1686833 | T | 2589 | 1674241 | 3037 | 6219 | 247 | 99.27 |
| 5290 | 1690407 | G | 2042 | 1535 | 1154 | 1685262 | 394 | 99.7 |
| 5291 | 1697086 | C | 1172 | 2203 | 1692556 | 736 | 419 | 99.73 |
| 5293 | 1707133 | C | 1246 | 1327 | 1702483 | 793 | 1088 | 99.73 |
| 5294 | 1716418 | A | 1703084 | 4346 | 1153 | 5545 | 290 | 99.34 |
| 5295 | 1979060 | C | 1730 | 2222 | 1958063 | 1228 | 15817 | 98.94 |
| 5296 | 2006306 | C | 2417 | 3243 | 1998215 | 1318 | 2913 | 99.5 |
| 5297 | 2033101 | A | 2030977 | 782 | 1268 | 1859 | 215 | 99.8 |
| 5301 | 2039146 | G | 1462 | 2162 | 552 | 2053793 | 1157 | 99.74 |
| 5302 | 2039138 | G | 2194 | 1762 | 512 | 2032544 | 2126 | 99.68 |
| 5303 | 2030748 | A | 2021477 | 1540 | 2777 | 3498 | 1436 | 99.54 |
| 5304 | 2006570 | C | 2137 | 2349 | 1993221 | 858 | 8205 | 99.32 |
| 5306 | 1889139 | G | 2294 | 1273 | 606 | 1891721 | 3245 | 99.61 |
| 5307 | 2089201 | C | 2295 | 2805 | 2082503 | 1213 | 385 | 99.68 |
| 5309 | 2099106 | A | 2094135 | 628 | 572 | 2073 | 1698 | 99.76 |
| 5310 | 2088754 | A | 2082727 | 866 | 772 | 3544 | 545 | 99.71 |
| 5311 | 2136251 | G | 3781 | 2616 | 785 | 2125911 | 3138 | 99.52 |
| 5312 | 2187266 | G | 2592 | 2357 | 570 | 2176964 | 4483 | 99.33 |
| 5313 | 2237667 | T | 12281 | 2222703 | 9666 | 12643 | 374 | 98.43 |
| 5314 | 2254795 | A | 2247806 | 2066 | 640 | 3557 | 729 | 99.69 |
| 5315 | 2218137 | C | 1902 | 4355 | 2209032 | 1027 | 1821 | 99.59 |
| 5318 | 2120897 | G | 1328 | 1706 | 426 | 2115792 | 1345 | 99.77 |
| 5319 | 2159428 | G | 1893 | 1919 | 745 | 2151279 | 3592 | 99.62 |
| 5320 | 2141419 | G | 3068 | 1883 | 911 | 2133022 | 2535 | 99.61 |
| 5321 | 2069011 | C | 1878 | 1974 | 2093517 | 1121 | 121 | 99.74 |
| 5322 | 2071448 | C | 1910 | 1819 | 2066404 | 1053 | 262 | 99.76 |
| 5323 | 2067311 | A | 2063033 | 963 | 899 | 2382 | 34 | 99.79 |
| 5324 | 2123750 | G | 1248 | 1791 | 316 | 2117133 | 3262 | 99.69 |
| 5325 | 2131122 | G | 1555 | 2514 | 399 | 2126418 | 236 | 99.78 |
| 5326 | 2136293 | G | 1833 | 1477 | 303 | 2131477 | 1181 | 99.77 |
| 5327 | 2065823 | T | 6539 | 2042526 | 6217 | 9093 | 1448 | 98.57 |

FIG. 5I

| | | | | | | | | |
|---|---|---|---|---|---|---|---|---|
| 5329 | 2039037 | C | 971 | 3401 | 2030833 | 1162 | 2670 | 99.6 |
| 5330 | 2044824 | G | 1731 | 1684 | 340 | 2040663 | 381 | 99.8 |
| 5331 | 2059290 | A | 2083865 | 651 | 700 | 1500 | 2374 | 99.74 |
| 5332 | 2059156 | T | 575 | 2092933 | 628 | 1142 | 3880 | 99.7 |
| 5334 | 2064253 | A | 2058717 | 1462 | 342 | 2163 | 1569 | 99.73 |
| 5335 | 2061023 | C | 4504 | 3481 | 2051223 | 1011 | 802 | 99.32 |
| 5336 | 2063694 | G | 3462 | 1585 | 1546 | 2056798 | 303 | 99.67 |
| 5337 | 2067822 | C | 1224 | 2024 | 2060136 | 1095 | 3343 | 99.63 |
| 5339 | 2034414 | G | 1333 | 1509 | 359 | 2023493 | 2620 | 99.71 |
| 5340 | 2031381 | T | 2664 | 2022364 | 1912 | 4386 | 33 | 99.56 |
| 5341 | 2110783 | G | 1361 | 1913 | 663 | 2100954 | 5892 | 99.53 |
| 5342 | 2128013 | G | 2533 | 2463 | 730 | 2120866 | 1401 | 99.66 |
| 5343 | 2115029 | C | 1668 | 2853 | 2108312 | 1336 | 660 | 99.68 |
| 5347 | 2134563 | C | 1585 | 1579 | 490 | 2134282 | 3627 | 99.66 |
| 5348 | 2132294 | G | 2380 | 1797 | 535 | 2132223 | 1379 | 99.72 |
| 5349 | 2069458 | C | 2006 | 2777 | 2061480 | 1674 | 5121 | 99.43 |
| 5350 | 2024042 | T | 1785 | 2019166 | 976 | 1119 | 1076 | 99.76 |
| 5354 | 1994610 | A | 1980088 | 360 | 373 | 5673 | 114 | 99.67 |
| 5355 | 1972502 | G | 2321 | 904 | 244 | 1966292 | 2541 | 99.69 |
| 5359 | 1948229 | C | 1360 | 1843 | 1942159 | 671 | 2196 | 99.69 |
| 5361 | 1991123 | T | 546 | 1964607 | 461 | 1325 | 3964 | 99.67 |
| 5363 | 2043543 | G | 1516 | 1929 | 461 | 2033903 | 4632 | 99.38 |
| 5364 | 2055314 | T | 1264 | 2049437 | 1469 | 2506 | 238 | 99.71 |
| 5366 | 2022643 | A | 2016874 | 1944 | 508 | 3187 | 128 | 99.71 |
| 5367 | 2029449 | C | 864 | 1996 | 2023861 | 514 | 2094 | 99.73 |
| 5369 | 2013383 | G | 1906 | 1324 | 705 | 2009402 | 2046 | 99.7 |
| 5370 | 2004340 | C | 1405 | 2669 | 1998720 | 773 | 771 | 99.72 |
| 5372 | 2002023 | A | 1996595 | 1728 | 328 | 2529 | 846 | 99.73 |
| 5373 | 2048417 | C | 994 | 898 | 2041509 | 700 | 4016 | 99.68 |
| 5375 | 2068897 | A | 2061303 | 2746 | 438 | 2872 | 1536 | 99.63 |
| 5376 | 2058828 | C | 1143 | 1698 | 2054104 | 501 | 1082 | 99.79 |
| 5377 | 2067367 | T | 575 | 2062735 | 873 | 1341 | 1563 | 99.79 |
| 5378 | 2108384 | A | 2103617 | 455 | 409 | 1643 | 2260 | 99.77 |
| 5379 | 2133113 | G | 2767 | 1830 | 560 | 2127388 | 2378 | 99.65 |
| 5380 | 2128564 | C | 1839 | 2373 | 2123514 | 947 | 891 | 99.72 |
| 5381 | 2118223 | A | 2111438 | 540 | 783 | 2002 | 3449 | 99.68 |
| 5382 | 2067785 | A | 2062945 | 859 | 805 | 2412 | 764 | 99.77 |
| 5383 | 2067297 | G | 1253 | 1700 | 407 | 2063198 | 739 | 99.8 |
| 5384 | 2108892 | G | 1620 | 1702 | 367 | 2103358 | 1845 | 99.74 |
| 5385 | 2112757 | G | 1197 | 1671 | 533 | 2107326 | 2010 | 99.74 |
| 5386 | 2089400 | A | 2080631 | 1282 | 2028 | 3228 | 233 | 99.58 |
| 5387 | 2104028 | G | 1166 | 1381 | 480 | 2097151 | 3650 | 99.67 |
| 5388 | 2062991 | A | 2053649 | 1473 | 2118 | 3564 | 167 | 99.65 |
| 5389 | 2103324 | G | 2032 | 1685 | 600 | 2097776 | 3441 | 99.63 |
| 5390 | 2122839 | T | 2665 | 2111952 | 2916 | 4767 | 339 | 99.49 |
| 5392 | 2134634 | C | 1337 | 2666 | 2127673 | 862 | 2104 | 99.67 |
| 5393 | 2112825 | A | 2105796 | 2564 | 1000 | 3379 | 86 | 99.67 |
| 5394 | 1983624 | C | 1532 | 3538 | 1972790 | 1193 | 4571 | 99.43 |
| 5395 | 1968108 | T | 505 | 1964993 | 842 | 1341 | 1027 | 99.79 |
| 5396 | 2164114 | A | 2146829 | 812 | 529 | 1724 | 14220 | 99.2 |
| 5397 | 2206868 | T | 827 | 2193706 | 1102 | 2668 | 8563 | 99.4 |
| 5398 | 2189832 | G | 1420 | 2482 | 385 | 2181103 | 4437 | 99.6 |
| 5399 | 2183215 | T | 1676 | 2177989 | 1990 | 2831 | 729 | 99.67 |

FIG. 5J

| | | | | | | | | |
|---|---|---|---|---|---|---|---|---|
| 5402 | 2161632 | G | 1918 | 2004 | 431 | 2136356 | 703 | 99.77 |
| 5403 | 2136931 | G | 1449 | 1418 | 385 | 2144683 | 8796 | 99.43 |
| 5404 | 2030767 | A | 2006414 | 601 | 576 | 2205 | 971 | 99.79 |
| 5405 | 2173806 | G | 2326 | 1902 | 612 | 2147693 | 21273 | 98.8 |
| 5406 | 2014760 | T | 2292 | 2003056 | 2719 | 3310 | 1383 | 99.42 |
| 5407 | 1976411 | C | 935 | 1494 | 1971928 | 658 | 1396 | 99.77 |
| 5409 | 1998362 | A | 1994173 | 1066 | 779 | 2161 | 203 | 99.79 |
| 5410 | 2000155 | C | 798 | 4225 | 1993323 | 671 | 1138 | 99.66 |
| 5411 | 1968191 | G | 2185 | 1173 | 396 | 1994055 | 180 | 99.79 |
| 5413 | 1935903 | C | 1907 | 2290 | 1923308 | 802 | 7596 | 99.33 |
| 5416 | 1837119 | C | 916 | 2016 | 1830025 | 676 | 383 | 99.77 |
| 5418 | 1833193 | T | 3123 | 1819259 | 3752 | 6137 | 922 | 99.24 |
| 5421 | 1844344 | C | 1227 | 1985 | 1839044 | 924 | 1164 | 99.71 |
| 5426 | 1865093 | T | 478 | 1860436 | 818 | 1229 | 2092 | 99.75 |
| 5428 | 1865340 | A | 1839088 | 2416 | 628 | 2972 | 236 | 99.66 |
| 5429 | 1838972 | C | 1049 | 1857 | 1834026 | 464 | 946 | 99.76 |
| 5430 | 1821866 | C | 1612 | 1983 | 1816635 | 540 | 1056 | 99.71 |
| 5432 | 1853743 | A | 1846510 | 1433 | 345 | 2124 | 3333 | 99.61 |
| 5433 | 1880655 | C | 1282 | 1135 | 1876060 | 629 | 1639 | 99.75 |
| 5434 | 1868673 | C | 1503 | 1174 | 1864323 | 665 | 1204 | 99.76 |
| 5436 | 1848140 | A | 1842274 | 1329 | 1338 | 2239 | 760 | 99.68 |
| 5437 | 1874099 | C | 914 | 2726 | 1867256 | 683 | 2320 | 99.63 |
| 5438 | 1875713 | G | 2392 | 1872 | 1196 | 1870092 | 161 | 99.7 |
| 5439 | 1871058 | C | 1271 | 1632 | 1866517 | 747 | 891 | 99.76 |
| 5440 | 1871886 | T | 792 | 1867088 | 1429 | 1459 | 1118 | 99.74 |
| 5442 | 1890061 | C | 1327 | 2220 | 1884823 | 715 | 976 | 99.72 |
| 5443 | 1928520 | A | 1919208 | 3174 | 1571 | 4454 | 113 | 99.52 |
| 5444 | 1951828 | C | 2166 | 2842 | 1944433 | 1052 | 1335 | 99.62 |
| 5445 | 1911332 | C | 1986 | 1972 | 1904802 | 753 | 2819 | 99.61 |
| 5447 | 1926119 | G | 1921 | 1366 | 314 | 1918554 | 3924 | 99.61 |
| 5448 | 1934406 | G | 1812 | 2204 | 326 | 1929158 | 706 | 99.73 |
| 5449 | 1927703 | T | 3773 | 1908373 | 3264 | 9920 | 171 | 99.01 |
| 5450 | 1933332 | G | 1542 | 990 | 305 | 1928948 | 1547 | 99.77 |
| 5452 | 1994724 | A | 1990283 | 816 | 817 | 1824 | 984 | 99.78 |
| 5454 | 1991435 | G | 2573 | 1031 | 663 | 1985782 | 1366 | 99.72 |
| 5455 | 2037060 | C | 1576 | 2690 | 2027913 | 1046 | 3833 | 99.55 |
| 5456 | 1999155 | A | 1995031 | 833 | 868 | 1731 | 690 | 99.79 |
| 5459 | 2009999 | G | 2473 | 2013 | 374 | 2002946 | 1989 | 99.65 |
| 5460 | 1977793 | T | 2079 | 1968358 | 2208 | 4870 | 248 | 99.52 |
| 5462 | 1952710 | A | 1947813 | 769 | 778 | 1891 | 1459 | 99.75 |
| 5463 | 1933383 | T | 899 | 1925513 | 644 | 1588 | 1739 | 99.75 |
| 5464 | 1855506 | C | 1069 | 2081 | 1851331 | 788 | 317 | 99.77 |
| 5466 | 1858964 | A | 1854329 | 802 | 1362 | 1798 | 673 | 99.75 |
| 5467 | 1861470 | T | 952 | 1855945 | 1024 | 1957 | 1392 | 99.7 |
| 5469 | 1854618 | G | 2394 | 1267 | 491 | 1849199 | 1247 | 99.71 |
| 5470 | 1848599 | C | 1350 | 2804 | 1842974 | 1192 | 279 | 99.7 |
| 5474 | 1886779 | G | 1423 | 1334 | 318 | 1880145 | 3557 | 99.63 |
| 5475 | 1883139 | A | 1878926 | 677 | 1124 | 1731 | 681 | 99.78 |
| 5477 | 1875797 | G | 1836 | 1176 | 390 | 1869594 | 2801 | 99.67 |
| 5478 | 1841170 | T | 6668 | 1818308 | 6282 | 9641 | 51 | 98.77 |
| 5480 | 1832965 | G | 1423 | 1525 | 305 | 1828807 | 705 | 99.77 |
| 5482 | 1887793 | G | 1495 | 1663 | 462 | 1878764 | 3407 | 99.63 |
| 5483 | 1856363 | A | 1851571 | 826 | 1326 | 1839 | 803 | 99.74 |

FIG. 5K

| | | | | | | | | |
|---|---|---|---|---|---|---|---|---|
| 5484 | 1870006 | T | 1094 | 1865349 | 800 | 2234 | 509 | 99.73 |
| 5485 | 1857668 | C | 1137 | 1715 | 1852764 | 562 | 1490 | 99.74 |
| 5490 | 2086517 | A | 2091108 | 925 | 943 | 2206 | 3315 | 99.65 |
| 5491 | 2078366 | T | 732 | 2073957 | 892 | 1743 | 1022 | 99.79 |
| 5492 | 2064317 | G | 2630 | 1468 | 648 | 2059113 | 458 | 99.75 |
| 5493 | 2063266 | C | 2142 | 3138 | 2056245 | 1235 | 506 | 99.66 |
| 5494 | 2072260 | C | 2400 | 2318 | 2065954 | 1179 | 409 | 99.7 |
| 5498 | 1844213 | G | 2537 | 1866 | 1222 | 1836718 | 1870 | 99.59 |
| 5499 | 1819381 | C | 961 | 2029 | 1815239 | 827 | 325 | 99.77 |
| 5501 | 1846672 | C | 1220 | 1133 | 1841280 | 859 | 2180 | 99.71 |
| 5502 | 1845892 | T | 1080 | 1841594 | 701 | 2466 | 51 | 99.77 |
| 5503 | 1848985 | C | 1243 | 2104 | 1844642 | 910 | 86 | 99.77 |
| 5507 | 1743009 | G | 1019 | 985 | 172 | 1738497 | 2336 | 99.74 |
| 5508 | 1749031 | T | 700 | 1744260 | 486 | 1247 | 2338 | 99.73 |
| 5512 | 1756456 | A | 1752430 | 797 | 351 | 1887 | 2991 | 99.66 |
| 5513 | 1763873 | G | 2283 | 1692 | 476 | 1758643 | 779 | 99.7 |
| 5514 | 1778896 | C | 1453 | 2260 | 1773274 | 1224 | 683 | 99.68 |
| 5519 | 1797589 | A | 1791425 | 2393 | 287 | 3398 | 86 | 99.66 |
| 5520 | 1796125 | C | 1307 | 1342 | 1790631 | 645 | 2183 | 99.7 |
| 5521 | 1770123 | C | 1603 | 1671 | 1765618 | 663 | 568 | 99.73 |
| 5523 | 1804552 | A | 1799304 | 512 | 578 | 1204 | 2954 | 99.71 |
| 5525 | 1807533 | C | 1227 | 1456 | 1802440 | 452 | 1928 | 99.72 |
| 5531 | 1817522 | A | 1813110 | 361 | 254 | 1330 | 2567 | 99.76 |
| 5533 | 1844530 | C | 962 | 1377 | 1833992 | 703 | 7336 | 99.43 |
| 5534 | 1877766 | A | 1867993 | 2736 | 280 | 3660 | 3047 | 99.48 |
| 5535 | 1996931 | C | 982 | 1647 | 1985063 | 606 | 8233 | 99.43 |
| 5541 | 2029904 | T | 1283 | 2021572 | 601 | 1957 | 4481 | 99.59 |
| 5542 | 2001320 | C | 1942 | 1796 | 1992645 | 720 | 4217 | 99.57 |
| 5543 | 1966687 | A | 1944270 | 7787 | 396 | 9295 | 4939 | 98.86 |
| 5544 | 2063319 | C | 1335 | 931 | 2069290 | 753 | 11210 | 99.32 |
| 5546 | 2055035 | C | 1561 | 1063 | 2049567 | 578 | 2166 | 99.74 |
| 5551 | 2080353 | G | 4197 | 1374 | 332 | 2071714 | 2736 | 99.58 |
| 5552 | 2058874 | A | 2053021 | 645 | 680 | 1746 | 3782 | 99.67 |
| 5553 | 2014912 | G | 1453 | 1068 | 240 | 2009043 | 3108 | 99.71 |
| 5554 | 2075082 | A | 2070874 | 552 | 686 | 1910 | 1060 | 99.8 |
| 5558 | 2117825 | G | 2709 | 863 | 234 | 2113345 | 674 | 99.79 |
| 5562 | 2223893 | A | 2217599 | 468 | 506 | 5172 | 148 | 99.72 |
| 5563 | 2281615 | G | 3725 | 1371 | 335 | 2277351 | 3833 | 99.64 |
| 5564 | 2293881 | T | 2723 | 2284207 | 2288 | 4430 | 234 | 99.58 |
| 5566 | 2297530 | C | 1067 | 2533 | 2292715 | 772 | 473 | 99.79 |
| 5570 | 2300500 | G | 1579 | 1403 | 417 | 2296355 | 746 | 99.82 |
| 5571 | 2367354 | A | 2332899 | 2063 | 1743 | 3810 | 6857 | 99.39 |
| 5572 | 2449904 | C | 1199 | 2494 | 2437023 | 829 | 8359 | 99.47 |
| 5576 | 2456513 | A | 2451978 | 458 | 431 | 1792 | 1854 | 99.82 |
| 5577 | 2467993 | G | 2516 | 2184 | 610 | 2461571 | 1112 | 99.74 |
| 5578 | 2467886 | A | 2463945 | 2691 | 771 | 4646 | 833 | 99.64 |
| 5579 | 2516334 | C | 2235 | 2384 | 2506615 | 801 | 4179 | 99.61 |
| 5580 | 2503052 | C | 2035 | 2121 | 2491213 | 912 | 6771 | 99.53 |
| 5581 | 2768218 | A | 2739730 | 3245 | 1317 | 4710 | 20216 | 98.94 |
| 5582 | 3028022 | C | 1609 | 4365 | 3002818 | 961 | 18269 | 99.17 |
| 5584 | 3025804 | T | 926 | 3021440 | 4190 | 1603 | 1645 | 99.72 |
| 5585 | 3013231 | A | 3009564 | 730 | 1621 | 2178 | 1138 | 99.81 |
| 5586 | 3232949 | T | 1124 | 3216957 | 1124 | 3277 | 10437 | 99.51 |

FIG. 5L

| | | | | | | | | |
|---|---|---|---|---|---|---|---|---|
| 5587 | 3226355 | A | 3103391 | 10501 | 760 | 11434 | 269 | 99.29 |
| 5588 | 3227994 | C | 5550 | 3235 | 3215847 | 1025 | 2334 | 99.62 |
| 5589 | 3183491 | C | 4644 | 2717 | 3157906 | 1136 | 17088 | 99.2 |
| 5590 | 2916887 | T | 1284 | 2907045 | 1888 | 1400 | 5090 | 99.66 |
| 5591 | 2943937 | A | 2927172 | 4842 | 780 | 5359 | 4684 | 99.46 |
| 5592 | 2930006 | C | 1725 | 1535 | 2945015 | 813 | 918 | 99.83 |
| 5593 | 2930844 | T | 1999 | 2944391 | 1251 | 3049 | 154 | 99.78 |
| 5594 | 2937004 | C | 2221 | 1567 | 2947360 | 690 | 5166 | 99.67 |
| 5598 | 2951625 | T | 2213 | 2944704 | 1040 | 3163 | 504 | 99.77 |
| 5599 | 2966304 | C | 1693 | 2461 | 2957939 | 870 | 3341 | 99.72 |
| 5600 | 2939135 | A | 2923625 | 5094 | 740 | 7427 | 246 | 99.54 |
| 5601 | 2921616 | C | 1338 | 1982 | 2917116 | 722 | 458 | 99.83 |
| 5602 | 2925097 | T | 1078 | 2920356 | 1296 | 2365 | 92 | 99.83 |
| 5603 | 2935059 | G | 2105 | 1737 | 544 | 2923614 | 1039 | 99.81 |
| 5604 | 2934932 | A | 2928542 | 1182 | 1122 | 3221 | 485 | 99.78 |
| 5605 | 2935948 | G | 2247 | 1699 | 491 | 2932842 | 1669 | 99.79 |
| 5606 | 2939174 | A | 2932263 | 1639 | 1567 | 3651 | 424 | 99.75 |
| 5607 | 2937810 | C | 2231 | 1935 | 2931473 | 913 | 1338 | 99.78 |
| 5608 | 2954483 | A | 2949069 | 735 | 693 | 2246 | 1720 | 99.82 |
| 5610 | 2976690 | A | 2970866 | 649 | 1105 | 2613 | 1557 | 99.8 |
| 5611 | 2976629 | T | 1138 | 2970767 | 1336 | 2633 | 755 | 99.8 |
| 5612 | 2974199 | G | 2231 | 2180 | 708 | 2968266 | 795 | 99.8 |
| 5613 | 3008004 | A | 2968765 | 1540 | 1865 | 3778 | 3036 | 99.66 |
| 5614 | 2979807 | T | 1433 | 2972413 | 1476 | 4341 | 142 | 99.75 |
| 5615 | 2980391 | G | 2543 | 2363 | 822 | 2974332 | 329 | 99.8 |
| 5616 | 2986593 | G | 2346 | 2593 | 1183 | 2978507 | 1966 | 99.73 |
| 5617 | 2976238 | A | 2967906 | 1325 | 1412 | 4185 | 1410 | 99.72 |
| 5618 | 3020096 | G | 2076 | 2502 | 919 | 3010976 | 3623 | 99.7 |
| 5619 | 3005765 | T | 5717 | 2983633 | 6931 | 9055 | 429 | 99.26 |
| 5620 | 3000623 | C | 2679 | 3232 | 2992520 | 1479 | 413 | 99.74 |
| 5621 | 3004190 | T | 954 | 2998245 | 1893 | 1942 | 1136 | 99.8 |
| 5622 | 3004630 | T | 510 | 3000414 | 1383 | 2221 | 102 | 99.86 |
| 5623 | 3006896 | G | 2568 | 3330 | 651 | 2999961 | 396 | 99.77 |
| 5624 | 3029793 | A | 3023310 | 1192 | 743 | 2362 | 2186 | 99.79 |
| 5625 | 3028949 | T | 1318 | 3020173 | 1422 | 2194 | 3600 | 99.71 |
| 5626 | 3004115 | C | 1938 | 3366 | 2994959 | 1466 | 2389 | 99.7 |
| 5627 | 2979015 | G | 3828 | 2366 | 1111 | 2968973 | 1737 | 99.7 |
| 5628 | 2943281 | T | 2799 | 2949907 | 3942 | 6588 | 45 | 99.35 |
| 5629 | 2968996 | G | 3316 | 2636 | 895 | 2961575 | 574 | 99.75 |
| 5631 | 3048397 | A | 3042710 | 1279 | 804 | 2578 | 1228 | 99.81 |
| 5632 | 3097565 | C | 2164 | 3312 | 3085614 | 1135 | 5640 | 99.6 |
| 5633 | 3072576 | A | 3064929 | 2321 | 1137 | 3566 | 123 | 99.75 |
| 5634 | 3030302 | C | 1548 | 3080 | 3019377 | 963 | 1034 | 99.64 |
| 5636 | 3060619 | A | 3053647 | 840 | 447 | 2349 | 3136 | 99.77 |
| 5637 | 3063978 | G | 4319 | 3310 | 1607 | 3053299 | 743 | 99.68 |
| 5638 | 3070040 | C | 2070 | 3738 | 3061727 | 1063 | 1442 | 99.73 |
| 5639 | 3075312 | A | 3069722 | 663 | 946 | 2183 | 1798 | 99.82 |
| 5640 | 3045595 | A | 3039916 | 659 | 815 | 2107 | 2401 | 99.8 |
| 5641 | 3033949 | G | 4768 | 2312 | 1021 | 3023514 | 2334 | 99.66 |
| 5642 | 3030723 | T | 8062 | 3004560 | 5744 | 7850 | 4467 | 99.14 |
| 5643 | 3028445 | A | 3011916 | 7469 | 760 | 6680 | 1320 | 99.41 |
| 5644 | 3028678 | C | 3860 | 3938 | 3008027 | 1043 | 9010 | 99.41 |
| 5645 | 3009762 | C | 2292 | 2584 | 3002997 | 1019 | 870 | 99.78 |

FIG. 5M

| | | | | | | | | |
|---|---|---|---|---|---|---|---|---|
| 5646 | 3000713 | C | 2403 | 2568 | 2993127 | 1078 | 1377 | 99.73 |
| 5647 | 3012032 | C | 3230 | 1971 | 3003137 | 1158 | 2336 | 99.7 |
| 5648 | 3040783 | A | 3033701 | 987 | 2175 | 2627 | 1293 | 99.77 |
| 5649 | 3116855 | A | 3102728 | 1893 | 1401 | 3257 | 7376 | 99.33 |
| 5650 | 3087704 | T | 1394 | 3060531 | 1413 | 1510 | 856 | 99.83 |
| 5651 | 3141330 | A | 3131913 | 1023 | 908 | 3334 | 4912 | 99.7 |
| 5652 | 3167895 | T | 815 | 3155112 | 1180 | 2167 | 8621 | 99.6 |
| 5653 | 3176610 | G | 3334 | 3203 | 693 | 3138230 | 9150 | 99.42 |
| 5654 | 3457023 | T | 3015 | 3439355 | 4842 | 7013 | 798 | 99.49 |
| 5655 | 3473063 | A | 3464781 | 1041 | 896 | 2429 | 3916 | 99.76 |
| 5656 | 3424288 | T | 900 | 3418568 | 1323 | 1949 | 1348 | 99.83 |
| 5657 | 3423233 | G | 3403 | 2031 | 696 | 3410976 | 6107 | 99.64 |
| 5658 | 3430624 | T | 2263 | 3420901 | 1677 | 3844 | 939 | 99.72 |
| 5659 | 3419304 | T | 1471 | 3410860 | 1145 | 3221 | 2607 | 99.75 |
| 5660 | 3469362 | C | 4292 | 2437 | 3393417 | 1369 | 5827 | 99.59 |
| 5661 | 3304634 | C | 2306 | 2003 | 3292138 | 1116 | 7061 | 99.62 |
| 5662 | 3214233 | T | 814 | 3209057 | 1370 | 2046 | 946 | 99.84 |
| 5663 | 3223841 | G | 3041 | 2581 | 965 | 3225371 | 1883 | 99.74 |
| 5664 | 3440788 | T | 2228 | 3430273 | 2248 | 5476 | 563 | 99.69 |
| 5665 | 3549946 | C | 2282 | 3191 | 3541774 | 1319 | 1380 | 99.77 |
| 5666 | 3529737 | G | 3381 | 2503 | 522 | 3523058 | 273 | 99.81 |
| 5667 | 3573174 | G | 3060 | 2472 | 1167 | 3563973 | 2502 | 99.74 |
| 5668 | 3591098 | T | 4859 | 3568318 | 6723 | 10082 | 1076 | 99.37 |
| 5669 | 3590618 | G | 4376 | 2188 | 727 | 3582781 | 786 | 99.78 |
| 5670 | 3462938 | C | 2257 | 3198 | 3472014 | 1573 | 1896 | 99.69 |
| 5671 | 3463561 | T | 1100 | 3457743 | 1783 | 2832 | 78 | 99.83 |
| 5672 | 3502333 | G | 2940 | 1897 | 562 | 3493948 | 2988 | 99.76 |
| 5673 | 3562900 | T | 3293 | 3546359 | 4360 | 7938 | 928 | 99.54 |
| 5674 | 3573333 | G | 2793 | 3132 | 856 | 3567832 | 720 | 99.79 |
| 5675 | 3611294 | A | 3601010 | 2266 | 1736 | 4711 | 1571 | 99.72 |
| 5676 | 3587183 | C | 2823 | 3140 | 3576384 | 1134 | 3502 | 99.7 |
| 5677 | 3534821 | T | 983 | 3529953 | 1420 | 2132 | 333 | 99.86 |
| 5678 | 3626928 | G | 3937 | 2571 | 734 | 3614303 | 5343 | 99.65 |
| 5679 | 3690578 | A | 3692038 | 1776 | 1628 | 3349 | 87 | 99.82 |
| 5680 | 3687288 | A | 3679237 | 2613 | 732 | 4535 | 111 | 99.78 |
| 5681 | 3473998 | C | 3280 | 4728 | 3461230 | 1580 | 3130 | 99.63 |
| 5682 | 3419134 | A | 3413183 | 1074 | 1137 | 3482 | 270 | 99.83 |
| 5683 | 3321140 | G | 2184 | 3013 | 795 | 3310770 | 4378 | 99.69 |
| 5684 | 3436206 | G | 2533 | 4010 | 939 | 3428122 | 600 | 99.76 |
| 5685 | 3431340 | G | 2778 | 2413 | 529 | 3444716 | 1104 | 99.8 |
| 5686 | 3463606 | A | 3438182 | 3572 | 3789 | 9378 | 8303 | 99.27 |
| 5687 | 3260736 | T | 1651 | 3254408 | 1309 | 2534 | 834 | 99.81 |
| 5688 | 3359654 | A | 3378084 | 1897 | 1141 | 2726 | 5806 | 99.66 |
| 5689 | 3400768 | T | 1468 | 3394971 | 1083 | 2405 | 841 | 99.83 |
| 5690 | 3358198 | C | 4086 | 4655 | 3347067 | 2050 | 920 | 99.67 |
| 5691 | 3349260 | T | 1870 | 3340984 | 912 | 1432 | 4042 | 99.73 |
| 5692 | 3298823 | A | 3294242 | 672 | 591 | 2145 | 1173 | 99.86 |
| 5694 | 3317112 | A | 3312067 | 1289 | 867 | 2188 | 701 | 99.83 |
| 5695 | 3319151 | T | 2682 | 3309542 | 1050 | 3145 | 732 | 99.71 |
| 5696 | 3310135 | C | 2242 | 2942 | 3298234 | 1249 | 5468 | 99.64 |
| 5697 | 3229974 | T | 2238 | 3219603 | 1344 | 4054 | 680 | 99.68 |
| 5698 | 3217398 | C | 2297 | 2732 | 3211086 | 1344 | 219 | 99.8 |
| 5699 | 3215373 | G | 3443 | 2236 | 894 | 3209252 | 48 | 99.79 |

| | | | | | | | | |
|---|---|---|---|---|---|---|---|---|
| 5737 | 3318673 | G | 2828 | 1692 | 322 | 3307159 | 6672 | 99.65 |
| 5738 | 3345144 | T | 4432 | 3318313 | 3233 | 9508 | 7658 | 99.2 |
| 5739 | 3255572 | G | 2676 | 1659 | 261 | 3250224 | 732 | 99.84 |
| 5740 | 3266075 | G | 4500 | 2088 | 464 | 3256866 | 2137 | 99.72 |
| 5761 | 3243815 | T | 7393 | 3211606 | 7764 | 15062 | 1988 | 99.01 |
| 5762 | 3224628 | G | 2355 | 1834 | 380 | 3219185 | 874 | 99.83 |
| 5763 | 3217646 | G | 1932 | 1834 | 540 | 3191588 | 21752 | 99.19 |
| 5764 | 2952144 | A | 2942492 | 1454 | 1250 | 6132 | 796 | 99.67 |
| 5765 | 2981994 | G | 2725 | 1736 | 631 | 2963657 | 13225 | 99.39 |
| 5766 | 2844511 | T | 2633 | 2831924 | 3331 | 6211 | 212 | 99.56 |
| 5767 | 2851295 | C | 2224 | 3176 | 2845239 | 1234 | 3402 | 99.65 |
| 5768 | 2906460 | A | 2899823 | 955 | 676 | 3074 | 1932 | 99.77 |
| 5769 | 2918784 | T | 1114 | 2913531 | 793 | 2122 | 1224 | 99.82 |
| 5770 | 2999735 | C | 2402 | 3339 | 2987484 | 1365 | 3168 | 99.59 |
| 5771 | 2995690 | A | 2964933 | 3839 | 646 | 5578 | 684 | 99.64 |
| 5772 | 3005447 | C | 3171 | 4437 | 2993409 | 907 | 3323 | 99.6 |
| 5773 | 2990478 | A | 2979252 | 1271 | 1282 | 1747 | 4926 | 99.62 |
| 5774 | 2923674 | T | 788 | 2925013 | 962 | 2430 | 481 | 99.84 |
| 5775 | 2991013 | G | 3018 | 1882 | 313 | 2978283 | 7315 | 99.57 |
| 5776 | 2989048 | T | 3270 | 2971007 | 3222 | 9080 | 2469 | 99.4 |
| 5777 | 2960940 | A | 2953810 | 3364 | 582 | 3782 | 402 | 99.73 |
| 5778 | 2935655 | C | 2082 | 3621 | 2919734 | 1493 | 8705 | 99.46 |
| 5779 | 2837345 | T | 857 | 2831383 | 1320 | 3131 | 144 | 99.81 |
| 5780 | 2864727 | G | 2625 | 1767 | 484 | 2856180 | 3671 | 99.7 |
| 5781 | 2846758 | G | 2082 | 2349 | 685 | 2835511 | 131 | 99.82 |
| 5782 | 2854430 | G | 2273 | 1645 | 486 | 2849514 | 310 | 99.83 |
| 5783 | 2854585 | A | 2830674 | 877 | 707 | 13555 | 8572 | 99.17 |
| 5784 | 2704641 | A | 2700213 | 793 | 731 | 2494 | 588 | 99.83 |
| 5785 | 2733503 | G | 3981 | 1632 | 505 | 2722913 | 3752 | 99.64 |
| 5786 | 2727355 | T | 3237 | 2713528 | 3390 | 7013 | 387 | 99.49 |
| 5787 | 2699680 | C | 2414 | 2994 | 2690300 | 1815 | 2157 | 99.65 |
| 5788 | 2685766 | T | 1323 | 2684227 | 974 | 2963 | 279 | 99.79 |
| 5789 | 2686936 | C | 1623 | 3173 | 2680040 | 2018 | 100 | 99.74 |
| 5790 | 2718207 | G | 1294 | 1371 | 347 | 2712693 | 2302 | 99.8 |
| 5791 | 2712782 | G | 2026 | 1461 | 666 | 2706234 | 2393 | 99.76 |
| 5792 | 2693693 | A | 2684365 | 1723 | 2323 | 4143 | 1139 | 99.65 |
| 5793 | 2700097 | T | 1252 | 2693193 | 1306 | 3717 | 429 | 99.74 |
| 5794 | 2717506 | G | 3164 | 1603 | 942 | 2710257 | 1540 | 99.73 |
| 5795 | 2752208 | C | 2281 | 4632 | 2743169 | 1646 | 449 | 99.67 |
| 5796 | 2779536 | A | 2772964 | 1351 | 1190 | 2661 | 1690 | 99.75 |
| 5797 | 2789973 | T | 708 | 2784762 | 1111 | 2706 | 683 | 99.81 |
| 5798 | 2789583 | G | 2182 | 1730 | 494 | 2781159 | 3838 | 99.71 |
| 5799 | 2744289 | T | 1139 | 2737735 | 1199 | 3097 | 1099 | 99.76 |
| 5800 | 2753145 | T | 507 | 2728871 | 933 | 1772 | 1062 | 99.84 |
| 5801 | 2765968 | G | 2739 | 1824 | 575 | 2757934 | 2876 | 99.71 |
| 5802 | 2755890 | G | 3028 | 2338 | 524 | 2746520 | 3490 | 99.66 |
| 5803 | 2777691 | T | 6019 | 2746564 | 7440 | 17228 | 646 | 98.87 |
| 5804 | 2770368 | G | 2014 | 1577 | 490 | 2763176 | 3111 | 99.74 |
| 5805 | 2729921 | G | 1426 | 2093 | 320 | 2725435 | 447 | 99.84 |
| 5806 | 2712290 | G | 2733 | 1660 | 883 | 2745142 | 1870 | 99.74 |
| 5807 | 2789310 | A | 2783487 | 1032 | 862 | 3873 | 236 | 99.78 |
| 5808 | 2788578 | A | 2781662 | 2200 | 592 | 3888 | 236 | 99.75 |
| 5809 | 2793813 | C | 1659 | 4214 | 2784450 | 1496 | 3994 | 99.59 |

FIG. 5P

| | | | | | | | | |
|---|---|---|---|---|---|---|---|---|
| 5813 | 2749130 | G | 2752 | 2367 | 852 | 2742521 | 428 | 99.76 |
| 5814 | 2809871 | G | 2607 | 1920 | 690 | 2800923 | 3731 | 99.68 |
| 5815 | 2803150 | T | 3349 | 2788060 | 4342 | 7319 | 80 | 99.46 |
| 5816 | 2835045 | T | 973 | 2827962 | 1065 | 2920 | 2125 | 99.75 |
| 5817 | 2831620 | C | 1903 | 3360 | 2823692 | 1209 | 1456 | 99.72 |
| 5818 | 2817051 | A | 2811815 | 1300 | 559 | 3172 | 205 | 99.81 |
| 5819 | 2822651 | C | 1820 | 3672 | 2815638 | 1062 | 459 | 99.75 |
| 5820 | 2845030 | A | 2837548 | 1995 | 613 | 4152 | 722 | 99.74 |
| 5821 | 2809059 | C | 2673 | 5123 | 2798247 | 1416 | 1600 | 99.62 |
| 5822 | 2789901 | G | 2019 | 2427 | 479 | 2780455 | 4481 | 99.66 |
| 5823 | 2874311 | G | 1530 | 1604 | 414 | 2863332 | 7431 | 99.62 |
| 5824 | 2829414 | G | 2048 | 3426 | 367 | 2820258 | 3315 | 99.68 |
| 5825 | 2846773 | T | 6317 | 2821076 | 6987 | 12328 | 65 | 99.1 |
| 5828 | 2783083 | G | 3404 | 1569 | 435 | 2779294 | 181 | 99.79 |
| 5829 | 2778118 | C | 1542 | 4422 | 2769917 | 1347 | 890 | 99.7 |
| 5830 | 2768229 | A | 2763396 | 1137 | 681 | 3000 | 15 | 99.83 |
| 5831 | 2767814 | G | 2118 | 1695 | 638 | 2753615 | 9748 | 99.49 |
| 5832 | 2615870 | C | 1274 | 4145 | 2608522 | 1443 | 486 | 99.72 |
| 5833 | 2617809 | G | 2264 | 1654 | 625 | 2612679 | 587 | 99.8 |
| 5834 | 2815311 | G | 3302 | 2418 | 1922 | 2794617 | 13052 | 99.26 |
| 5835 | 2838836 | C | 2399 | 2965 | 2831016 | 2171 | 285 | 99.72 |
| 5836 | 2844631 | C | 2574 | 2797 | 2836341 | 2066 | 553 | 99.71 |
| 5837 | 2842039 | C | 2385 | 2072 | 2835400 | 1338 | 844 | 99.77 |
| 5838 | 2832637 | T | 717 | 2828436 | 1361 | 2104 | 19 | 99.85 |
| 5839 | 2842579 | G | 2489 | 1247 | 424 | 2837699 | 720 | 99.83 |
| 5840 | 2853857 | A | 2849241 | 1018 | 1243 | 2296 | 59 | 99.84 |
| 5841 | 2841652 | A | 2836236 | 1250 | 1047 | 2807 | 312 | 99.81 |
| 5842 | 2847418 | G | 2412 | 1423 | 527 | 2823276 | 19780 | 99.15 |
| 5843 | 2562714 | C | 1323 | 2532 | 2555350 | 1901 | 1608 | 99.71 |
| 5844 | 2572464 | G | 1892 | 1887 | 489 | 2566963 | 1233 | 99.79 |
| 5845 | 2759612 | A | 2743613 | 1833 | 1316 | 3176 | 9674 | 99.42 |
| 5846 | 2527859 | T | 1022 | 2523516 | 1043 | 1961 | 317 | 99.83 |
| 5847 | 2561079 | C | 1547 | 2446 | 2555413 | 895 | 778 | 99.78 |
| 5848 | 2583624 | A | 2577337 | 662 | 1094 | 2383 | 1948 | 99.76 |
| 5849 | 2613655 | T | 527 | 2608909 | 766 | 1340 | 2113 | 99.82 |
| 5850 | 2661570 | A | 2646218 | 5503 | 465 | 6085 | 3299 | 99.42 |
| 5851 | 2616849 | C | 1714 | 3406 | 2608189 | 705 | 2835 | 99.67 |
| 5852 | 2615878 | T | 1072 | 2611104 | 1041 | 1634 | 1027 | 99.82 |
| 5853 | 2606259 | T | 885 | 2596925 | 1081 | 1530 | 5838 | 99.64 |
| 5854 | 2515588 | C | 1433 | 2467 | 2509370 | 1065 | 1053 | 99.76 |
| 5855 | 2529629 | A | 2517651 | 3789 | 994 | 5773 | 1422 | 99.53 |
| 5856 | 2358336 | C | 1321 | 3329 | 2349979 | 1001 | 2706 | 99.65 |
| 5857 | 2364536 | T | 1233 | 2360017 | 837 | 2321 | 128 | 99.81 |
| 5858 | 2362942 | C | 1397 | 2088 | 2354872 | 958 | 3627 | 99.66 |
| 5860 | 2363786 | G | 1467 | 1711 | 410 | 2355918 | 4280 | 99.67 |
| 5861 | 2458727 | A | 2453260 | 1068 | 1147 | 3005 | 247 | 99.78 |
| 5862 | 2482887 | G | 2238 | 1222 | 609 | 2476836 | 1982 | 99.76 |
| 5863 | 2523204 | T | 3405 | 2507453 | 4483 | 6391 | 1472 | 99.38 |
| 5864 | 2527118 | C | 2149 | 2201 | 2520483 | 1240 | 1045 | 99.74 |
| 5866 | 2526587 | A | 2520926 | 1039 | 818 | 3025 | 779 | 99.78 |
| 5867 | 2551869 | G | 2887 | 2290 | 291 | 2544868 | 1543 | 99.73 |
| 5868 | 2590153 | G | 3038 | 1796 | 482 | 2578539 | 6298 | 99.55 |
| 5869 | 2562966 | T | 9040 | 2525693 | 10115 | 17919 | 199 | 98.55 |

FIG. 5Q

| | | | | | | | | |
|---|---|---|---|---|---|---|---|---|
| 5870 | 2553717 | G | 2516 | 1354 | 328 | 2547129 | 2390 | 99.74 |
| 5873 | 2624783 | A | 2620449 | 710 | 529 | 2012 | 1063 | 99.84 |
| 5874 | 2622263 | T | 1483 | 2619100 | 1166 | 2738 | 746 | 99.77 |
| 5875 | 2587568 | C | 2433 | 2102 | 2580846 | 943 | 1239 | 99.74 |
| 5876 | 2585228 | C | 1684 | 1826 | 2576512 | 983 | 3883 | 99.68 |
| 5877 | 2534111 | A | 2529989 | 936 | 827 | 2318 | 41 | 99.84 |
| 5878 | 2551283 | G | 2210 | 1627 | 329 | 2545535 | 1582 | 99.77 |
| 5879 | 2534180 | T | 3010 | 2520377 | 2987 | 7679 | 127 | 99.46 |
| 5880 | 2598933 | G | 1821 | 1604 | 416 | 2591352 | 3540 | 99.71 |
| 5881 | 2614306 | G | 1851 | 2115 | 501 | 2606917 | 2922 | 99.72 |
| 5882 | 2651824 | A | 2649914 | 1143 | 1281 | 3373 | 109 | 99.78 |
| 5883 | 2662236 | T | 1102 | 2656903 | 1324 | 2456 | 451 | 99.8 |
| 5884 | 2656748 | G | 2303 | 2173 | 837 | 2650307 | 1126 | 99.76 |
| 5885 | 2648840 | A | 2641239 | 949 | 739 | 2802 | 111 | 99.83 |
| 5886 | 2648823 | G | 2744 | 2633 | 712 | 2649975 | 1759 | 99.7 |
| 5887 | 2569580 | A | 2556053 | 5130 | 700 | 7702 | 215 | 99.47 |
| 5888 | 2644789 | C | 2573 | 2945 | 2633394 | 1582 | 3648 | 99.6 |
| 5889 | 2619823 | C | 3170 | 2380 | 2608806 | 1740 | 3347 | 99.59 |
| 5890 | 2643984 | T | 851 | 2641274 | 961 | 1887 | 977 | 99.82 |
| 5891 | 2655252 | C | 1714 | 2306 | 2649527 | 1468 | 237 | 99.78 |
| 5892 | 2656197 | G | 2821 | 1290 | 410 | 2651488 | 188 | 99.82 |
| 5894 | 2658180 | A | 2652871 | 810 | 1111 | 2403 | 985 | 99.8 |
| 5895 | 2648894 | A | 2644213 | 947 | 943 | 2604 | 167 | 99.82 |
| 5896 | 2656126 | G | 1390 | 1995 | 440 | 2650018 | 2230 | 99.77 |
| 5897 | 2696361 | G | 1760 | 1821 | 175 | 2689361 | 5044 | 99.66 |
| 5898 | 2700625 | A | 2683410 | 1106 | 1160 | 3136 | 1813 | 99.73 |
| 5899 | 2676310 | A | 2671443 | 925 | 934 | 2832 | 176 | 99.82 |
| 5900 | 2680782 | G | 3753 | 1871 | 620 | 2672626 | 1912 | 99.7 |
| 5901 | 2681118 | T | 7836 | 2650361 | 7347 | 11205 | 369 | 98.85 |
| 5902 | 2739463 | G | 2254 | 2121 | 638 | 2730112 | 4340 | 99.66 |
| 5903 | 2740718 | G | 1643 | 2446 | 373 | 2733808 | 448 | 99.82 |
| 5904 | 2781644 | G | 2224 | 1563 | 298 | 2778268 | 1289 | 99.81 |
| 5905 | 2761109 | A | 2747056 | 1331 | 1367 | 5424 | 3731 | 99.49 |
| 5906 | 2681166 | T | 1291 | 2675916 | 1459 | 1726 | 774 | 99.8 |
| 5907 | 2714152 | A | 2707312 | 1398 | 515 | 1975 | 2732 | 99.76 |
| 5908 | 2724798 | T | 1191 | 2718676 | 1275 | 2027 | 1629 | 99.78 |
| 5909 | 2703871 | C | 2808 | 2495 | 2695877 | 1172 | 1519 | 99.7 |
| 5910 | 2685474 | C | 2473 | 1843 | 2679962 | 868 | 4328 | 99.65 |
| 5911 | 2646085 | A | 2640256 | 1024 | 1016 | 2481 | 1308 | 99.78 |
| 5912 | 2695196 | A | 2689542 | 1377 | 692 | 2694 | 3891 | 99.68 |
| 5913 | 2690152 | T | 1318 | 2684514 | 874 | 2704 | 742 | 99.79 |
| 5914 | 2715295 | C | 2247 | 2616 | 2704804 | 1294 | 4334 | 99.61 |
| 5915 | 2722016 | A | 2716081 | 614 | 653 | 2097 | 2571 | 99.78 |
| 5916 | 2831741 | T | 1178 | 2836447 | 921 | 2295 | 10900 | 99.46 |
| 5919 | 2810504 | A | 2804320 | 719 | 1545 | 2228 | 1492 | 99.79 |
| 5920 | 2793302 | T | 1653 | 2784754 | 1361 | 2824 | 2478 | 99.7 |
| 5921 | 2764503 | G | 4128 | 2259 | 12331 | 2745233 | 354 | 99.3 |
| 5922 | 2804080 | C | 1931 | 3362 | 2794531 | 1722 | 2514 | 99.66 |
| 5923 | 2673810 | C | 3601 | 2502 | 2665495 | 1936 | 256 | 99.69 |
| 5924 | 2670038 | C | 2060 | 2140 | 2658057 | 1664 | 6135 | 99.55 |
| 5925 | 2584019 | C | 1697 | 2610 | 2578062 | 1491 | 129 | 99.77 |
| 5926 | 2687137 | G | 3522 | 1464 | 571 | 2675663 | 5915 | 99.57 |
| 5927 | 2700159 | T | 2933 | 2686256 | 4157 | 6642 | 171 | 99.49 |

FIG. 5R

| | | | | | | | | |
|---|---|---|---|---|---|---|---|---|
| 5928 | 2699049 | C | 1885 | 2313 | 2695613 | 1103 | 133 | 99.8 |
| 5929 | 2686580 | C | 3437 | 2255 | 2609685 | 913 | 290 | 99.74 |
| 5933 | 2760232 | A | 2747773 | 4180 | 1962 | 3834 | 503 | 99.55 |
| 5934 | 2603271 | C | 6771 | 1605 | 2588946 | 900 | 1005 | 99.43 |
| 5935 | 2513565 | C | 1937 | 1367 | 2509241 | 680 | 620 | 99.82 |
| 5937 | 2587221 | A | 2577129 | 847 | 1011 | 2319 | 5915 | 99.61 |
| 5938 | 2617100 | G | 2713 | 3430 | 873 | 2608089 | 1003 | 99.66 |
| 5939 | 2635378 | C | 1598 | 2741 | 2631530 | 1227 | 2282 | 99.7 |
| 5940 | 2635914 | T | 1069 | 2633774 | 897 | 2377 | 797 | 99.81 |
| 5942 | 2627386 | G | 3113 | 1982 | 701 | 2621372 | 178 | 99.77 |
| 5943 | 2632789 | A | 2628586 | 973 | 760 | 2133 | 337 | 99.84 |
| 5944 | 2667136 | A | 2647432 | 6634 | 619 | 9022 | 3449 | 99.26 |
| 5945 | 2557379 | C | 1647 | 2082 | 2548108 | 834 | 4708 | 99.64 |
| 5946 | 2491666 | C | 1936 | 1480 | 2486734 | 599 | 867 | 99.8 |
| 5947 | 2480241 | C | 1351 | 1739 | 2473327 | 533 | 3269 | 99.72 |
| 5949 | 2444671 | G | 3162 | 1876 | 704 | 2436684 | 2245 | 99.67 |
| 5950 | 2425632 | T | 3346 | 2415161 | 3126 | 7518 | 101 | 99.4 |
| 5951 | 2515626 | G | 2673 | 1899 | 913 | 2501536 | 8605 | 99.44 |
| 5952 | 2520146 | C | 1581 | 4712 | 2509246 | 1245 | 3362 | 99.57 |
| 5953 | 2496527 | T | 623 | 2491533 | 1360 | 1842 | 1169 | 99.8 |
| 5954 | 2517389 | T | 1004 | 2512394 | 1136 | 1486 | 1369 | 99.8 |
| 5955 | 2528410 | T | 946 | 2523861 | 1002 | 1910 | 289 | 99.82 |
| 5956 | 2374216 | C | 2110 | 2329 | 2363251 | 1075 | 3431 | 99.57 |
| 5957 | 2626185 | C | 1866 | 2406 | 2617876 | 835 | 3202 | 99.68 |
| 5958 | 2596764 | A | 2585639 | 4239 | 1031 | 5479 | 356 | 99.57 |
| 5959 | 2579649 | C | 1843 | 4299 | 2561286 | 1106 | 11113 | 99.29 |
| 5960 | 2432942 | T | 856 | 2428493 | 1611 | 1613 | 139 | 99.83 |
| 5961 | 2499906 | A | 2490349 | 1087 | 686 | 2273 | 1511 | 99.62 |
| 5962 | 2474431 | T | 602 | 2469949 | 1246 | 2042 | 592 | 99.82 |
| 5963 | 2355504 | G | 3556 | 1864 | 605 | 2340926 | 8343 | 99.43 |
| 5964 | 2543723 | T | 2974 | 2527092 | 3682 | 8094 | 3881 | 99.27 |
| 5965 | 2563354 | G | 2499 | 2000 | 599 | 2551849 | 6407 | 99.55 |
| 5966 | 2544538 | T | 1974 | 2534959 | 2390 | 4832 | 403 | 99.62 |
| 5967 | 2544404 | T | 616 | 2538136 | 987 | 1761 | 2904 | 99.75 |
| 5969 | 2472000 | G | 2097 | 1374 | 376 | 2463322 | 4631 | 99.65 |
| 5970 | 2423892 | A | 2419102 | 970 | 1063 | 2381 | 376 | 99.8 |
| 5971 | 2414364 | A | 2402948 | 1279 | 979 | 3304 | 5874 | 99.53 |
| 5972 | 2347483 | G | 2033 | 1926 | 549 | 2337155 | 3820 | 99.56 |
| 5973 | 2336052 | G | 1616 | 1891 | 738 | 2325809 | 5958 | 99.56 |
| 5974 | 2302783 | G | 2110 | 2347 | 798 | 2295076 | 2452 | 99.67 |
| 5975 | 2350645 | G | 2574 | 2118 | 485 | 2343236 | 2172 | 99.68 |
| 5976 | 2334463 | T | 13053 | 2277934 | 16229 | 27343 | 104 | 97.57 |
| 5977 | 2345179 | G | 2208 | 1501 | 685 | 2339520 | 1273 | 99.76 |
| 5978 | 2345727 | A | 2340478 | 1058 | 1187 | 2830 | 144 | 99.78 |
| 5979 | 2334699 | A | 2330431 | 982 | 783 | 2260 | 243 | 99.82 |
| 5980 | 2361269 | G | 2312 | 2288 | 430 | 2353096 | 3143 | 99.63 |
| 5981 | 2354361 | G | 1919 | 1973 | 527 | 2346567 | 3373 | 99.67 |
| 5982 | 2400186 | A | 2387425 | 748 | 773 | 2493 | 8743 | 99.47 |
| 5983 | 2359093 | A | 2352227 | 1987 | 354 | 3512 | 813 | 99.71 |
| 5984 | 2381043 | C | 1597 | 2247 | 2375088 | 826 | 1335 | 99.75 |
| 5985 | 2391348 | C | 1573 | 2588 | 2384060 | 799 | 2328 | 99.7 |
| 5987 | 2381877 | G | 3730 | 1524 | 1050 | 2373940 | 613 | 99.71 |
| 5988 | 2392497 | C | 1331 | 3116 | 2384915 | 1110 | 2025 | 99.68 |

FIG. 5S

| | | | | | | | |
|---|---|---|---|---|---|---|---|
| 5990 | 2383430 | G | 2402 | 1407 | 935 | 2374462 | 6204 | 99.54 |
| 5991 | 2417390 | T | 2221 | 2408057 | 3013 | 4236 | 63 | 99.61 |
| 5992 | 2435161 | C | 2207 | 1809 | 2425701 | 1218 | 1186 | 99.73 |
| 5993 | 2472790 | C | 2029 | 1332 | 2466229 | 1130 | 2080 | 99.73 |
| 5994 | 2457244 | T | 1178 | 2452864 | 1330 | 1794 | 78 | 99.82 |
| 5995 | 2528212 | C | 1568 | 2390 | 2517991 | 950 | 5313 | 99.6 |
| 5996 | 2563585 | A | 2555590 | 2577 | 1228 | 3661 | 329 | 99.69 |
| 5997 | 2555931 | C | 2719 | 2517 | 2546334 | 796 | 3565 | 99.62 |
| 5998 | 2356320 | T | 2267 | 2348365 | 1342 | 938 | 3208 | 99.7 |
| 6003 | 2469414 | A | 2469127 | 1643 | 1799 | 3317 | 3528 | 99.59 |
| 6004 | 2463386 | C | 1794 | 2449 | 2457139 | 1217 | 787 | 99.73 |
| 6005 | 2451810 | G | 2186 | 1277 | 674 | 2446232 | 1421 | 99.77 |
| 6006 | 2540634 | A | 2533886 | 1028 | 1195 | 1883 | 2842 | 99.73 |
| 6007 | 2547092 | T | 1595 | 2538604 | 3834 | 2439 | 630 | 99.67 |
| 6008 | 2522812 | C | 1861 | 1951 | 2517688 | 964 | 318 | 99.8 |
| 6009 | 2534063 | C | 1911 | 1654 | 2528933 | 1046 | 477 | 99.8 |
| 6010 | 2524693 | C | 1755 | 1987 | 2519907 | 826 | 218 | 99.81 |
| 6011 | 2523282 | A | 2518119 | 921 | 1628 | 2527 | 87 | 99.8 |
| 6012 | 2577462 | G | 1437 | 2975 | 782 | 2567782 | 4486 | 99.62 |
| 6013 | 2688976 | G | 3223 | 2783 | 1253 | 2678347 | 3161 | 99.61 |
| 6014 | 2651637 | C | 2361 | 2989 | 2642397 | 2159 | 1531 | 99.66 |
| 6018 | 2593762 | A | 2588959 | 964 | 879 | 2468 | 492 | 99.81 |
| 6019 | 2608005 | G | 2233 | 1862 | 729 | 2602138 | 1043 | 99.78 |
| 6020 | 2609047 | A | 2600935 | 1905 | 1907 | 3185 | 712 | 99.69 |
| 6021 | 2604745 | C | 2277 | 2363 | 2614621 | 960 | 4324 | 99.61 |
| 6023 | 2559955 | A | 2554239 | 1082 | 1189 | 2373 | 1047 | 99.73 |
| 6024 | 2610859 | A | 2596731 | 4065 | 1218 | 5671 | 3174 | 99.46 |
| 6025 | 2556072 | C | 1924 | 1694 | 2549950 | 1126 | 1378 | 99.76 |
| 6026 | 2609720 | T | 1071 | 2604272 | 1723 | 2392 | 262 | 99.79 |
| 6027 | 2607622 | T | 705 | 2603307 | 921 | 1619 | 870 | 99.84 |
| 6030 | 2602320 | A | 2594647 | 1189 | 1926 | 3912 | 46 | 99.71 |
| 6031 | 2605336 | G | 1364 | 2123 | 409 | 2600684 | 726 | 99.82 |
| 6032 | 2641922 | G | 1338 | 1677 | 559 | 2638734 | 3614 | 99.73 |
| 6033 | 2389763 | A | 2382279 | 1337 | 1648 | 3768 | 731 | 99.71 |
| 6034 | 2604500 | G | 1943 | 2342 | 696 | 2597839 | 1631 | 99.75 |
| 6035 | 2654779 | G | 2957 | 2284 | 792 | 2648564 | 142 | 99.77 |
| 6036 | 2672155 | C | 2341 | 3420 | 2663387 | 2129 | 374 | 99.69 |
| 6038 | 2606442 | A | 2606796 | 6885 | 1487 | 2357 | 917 | 99.56 |
| 6042 | 2691122 | T | 1061 | 2686391 | 873 | 2362 | 330 | 99.82 |
| 6043 | 2664280 | C | 1356 | 4269 | 2656057 | 1005 | 1393 | 99.69 |
| 6044 | 2659159 | T | 1928 | 2652046 | 1445 | 3659 | 81 | 99.73 |
| 6045 | 2671034 | C | 1825 | 1805 | 2664029 | 1161 | 1414 | 99.77 |
| 6046 | 2699563 | C | 2219 | 2234 | 2693430 | 819 | 841 | 99.77 |
| 6047 | 2708556 | A | 2703937 | 533 | 337 | 2854 | 1195 | 99.82 |
| 6049 | 2790906 | G | 2368 | 1914 | 507 | 2780934 | 3182 | 99.64 |
| 6050 | 2777369 | T | 4708 | 2757244 | 3858 | 6177 | 582 | 99.43 |
| 6051 | 2547855 | A | 2539203 | 3090 | 507 | 3802 | 1233 | 99.7 |
| 6052 | 2727290 | C | 1635 | 5015 | 2719232 | 1019 | 386 | 99.7 |
| 6053 | 2731063 | G | 3389 | 1176 | 731 | 2724260 | 1107 | 99.73 |
| 6054 | 2716538 | T | 2612 | 2704207 | 2742 | 6861 | 196 | 99.55 |
| 6055 | 2713991 | G | 1621 | 2063 | 573 | 2707659 | 2125 | 99.77 |
| 6056 | 2722263 | G | 2256 | 2523 | 586 | 2714934 | 1864 | 99.73 |
| 6057 | 2668944 | G | 2313 | 2813 | 481 | 2659441 | 4636 | 99.64 |

FIG. 5T

| | | | | | | | | |
|---|---|---|---|---|---|---|---|---|
| 6018 | 2607935 | T | 9915 | 2575066 | 9919 | 12242 | 754 | 99.74 |
| 6061 | 2633971 | C | 3382 | 2907 | 2626593 | 849 | 2240 | 99.64 |
| 6063 | 2655641 | A | 2652817 | 622 | 776 | 2100 | 2326 | 99.78 |
| 6064 | 2558223 | A | 2533386 | 788 | 916 | 2320 | 813 | 99.81 |
| 6065 | 2551136 | A | 2546427 | 1162 | 550 | 1767 | 1230 | 99.82 |
| 6066 | 2544034 | T | 2019 | 2535561 | 518 | 2635 | 3245 | 99.67 |
| 6068 | 2546704 | A | 2540849 | 1859 | 274 | 2514 | 812 | 99.77 |
| 6069 | 2553403 | C | 1360 | 2267 | 2547280 | 964 | 1512 | 99.76 |
| 6071 | 2610105 | G | 3198 | 1303 | 324 | 2601214 | 3849 | 99.66 |
| 6072 | 2657468 | A | 2661235 | 957 | 828 | 2670 | 1768 | 99.77 |
| 6073 | 2666131 | A | 2661145 | 1013 | 808 | 2360 | 264 | 99.81 |
| 6074 | 2671351 | G | 2203 | 1549 | 312 | 2662315 | 4912 | 99.66 |
| 6075 | 2675491 | T | 5061 | 2615419 | 4321 | 10384 | 276 | 99.25 |
| 6076 | 2712260 | G | 2000 | 1997 | 319 | 2704230 | 3714 | 99.7 |
| 6077 | 2739255 | G | 2444 | 2450 | 320 | 2731747 | 2094 | 99.73 |
| 6078 | 2869822 | A | 2864568 | 1233 | 845 | 3053 | 123 | 99.82 |
| 6079 | 2871389 | T | 1135 | 2865799 | 1047 | 2407 | 991 | 99.81 |
| 6080 | 2865669 | G | 2730 | 1797 | 412 | 2877759 | 2901 | 99.73 |
| 6081 | 2821365 | A | 2816207 | 1077 | 717 | 3214 | 150 | 99.82 |
| 6082 | 2889614 | G | 3434 | 2261 | 326 | 2876282 | 7091 | 99.54 |
| 6083 | 2844710 | C | 2689 | 4430 | 2834716 | 1666 | 1209 | 99.65 |
| 6084 | 2842275 | A | 2832226 | 2027 | 284 | 4469 | 2472 | 99.65 |
| 6085 | 2903174 | C | 2287 | 5121 | 2893312 | 1458 | 8996 | 99.38 |
| 6086 | 2882596 | A | 2877996 | 874 | 526 | 3079 | 221 | 99.84 |
| 6087 | 2910919 | T | 647 | 2905414 | 777 | 2330 | 1751 | 99.81 |
| 6088 | 2965489 | G | 2993 | 1837 | 491 | 2955532 | 4636 | 99.66 |
| 6089 | 2971133 | A | 2970735 | 712 | 696 | 2470 | 520 | 99.83 |
| 6090 | 2985457 | A | 2973267 | 1290 | 853 | 2893 | 7104 | 99.59 |
| 6091 | 2859123 | A | 2853432 | 858 | 879 | 3136 | 803 | 99.8 |
| 6092 | 2857971 | G | 10903 | 2567 | 342 | 2843057 | 1102 | 99.48 |
| 6093 | 3073300 | A | 3064215 | 1071 | 556 | 3056 | 6102 | 99.64 |
| 6094 | 3032027 | G | 2372 | 3609 | 602 | 3023195 | 2249 | 99.71 |
| 6095 | 3057119 | G | 4445 | 2195 | 857 | 3046733 | 2886 | 99.66 |
| 6096 | 3030087 | C | 2457 | 3449 | 3017068 | 2294 | 4739 | 99.57 |
| 6097 | 2985980 | A | 2981306 | 1037 | 658 | 2840 | 119 | 99.84 |
| 6098 | 3064919 | G | 3744 | 1739 | 457 | 3051798 | 7131 | 99.57 |
| 6099 | 3077364 | T | 2265 | 3068962 | 1830 | 3927 | 600 | 99.72 |
| 6100 | 3081246 | A | 3075972 | 662 | 335 | 3439 | 838 | 99.83 |
| 6101 | 3099665 | G | 4304 | 3091 | 1241 | 3067833 | 3146 | 99.62 |
| 6102 | 3103735 | A | 3089148 | 5463 | 877 | 7822 | 426 | 99.53 |
| 6103 | 3265189 | C | 2258 | 4210 | 3247891 | 1287 | 12343 | 99.38 |
| 6104 | 3244848 | C | 2563 | 2398 | 3236163 | 1164 | 2560 | 99.73 |
| 6105 | 3228733 | A | 3210675 | 7316 | 771 | 9144 | 827 | 99.44 |
| 6106 | 3234028 | C | 2481 | 4773 | 3216796 | 1311 | 8625 | 99.47 |
| 6108 | 3331289 | A | 3316249 | 1140 | 478 | 2097 | 11325 | 99.55 |
| 6109 | 3316214 | T | 556 | 3310703 | 1163 | 2381 | 1181 | 99.83 |
| 6110 | 3302370 | G | 5907 | 2365 | 1304 | 3292075 | 319 | 99.69 |
| 6111 | 3274482 | C | 2374 | 3305 | 3256210 | 2131 | 8462 | 99.44 |
| 6112 | 3147351 | T | 954 | 3142109 | 1420 | 2991 | 77 | 99.83 |
| 6113 | 3210431 | G | 3069 | 2540 | 911 | 3199437 | 4534 | 99.66 |
| 6114 | 3228509 | G | 3547 | 2351 | 929 | 3220831 | 851 | 99.76 |
| 6115 | 3220866 | C | 2600 | 3671 | 3212424 | 1565 | 606 | 99.74 |
| 6116 | 3214047 | C | 2602 | 2338 | 3201516 | 1441 | 5830 | 99.61 |

FIG. 5U

| | | | | | | | | |
|---|---|---|---|---|---|---|---|---|
| 6117 | 3133293 | A | 3129005 | 939 | 906 | 2338 | 105 | 99.86 |
| 6118 | 3218694 | G | 3609 | 1946 | 834 | 3206151 | 6132 | 99.61 |
| 6119 | 3343832 | C | 2819 | 4545 | 3333468 | 2223 | 377 | 99.69 |
| 6120 | 3343838 | T | 1678 | 3338608 | 1463 | 3412 | 137 | 99.8 |
| 6121 | 3364157 | C | 3417 | 3150 | 3352172 | 1798 | 3620 | 99.64 |
| 6122 | 3347509 | A | 3343318 | 900 | 692 | 2470 | 129 | 99.87 |
| 6123 | 3466245 | T | 793 | 3455877 | 1356 | 3140 | 5079 | 99.7 |
| 6124 | 3466196 | G | 3661 | 3211 | 961 | 3457389 | 974 | 99.73 |
| 6125 | 3571386 | T | 1849 | 3554611 | 2802 | 4522 | 7202 | 99.33 |
| 6126 | 3598311 | C | 2292 | 3564 | 3582789 | 1641 | 5025 | 99.57 |
| 6127 | 3545649 | A | 3531728 | 4639 | 1544 | 6957 | 451 | 99.61 |
| 6128 | 3773434 | C | 3004 | 3278 | 3764146 | 1246 | 1762 | 99.75 |
| 6129 | 3772821 | T | 1136 | 3767446 | 1126 | 2342 | 771 | 99.86 |
| 6130 | 3773657 | A | 3767377 | 1040 | 437 | 3927 | 576 | 99.83 |
| 6131 | 3810800 | G | 4198 | 2431 | 896 | 3796217 | 7038 | 99.62 |
| 6132 | 3826515 | A | 3816458 | 2537 | 822 | 5762 | 936 | 99.74 |
| 6133 | 4041023 | C | 2347 | 4393 | 4018841 | 1693 | 13549 | 99.45 |
| 6134 | 3991957 | A | 3964876 | 1229 | 1172 | 3451 | 1229 | 99.82 |
| 6135 | 3971463 | T | 1874 | 3964057 | 1325 | 3266 | 911 | 99.81 |
| 6136 | 3973349 | C | 3194 | 4736 | 3962220 | 1806 | 1373 | 99.72 |
| 6137 | 3962623 | A | 3957897 | 643 | 894 | 3167 | 27 | 99.58 |
| 6138 | 4061364 | A | 4048550 | 1760 | 916 | 3837 | 6301 | 99.68 |
| 6139 | 4057192 | C | 2858 | 3229 | 4047728 | 1229 | 2118 | 99.77 |
| 6140 | 4023774 | A | 4014940 | 3347 | 1347 | 6093 | 47 | 99.73 |
| 6141 | 4037614 | C | 3205 | 3794 | 4021184 | 1242 | 8189 | 99.39 |
| 6142 | 3895322 | A | 3893846 | 1238 | 1194 | 3179 | 23 | 99.85 |
| 6143 | 4076793 | G | 3707 | 3568 | 1173 | 4056696 | 11649 | 99.51 |
| 6144 | 4097955 | A | 4089667 | 1125 | 1415 | 3574 | 207 | 99.85 |
| 6145 | 4113736 | A | 4103785 | 3041 | 696 | 5615 | 599 | 99.76 |
| 6146 | 4125696 | C | 3373 | 3146 | 4113718 | 1189 | 4270 | 99.71 |
| 6147 | 4081796 | A | 4075506 | 1319 | 733 | 3250 | 918 | 99.85 |
| 6148 | 4141257 | A | 4139033 | 1260 | 1057 | 2636 | 1219 | 99.85 |
| 6149 | 4076984 | T | 1682 | 4070278 | 1444 | 3339 | 221 | 99.84 |
| 6150 | 4104257 | G | 3300 | 3464 | 705 | 4088308 | 5460 | 99.61 |
| 6151 | 4060131 | T | 7192 | 4027372 | 7279 | 15165 | 3123 | 99.19 |
| 6152 | 4133017 | G | 3948 | 3718 | 1027 | 4121789 | 4533 | 99.68 |
| 6153 | 4120239 | C | 2176 | 5553 | 4113271 | 2079 | 1180 | 99.73 |
| 6154 | 4122611 | T | 1023 | 4116300 | 1564 | 3928 | 196 | 99.85 |
| 6155 | 4124491 | T | 826 | 4119154 | 1210 | 2567 | 734 | 99.87 |
| 6156 | 4106524 | G | 2515 | 2419 | 592 | 4100221 | 677 | 99.85 |
| 6157 | 4173035 | G | 2224 | 2420 | 799 | 4165191 | 2421 | 99.81 |
| 6158 | 4166481 | A | 4154953 | 1792 | 2062 | 5737 | 1937 | 99.72 |
| 6159 | 4145094 | G | 2519 | 3061 | 706 | 4135993 | 2813 | 99.78 |
| 6160 | 4121738 | G | 3178 | 2295 | 618 | 4110600 | 5007 | 99.73 |
| 6161 | 4113005 | A | 4098756 | 2160 | 2749 | 6117 | 3223 | 99.65 |
| 6162 | 4114442 | T | 2028 | 4104803 | 2325 | 4850 | 436 | 99.77 |
| 6163 | 4201800 | G | 4535 | 2444 | 2023 | 4186149 | 6349 | 99.63 |
| 6164 | 4210235 | C | 2805 | 6320 | 4197291 | 2592 | 1227 | 99.69 |
| 6165 | 4177434 | C | 3175 | 4022 | 4166754 | 1728 | 1755 | 99.74 |
| 6166 | 4230365 | A | 4236445 | 2110 | 3349 | 4049 | 5412 | 99.67 |
| 6167 | 4231125 | T | 1105 | 4244318 | 1769 | 3198 | 345 | 99.84 |
| 6168 | 4382356 | G | 6750 | 3449 | 1038 | 4351694 | 19425 | 99.33 |
| 6169 | 4572148 | T | 4648 | 4548757 | 4365 | 10170 | 4008 | 99.49 |

FIG. 5V

| | | | | | | | | |
|---|---|---|---|---|---|---|---|---|
| 6171 | 4544135 | A | 4537793 | 1313 | 777 | 3172 | 880 | 99.86 |
| 6172 | 4518493 | T | 1882 | 4502702 | 2435 | 4012 | 7462 | 99.65 |
| 6173 | 4399670 | G | 5730 | 6148 | 3157 | 4388869 | 773 | 99.64 |
| 6174 | 4442930 | G | 6813 | 4010 | 2702 | 4425839 | 3386 | 99.61 |
| 6175 | 4426943 | C | 2715 | 6190 | 4405704 | 2399 | 6955 | 99.59 |
| 6176 | 4348202 | A | 4355344 | 4728 | 2066 | 6911 | 153 | 99.68 |
| 6177 | 4338280 | C | 3143 | 4705 | 4312519 | 1731 | 16164 | 99.41 |
| 6178 | 4090980 | T | 843 | 4085306 | 1881 | 2735 | 215 | 99.86 |
| 6179 | 4108806 | G | 2687 | 2272 | 672 | 4101708 | 1467 | 99.83 |
| 6180 | 4126296 | A | 4113437 | 2359 | 2793 | 4540 | 1165 | 99.74 |
| 6181 | 4114601 | T | 1222 | 4108057 | 1482 | 3115 | 725 | 99.84 |
| 6182 | 4127268 | G | 3294 | 2940 | 806 | 4116180 | 4048 | 99.73 |
| 6183 | 4362643 | G | 3744 | 3942 | 1289 | 4334657 | 19011 | 99.36 |
| 6184 | 4365010 | T | 4104 | 4344684 | 5752 | 10098 | 372 | 99.53 |
| 6185 | 4519582 | C | 2967 | 4414 | 4509406 | 1655 | 1140 | 99.77 |
| 6187 | 4509372 | A | 4503741 | 1153 | 525 | 3398 | 555 | 99.88 |
| 6188 | 4489409 | G | 5042 | 4044 | 1641 | 4477631 | 1051 | 99.74 |
| 6189 | 4456825 | A | 4451652 | 907 | 1136 | 2569 | 561 | 99.88 |
| 6190 | 4445700 | A | 4438889 | 1433 | 954 | 3428 | 976 | 99.83 |
| 6191 | 4442219 | G | 6167 | 2867 | 1606 | 4409746 | 21833 | 99.27 |
| 6192 | 4153379 | C | 2369 | 3303 | 4142809 | 1785 | 2911 | 99.73 |
| 6193 | 4140545 | A | 4123915 | 6357 | 1353 | 5727 | 193 | 99.6 |
| 6194 | 4161183 | C | 2436 | 2473 | 4107500 | 1387 | 2387 | 99.79 |
| 6195 | 4113090 | T | 1387 | 4110224 | 1243 | 2063 | 173 | 99.88 |
| 6197 | 4184936 | G | 3144 | 2292 | 577 | 4177793 | 1130 | 99.83 |
| 6198 | 4186334 | A | 4178912 | 1764 | 2136 | 3353 | 167 | 99.82 |
| 6199 | 4117606 | T | 1484 | 4110384 | 1540 | 2641 | 1537 | 99.82 |
| 6200 | 4117459 | T | 1130 | 4108990 | 1377 | 2064 | 3848 | 99.79 |
| 6201 | 4137537 | G | 4516 | 3755 | 839 | 4122798 | 5529 | 99.64 |
| 6202 | 4119736 | T | 2936 | 4107435 | 2978 | 6277 | 90 | 99.7 |
| 6204 | 4025541 | C | 2093 | 3590 | 4018049 | 1364 | 443 | 99.81 |
| 6205 | 4045772 | C | 2173 | 3303 | 4035936 | 1138 | 3222 | 99.76 |
| 6206 | 4012017 | A | 4034321 | 6930 | 1377 | 9264 | 125 | 99.56 |
| 6207 | 4045573 | C | 2314 | 4886 | 4035311 | 1288 | 1774 | 99.75 |
| 6208 | 3930463 | C | 2948 | 3886 | 3920565 | 1425 | 1639 | 99.75 |
| 6209 | 3907266 | A | 3900806 | 1139 | 2003 | 3071 | 247 | 99.83 |
| 6210 | 4108177 | G | 3608 | 2319 | 867 | 4084143 | 16740 | 99.41 |
| 6211 | 4109583 | T | 4967 | 4087153 | 3490 | 11918 | 55 | 99.45 |
| 6212 | 4120164 | G | 5566 | 2667 | 1394 | 4109876 | 761 | 99.73 |
| 6213 | 4108329 | C | 4176 | 6096 | 4094929 | 1819 | 2309 | 99.65 |
| 6214 | 4191603 | T | 1582 | 4183035 | 2352 | 4071 | 562 | 99.8 |
| 6215 | 4289612 | G | 3303 | 3546 | 1645 | 4274805 | 6313 | 99.65 |
| 6216 | 4327699 | G | 5024 | 3455 | 1533 | 4317423 | 224 | 99.76 |
| 6217 | 4292125 | C | 6109 | 5751 | 4276193 | 2430 | 1642 | 99.63 |
| 6218 | 4279381 | T | 1696 | 4258100 | 2355 | 3110 | 13920 | 99.5 |
| 6219 | 4114724 | A | 4085454 | 13665 | 982 | 12566 | 2137 | 99.29 |
| 6220 | 4386410 | C | 2709 | 6462 | 4360435 | 1945 | 14839 | 99.41 |
| 6221 | 4378737 | C | 4445 | 3285 | 4368164 | 2085 | 738 | 99.76 |
| 6222 | 4375845 | C | 5782 | 4768 | 4358196 | 1890 | 1209 | 99.6 |
| 6223 | 4386793 | T | 2267 | 4368051 | 2713 | 3602 | 10160 | 99.57 |
| 6224 | 4396290 | T | 882 | 4290060 | 1463 | 2472 | 1413 | 99.83 |
| 6225 | 4367661 | A | 4354520 | 1787 | 1020 | 4682 | 5612 | 99.7 |
| 6226 | 4366833 | T | 1411 | 4360213 | 1681 | 3354 | 174 | 99.85 |

FIG. 5W

| | | | | | | | | |
|---|---|---|---|---|---|---|---|---|
| 6227 | 4347086 | G | 4893 | 1940 | 446 | 4336905 | 2900 | 99.77 |
| 6228 | 4121053 | T | 4998 | 4281541 | 4609 | 7349 | 22356 | 99.09 |
| 6229 | 3966611 | A | 3958828 | 1228 | 1321 | 4556 | 645 | 99.8 |
| 6230 | 3978133 | G | 4141 | 2460 | 871 | 3966754 | 3907 | 99.71 |
| 6231 | 3964273 | C | 3193 | 3049 | 3951548 | 1904 | 4579 | 99.63 |
| 6232 | 3904632 | A | 3896976 | 1322 | 1837 | 3641 | 856 | 99.8 |
| 6233 | 3903306 | A | 3886294 | 2111 | 1316 | 3736 | 5839 | 99.67 |
| 6234 | 3783923 | T | 706 | 3782259 | 1188 | 4304 | 471 | 99.82 |
| 6235 | 3819253 | G | 2844 | 3068 | 345 | 3811417 | 2379 | 99.79 |
| 6236 | 3830361 | G | 2248 | 3063 | 491 | 3823213 | 1941 | 99.81 |
| 6237 | 3843526 | G | 2474 | 2452 | 640 | 3836417 | 1543 | 99.82 |
| 6238 | 3857360 | A | 3844706 | 1240 | 1693 | 9111 | 759 | 99.67 |
| 6239 | 3836464 | A | 3828964 | 1024 | 1310 | 4026 | 1140 | 99.8 |
| 6240 | 3827556 | A | 3820772 | 1470 | 1222 | 3873 | 219 | 99.82 |
| 6241 | 3931483 | G | 10835 | 2762 | 679 | 3929528 | 7979 | 99.44 |
| 6242 | 4065177 | A | 4057685 | 1012 | 1514 | 4165 | 801 | 99.82 |
| 6243 | 4058970 | A | 4052316 | 1278 | 945 | 3741 | 690 | 99.84 |
| 6244 | 3981457 | G | 1515 | 2999 | 308 | 3969402 | 5032 | 99.7 |
| 6245 | 4078410 | A | 4070632 | 1143 | 1431 | 3770 | 1434 | 99.81 |
| 6246 | 4056814 | A | 4050211 | 1526 | 960 | 3790 | 327 | 99.84 |
| 6247 | 4065168 | G | 2669 | 2575 | 495 | 4057353 | 2076 | 99.81 |
| 6248 | 4266544 | A | 4258193 | 1513 | 1779 | 4863 | 196 | 99.79 |
| 6249 | 4120529 | G | 2616 | 3243 | 969 | 4102344 | 11355 | 99.36 |
| 6250 | 4000669 | A | 3987516 | 2165 | 3473 | 7382 | 133 | 99.67 |
| 6251 | 4011183 | G | 5353 | 5086 | 637 | 3999110 | 997 | 99.7 |
| 6252 | 4085386 | A | 4076060 | 2327 | 2710 | 4822 | 2267 | 99.7 |
| 6253 | 4000896 | T | 4303 | 4006485 | 3028 | 5370 | 407 | 99.69 |
| 6254 | 4051255 | A | 4040078 | 1737 | 865 | 3334 | 5041 | 99.72 |
| 6255 | 4054164 | T | 5234 | 4039299 | 1122 | 7164 | 1365 | 99.63 |
| 6256 | 4042301 | C | 3073 | 3632 | 4033748 | 1339 | 509 | 99.79 |
| 6257 | 4074591 | T | 2268 | 4062883 | 1410 | 3731 | 4279 | 99.71 |
| 6258 | 4032908 | T | 1243 | 4026605 | 1561 | 2925 | 574 | 99.84 |
| 6259 | 4017830 | G | 3904 | 2325 | 1010 | 4009325 | 1285 | 99.79 |
| 6260 | 4003829 | A | 3967937 | 1097 | 1418 | 3317 | 40 | 99.85 |
| 6261 | 3968732 | A | 3991287 | 2214 | 805 | 4328 | 98 | 99.81 |
| 6262 | 3978957 | C | 2897 | 3069 | 3963207 | 1427 | 4337 | 99.65 |
| 6263 | 3959741 | A | 3954352 | 478 | 493 | 2450 | 1988 | 99.86 |
| 6264 | 3966680 | A | 3961560 | 891 | 794 | 2498 | 937 | 99.87 |
| 6265 | 3904021 | A | 3895872 | 2012 | 1211 | 4647 | 279 | 99.79 |
| 6266 | 3899574 | C | 2538 | 2829 | 3892338 | 967 | 891 | 99.81 |
| 6267 | 3897884 | A | 3893397 | 443 | 661 | 2745 | 636 | 99.88 |
| 6268 | 3912800 | A | 3904485 | 844 | 766 | 2745 | 3939 | 99.79 |
| 6269 | 3983014 | A | 3973407 | 3341 | 800 | 5500 | 1966 | 99.71 |
| 6270 | 3824376 | C | 2309 | 2230 | 3814959 | 1335 | 3443 | 99.76 |
| 6271 | 3819214 | C | 2016 | 3121 | 3809929 | 1448 | 2700 | 99.76 |
| 6272 | 3781051 | A | 3775608 | 892 | 1333 | 3000 | 218 | 99.86 |
| 6273 | 3780101 | G | 2305 | 2808 | 610 | 3773676 | 702 | 99.83 |
| 6274 | 3778232 | A | 3770237 | 1496 | 1474 | 4829 | 196 | 99.79 |
| 6275 | 3747829 | G | 4040 | 3131 | 974 | 3738387 | 877 | 99.75 |
| 6276 | 3805721 | A | 3790522 | 3802 | 2261 | 7354 | 4032 | 99.52 |
| 6277 | 3984772 | C | 2511 | 3170 | 3970684 | 1648 | 16759 | 99.4 |
| 6278 | 3974347 | A | 3957502 | 6470 | 1086 | 5504 | 465 | 99.38 |
| 6279 | 4014096 | C | 2446 | 3186 | 4003966 | 1311 | 3187 | 99.75 |

FIG. 5X

| | | | | | | | | |
|---|---|---|---|---|---|---|---|---|
| 6280 | 3989060 | T | 2420 | 3981205 | 2111 | 3126 | 98 | 99.8 |
| 6281 | 3989307 | A | 3993579 | 712 | 864 | 3285 | 867 | 99.86 |
| 6282 | 3994635 | A | 3987526 | 1734 | 1349 | 3753 | 283 | 99.82 |
| 6283 | 3996210 | G | 2269 | 2701 | 479 | 3989303 | 1258 | 99.83 |
| 6284 | 3792626 | G | 2473 | 2240 | 359 | 3785170 | 2184 | 99.8 |
| 6285 | 3847479 | A | 3820769 | 1170 | 1048 | 3152 | 21331 | 99.31 |
| 6287 | 3537868 | A | 3530423 | 697 | 635 | 2065 | 4048 | 99.79 |
| 6288 | 3605646 | T | 2243 | 3591444 | 1328 | 4123 | 6305 | 99.61 |
| 6289 | 3613263 | G | 4892 | 3438 | 1009 | 3603044 | 860 | 99.72 |
| 6290 | 3645164 | C | 2340 | 4129 | 3637032 | 1247 | 416 | 99.78 |
| 6291 | 3641483 | A | 3636762 | 780 | 1079 | 2781 | 161 | 99.87 |
| 6292 | 3630117 | A | 3625735 | 750 | 597 | 2612 | 383 | 99.88 |
| 6293 | 3607816 | A | 3599475 | 2313 | 1760 | 4001 | 267 | 99.77 |
| 6294 | 3603243 | C | 2189 | 1293 | 3591493 | 761 | 7507 | 99.67 |
| 6297 | 3493010 | T | 1211 | 3487317 | 1237 | 2978 | 67 | 99.84 |
| 6298 | 3523723 | G | 4590 | 2037 | 960 | 3515982 | 2154 | 99.72 |
| 6299 | 3532655 | C | 2140 | 3934 | 3124867 | 1433 | 161 | 99.78 |
| 6300 | 3539809 | T | 1956 | 3529857 | 1535 | 3405 | 56 | 99.8 |
| 6301 | 3543499 | C | 1901 | 3847 | 3537282 | 1631 | 837 | 99.77 |
| 6302 | 3544492 | G | 3130 | 1699 | 643 | 3538848 | 152 | 99.84 |
| 6303 | 3673263 | A | 3652391 | 2290 | 1455 | 4280 | 13547 | 99.43 |
| 6304 | 3684753 | C | 2794 | 3613 | 3674369 | 1605 | 2172 | 99.72 |
| 6305 | 3682431 | A | 3670415 | 4126 | 839 | 6918 | 133 | 99.67 |
| 6306 | 3836216 | C | 2005 | 6660 | 3812494 | 1600 | 13457 | 99.38 |
| 6307 | 3923097 | A | 3918417 | 1319 | 1108 | 4307 | 2946 | 99.75 |
| 6308 | 3948443 | T | 1214 | 3939774 | 2604 | 2397 | 2436 | 99.78 |
| 6309 | 3951747 | A | 3945409 | 1062 | 1574 | 3026 | 354 | 99.84 |
| 6310 | 3946336 | T | 1321 | 3939817 | 1384 | 2895 | 739 | 99.83 |
| 6311 | 3802373 | G | 3560 | 2377 | 473 | 3786832 | 9131 | 99.59 |
| 6312 | 3743247 | G | 2871 | 2214 | 637 | 3731327 | 6198 | 99.68 |
| 6313 | 3767124 | A | 3760478 | 1236 | 816 | 4355 | 239 | 99.82 |
| 6314 | 3778538 | A | 3763153 | 1261 | 912 | 2333 | 10879 | 99.59 |
| 6315 | 3621070 | T | 2073 | 3611196 | 1149 | 3433 | 4219 | 99.73 |
| 6316 | 3499294 | C | 2451 | 3530 | 3490301 | 1145 | 1847 | 99.74 |
| 6318 | 3613418 | A | 3593723 | 6023 | 833 | 8386 | 6453 | 99.4 |
| 6319 | 3604379 | C | 2363 | 3433 | 3595190 | 1440 | 1733 | 99.75 |
| 6320 | 3417278 | C | 1858 | 1489 | 3410521 | 702 | 2708 | 99.8 |
| 6321 | 3430847 | T | 2441 | 3417169 | 3698 | 4299 | 3240 | 99.6 |
| 6322 | 3479078 | C | 1769 | 2288 | 3471578 | 985 | 2508 | 99.78 |
| 6323 | 3473397 | C | 2145 | 2136 | 3467547 | 1101 | 465 | 99.83 |
| 6324 | 3460239 | C | 2343 | 2366 | 3453417 | 883 | 720 | 99.8 |
| 6325 | 3482035 | A | 3468529 | 4239 | 2004 | 6285 | 978 | 99.61 |
| 6326 | 3499227 | C | 2158 | 4314 | 3479213 | 1272 | 12268 | 99.43 |
| 6327 | 3439210 | T | 973 | 3433787 | 1232 | 2710 | 306 | 99.84 |
| 6328 | 3463645 | G | 3230 | 1881 | 678 | 3457698 | 2158 | 99.77 |
| 6329 | 3466412 | G | 3413 | 2630 | 702 | 3455715 | 3930 | 99.69 |
| 6330 | 3451972 | T | 9136 | 3413938 | 10097 | 17622 | 1179 | 98.9 |
| 6331 | 3467930 | G | 2330 | 2019 | 626 | 3459409 | 3346 | 99.75 |
| 6332 | 3463354 | A | 3455118 | 2772 | 2306 | 4569 | 289 | 99.7 |
| 6333 | 3574535 | C | 3271 | 4234 | 3556713 | 1646 | 8671 | 99.5 |
| 6334 | 3566549 | T | 1528 | 3554913 | 1356 | 2472 | 6280 | 99.67 |
| 6335 | 3518074 | T | 735 | 3513394 | 1120 | 1547 | 1378 | 99.86 |
| 6336 | 3646914 | A | 3629637 | 1368 | 1349 | 3117 | 11443 | 99.53 |

FIG. 5Y

| | | | | | | | | |
|---|---|---|---|---|---|---|---|---|
| 6337 | 3419604 | T | 842 | 3613376 | 1826 | 2386 | 974 | 99.83 |
| 6338 | 3624504 | G | 4388 | 2145 | 334 | 3615614 | 1223 | 99.75 |
| 6339 | 3620803 | T | 4685 | 3602962 | 3738 | 3935 | 3483 | 99.31 |
| 6340 | 3569029 | A | 3564145 | 846 | 609 | 3340 | 89 | 99.86 |
| 6341 | 3573298 | A | 3556900 | 1097 | 882 | 3461 | 10958 | 99.54 |
| 6342 | 3325411 | A | 3319411 | 1111 | 1286 | 3276 | 327 | 99.81 |
| 6343 | 3405174 | G | 3072 | 2889 | 922 | 3391997 | 6294 | 99.61 |
| 6344 | 3475127 | G | 2967 | 3239 | 932 | 3458277 | 9692 | 99.52 |
| 6345 | 3341786 | A | 3331278 | 1701 | 1864 | 1542 | 3404 | 99.69 |
| 6346 | 3399262 | T | 1459 | 3391710 | 2379 | 3227 | 487 | 99.77 |
| 6347 | 3256397 | G | 2640 | 2328 | 691 | 3289796 | 942 | 99.8 |
| 6348 | 3298801 | A | 3292319 | 1302 | 1275 | 2658 | 1247 | 99.8 |
| 6349 | 3361914 | A | 3345460 | 3273 | 932 | 3061 | 4188 | 99.6 |
| 6350 | 3347005 | C | 2583 | 2224 | 3338163 | 1156 | 2879 | 99.74 |
| 6351 | 3333887 | T | 1012 | 3326999 | 1070 | 2026 | 2788 | 99.79 |
| 6352 | 3303559 | T | 779 | 3294979 | 1426 | 1439 | 4946 | 99.74 |
| 6353 | 3229218 | A | 3223880 | 937 | 733 | 2381 | 67 | 99.87 |
| 6354 | 3238032 | G | 3359 | 2578 | 832 | 3230623 | 622 | 99.77 |
| 6355 | 3445100 | A | 3437087 | 1302 | 1304 | 3294 | 2111 | 99.77 |
| 6356 | 3465483 | T | 1845 | 3457755 | 1776 | 2735 | 1372 | 99.78 |
| 6357 | 3447105 | C | 3079 | 2890 | 3436227 | 1219 | 3690 | 99.68 |
| 6358 | 3401431 | C | 4863 | 2132 | 3391568 | 1030 | 1838 | 99.71 |
| 6360 | 3423376 | A | 3418914 | 665 | 723 | 1860 | 3214 | 99.81 |
| 6361 | 3460542 | A | 3454120 | 766 | 1076 | 2570 | 2030 | 99.81 |
| 6362 | 3470813 | A | 3462382 | 2215 | 1248 | 4187 | 731 | 99.76 |
| 6363 | 3463301 | C | 2785 | 2094 | 3455435 | 1078 | 1939 | 99.77 |
| 6364 | 3438493 | A | 3433865 | 858 | 1293 | 2646 | 31 | 99.86 |
| 6365 | 3433927 | A | 3427236 | 1405 | 1736 | 3187 | 363 | 99.81 |
| 6366 | 3460471 | A | 3450396 | 1785 | 2255 | 4049 | 1966 | 99.71 |
| 6367 | 3513118 | G | 2440 | 3803 | 515 | 3502860 | 3500 | 99.71 |
| 6368 | 3519327 | G | 2187 | 3188 | 706 | 3511203 | 2241 | 99.76 |
| 6369 | 3437937 | T | 8206 | 3425321 | 7918 | 12054 | 4456 | 99.06 |
| 6371 | 3377382 | G | 2301 | 2239 | 771 | 3369301 | 2770 | 99.76 |
| 6372 | 3378780 | A | 3370965 | 1542 | 1804 | 4262 | 207 | 99.77 |
| 6373 | 3379974 | G | 4312 | 2460 | 1241 | 3371741 | 220 | 99.76 |
| 6374 | 3376712 | C | 2844 | 4574 | 3361918 | 2442 | 4934 | 99.56 |
| 6375 | 3303480 | A | 3293910 | 1382 | 1583 | 3028 | 577 | 99.74 |
| 6376 | 3398392 | G | 4969 | 2966 | 762 | 3382176 | 7719 | 99.52 |
| 6377 | 3507150 | G | 3131 | 4456 | 759 | 3498079 | 723 | 99.74 |
| 6378 | 3343447 | G | 2284 | 2479 | 719 | 3337720 | 243 | 99.83 |
| 6379 | 3343809 | G | 4220 | 1678 | 689 | 3333006 | 3616 | 99.68 |
| 6380 | 3277568 | A | 3246666 | 1311 | 2415 | 2789 | 387 | 99.03 |
| 6381 | 3300972 | A | 3294446 | 1066 | 1065 | 3523 | 872 | 99.8 |
| 6382 | 3321123 | A | 3313570 | 1444 | 1325 | 3196 | 1588 | 99.77 |
| 6383 | 3398219 | T | 2905 | 3389736 | 1733 | 3778 | 87 | 99.75 |
| 6384 | 3397292 | C | 4071 | 3027 | 3388578 | 3018 | 1598 | 99.68 |
| 6385 | 3375993 | C | 3421 | 3302 | 3360660 | 2090 | 6490 | 99.55 |
| 6386 | 3282449 | A | 3275348 | 1431 | 2191 | 3341 | 138 | 99.78 |
| 6387 | 3322673 | G | 2356 | 2368 | 321 | 3314947 | 2481 | 99.77 |
| 6388 | 3371360 | A | 3362437 | 1866 | 2585 | 4189 | 181 | 99.74 |
| 6389 | 3307092 | T | 1152 | 3301492 | 1163 | 2258 | 1027 | 99.83 |
| 6390 | 3296103 | T | 835 | 3289982 | 818 | 1318 | 3150 | 99.81 |
| 6391 | 3298142 | A | 3291390 | 779 | 552 | 2991 | 2430 | 99.8 |

FIG. 5Z

| | | | | | | | | |
|---|---|---|---|---|---|---|---|---|
| 6392 | 3345599 | A | 3340932 | 978 | 834 | 2151 | 664 | 99.86 |
| 6393 | 3349898 | T | 975 | 3345701 | 833 | 2117 | 270 | 99.87 |
| 6394 | 3396206 | T | 1086 | 3391517 | 1509 | 1980 | 164 | 99.86 |
| 6395 | 3393555 | G | 3272 | 1982 | 338 | 3387367 | 2396 | 99.76 |
| 6396 | 3373229 | A | 3365433 | 1100 | 1095 | 2481 | 100 | 99.86 |
| 6397 | 3374763 | A | 3367989 | 1470 | 1089 | 3304 | 911 | 99.8 |
| 6398 | 3381141 | G | 2210 | 2063 | 674 | 3375135 | 1059 | 99.82 |
| 6399 | 3632205 | C | 2153 | 3295 | 3619059 | 1532 | 6166 | 99.64 |
| 6400 | 3609388 | T | 1469 | 3602861 | 1318 | 2908 | 622 | 99.82 |
| 6401 | 3612999 | T | 947 | 3608514 | 1115 | 2210 | 213 | 99.88 |
| 6402 | 3481099 | C | 2042 | 2486 | 3475164 | 1317 | 80 | 99.83 |
| 6403 | 3483527 | T | 1326 | 3478528 | 1237 | 2189 | 247 | 99.86 |
| 6404 | 3579402 | A | 3568277 | 1362 | 876 | 2991 | 5596 | 99.69 |
| 6405 | 3578286 | G | 1904 | 3569 | 506 | 3570430 | 1877 | 99.78 |
| 6406 | 3573087 | T | 2637 | 3563755 | 3073 | 3314 | 258 | 99.68 |
| 6407 | 3479478 | T | 1164 | 3466240 | 1205 | 2836 | 8013 | 99.62 |
| 6408 | 3341335 | T | 332 | 3337934 | 957 | 2707 | 205 | 99.87 |
| 6409 | 3372268 | G | 2204 | 1481 | 289 | 3364406 | 3887 | 99.77 |
| 6410 | 3369903 | A | 3363814 | 1048 | 687 | 4299 | 35 | 99.82 |
| 6412 | 3418375 | T | 1073 | 3407406 | 1126 | 2153 | 6615 | 99.68 |
| 6413 | 3290895 | G | 2696 | 2141 | 430 | 3284601 | 1027 | 99.81 |
| 6414 | 3397347 | A | 3373987 | 3718 | 772 | 6545 | 7325 | 99.45 |
| 6415 | 3418678 | C | 1727 | 2837 | 3409193 | 1269 | 3652 | 99.72 |
| 6416 | 3403524 | T | 1379 | 3398403 | 1439 | 2269 | 34 | 99.85 |
| 6417 | 3422928 | C | 1832 | 2632 | 3412158 | 1485 | 4781 | 99.69 |
| 6418 | 3365496 | A | 3359995 | 1161 | 1224 | 4065 | 41 | 99.81 |
| 6419 | 3346445 | G | 2746 | 2164 | 429 | 3337017 | 4069 | 99.72 |
| 6420 | 3355602 | T | 3712 | 3342572 | 3604 | 8379 | 333 | 99.52 |
| 6421 | 3393981 | G | 2562 | 2265 | 387 | 3385547 | 3220 | 99.77 |
| 6422 | 3354510 | G | 3500 | 2376 | 643 | 3342213 | 5778 | 99.63 |
| 6423 | 3265137 | C | 2555 | 4630 | 3252569 | 2009 | 3374 | 99.62 |
| 6424 | 3226161 | A | 3220454 | 1080 | 936 | 3316 | 373 | 99.82 |
| 6425 | 3224953 | A | 3219459 | 1022 | 798 | 2233 | 1441 | 99.83 |
| 6426 | 3200163 | T | 817 | 3195730 | 897 | 2143 | 376 | 99.86 |
| 6427 | 3170962 | G | 1995 | 1630 | 318 | 3159762 | 7257 | 99.65 |
| 6428 | 3106023 | A | 3101748 | 809 | 324 | 2836 | 306 | 99.86 |
| 6429 | 3102282 | G | 1775 | 1764 | 367 | 3093519 | 4857 | 99.72 |
| 6431 | 3033634 | A | 3031269 | 887 | 591 | 2174 | 713 | 99.86 |
| 6432 | 3016847 | T | 1022 | 3011904 | 951 | 2367 | 603 | 99.84 |
| 6433 | 3035192 | G | 1853 | 1618 | 352 | 3029712 | 1657 | 99.82 |
| 6434 | 2990520 | G | 2457 | 2018 | 771 | 2982455 | 2819 | 99.73 |
| 6435 | 2966071 | C | 1676 | 5847 | 2953721 | 2547 | 2330 | 99.57 |
| 6436 | 2850246 | T | 871 | 2836447 | 10127 | 2317 | 484 | 99.52 |
| 6437 | 2861384 | T | 821 | 2855563 | 1006 | 1855 | 2139 | 99.8 |
| 6438 | 2852414 | T | 656 | 2847525 | 929 | 2197 | 1077 | 99.83 |
| 6439 | 2845022 | T | 451 | 2832473 | 1111 | 10821 | 166 | 99.56 |
| 6440 | 2845613 | G | 2518 | 4297 | 936 | 2840360 | 502 | 99.71 |
| 6441 | 2850481 | G | 2892 | 3181 | 1427 | 2842391 | 390 | 99.72 |
| 6442 | 2870883 | G | 2730 | 1960 | 572 | 2858983 | 6638 | 99.59 |
| 6443 | 2841290 | A | 2832105 | 1196 | 1375 | 5187 | 1427 | 99.68 |
| 6444 | 2783397 | A | 2768331 | 3133 | 729 | 7238 | 746 | 99.5 |
| 6445 | 3191373 | C | 2495 | 3600 | 3182741 | 2035 | 30500 | 98.79 |
| 6446 | 3190222 | C | 3835 | 2719 | 3180000 | 1733 | 1435 | 99.7 |

| | | | | | | | | |
|---|---|---|---|---|---|---|---|---|
| 6508 | 4165233 | A | 4158843 | 1507 | 1116 | 3488 | 259 | 99.85 |
| 6509 | 4200066 | G | 2373 | 2240 | 341 | 4193074 | 2038 | 99.83 |
| 6510 | 4197447 | A | 4188539 | 2439 | 2533 | 3808 | 128 | 99.79 |
| 6511 | 4197504 | T | 1338 | 4192277 | 1301 | 2357 | 431 | 99.88 |
| 6512 | 4193122 | T | 936 | 4183556 | 1134 | 2086 | 5410 | 99.77 |
| 6514 | 4125445 | G | 1814 | 3682 | 379 | 4118247 | 1323 | 99.83 |
| 6515 | 4050733 | T | 3327 | 4034756 | 3989 | 8371 | 260 | 99.61 |
| 6517 | 4168356 | T | 642 | 4163400 | 658 | 2048 | 1608 | 99.88 |
| 6518 | 4161435 | T | 539 | 4156726 | 790 | 3161 | 119 | 99.89 |
| 6519 | 4162862 | G | 2216 | 5454 | 489 | 4154459 | 244 | 99.8 |
| 6520 | 4132097 | G | 2741 | 2368 | 669 | 4125319 | 803 | 99.54 |
| 6521 | 4210606 | A | 4196570 | 2924 | 3744 | 7339 | 29 | 99.67 |
| 6522 | 4188062 | G | 4836 | 2334 | 811 | 4178763 | 1318 | 99.78 |
| 6523 | 4191740 | C | 5069 | 6727 | 4176844 | 2794 | 186 | 99.64 |
| 6525 | 4211226 | A | 4205365 | 850 | 1380 | 2623 | 1108 | 99.86 |
| 6527 | 4220277 | A | 4213680 | 2409 | 959 | 2303 | 926 | 99.54 |
| 6528 | 4250925 | T | 1422 | 4244222 | 931 | 2677 | 1676 | 99.54 |
| 6529 | 4242985 | T | 1220 | 4237077 | 1728 | 3911 | 49 | 99.86 |
| 6530 | 4236343 | C | 3394 | 3839 | 4225272 | 2909 | 939 | 99.74 |
| 6531 | 4229677 | C | 3096 | 3935 | 4218352 | 3393 | 101 | 99.73 |
| 6532 | 4233489 | G | 1852 | 2782 | 452 | 4226124 | 279 | 99.83 |
| 6533 | 4274832 | G | 3039 | 1966 | 651 | 4265544 | 3632 | 99.78 |
| 6534 | 4243065 | T | 11085 | 4204134 | 1049 | 17262 | 128 | 99.08 |
| 6535 | 4267799 | A | 4236813 | 1848 | 985 | 3917 | 4244 | 99.74 |
| 6536 | 4255176 | T | 907 | 4248426 | 774 | 2600 | 1469 | 99.86 |
| 6537 | 4274288 | T | 603 | 4267491 | 996 | 2723 | 2473 | 99.84 |
| 6538 | 4304851 | G | 2966 | 3203 | 564 | 4294545 | 3171 | 99.77 |
| 6539 | 4324979 | A | 4312776 | 2578 | 1698 | 5707 | 2230 | 99.73 |
| 6540 | 4328530 | T | 1338 | 4320459 | 1014 | 5015 | 704 | 99.81 |
| 6541 | 4320603 | G | 3952 | 4480 | 516 | 4309750 | 1905 | 99.75 |
| 6542 | 4351467 | G | 4541 | 2425 | 468 | 4339064 | 4169 | 99.73 |
| 6543 | 4358583 | A | 4343949 | 2260 | 2466 | 3426 | 4402 | 99.67 |
| 6544 | 4297935 | A | 4291162 | 1181 | 1023 | 4162 | 327 | 99.84 |
| 6545 | 4314121 | G | 3015 | 2566 | 396 | 4303696 | 4448 | 99.76 |
| 6546 | 3952917 | A | 3946067 | 1234 | 912 | 4076 | 188 | 99.83 |
| 6547 | 3944913 | G | 2529 | 2044 | 371 | 3936800 | 3171 | 99.79 |
| 6548 | 3941215 | A | 3936070 | 937 | 1094 | 2764 | 350 | 99.87 |
| 6549 | 3887887 | A | 3881416 | 1732 | 800 | 3777 | 162 | 99.83 |
| 6550 | 3900420 | G | 3957 | 2140 | 587 | 3891576 | 2160 | 99.77 |
| 6551 | 3911995 | C | 2241 | 4111 | 3900474 | 1812 | 3397 | 99.71 |
| 6552 | 3873346 | T | 796 | 3870724 | 848 | 2904 | 74 | 99.88 |
| 6553 | 3893009 | G | 3188 | 2069 | 412 | 3886646 | 2494 | 99.79 |
| 6554 | 3877265 | T | 1849 | 3869574 | 1747 | 4012 | 63 | 99.8 |
| 6555 | 3887702 | T | 977 | 3881143 | 1023 | 1991 | 568 | 99.88 |
| 6557 | 3994835 | G | 3022 | 1816 | 399 | 3986215 | 3183 | 99.78 |
| 6558 | 4052304 | C | 2702 | 5740 | 4040118 | 2353 | 1391 | 99.7 |
| 6559 | 4045225 | C | 3222 | 3610 | 4034532 | 1900 | 1564 | 99.74 |
| 6560 | 4090769 | T | 1576 | 4084002 | 1429 | 2604 | 1158 | 99.83 |
| 6561 | 4104568 | T | 871 | 4099067 | 793 | 2376 | 1461 | 99.87 |
| 6562 | 4429308 | T | 786 | 4399408 | 1601 | 4825 | 22588 | 99.32 |
| 6563 | 4483159 | G | 3075 | 7977 | 812 | 4467825 | 3470 | 99.66 |
| 6564 | 4512391 | A | 4500150 | 3082 | 681 | 6828 | 1340 | 99.73 |
| 6565 | 4559261 | C | 2478 | 5942 | 4542950 | 1544 | 5867 | 99.64 |

FIG. 5CC

| | | | | | | | | |
|---|---|---|---|---|---|---|---|---|
| 6566 | 4509730 | T | 1174 | 4504221 | 1065 | 2019 | 1251 | 99.68 |
| 6567 | 4654740 | A | 4633784 | 4206 | 336 | 5796 | 10438 | 99.53 |
| 6568 | 4550327 | C | 2271 | 7386 | 4537327 | 1201 | 2342 | 99.71 |
| 6569 | 4549306 | A | 4538607 | 3138 | 896 | 5707 | 918 | 99.76 |
| 6570 | 4542240 | C | 2555 | 8463 | 4113143 | 1738 | 16039 | 99.36 |
| 6571 | 4257030 | A | 4248765 | 1638 | 1579 | 4691 | 377 | 99.81 |
| 6572 | 4892005 | G | 3393 | 5696 | 897 | 4843400 | 41619 | 98.93 |
| 6573 | 4921105 | G | 3304 | 12767 | 1037 | 4801019 | 3078 | 99.59 |
| 6574 | 5109213 | G | 6972 | 3666 | 1047 | 5083666 | 13860 | 99.5 |
| 6575 | 5067361 | T | 17980 | 5196394 | 21531 | 24294 | 7182 | 98.65 |
| 6576 | 5172232 | A | 5161699 | 980 | 329 | 3384 | 3630 | 99.8 |
| 6577 | 5113833 | T | 1026 | 5104560 | 2055 | 4430 | 1772 | 99.82 |
| 6578 | 5093343 | G | 4524 | 2626 | 629 | 5086948 | 616 | 99.84 |
| 6579 | 5118213 | A | 5141649 | 1868 | 1415 | 3841 | 9439 | 99.68 |
| 6580 | 5093902 | T | 2011 | 3054859 | 2307 | 3669 | 33156 | 99.19 |
| 6581 | 4626561 | G | 6139 | 2770 | 906 | 4604926 | 11800 | 99.53 |
| 6582 | 4526079 | C | 2320 | 7678 | 4505681 | 1543 | 9757 | 99.33 |
| 6583 | 4406386 | A | 4393664 | 2041 | 1185 | 4205 | 291 | 99.82 |
| 6584 | 4538422 | T | 1393 | 4538958 | 1461 | 3722 | 12388 | 99.57 |
| 6585 | 4443633 | C | 2168 | 3393 | 4437251 | 1103 | 1718 | 99.81 |
| 6586 | 4816857 | T | 1916 | 4789721 | 2393 | 4635 | 18220 | 99.44 |
| 6587 | 4821958 | C | 3531 | 2019 | 4810411 | 1187 | 4840 | 99.76 |
| 6588 | 4806671 | T | 1777 | 4800165 | 1662 | 2995 | 72 | 99.86 |
| 6589 | 4711577 | C | 2503 | 3943 | 4706175 | 1172 | 1784 | 99.8 |
| 6590 | 4693559 | A | 4687376 | 1076 | 1128 | 3937 | 42 | 99.87 |
| 6591 | 4781594 | G | 3841 | 3449 | 1642 | 4768757 | 5905 | 99.65 |
| 6592 | 4878596 | C | 2761 | 6718 | 4843732 | 2100 | 3185 | 99.7 |
| 6593 | 4871354 | C | 6309 | 1391 | 4850262 | 2615 | 777 | 99.73 |
| 6594 | 4877837 | C | 3663 | 2616 | 4857448 | 2210 | 11900 | 99.58 |
| 6595 | 4733347 | T | 1046 | 4726212 | 2081 | 2583 | 1425 | 99.85 |
| 6596 | 4916276 | G | 4965 | 2614 | 1164 | 4896748 | 10765 | 99.6 |
| 6597 | 5055803 | C | 3841 | 8151 | 5040793 | 2683 | 333 | 99.7 |
| 6598 | 5031713 | T | 1473 | 5045635 | 1660 | 2762 | 183 | 99.88 |
| 6599 | 5058141 | T | 1048 | 5047278 | 1602 | 2371 | 3842 | 99.79 |
| 6600 | 4972331 | G | 2631 | 3615 | 589 | 4864817 | 679 | 99.85 |
| 6601 | 5035601 | G | 4471 | 2638 | 1529 | 5023323 | 3629 | 99.76 |
| 6602 | 5150809 | T | 3445 | 5132262 | 3886 | 5700 | 516 | 99.64 |
| 6603 | 5146911 | T | 1180 | 5139163 | 1299 | 2844 | 2425 | 99.85 |
| 6604 | 5065780 | C | 2036 | 6881 | 5074491 | 1790 | 3582 | 99.72 |
| 6605 | 5035913 | G | 3214 | 2595 | 1407 | 5025575 | 122 | 99.85 |
| 6606 | 5054036 | A | 5043484 | 1907 | 2656 | 4813 | 1126 | 99.79 |
| 6607 | 5050859 | G | 4003 | 4926 | 2028 | 5039413 | 489 | 99.77 |
| 6608 | 5355539 | G | 8530 | 3450 | 1812 | 5333056 | 8361 | 99.58 |
| 6609 | 5463962 | C | 3095 | 5307 | 5446018 | 3030 | 3342 | 99.69 |
| 6610 | 5470620 | A | 5447344 | 7667 | 1484 | 10696 | 3429 | 99.57 |
| 6611 | 5671278 | C | 3808 | 3627 | 5649268 | 2403 | 10172 | 99.61 |
| 6612 | 5681535 | T | 1299 | 5674072 | 2629 | 3156 | 399 | 99.87 |
| 6613 | 5722905 | A | 5714021 | 1492 | 1350 | 4468 | 1577 | 99.84 |
| 6614 | 5732097 | A | 5723314 | 1138 | 1899 | 4075 | 1651 | 99.85 |
| 6615 | 5732515 | A | 5723715 | 1394 | 1269 | 4119 | 2018 | 99.85 |
| 6616 | 5742998 | G | 11416 | 4242 | 1130 | 5716719 | 9471 | 99.54 |
| 6617 | 5763846 | A | 5748037 | 2677 | 2371 | 5512 | 5049 | 99.73 |
| 6618 | 5777285 | T | 2736 | 5762736 | 3276 | 5277 | 3240 | 99.73 |

| | | | | | | | | |
|---|---|---|---|---|---|---|---|---|
| 6674 | 5160190 | C | 3780 | 3674 | 5131807 | 1816 | 19113 | 99.45 |
| 6675 | 4923267 | A | 4886711 | 9740 | 1060 | 11309 | 4447 | 99.46 |
| 6676 | 4895746 | C | 2201 | 4479 | 4888971 | 1330 | 2765 | 99.75 |
| 6677 | 4911386 | T | 3140 | 4803022 | 1866 | 5134 | 222 | 99.79 |
| 6678 | 5063694 | C | 2716 | 4456 | 5041601 | 1832 | 13059 | 99.56 |
| 6679 | 5048884 | A | 5080575 | 6532 | 1665 | 9945 | 164 | 99.64 |
| 6680 | 5057361 | C | 1764 | 4510 | 5044423 | 684 | 6000 | 99.74 |
| 6681 | 5061635 | A | 5050992 | 11471 | 1638 | 11500 | 714 | 99.4 |
| 6682 | 5143463 | C | 2646 | 6310 | 5123577 | 1277 | 9673 | 99.61 |
| 6683 | 5142174 | C | 3188 | 4697 | 5126829 | 1308 | 6122 | 99.7 |
| 6684 | 5246880 | A | 5156395 | 22747 | 1705 | 23694 | 10338 | 99.85 |
| 6685 | 5232120 | C | 4339 | 6199 | 5210826 | 1470 | 9786 | 99.58 |
| 6686 | 5131593 | C | 4239 | 3869 | 5110282 | 1962 | 11191 | 99.58 |
| 6687 | 5001733 | T | 1963 | 4993711 | 2166 | 3804 | 89 | 99.84 |
| 6688 | 5208403 | G | 12363 | 3907 | 1048 | 5173013 | 16572 | 99.36 |
| 6689 | 5172329 | T | 4106 | 5155068 | 4795 | 8271 | 289 | 99.66 |
| 6690 | 5200436 | A | 5190692 | 2996 | 1169 | 5103 | 496 | 99.81 |
| 6691 | 5186530 | C | 4831 | 10295 | 5162340 | 2144 | 6440 | 99.54 |
| 6692 | 5075115 | A | 5061027 | 1148 | 1338 | 4404 | 7198 | 99.72 |
| 6693 | 4963394 | A | 4931035 | 2117 | 1182 | 4811 | 4238 | 99.75 |
| 6694 | 5095937 | G | 5223 | 4149 | 1163 | 5066830 | 18582 | 99.43 |
| 6695 | 5043174 | A | 5035004 | 1042 | 1494 | 4229 | 1405 | 99.84 |
| 6696 | 5289620 | A | 5271687 | 1301 | 946 | 3320 | 12366 | 99.66 |
| 6697 | 5069625 | T | 2831 | 5055632 | 1742 | 2274 | 7146 | 99.72 |
| 6698 | 5328702 | A | 5302279 | 2740 | 572 | 3495 | 16616 | 99.56 |
| 6699 | 5350303 | A | 5340726 | 1336 | 1398 | 5249 | 1464 | 99.82 |
| 6700 | 5470084 | A | 5454230 | 1511 | 1952 | 3808 | 8593 | 99.71 |
| 6701 | 5491755 | A | 5472239 | 3221 | 2866 | 6149 | 1290 | 99.75 |
| 6702 | 3469474 | C | 2964 | 4230 | 3452010 | 1154 | 9066 | 99.65 |
| 6703 | 5356240 | A | 5347189 | 1490 | 2123 | 3643 | 3795 | 99.79 |
| 6704 | 5364128 | T | 1457 | 5355667 | 1738 | 2148 | 3118 | 99.84 |
| 6705 | 5346564 | A | 5335867 | 4328 | 1251 | 5315 | 1803 | 99.76 |
| 6706 | 5258774 | C | 3527 | 6573 | 5232238 | 1917 | 14519 | 99.5 |
| 6707 | 4993075 | T | 1641 | 4985513 | 2305 | 3313 | 303 | 99.85 |
| 6708 | 5214049 | G | 5555 | 3165 | 663 | 5184553 | 20113 | 99.43 |
| 6709 | 5201477 | T | 6462 | 5178833 | 8027 | 14772 | 1383 | 99.41 |
| 6710 | 5429324 | G | 5895 | 3305 | 895 | 5404700 | 14629 | 99.55 |
| 6711 | 5460068 | T | 4470 | 5437084 | 5291 | 9397 | 3626 | 99.58 |
| 6712 | 5322303 | C | 3280 | 6039 | 5309814 | 2191 | 979 | 99.77 |
| 6713 | 5324126 | A | 5314540 | 1053 | 2136 | 4601 | 1496 | 99.82 |
| 6714 | 5289207 | A | 5281582 | 1367 | 1620 | 4336 | 382 | 99.87 |
| 6715 | 5300198 | G | 5010 | 4632 | 1142 | 5287455 | 1959 | 99.76 |
| 6716 | 5298135 | G | 3237 | 4135 | 1496 | 5284016 | 3254 | 99.73 |
| 6717 | 5323664 | G | 4490 | 3871 | 2668 | 5304273 | 13362 | 99.54 |
| 6718 | 5343355 | C | 3468 | 6412 | 5320582 | 3574 | 9379 | 99.54 |
| 6719 | 5216174 | G | 5176 | 3613 | 1102 | 5205095 | 388 | 99.8 |
| 6720 | 5304943 | G | 6230 | 2746 | 1192 | 5289803 | 4972 | 99.71 |
| 6721 | 5269806 | T | 16038 | 5217235 | 15231 | 21093 | 189 | 99 |
| 6722 | 5310644 | A | 5302203 | 1275 | 1395 | 2838 | 2844 | 99.84 |
| 6723 | 5631149 | T | 1689 | 5621695 | 2383 | 3957 | 1435 | 99.83 |
| 6724 | 5648810 | G | 7399 | 3933 | 3817 | 5630838 | 2823 | 99.68 |
| 6725 | 5741630 | C | 3777 | 8900 | 5719043 | 2933 | 6977 | 99.61 |
| 6726 | 5681514 | C | 3578 | 4315 | 5669514 | 1832 | 2075 | 99.79 |

FIG. 5FF

| | | | | | | | | |
|---|---|---|---|---|---|---|---|---|
| 6727 | 5679272 | A | 5666129 | 2388 | 3214 | 5486 | 1335 | 99.77 |
| 6728 | 5677687 | T | 1985 | 5667413 | 2722 | 3146 | 2021 | 99.82 |
| 6729 | 5669224 | C | 3380 | 4275 | 5653092 | 1967 | 6510 | 99.72 |
| 6730 | 5601218 | T | 1723 | 5592420 | 3268 | 4812 | 2985 | 99.77 |
| 6731 | 5589633 | G | 4294 | 4494 | 1590 | 5578080 | 1173 | 99.79 |
| 6732 | 5593233 | G | 3933 | 4335 | 2117 | 5580419 | 2448 | 99.77 |
| 6733 | 5679120 | T | 3891 | 5646079 | 8383 | 12200 | 6367 | 99.42 |
| 6734 | 5669786 | T | 1338 | 5660200 | 2886 | 3766 | 1396 | 99.83 |
| 6735 | 5709230 | G | 9214 | 5143 | 2775 | 5688458 | 3660 | 99.64 |
| 6736 | 5702308 | C | 3231 | 6699 | 5767008 | 2950 | 2420 | 99.74 |
| 6737 | 5793516 | T | 2579 | 5782413 | 3838 | 3913 | 771 | 99.77 |
| 6738 | 5738954 | C | 3071 | 4627 | 5726736 | 2033 | 2487 | 99.79 |
| 6739 | 5702610 | A | 5691561 | 1925 | 2665 | 6014 | 445 | 99.81 |
| 6740 | 5705879 | G | 4598 | 5021 | 2035 | 5696104 | 1101 | 99.78 |
| 6741 | 5702334 | G | 5831 | 4696 | 2723 | 5685404 | 680 | 99.7 |
| 6742 | 5709253 | C | 1873 | 5106 | 5695272 | 2308 | 2097 | 99.76 |
| 6743 | 5680317 | A | 5654617 | 10474 | 2499 | 10988 | 1739 | 99.55 |
| 6744 | 5718918 | C | 2941 | 4295 | 5702560 | 1843 | 7299 | 99.71 |
| 6745 | 5682220 | T | 2236 | 5674359 | 2093 | 3500 | 32 | 99.86 |
| 6746 | 5814910 | T | 2265 | 5807289 | 1581 | 3498 | 277 | 99.87 |
| 6747 | 5578808 | C | 3969 | 5036 | 5567896 | 1736 | 301 | 99.81 |
| 6748 | 5914663 | A | 5907118 | 1215 | 1674 | 4400 | 256 | 99.87 |
| 6749 | 5906187 | A | 5881077 | 13619 | 3534 | 4466 | 3491 | 99.57 |
| 6750 | 5903236 | T | 3180 | 5895227 | 1398 | 2691 | 840 | 99.86 |
| 6751 | 5915697 | T | 1780 | 5907445 | 1367 | 3191 | 1714 | 99.86 |
| 6752 | 5930401 | T | 1733 | 5920125 | 1467 | 3069 | 4007 | 99.83 |
| 6754 | 5864045 | T | 8293 | 5851958 | 2026 | 1617 | 151 | 99.79 |
| 6756 | 5873603 | A | 5863828 | 2637 | 1125 | 5160 | 1063 | 99.83 |
| 6757 | 5879705 | C | 3328 | 4137 | 5867717 | 1968 | 2338 | 99.8 |
| 6758 | 5877706 | T | 4762 | 5861392 | 1780 | 7124 | 246 | 99.76 |
| 6759 | 5891140 | C | 3364 | 3166 | 5879232 | 2419 | 2839 | 99.8 |
| 6760 | 5962864 | A | 5954323 | 1682 | 1903 | 4637 | 119 | 99.86 |
| 6761 | 5992561 | A | 5984453 | 1897 | 2323 | 3802 | 26 | 99.86 |
| 6762 | 5960030 | T | 2210 | 5971739 | 1979 | 3933 | 169 | 99.86 |
| 6763 | 5995773 | G | 4703 | 4603 | 878 | 5984857 | 1332 | 99.82 |
| 6764 | 5986934 | A | 5984034 | 2911 | 3299 | 5747 | 903 | 99.78 |
| 6765 | 5976065 | T | 2182 | 5967037 | 1540 | 4330 | 976 | 99.83 |
| 6766 | 5956460 | T | 1856 | 5949641 | 1997 | 2683 | 283 | 99.89 |
| 6767 | 5572489 | A | 5566016 | 1301 | 857 | 3163 | 1132 | 99.89 |
| 6768 | 5544365 | A | 5533924 | 3307 | 1169 | 5743 | 222 | 99.81 |
| 6769 | 5615917 | C | 3176 | 5335 | 5596788 | 1805 | 8813 | 99.66 |
| 6770 | 5521633 | A | 5515537 | 834 | 1184 | 3861 | 217 | 99.89 |
| 6771 | 5591595 | A | 5574240 | 5011 | 1354 | 6360 | 4430 | 99.65 |
| 6772 | 5566547 | C | 3516 | 4340 | 5558796 | 1510 | 6385 | 99.72 |
| 6773 | 5530825 | T | 2904 | 5518819 | 2031 | 5616 | 1435 | 99.73 |
| 6774 | 5514301 | T | 1139 | 5507150 | 1854 | 3822 | 336 | 99.87 |
| 6775 | 5511886 | G | 4089 | 3677 | 820 | 5501154 | 2146 | 99.81 |
| 6776 | 5528017 | A | 5516902 | 2143 | 2256 | 4138 | 2138 | 99.8 |
| 6777 | 5503531 | T | 1917 | 5493679 | 1430 | 4008 | 2497 | 99.82 |
| 6778 | 5656860 | T | 911 | 5640714 | 1966 | 3973 | 9296 | 99.71 |
| 6779 | 5575184 | A | 5566453 | 1320 | 721 | 3777 | 2913 | 99.84 |
| 6780 | 5603637 | T | 1929 | 5593583 | 1712 | 3774 | 4639 | 99.78 |
| 6781 | 5553170 | C | 2639 | 5353 | 5537949 | 2251 | 4978 | 99.73 |

FIG. 5GG

| | | | | | | | | |
|---|---|---|---|---|---|---|---|---|
| 6782 | 5303208 | A | 5495787 | 1629 | 1564 | 5397 | 831 | 99.83 |
| 6783 | 5347884 | G | 4872 | 6239 | 1274 | 5128356 | 9143 | 99.61 |
| 6784 | 5492694 | G | 4661 | 6133 | 1570 | 5477722 | 2568 | 99.73 |
| 6785 | 5379164 | A | 5361562 | 3107 | 2129 | 10154 | 213 | 99.67 |
| 6786 | 5286872 | C | 3389 | 3584 | 3286672 | 1632 | 7373 | 99.69 |
| 6787 | 5195735 | A | 5153711 | 19234 | 1586 | 20735 | 439 | 99.19 |
| 6788 | 5401740 | C | 2874 | 7432 | 5363990 | 2278 | 25146 | 99.3 |
| 6789 | 5366882 | T | 2251 | 5356021 | 1525 | 4033 | 232 | 99.83 |
| 6790 | 5426680 | C | 4359 | 3582 | 5411574 | 1446 | 3117 | 99.73 |
| 6791 | 5393915 | T | 1648 | 5361603 | 2095 | 2700 | 3672 | 99.77 |
| 6793 | 5369133 | A | 5351748 | 1969 | 963 | 8084 | 2372 | 99.68 |
| 6794 | 5191943 | C | 3118 | 5395 | 3177316 | 1836 | 4075 | 99.72 |
| 6795 | 5157045 | T | 1431 | 5150379 | 1605 | 3278 | 352 | 99.87 |
| 6796 | 5164555 | G | 7324 | 3027 | 848 | 5133044 | 20112 | 99.39 |
| 6797 | 4844696 | A | 4838322 | 1064 | 1431 | 3476 | 383 | 99.87 |
| 6798 | 4936686 | A | 4929297 | 872 | 870 | 2782 | 2845 | 99.85 |
| 6799 | 4749324 | A | 4743812 | 943 | 869 | 3316 | 384 | 99.88 |
| 6800 | 4827232 | A | 4800914 | 7310 | 2226 | 9803 | 6779 | 99.45 |
| 6801 | 4839318 | C | 8568 | 2621 | 4817413 | 1431 | 9263 | 99.55 |
| 6802 | 4827277 | C | 4033 | 2806 | 4812179 | 3808 | 4449 | 99.69 |
| 6804 | 4837807 | A | 4827012 | 4285 | 1144 | 5134 | 232 | 99.78 |
| 6805 | 4820971 | C | 2540 | 7601 | 4807969 | 1162 | 1299 | 99.73 |
| 6806 | 4812591 | A | 4803902 | 843 | 700 | 4232 | 894 | 99.86 |
| 6807 | 4799247 | A | 4791296 | 1995 | 1316 | 4026 | 611 | 99.83 |
| 6808 | 4841612 | G | 3375 | 4347 | 969 | 4823676 | 9245 | 99.63 |
| 6809 | 4816869 | G | 3583 | 4764 | 1466 | 4789436 | 17318 | 99.43 |
| 6810 | 4818839 | G | 5808 | 6593 | 1341 | 4799359 | 5926 | 99.6 |
| 6811 | 4806623 | C | 2468 | 4342 | 4596227 | 1949 | 1042 | 99.79 |
| 6812 | 4605188 | A | 4597743 | 1515 | 2040 | 3830 | 70 | 99.84 |
| 6813 | 4711250 | T | 1129 | 4705650 | 1089 | 2364 | 818 | 99.88 |
| 6814 | 4706606 | A | 4700048 | 1397 | 721 | 4072 | 368 | 99.86 |
| 6815 | 5258055 | G | 3779 | 5055 | 1022 | 5212430 | 35779 | 99.13 |
| 6816 | 5278161 | A | 5263629 | 2289 | 1617 | 4535 | 6091 | 99.72 |
| 6817 | 5204899 | T | 2233 | 5154895 | 1899 | 3136 | 12736 | 99.62 |
| 6818 | 5010790 | T | 1721 | 5002537 | 2308 | 2939 | 1045 | 99.84 |
| 6819 | 4999297 | T | 1238 | 4992797 | 1524 | 2571 | 1167 | 99.87 |
| 6820 | 4982304 | A | 4975249 | 2309 | 739 | 4123 | 103 | 99.83 |
| 6821 | 4930964 | G | 4077 | 3609 | 1087 | 4921751 | 360 | 99.81 |
| 6822 | 5080905 | A | 5009401 | 7418 | 2272 | 11700 | 114 | 99.57 |
| 6823 | 5001430 | C | 4661 | 4315 | 4965813 | 1790 | 25441 | 99.29 |
| 6824 | 4556187 | C | 3077 | 3844 | 4543530 | 1334 | 4402 | 99.72 |
| 6825 | 4628111 | A | 4583337 | 15731 | 1773 | 18469 | 6801 | 99.08 |
| 6826 | 4914345 | C | 2877 | 4726 | 4899947 | 1621 | 14174 | 99.52 |
| 6827 | 4907786 | C | 4471 | 3090 | 4898186 | 1731 | 308 | 99.8 |
| 6828 | 4920746 | T | 6551 | 4906055 | 6240 | 1762 | 138 | 99.7 |
| 6829 | 4940775 | A | 4927645 | 7460 | 1545 | 2517 | 1608 | 99.73 |
| 6832 | 5122354 | A | 5116897 | 1187 | 935 | 3362 | 273 | 99.88 |
| 6833 | 5151801 | A | 5126818 | 10029 | 1306 | 3474 | 10274 | 99.52 |
| 6834 | 5011922 | T | 2369 | 4902735 | 1330 | 9020 | 6468 | 99.62 |
| 6835 | 4913958 | G | 4040 | 3554 | 1063 | 4896710 | 3591 | 99.71 |
| 6836 | 4824623 | A | 4817338 | 1843 | 1011 | 3994 | 242 | 99.85 |
| 6837 | 4810397 | T | 1914 | 4802259 | 1225 | 3144 | 1755 | 99.83 |
| 6838 | 4904433 | T | 1232 | 4896255 | 1458 | 4739 | 6719 | 99.71 |

FIG. 5HH

| | | | | | | | | |
|---|---|---|---|---|---|---|---|---|
| 6839 | 5049137 | G | 4328 | 3286 | 2302 | 5028433 | 8888 | 99.39 |
| 6840 | 5095358 | C | 3022 | 6028 | 5078911 | 3685 | 3692 | 99.68 |
| 6841 | 5116653 | C | 3382 | 4269 | 5102008 | 2384 | 2610 | 99.71 |
| 6842 | 5102893 | T | 1800 | 5093142 | 2072 | 2645 | 1334 | 99.85 |
| 6843 | 5154399 | A | 5143276 | 1544 | 838 | 3142 | 3499 | 99.82 |
| 6844 | 5170649 | T | 2367 | 5160108 | 2440 | 4878 | 1136 | 99.8 |
| 6845 | 5133233 | G | 4883 | 3807 | 844 | 5122594 | 1105 | 99.79 |
| 6846 | 5243871 | G | 3810 | 3803 | 1226 | 5218544 | 16984 | 99.31 |
| 6847 | 5075397 | T | 13756 | 5012267 | 13177 | 27660 | 6737 | 95.73 |
| 6848 | 4988679 | G | 3194 | 2770 | 1334 | 4978171 | 4210 | 99.77 |
| 6849 | 4955624 | A | 4942446 | 2227 | 2833 | 4894 | 3124 | 99.73 |
| 6850 | 4924927 | T | 1425 | 4915001 | 1957 | 4011 | 2533 | 99.8 |
| 6851 | 4943779 | G | 4414 | 3709 | 691 | 4929322 | 3443 | 99.71 |
| 6852 | 5054317 | A | 5032574 | 2532 | 1983 | 4586 | 12840 | 99.37 |
| 6853 | 5072740 | T | 1802 | 5062829 | 2064 | 3642 | 2683 | 99.8 |
| 6854 | 5080060 | G | 4773 | 3500 | 1736 | 5062015 | 8514 | 99.63 |
| 6855 | 5084541 | T | 6112 | 5012976 | 6711 | 7760 | 982 | 99.57 |
| 6856 | 5053748 | A | 5044975 | 1381 | 1173 | 4182 | 2037 | 99.83 |
| 6857 | 5044102 | A | 5037473 | 1703 | 1069 | 3154 | 763 | 99.87 |
| 6858 | 5101740 | T | 1444 | 5092613 | 1221 | 2848 | 3614 | 99.82 |
| 6859 | 5068972 | T | 1065 | 5063196 | 1748 | 2311 | 632 | 99.89 |
| 6860 | 5075660 | G | 5789 | 4128 | 1717 | 5052213 | 11813 | 99.54 |
| 6861 | 5142097 | C | 2309 | 5191 | 5126564 | 2027 | 3506 | 99.7 |
| 6862 | 5137676 | T | 1823 | 5148114 | 2443 | 2835 | 2441 | 99.81 |
| 6863 | 5282553 | T | 2133 | 5265310 | 1904 | 4604 | 8602 | 99.67 |
| 6864 | 5275434 | C | 2595 | 3719 | 5267230 | 1498 | 372 | 99.84 |
| 6865 | 5277794 | C | 5157 | 3751 | 5266708 | 1603 | 575 | 99.79 |
| 6866 | 5277346 | T | 1510 | 5271124 | 2017 | 2394 | 301 | 99.88 |
| 6867 | 5290818 | A | 5262288 | 13136 | 1941 | 12458 | 995 | 99.46 |
| 6868 | 5338888 | C | 6041 | 7236 | 5320830 | 1460 | 3321 | 99.66 |
| 6869 | 5314207 | C | 3663 | 3523 | 5300916 | 1340 | 4765 | 99.75 |
| 6870 | 5354481 | C | 4991 | 3098 | 5333630 | 1727 | 9015 | 99.65 |
| 6871 | 5416362 | C | 2988 | 2438 | 5399794 | 1344 | 9798 | 99.69 |
| 6872 | 5272852 | C | 3867 | 4080 | 5263101 | 834 | 970 | 99.82 |
| 6873 | 5368194 | A | 5355339 | 1548 | 7087 | 3430 | 770 | 99.76 |
| 6874 | 5426379 | T | 2241 | 5417339 | 2111 | 4547 | 141 | 99.83 |
| 6875 | 5428405 | G | 3194 | 3318 | 771 | 5417942 | 1140 | 99.81 |
| 6876 | 5433955 | A | 5422303 | 1931 | 1855 | 4818 | 3048 | 99.79 |
| 6877 | 5392138 | A | 5380145 | 2686 | 2780 | 5478 | 1049 | 99.78 |
| 6878 | 5432805 | G | 4146 | 3946 | 1688 | 5415216 | 7809 | 99.68 |
| 6879 | 5366673 | T | 7131 | 5332433 | 7381 | 11370 | 2157 | 99.47 |
| 6880 | 5319717 | T | 936 | 5312744 | 1996 | 3188 | 853 | 99.87 |
| 6881 | 5276030 | G | 7119 | 6556 | 3225 | 5255795 | 353 | 99.67 |
| 6882 | 5374641 | A | 5363133 | 2427 | 1359 | 4838 | 2884 | 99.79 |
| 6883 | 5437553 | C | 2479 | 7839 | 5423048 | 2069 | 1318 | 99.73 |
| 6884 | 5434777 | G | 3504 | 3920 | 2895 | 5421232 | 506 | 99.75 |
| 6885 | 5481751 | C | 3355 | 3941 | 5463017 | 2238 | 5200 | 99.69 |
| 6886 | 5464112 | T | 2015 | 5449866 | 3340 | 3977 | 4714 | 99.74 |
| 6887 | 5413303 | A | 5405378 | 1284 | 1242 | 3801 | 1598 | 99.85 |
| 6888 | 5418806 | G | 4664 | 3860 | 1014 | 5406555 | 683 | 99.81 |
| 6889 | 5188253 | T | 6793 | 5159798 | 8598 | 12397 | 665 | 99.45 |
| 6890 | 5416907 | C | 3473 | 4738 | 5386254 | 2300 | 19590 | 99.43 |
| 6891 | 5541288 | T | 2199 | 5528113 | 3083 | 4804 | 3089 | 99.76 |

FIG. 5II

| | | | | | | | | |
|---|---|---|---|---|---|---|---|---|
| 6892 | 5139441 | C | 3329 | 4445 | 5124532 | 3509 | 1626 | 99.73 |
| 6893 | 5144630 | C | 5731 | 4862 | 5128983 | 2443 | 2591 | 99.72 |
| 6894 | 5507025 | T | 1465 | 5501007 | 1457 | 2233 | 776 | 99.89 |
| 6895 | 5524437 | A | 5512811 | 1619 | 804 | 4070 | 3133 | 99.83 |
| 6896 | 5518126 | G | 6409 | 3993 | 3052 | 5503144 | 1326 | 99.73 |
| 6897 | 5531050 | C | 6703 | 6022 | 5514507 | 2929 | 887 | 99.7 |
| 6898 | 5515316 | C | 8155 | 5602 | 5482150 | 4152 | 13057 | 99.4 |
| 6899 | 5267255 | C | 5149 | 3178 | 5253319 | 2554 | 3055 | 99.74 |
| 6900 | 5306961 | A | 5300211 | 1373 | 1115 | 3462 | 787 | 99.87 |
| 6901 | 5237857 | A | 5276327 | 1923 | 1524 | 4250 | 3613 | 99.79 |
| 6902 | 5210199 | T | 1830 | 5203028 | 1691 | 3402 | 248 | 99.86 |
| 6903 | 5193824 | C | 3749 | 4730 | 5180649 | 3095 | 3601 | 99.71 |
| 6904 | 5170639 | A | 5160129 | 1557 | 1770 | 6181 | 1002 | 99.8 |
| 6905 | 5350254 | G | 4176 | 4486 | 895 | 5327212 | 13473 | 99.57 |
| 6906 | 5499168 | G | 12761 | 6178 | 1372 | 5478254 | 573 | 99.62 |
| 6907 | 5497704 | A | 5482251 | 2237 | 3355 | 9476 | 383 | 99.72 |
| 6908 | 5464745 | A | 5453065 | 1453 | 2359 | 4711 | 1157 | 99.82 |
| 6909 | 5450142 | A | 5439173 | 1397 | 1612 | 5036 | 3004 | 99.8 |
| 6910 | 5271228 | A | 5246786 | 1573 | 1675 | 16769 | 2425 | 99.57 |
| 6911 | 5330157 | G | 5801 | 4441 | 1369 | 5331364 | 7182 | 99.65 |
| 6912 | 5473443 | A | 5443565 | 6672 | 1822 | 10199 | 8855 | 99.5 |
| 6913 | 5493778 | C | 2867 | 5139 | 5473081 | 1572 | 11169 | 99.62 |
| 6915 | 5435647 | A | 5430224 | 2152 | 1320 | 3298 | 1653 | 99.85 |
| 6916 | 5041641 | T | 2033 | 5033084 | 1901 | 3919 | 682 | 99.83 |
| 6917 | 5068120 | G | 3676 | 3357 | 851 | 5074874 | 3362 | 99.74 |
| 6918 | 5181476 | G | 3432 | 2243 | 1177 | 5162412 | 9212 | 99.63 |
| 6919 | 5176093 | A | 5151990 | 6709 | 3725 | 12143 | 1326 | 99.53 |
| 6920 | 5237620 | C | 3521 | 4653 | 5218122 | 2786 | 8536 | 99.63 |
| 6921 | 5109072 | T | 1669 | 5098799 | 1721 | 5463 | 1420 | 99.8 |
| 6922 | 5437562 | A | 5401390 | 1809 | 901 | 7996 | 25466 | 99.33 |
| 6923 | 5471050 | A | 5453646 | 5115 | 871 | 8712 | 2466 | 99.69 |
| 6924 | 5545401 | C | 4032 | 3664 | 5524959 | 1941 | 10805 | 99.63 |
| 6925 | 5382636 | T | 2427 | 5370259 | 2398 | 3804 | 3648 | 99.78 |
| 6926 | 5541281 | A | 5526082 | 1942 | 1237 | 2742 | 9278 | 99.73 |
| 6927 | 5237636 | T | 1749 | 5229793 | 1875 | 4068 | 311 | 99.85 |
| 6928 | 5260294 | G | 4648 | 3358 | 925 | 5247793 | 3379 | 99.76 |
| 6929 | 5277503 | A | 5236430 | 9639 | 1510 | 11546 | 378 | 99.49 |
| 6930 | 5349374 | C | 4268 | 5484 | 5323768 | 2187 | 13367 | 99.52 |
| 6931 | 5186709 | T | 3824 | 5172411 | 2558 | 6755 | 1161 | 99.72 |
| 6932 | 5183320 | C | 3440 | 2969 | 5168005 | 2112 | 6794 | 99.7 |
| 6933 | 5074447 | C | 2948 | 3388 | 5064853 | 1748 | 1510 | 99.81 |
| 6934 | 5055945 | A | 5047708 | 1710 | 1955 | 4436 | 136 | 99.84 |
| 6935 | 5062263 | G | 5753 | 3804 | 1493 | 5049923 | 1288 | 99.76 |
| 6936 | 5037695 | C | 2966 | 6393 | 5024515 | 1875 | 1946 | 99.74 |
| 6937 | 5026009 | T | 1347 | 5019197 | 2103 | 3398 | 864 | 99.85 |
| 6938 | 5036013 | G | 4622 | 3421 | 1171 | 5025538 | 2161 | 99.77 |
| 6939 | 5058237 | A | 5044311 | 3647 | 2536 | 7632 | 111 | 99.72 |
| 6940 | 5040502 | C | 4253 | 6438 | 5025437 | 2511 | 2141 | 99.7 |
| 6941 | 5031718 | A | 5026147 | 817 | 1091 | 3356 | 307 | 99.89 |
| 6942 | 5034430 | A | 5028034 | 1199 | 911 | 2787 | 1499 | 99.87 |
| 6943 | 5101672 | A | 5093064 | 1819 | 1447 | 3692 | 1630 | 99.83 |
| 6944 | 5066204 | T | 2970 | 5066787 | 1183 | 5025 | 238 | 99.82 |
| 6945 | 5066505 | C | 3337 | 4139 | 5074875 | 2005 | 2649 | 99.76 |

FIG. 5JJ

| | | | | | | | | |
|---|---|---|---|---|---|---|---|---|
| 6946 | 5062688 | A | 5064199 | 1359 | 1768 | 4720 | 442 | 99.83 |
| 6947 | 5073193 | G | 6277 | 3430 | 1322 | 5066480 | 5654 | 99.67 |
| 6948 | 5092913 | C | 4007 | 5165 | 5078748 | 3186 | 1807 | 99.72 |
| 6949 | 5097997 | T | 1333 | 5091367 | 1697 | 3526 | 74 | 99.87 |
| 6950 | 5201592 | A | 5188220 | 1265 | 1014 | 2727 | 8366 | 99.74 |
| 6951 | 5180348 | T | 1253 | 5173573 | 1556 | 2152 | 1814 | 99.87 |
| 6952 | 5418461 | A | 5394239 | 2050 | 1239 | 3567 | 17386 | 99.55 |
| 6953 | 5311029 | T | 1632 | 5304621 | 953 | 2310 | 1313 | 99.88 |
| 6954 | 5273646 | T | 1595 | 5266351 | 1521 | 2642 | 1537 | 99.86 |
| 6955 | 5248016 | T | 1417 | 5236116 | 2027 | 4128 | 4328 | 99.77 |
| 6956 | 5186120 | G | 4518 | 3910 | 928 | 5175837 | 927 | 99.8 |
| 6957 | 5191497 | A | 5184236 | 1425 | 1512 | 3762 | 562 | 99.86 |
| 6958 | 5195685 | A | 5181500 | 1616 | 1557 | 4367 | 6645 | 99.73 |
| 6959 | 5063268 | A | 5060351 | 3263 | 1042 | 6798 | 1814 | 99.75 |
| 6960 | 5077703 | C | 3522 | 3280 | 5048156 | 4270 | 16475 | 99.42 |
| 6961 | 4838660 | A | 4830544 | 1288 | 1526 | 4457 | 854 | 99.83 |
| 6962 | 4870713 | G | 4016 | 3216 | 1381 | 4855714 | 5986 | 99.7 |
| 6963 | 4928343 | T | 5673 | 4893155 | 6037 | 18383 | 2895 | 99.33 |
| 6964 | 4890078 | C | 3890 | 13361 | 4867677 | 2343 | 2807 | 99.54 |
| 6965 | 4962719 | A | 4940935 | 5030 | 1375 | 9632 | 5747 | 99.56 |
| 6966 | 5035930 | C | 2653 | 6004 | 5017299 | 3390 | 6544 | 99.63 |
| 6967 | 5033991 | A | 5022685 | 2054 | 1970 | 6724 | 355 | 99.78 |
| 6968 | 5040797 | T | 1344 | 5027902 | 1816 | 5990 | 3745 | 99.74 |
| 6969 | 4992752 | G | 4670 | 3671 | 840 | 4981850 | 1691 | 99.78 |
| 6970 | 5089004 | G | 4357 | 3795 | 1034 | 5069690 | 10128 | 99.62 |
| 6971 | 5009000 | G | 2902 | 4345 | 968 | 4990603 | 9900 | 99.63 |
| 6972 | 4866046 | A | 4546217 | 2769 | 3829 | 12771 | 461 | 99.59 |
| 6973 | 4919869 | G | 4098 | 3683 | 983 | 4898224 | 12881 | 99.56 |
| 6974 | 4925417 | A | 4906284 | 2234 | 3386 | 6423 | 7140 | 99.61 |
| 6975 | 4995793 | A | 4973655 | 2025 | 1455 | 7864 | 10790 | 99.56 |
| 6976 | 4987111 | T | 1198 | 4977370 | 1765 | 5326 | 1452 | 99.8 |
| 6977 | 4998002 | G | 5041 | 3090 | 730 | 4985490 | 3631 | 99.75 |
| 6978 | 4994238 | T | 8978 | 4956293 | 8020 | 11411 | 9536 | 99.24 |
| 6979 | 4834454 | A | 4828599 | 1366 | 591 | 3760 | 138 | 99.88 |
| 6980 | 4649441 | A | 4838033 | 2911 | 973 | 6749 | 773 | 99.76 |
| 6981 | 4845886 | C | 3074 | 4920 | 4828502 | 3038 | 6312 | 99.64 |
| 6982 | 4812427 | A | 4804995 | 1253 | 1321 | 3852 | 1006 | 99.85 |
| 6983 | 4988539 | T | 1423 | 4958188 | 1438 | 4316 | 23174 | 99.39 |
| 6984 | 4802639 | T | 1357 | 4796121 | 1527 | 3337 | 297 | 99.88 |
| 6985 | 4860489 | C | 2723 | 4296 | 4844768 | 1352 | 7350 | 99.68 |
| 6986 | 4833394 | T | 1563 | 4826352 | 2216 | 2742 | 521 | 99.83 |
| 6987 | 4843565 | T | 916 | 4837391 | 2067 | 2365 | 426 | 99.88 |
| 6988 | 4835989 | G | 4064 | 2353 | 553 | 4827552 | 1247 | 99.83 |
| 6989 | 4830186 | A | 4821428 | 1746 | 2087 | 4708 | 617 | 99.81 |
| 6990 | 4821468 | A | 4813984 | 1861 | 1128 | 4363 | 132 | 99.84 |
| 6991 | 4656765 | G | 3011 | 3199 | 1038 | 4637710 | 13807 | 99.55 |
| 6992 | 4636344 | A | 4625196 | 1622 | 1545 | 4573 | 3406 | 99.76 |
| 6993 | 4641010 | G | 2920 | 3739 | 693 | 4628064 | 5594 | 99.72 |
| 6994 | 4677350 | A | 4668396 | 1577 | 2151 | 4561 | 665 | 99.81 |
| 6995 | 4725370 | T | 1680 | 4717754 | 1814 | 3314 | 808 | 99.84 |
| 6996 | 4704017 | T | 1422 | 4696150 | 1375 | 2554 | 516 | 99.88 |
| 6997 | 4911407 | C | 3182 | 4787 | 4885014 | 2791 | 13633 | 99.46 |
| 6998 | 4899441 | T | 2086 | 4891459 | 1914 | 3874 | 108 | 99.84 |

FIG. 5KK

| | | | | | | | | |
|---|---|---|---|---|---|---|---|---|
| 6999 | 4901415 | T | 1493 | 4894730 | 1611 | 3401 | 180 | 99.86 |
| 7000 | 4891031 | C | 2553 | 6121 | 4873091 | 1904 | 7362 | 99.63 |
| 7001 | 4789155 | A | 4781730 | 1311 | 1633 | 4411 | 70 | 99.84 |
| 7002 | 4799455 | G | 4219 | 5013 | 1743 | 4780710 | 3770 | 99.69 |
| 7003 | 4824128 | G | 4776 | 7438 | 2617 | 4809003 | 294 | 99.69 |
| 7004 | 4944371 | G | 7175 | 4031 | 2456 | 4929717 | 992 | 99.7 |
| 7005 | 4806341 | C | 3602 | 5021 | 4777934 | 5242 | 13942 | 99.41 |
| 7006 | 4801147 | A | 4794291 | 1495 | 1230 | 3978 | 153 | 99.85 |
| 7007 | 4702317 | G | 3491 | 3590 | 881 | 4685082 | 8473 | 99.65 |
| 7008 | 4820368 | A | 4810594 | 2414 | 1629 | 5630 | 111 | 99.8 |
| 7009 | 4837123 | C | 3237 | 6814 | 4823033 | 2441 | 1603 | 99.71 |
| 7010 | 4850289 | G | 4308 | 3009 | 840 | 4838149 | 3983 | 99.75 |
| 7011 | 4812285 | A | 4799518 | 2078 | 2127 | 6267 | 2295 | 99.73 |
| 7012 | 4819192 | G | 4099 | 4223 | 1073 | 4803705 | 6090 | 99.68 |
| 7013 | 4814473 | A | 4803411 | 2020 | 3241 | 5285 | 516 | 99.77 |
| 7014 | 4796492 | A | 4789390 | 1274 | 1602 | 3965 | 261 | 99.85 |
| 7015 | 4822185 | A | 4805932 | 1096 | 1466 | 3413 | 10258 | 99.66 |
| 7016 | 4660233 | T | 1793 | 4653457 | 1646 | 2518 | 821 | 99.85 |
| 7017 | 4789942 | A | 4716037 | 19718 | 898 | 17353 | 3736 | 99.06 |
| 7018 | 4667931 | C | 2933 | 5168 | 4654334 | 1510 | 3966 | 99.71 |
| 7019 | 4643461 | C | 4252 | 3415 | 4634633 | 1536 | 1325 | 99.77 |
| 7020 | 4643347 | C | 3346 | 3417 | 4627718 | 1544 | 6822 | 99.67 |
| 7021 | 4694616 | A | 4684733 | 2506 | 2147 | 3532 | 1258 | 99.79 |
| 7022 | 4813966 | T | 1289 | 4799849 | 1111 | 3015 | 8702 | 99.71 |
| 7023 | 4709076 | T | 880 | 4701993 | 1067 | 1943 | 3193 | 99.85 |
| 7025 | 4743603 | C | 3847 | 3506 | 4727584 | 1344 | 6612 | 99.67 |
| 7026 | 4674687 | T | 1598 | 4667071 | 1611 | 2515 | 1892 | 99.84 |
| 7027 | 4733094 | T | 883 | 4744267 | 1759 | 2491 | 3724 | 99.81 |
| 7028 | 4908563 | A | 4900306 | 1400 | 906 | 4053 | 1895 | 99.83 |
| 7029 | 4937337 | T | 1731 | 4929574 | 1352 | 2400 | 2230 | 99.84 |
| 7030 | 4922859 | T | 1646 | 4939499 | 1332 | 2773 | 7609 | 99.73 |
| 7031 | 4876198 | C | 3184 | 4625 | 4861082 | 2031 | 5276 | 99.69 |
| 7032 | 4930322 | A | 4936066 | 1672 | 1233 | 3790 | 7761 | 99.71 |
| 7033 | 4933055 | T | 3273 | 4943129 | 1797 | 5198 | 1656 | 99.76 |
| 7034 | 4941838 | C | 3573 | 4501 | 4930466 | 2365 | 733 | 99.77 |
| 7035 | 5016832 | C | 4208 | 4040 | 4995945 | 3213 | 9423 | 99.35 |
| 7036 | 5010868 | A | 4996486 | 1910 | 1892 | 5219 | 3361 | 99.75 |
| 7037 | 5047706 | G | 3847 | 3513 | 1070 | 5035666 | 3410 | 99.77 |
| 7038 | 5178651 | T | 5247 | 5160031 | 4466 | 7301 | 1606 | 99.64 |
| 7039 | 5151708 | A | 5142804 | 1021 | 764 | 4781 | 2358 | 99.83 |
| 7040 | 5207601 | A | 5191873 | 1298 | 1039 | 3829 | 9362 | 99.7 |
| 7041 | 5083645 | T | 1635 | 5074681 | 1247 | 3732 | 2330 | 99.82 |
| 7042 | 5066913 | G | 5074 | 3493 | 1181 | 5076282 | 883 | 99.79 |
| 7043 | 5098187 | C | 4794 | 6409 | 5077528 | 2855 | 6601 | 99.59 |
| 7044 | 5015533 | C | 4266 | 4099 | 4999173 | 1970 | 6025 | 99.67 |
| 7045 | 4969301 | A | 4935785 | 1832 | 1004 | 4491 | 2187 | 99.81 |
| 7046 | 4950318 | A | 4943090 | 1678 | 1307 | 3877 | 366 | 99.85 |
| 7047 | 4965170 | T | 1173 | 4959708 | 1242 | 2491 | 556 | 99.89 |
| 7048 | 4931837 | G | 3676 | 2730 | 722 | 4923406 | 3303 | 99.79 |
| 7049 | 4965312 | A | 4955043 | 1674 | 1604 | 4066 | 2925 | 99.79 |
| 7050 | 4932185 | A | 4923651 | 1745 | 858 | 3190 | 741 | 99.87 |
| 7051 | 4873023 | G | 3806 | 4720 | 842 | 4864112 | 1348 | 99.78 |
| 7052 | 4886145 | G | 4880 | 3781 | 908 | 4868696 | 1700 | 99.77 |

FIG. 5LL

| | | | | | | | | |
|---|---|---|---|---|---|---|---|---|
| 7053 | 4769342 | A | 4760645 | 1305 | 1084 | 4097 | 2209 | 99.82 |
| 7055 | 4759736 | A | 4732031 | 1372 | 1001 | 4003 | 1329 | 99.84 |
| 7056 | 4925403 | T | 4527 | 4913943 | 1099 | 4318 | 4525 | 99.71 |
| 7057 | 4912130 | T | 1420 | 4963054 | 1461 | 4176 | 1189 | 99.83 |
| 7058 | 4948206 | C | 3798 | 4653 | 4936311 | 2586 | 858 | 99.76 |
| 7059 | 4941433 | A | 4935117 | 1068 | 639 | 3396 | 1193 | 99.87 |
| 7060 | 4927257 | T | 1309 | 4921760 | 1367 | 2386 | 331 | 99.89 |
| 7061 | 4916047 | G | 4177 | 2788 | 842 | 4905773 | 2467 | 99.79 |
| 7062 | 4944784 | A | 4938045 | 1219 | 729 | 3624 | 1167 | 99.86 |
| 7063 | 4913554 | A | 4903830 | 1804 | 1436 | 3901 | 2563 | 99.8 |
| 7064 | 4858525 | T | 2773 | 4876923 | 939 | 4217 | 3671 | 99.76 |
| 7065 | 4856645 | C | 3121 | 3534 | 4880303 | 1859 | 9638 | 99.63 |
| 7066 | 4913315 | A | 4903263 | 1506 | 940 | 3883 | 1723 | 99.84 |
| 7067 | 4869882 | A | 4863963 | 856 | 637 | 3053 | 1371 | 99.83 |
| 7068 | 4886590 | T | 2023 | 4881133 | 1004 | 2241 | 189 | 99.89 |
| 7069 | 4880727 | T | 1289 | 4873207 | 1251 | 2933 | 2047 | 99.85 |
| 7070 | 4860609 | A | 4854316 | 1144 | 624 | 3225 | 1297 | 99.87 |
| 7071 | 4769721 | G | 2303 | 3478 | 982 | 4761456 | 1104 | 99.83 |
| 7072 | 4761279 | A | 4751720 | 1759 | 1513 | 4091 | 2186 | 99.8 |
| 7073 | 4745430 | T | 2270 | 4725737 | 1250 | 4399 | 8774 | 99.65 |
| 7074 | 4629560 | G | 3329 | 3539 | 928 | 4614863 | 6401 | 99.68 |
| 7075 | 4663502 | G | 3726 | 3773 | 1159 | 4650873 | 3964 | 99.73 |
| 7076 | 4539125 | A | 4526573 | 3451 | 1361 | 7408 | 337 | 99.72 |
| 7077 | 4637796 | C | 4545 | 3132 | 4623358 | 2298 | 4263 | 99.69 |
| 7078 | 4623631 | A | 4621939 | 1074 | 1095 | 4229 | 274 | 99.86 |
| 7079 | 5020707 | A | 5014020 | 1139 | 1009 | 3265 | 1274 | 99.87 |
| 7080 | 5019931 | A | 5012917 | 1667 | 1276 | 3302 | 769 | 99.86 |
| 7081 | 5005494 | A | 4967507 | 1490 | 1044 | 35073 | 378 | 99.13 |
| 7082 | 5048299 | G | 25661 | 4892 | 1099 | 5008560 | 8087 | 99.21 |
| 7083 | 5069191 | A | 5051441 | 2079 | 1430 | 4483 | 9758 | 99.65 |
| 7084 | 4997247 | T | 3036 | 4978847 | 2368 | 3860 | 7244 | 99.63 |
| 7085 | 4986455 | C | 3160 | 3154 | 4981122 | 2151 | 6768 | 99.69 |
| 7086 | 4972231 | C | 4819 | 3467 | 4959102 | 2256 | 2187 | 99.74 |
| 7087 | 5040054 | T | 1796 | 5025909 | 1905 | 4867 | 5577 | 99.72 |
| 7088 | 5036904 | A | 5027554 | 1512 | 940 | 5998 | 900 | 99.81 |
| 7089 | 5052627 | G | 2361 | 4601 | 829 | 5042379 | 1957 | 99.8 |
| 7090 | 5124334 | G | 5052 | 3735 | 1393 | 5105098 | 5354 | 99.7 |
| 7091 | 5064792 | A | 5076889 | 1496 | 1619 | 5544 | 9244 | 99.65 |
| 7092 | 4971413 | A | 4933725 | 3699 | 780 | 7160 | 6040 | 99.64 |
| 7093 | 4877737 | C | 3667 | 4974 | 4861331 | 2901 | 4864 | 99.66 |
| 7094 | 4962636 | A | 4933420 | 10051 | 988 | 12670 | 5507 | 99.41 |
| 7095 | 5010945 | C | 3390 | 4134 | 4993645 | 1998 | 7878 | 99.65 |
| 7096 | 4959747 | T | 2517 | 4950307 | 1820 | 4854 | 49 | 99.81 |
| 7097 | 4838633 | C | 4123 | 5195 | 4822797 | 2527 | 4013 | 99.67 |
| 7098 | 4801543 | A | 4792797 | 1241 | 993 | 5050 | 1431 | 99.82 |
| 7099 | 4876717 | G | 2803 | 4110 | 791 | 4861881 | 7030 | 99.7 |
| 7100 | 4911198 | G | 3891 | 4280 | 934 | 4899149 | 2944 | 99.75 |
| 7101 | 4589606 | A | 4578620 | 1925 | 1388 | 3958 | 2285 | 99.8 |
| 7102 | 4900719 | T | 2606 | 4883377 | 1749 | 4109 | 8638 | 99.65 |
| 7103 | 4757073 | C | 2787 | 3997 | 4742203 | 1358 | 3728 | 99.75 |
| 7104 | 4830031 | A | 4813190 | 6309 | 985 | 9019 | 548 | 99.65 |
| 7105 | 4908904 | C | 3464 | 7303 | 4889646 | 2576 | 3685 | 99.61 |
| 7106 | 4910967 | G | 5450 | 3845 | 606 | 4897612 | 3424 | 99.73 |

FIG. 5MM

| | | | | | | | | |
|---|---|---|---|---|---|---|---|---|
| 7107 | 4917806 | T | 2704 | 4901705 | 2671 | 4810 | 5916 | 99.67 |
| 7108 | 4773343 | T | 1893 | 4763333 | 1375 | 3826 | 2696 | 99.79 |
| 7109 | 4760180 | C | 1888 | 3838 | 4730780 | 1778 | 1596 | 99.8 |
| 7110 | 4758329 | G | 7482 | 2960 | 1389 | 4746404 | 94 | 99.75 |
| 7111 | 4720238 | C | 2996 | 4757 | 4714007 | 2345 | 2133 | 99.74 |
| 7112 | 4741130 | T | 1878 | 4733055 | 1433 | 4289 | 475 | 99.83 |
| 7113 | 5107032 | C | 3326 | 3327 | 3078901 | 1755 | 19723 | 99.43 |
| 7114 | 5065330 | T | 2245 | 5017321 | 1557 | 4019 | 188 | 99.84 |
| 7115 | 5076699 | C | 3681 | 3872 | 5060438 | 1217 | 7491 | 99.68 |
| 7116 | 5083793 | T | 1633 | 5087013 | 1497 | 3565 | 85 | 99.87 |
| 7117 | 5194634 | G | 7255 | 3821 | 1206 | 5173201 | 9331 | 99.58 |
| 7118 | 5180961 | T | 3333 | 5165752 | 3676 | 7949 | 229 | 99.71 |
| 7119 | 5269541 | G | 3004 | 3422 | 1413 | 5252663 | 7339 | 99.67 |
| 7120 | 5408783 | C | 6746 | 10347 | 3378302 | 2937 | 9953 | 99.43 |
| 7121 | 5339827 | C | 7682 | 5741 | 5307686 | 2251 | 16437 | 99.42 |
| 7122 | 5379675 | T | 1297 | 5371594 | 1279 | 3162 | 2343 | 99.83 |
| 7123 | 5561977 | A | 5545446 | 2754 | 1588 | 3607 | 8582 | 99.7 |
| 7124 | 5413837 | T | 1477 | 5407325 | 1523 | 2837 | 673 | 99.88 |
| 7125 | 5412383 | T | 848 | 5395469 | 1046 | 2703 | 12776 | 99.68 |
| 7126 | 5236701 | A | 5228999 | 1102 | 792 | 4501 | 1347 | 99.83 |
| 7127 | 5333672 | G | 4929 | 4203 | 1413 | 5312868 | 10259 | 99.61 |
| 7128 | 5474580 | C | 5337 | 5687 | 5447070 | 2746 | 14040 | 99.49 |
| 7129 | 5275383 | T | 2513 | 5260060 | 1876 | 5180 | 5732 | 99.71 |
| 7130 | 5227217 | T | 1934 | 5215254 | 1542 | 4249 | 4338 | 99.77 |
| 7131 | 5191733 | G | 4165 | 4711 | 757 | 5181431 | 691 | 99.8 |
| 7132 | 5266673 | G | 8383 | 3270 | 1079 | 5248638 | 3305 | 99.66 |
| 7133 | 5204474 | C | 2679 | 11104 | 5187342 | 2281 | 963 | 99.67 |
| 7134 | 5193197 | A | 5179974 | 4385 | 1219 | 7252 | 367 | 99.75 |
| 7135 | 5113823 | C | 4036 | 7892 | 5128386 | 1464 | 13050 | 99.31 |
| 7136 | 4996610 | A | 4990670 | 1262 | 921 | 3634 | 123 | 99.88 |
| 7137 | 4980823 | A | 4973747 | 1355 | 826 | 3563 | 834 | 99.87 |
| 7138 | 4970432 | T | 1643 | 4961565 | 1318 | 3137 | 2769 | 99.82 |
| 7139 | 4974951 | G | 4267 | 4114 | 980 | 4962587 | 3003 | 99.75 |
| 7140 | 5027472 | G | 4391 | 3725 | 1055 | 5009836 | 8362 | 99.45 |
| 7141 | 4902674 | C | 3086 | 3826 | 4890626 | 3032 | 104 | 99.75 |
| 7142 | 4907465 | G | 5317 | 2338 | 705 | 4898625 | 479 | 99.82 |
| 7143 | 4925936 | A | 4917769 | 1303 | 1540 | 3474 | 3870 | 99.79 |
| 7144 | 4887970 | A | 4881313 | 1852 | 874 | 3847 | 82 | 99.86 |
| 7145 | 4918001 | G | 5278 | 3008 | 1094 | 4942274 | 6347 | 99.68 |
| 7146 | 4965523 | A | 4957858 | 1089 | 1580 | 3208 | 588 | 99.83 |
| 7147 | 4957743 | A | 4948312 | 1703 | 784 | 4400 | 1544 | 99.83 |
| 7148 | 5073014 | G | 5183 | 5607 | 744 | 5049979 | 13501 | 99.55 |
| 7149 | 5012136 | A | 5003561 | 1711 | 1903 | 4802 | 149 | 99.83 |
| 7150 | 5084263 | A | 5072899 | 1805 | 919 | 4977 | 3663 | 99.78 |
| 7151 | 5073494 | T | 4345 | 5063646 | 1049 | 2742 | 1712 | 99.81 |
| 7152 | 5054482 | A | 5048690 | 1372 | 805 | 2844 | 371 | 99.89 |
| 7153 | 5147721 | T | 9311 | 5125156 | 1932 | 2710 | 8562 | 99.56 |
| 7154 | 5080823 | A | 5073326 | 769 | 740 | 3014 | 2974 | 99.83 |
| 7155 | 5110820 | A | 5099971 | 3306 | 317 | 5414 | 1612 | 99.79 |
| 7156 | 5115706 | C | 11004 | 5219 | 5087831 | 1378 | 13274 | 99.4 |
| 7158 | 5087768 | A | 5078913 | 1037 | 947 | 2744 | 4145 | 99.83 |
| 7159 | 5024825 | A | 5012327 | 7509 | 1572 | 2832 | 585 | 99.75 |
| 7160 | 5041658 | T | 3170 | 5031944 | 1402 | 3411 | 1731 | 99.81 |

FIG. 5NN

| | | | | | | | | |
|---|---|---|---|---|---|---|---|---|
| 7161 | 5087976 | T | 3324 | 5025177 | 1239 | 7310 | 326 | 99.73 |
| 7162 | 5038574 | C | 2414 | 3123 | 5047808 | 1555 | 3574 | 99.79 |
| 7163 | 5117064 | C | 5163 | 8964 | 5099404 | 2333 | 1200 | 99.65 |
| 7164 | 5422210 | T | 10336 | 5406189 | 1088 | 3666 | 731 | 99.7 |
| 7165 | 5429734 | A | 5415531 | 2225 | 895 | 10155 | 928 | 99.74 |
| 7166 | 5383957 | G | 6776 | 6249 | 1385 | 5367854 | 1793 | 99.7 |
| 7167 | 5377209 | C | 10432 | 14943 | 5347203 | 3825 | 486 | 99.45 |
| 7168 | 5389062 | T | 37628 | 5345300 | 945 | 3199 | 1790 | 99.19 |
| 7169 | 5417239 | A | 5410621 | 950 | 537 | 2183 | 2938 | 99.88 |
| 7171 | 5844276 | A | 5814044 | 1211 | 671 | 2981 | 2769 | 99.45 |
| 7172 | 5864002 | A | 5847383 | 9691 | 801 | 5122 | 805 | 99.72 |
| 7173 | 5865960 | T | 8418 | 5839162 | 1630 | 15432 | 1318 | 99.54 |
| 7174 | 5811488 | C | 14036 | 7203 | 5781933 | 5681 | 2633 | 99.49 |
| 7175 | 5773789 | A | 5747767 | 1838 | 1247 | 22770 | 147 | 99.55 |
| 7176 | 5774844 | G | 4181 | 5683 | 1414 | 5762007 | 1659 | 99.78 |
| 7177 | 5812946 | G | 8573 | 5797 | 1718 | 5785810 | 8048 | 99.58 |
| 7178 | 5745807 | A | 5704305 | 5412 | 2000 | 33806 | 84 | 99.28 |
| 7179 | 5763336 | G | 4799 | 9256 | 985 | 5710666 | 36630 | 99.1 |
| 7180 | 5203365 | T | 11354 | 5147137 | 11003 | 33396 | 275 | 98.92 |
| 7181 | 5243109 | G | 5773 | 8344 | 733 | 5225127 | 3132 | 99.66 |
| 7182 | 5370302 | T | 6509 | 5324852 | 5975 | 32500 | 386 | 99.15 |
| 7183 | 5359119 | G | 6543 | 4551 | 1242 | 5346305 | 278 | 99.76 |
| 7184 | 5276273 | C | 4265 | 9191 | 5257039 | 4083 | 1683 | 99.64 |
| 7185 | 5225330 | C | 62472 | 8261 | 5147870 | 5687 | 1260 | 98.51 |
| 7186 | 5238027 | A | 5247065 | 1947 | 1301 | 4439 | 3275 | 99.79 |
| 7187 | 5708654 | A | 5618884 | 79424 | 1212 | 7139 | 1565 | 98.43 |
| 7188 | 5725782 | T | 1594 | 5718063 | 1260 | 3575 | 1290 | 99.87 |
| 7189 | 5781730 | T | 3621 | 5706850 | 1332 | 62982 | 4945 | 98.74 |
| 7190 | 5706382 | G | 4230 | 3793 | 775 | 5693304 | 2460 | 99.8 |
| 7191 | 5710586 | G | 53184 | 6163 | 947 | 5649458 | 834 | 98.93 |
| 7192 | 5840230 | A | 5831927 | 1734 | 1186 | 4840 | 543 | 99.86 |
| 7193 | 5821701 | A | 5792612 | 2605 | 697 | 25742 | 45 | 99.5 |
| 7194 | 5828402 | G | 13502 | 5108 | 835 | 5801457 | 7470 | 99.54 |
| 7195 | 5744267 | A | 5681886 | 10125 | 1831 | 52046 | 379 | 98.88 |
| 7196 | 5840280 | G | 8197 | 26839 | 922 | 5786259 | 6063 | 99.28 |
| 7197 | 5974211 | C | 9733 | 191765 | 5764236 | 7428 | 1046 | 98.49 |
| 7198 | 5985883 | T | 1744 | 5978133 | 2136 | 3382 | 478 | 99.87 |
| 7199 | 5993402 | T | 1640 | 5986377 | 1068 | 2789 | 1528 | 99.88 |
| 7200 | 5926305 | T | 9221 | 5912942 | 793 | 3468 | 80 | 99.77 |
| 7201 | 5912331 | A | 5837979 | 67087 | 442 | 6023 | 500 | 98.73 |
| 7202 | 5930406 | T | 1493 | 5920963 | 941 | 2912 | 4090 | 99.84 |
| 7203 | 5908735 | T | 2329 | 5877460 | 957 | 27293 | 714 | 99.47 |
| 7204 | 5926084 | G | 9542 | 11889 | 1155 | 5890704 | 12734 | 99.4 |
| 7205 | 5777380 | C | 4927 | 18738 | 5745536 | 3368 | 4811 | 99.43 |
| 7206 | 5807407 | T | 19608 | 5738037 | 7535 | 19373 | 2654 | 99.15 |
| 7207 | 5826662 | C | 3230 | 3389 | 5813743 | 1689 | 4611 | 99.78 |
| 7208 | 5808700 | C | 8008 | 4722 | 5778887 | 11649 | 1434 | 99.49 |
| 7209 | 5797107 | C | 95199 | 12264 | 5663186 | 24410 | 2048 | 97.69 |
| 7210 | 5780616 | A | 5718826 | 4483 | 1764 | 54976 | 367 | 98.93 |
| 7211 | 5823183 | G | 20234 | 6005 | 1542 | 5791415 | 3987 | 99.45 |
| 7212 | 5776592 | A | 5707200 | 11276 | 1574 | 54839 | 1703 | 98.8 |
| 7213 | 5804114 | G | 15139 | 64515 | 674 | 5801426 | 24366 | 98.33 |
| 7214 | 5802838 | T | 22378 | 5432609 | 7493 | 14747 | 5611 | 99.09 |

FIG. 500

| | | | | | | | | |
|---|---|---|---|---|---|---|---|---|
| 7215 | 5583622 | A | 5482102 | 59769 | 569 | 32639 | 8544 | 98.18 |
| 7216 | 5477333 | C | 6889 | 24402 | 5437632 | 3771 | 4644 | 99.23 |
| 7217 | 5412647 | T | 14891 | 5318172 | 1232 | 18257 | 95 | 98.99 |
| 7218 | 5449024 | C | 162903 | 9887 | 5265027 | 6840 | 4367 | 98.62 |
| 7219 | 5409178 | A | 5398036 | 1730 | 1063 | 3737 | 4570 | 99.79 |
| 7220 | 5514507 | A | 5475500 | 13150 | 552 | 13568 | 11737 | 99.29 |
| 7221 | 5412931 | C | 92316 | 24235 | 5269565 | 9105 | 17310 | 97.36 |
| 7222 | 5141962 | A | 4990185 | 138576 | 963 | 12044 | 192 | 97.05 |
| 7223 | 5171234 | T | 1998 | 5145019 | 1340 | 4868 | 17981 | 99.49 |
| 7224 | 4906213 | T | 2759 | 4848854 | 1021 | 53235 | 316 | 98.83 |
| 7225 | 4948313 | G | 11170 | 72581 | 576 | 4861329 | 2657 | 98.24 |
| 7226 | 4935310 | T | 23678 | 4891048 | 3844 | 14943 | 5797 | 99.02 |
| 7227 | 4844204 | A | 4717525 | 63999 | 383 | 62182 | 103 | 97.38 |
| 7228 | 4790311 | C | 1470 | 7355 | 4764646 | 753 | 16085 | 99.46 |
| 7229 | 4521352 | C | 1873 | 4209 | 4514200 | 746 | 319 | 99.84 |
| 7230 | 4534835 | G | 3977 | 2054 | 1017 | 4526713 | 1074 | 99.82 |
| 7231 | 4555661 | C | 1134 | 2428 | 4550097 | 1344 | 4658 | 99.79 |
| 7232 | 4475732 | C | 3084 | 3191 | 4468360 | 939 | 118 | 99.84 |
| 7233 | 4475023 | G | 3640 | 1169 | 574 | 4467995 | 1245 | 99.84 |
| 7234 | 4442065 | T | 1930 | 4433462 | 2713 | 3851 | 109 | 99.81 |
| 7236 | 4452108 | G | 1461 | 2446 | 802 | 4446351 | 1018 | 99.87 |
| 7237 | 4451323 | G | 3834 | 1736 | 641 | 4448933 | 179 | 99.86 |
| 7238 | 4427720 | C | 2902 | 7571 | 4414767 | 2111 | 369 | 99.71 |
| 7239 | 4410533 | T | 908 | 4405407 | 1061 | 1763 | 1414 | 99.88 |
| 7241 | 4353286 | G | 2331 | 3176 | 616 | 4346790 | 373 | 99.85 |
| 7242 | 4367306 | A | 4351819 | 4409 | 1560 | 6483 | 735 | 99.65 |
| 7243 | 4355979 | C | 2346 | 3704 | 4349247 | 1331 | 351 | 99.82 |
| 7244 | 4351447 | T | 1333 | 4346187 | 927 | 1908 | 1092 | 99.88 |
| 7245 | 4320003 | C | 2404 | 2839 | 4312014 | 616 | 2028 | 99.82 |
| 7246 | 4310519 | A | 4203287 | 1623 | 2837 | 3269 | 303 | 99.83 |
| 7250 | 4290663 | T | 939 | 4284384 | 479 | 1108 | 3753 | 99.85 |
| 7251 | 4229163 | A | 4222820 | 3543 | 587 | 2293 | 200 | 99.85 |
| 7252 | 4227953 | G | 3072 | 2028 | 768 | 4220787 | 798 | 99.83 |
| 7253 | 4214193 | T | 4109 | 4193558 | 3500 | 5613 | 7413 | 99.51 |
| 7254 | 4105077 | A | 4099872 | 731 | 487 | 2322 | 1663 | 99.87 |
| 7255 | 4121950 | A | 4104173 | 4515 | 486 | 7464 | 3314 | 99.62 |
| 7256 | 4160634 | C | 2966 | 1700 | 4149833 | 1422 | 4891 | 99.74 |
| 7257 | 4117371 | C | 3896 | 1781 | 4105449 | 907 | 5338 | 99.71 |
| 7258 | 4023897 | C | 3123 | 1495 | 4008636 | 746 | 9897 | 99.62 |
| 7259 | 3863437 | T | 1126 | 3838437 | 1756 | 1726 | 402 | 99.87 |
| 7260 | 3865537 | A | 3822357 | 22248 | 1192 | 19462 | 278 | 98.88 |
| 7261 | 3851979 | C | 2602 | 4031 | 3848160 | 663 | 303 | 99.8 |
| 7262 | 3850970 | C | 1463 | 1963 | 3838834 | 589 | 4121 | 99.63 |
| 7263 | 3776644 | T | 1717 | 3735646 | 1154 | 2825 | 12272 | 99.52 |
| 7264 | 3362791 | C | 1599 | 1808 | 3329179 | 766 | 29439 | 99.06 |
| 7265 | 3060318 | A | 3053323 | 1007 | 1527 | 2451 | 10 | 99.84 |
| 7266 | 3053073 | G | 2254 | 1306 | 581 | 3050897 | 120 | 99.86 |
| 7267 | 3042417 | T | 3036 | 3025346 | 3856 | 5604 | 1375 | 99.34 |
| 7268 | 3013374 | C | 1329 | 2421 | 3009263 | 790 | 1571 | 99.8 |
| 7269 | 2985924 | G | 2371 | 1303 | 532 | 2981036 | 680 | 99.84 |
| 7270 | 2956494 | A | 2947305 | 2105 | 3359 | 3721 | 4 | 99.69 |
| 7271 | 2954836 | A | 2950210 | 1288 | 1089 | 2282 | 37 | 99.84 |
| 7274 | 2716372 | G | 1243 | 1533 | 305 | 2712464 | 2837 | 99.79 |
| 7276 | 2705478 | A | 2698029 | 2031 | 1841 | 3516 | 21 | 99.72 |
| 7277 | 2694199 | T | 1143 | 2684875 | 654 | 1132 | 6335 | 99.66 |
| 7282 | 2520291 | T | 4133 | 2488674 | 1599 | 8571 | 13292 | 98.73 |
| 7283 | 2312052 | C | 1109 | 3006 | 2305341 | 472 | 2124 | 99.71 |
| 7284 | 2276273 | A | 2272142 | 931 | 867 | 2290 | 43 | 99.82 |
| 7287 | 2247527 | C | 3630 | 2718 | 2196574 | 764 | 43821 | 97.73 |
| 7288 | 1500620 | T | 604 | 1491236 | 383 | 833 | 7384 | 99.37 |
| 7289 | 1385133 | G | 2956 | 891 | 439 | 1374128 | 6719 | 99.21 |
| 7290 | 1271215 | C | 1383 | 2473 | 1262500 | 414 | 4341 | 99.32 |
| 7292 | 1204827 | G | 1831 | 917 | 232 | 1186573 | 14734 | 98.53 |
| 7293 | 972301 | T | 723 | 964953 | 868 | 1209 | 4318 | 99.24 |
| 7295 | 897681 | G | 666 | 1061 | 354 | 870306 | 25094 | 96.85 |
| 7297 | 410093 | G | 369 | 378 | 121 | 399215 | 10010 | 97.35 |
| 7298 | 211393 | G | 264 | 217 | 74 | 206634 | 4204 | 97.73 |

METHODS OF ANALYZING VIRUS-DERIVED THERAPEUTICS

CROSS-REFERENCE TO RELATED APPLICATION

This application claims priority to U.S. Provisional Application No. 62/199,663, filed Jul. 31, 2015, herein incorporated by reference.

FIELD

The present disclosure is related to library-based deep sequencing methods to analyze batches of virus-derived therapeutics, such as live attenuated poliovirus vaccines.

BACKGROUND

PVS-RIPO is a chimeric poliovirus (PV), consisting of the live attenuated, oral type-1 Sabin vaccine strain carrying a foreign internal ribosome entry site (IRES) from human rhinovirus type 2 (HRV2) (Brown et al., (2014) Cancer 120:3277-86; Goetz et al., (2011) Future Virol. 9:1045-1058; Goetz & Gromeier (2010) Cytokine & Growth Fact Rev; 21:197-203). Poliovirus is the causative agent of Poliomyelitis, a severe neuro-degenerative disease. PVS-RIPO was engineered to be a non-pathogenic therapeutic virus for the treatment of Glioblastoma Multiforme (GBM) and other CD155$^+$ cancers (WO 2014/081937).

The IRES is a critical non-coding sequence element within the 5' untranslated region of picornaviral genomic RNA, as it mediates translation initiation in a 5' end-, 7-methyl-guanosine ('cap')-independent fashion (Dobrikova et al., (2003) PNAS USA 100:15125-15130; Dobrikova et al., (2003) Virology 311:241-253; Dufresne et al., (2002) J Virol 76:8966-8972). The IRES is the principal determinant of the neuro-attenuated phenotype of all three PV Sabin vaccine strains and of PVSRIPO (Campbell et al. (2005) J Virol 79:6281-6290; Dobrikova et al. (2006) J Virol 80:3310-3321; Brown & Gromeier (2015) Curr Opinion Virol 13:81-85). Mechanistically, neuro-attenuation results from formation of neuron-specific (IRES) ribonucleoprotein complexes that preclude ribosome recruitment. In the Sabin vaccine strains, neuronal IRES incompetence rests on single point mutations mapping to a discrete region of stem loop domain 5; this scant base for neuro-attenuation is the likely cause for their notorious propensity to revert to neurovirulence. Back-reversion can occur through random genetic mutation or homologous recombination with wild-type sequences either during vaccine manufacture or, if live virus is used, following patient administration. PVSRIPO features an intact and functionally integrated HRV2 IRES, a naturally occurring enterovirus. In contrast to the Sabin type 1/3 IRESs, whose deficits were selected for in tissue culture, the HRV2 IRES is inherently neuron-incompetent to a far greater extent than the Sabin IRESs. The genetic footprint for neuronal incompetence in the HRV2 IRES spans at least the upper parts of stem loop domain 5 (~40 nt) and domain 6 (~25 nt) (Brown et al., (2014) Cancer 120:3277-86; Dobrikova et al., (2003) PNAS USA 100:15125-15130; Dobrikova et al., (2003) Virology 311:241-253; Dufresne et al., (2002) J Virol 76:8966-8972). Because the consensus HRV2 IRES sequence likely resulted from thousands of years of evolution in humans, it may represent an idealized version of a translation initiation mediator in HRV2 target cells (mitotically active cells in respiratory tract epithelium).

Since polioviruses and PVS-RIPO are single-stranded RNA (ssRNA) viruses, the natural frequency of mutation during viral replication (such as during construct development and manufacturing) is higher than observed with dsDNA viruses and organisms with DNA genomes. Currently, each clinical lot of live or inactivated poliovirus virus must be validated prior to clinical release by in vivo primate neurotoxicity safety testing and in vitro plaque-sequencing methods to verify that the lot does not contain rare genetic reversion mutations that can regenerate a neurotoxic phenotype leading to poliomyelitis. Primate neurotoxicity testing of vaccine lots typically requires several months to complete and in vitro plaque-sequencing methods have relatively poor sensitivity.

Because of their prominent role in the neuro-attenuation of PVs, most of the methods described in the literature for assessing potential polio vaccine neurotoxicity focus on well-defined sites in the IRES (Martin et al., (2011) WHO working group discussion on revision of the WHO recommendation for the production and control of poliomyelitis vaccines (oral): TRS Nos. 904 and 910. Report on Meeting held on 20-22 Jul. 2010, Geneva, Switzerland. Vaccine; 29:6432-6436; Rezapkin et al., (1998) Virology 245:183-187; Chumakov et al., (1994) J Med Virol 42:79-85; Laassri et al., (2006) J Infect Diseases 193:1344-1349). The complete replacement of the polio IRES with the HRV2 IRES in PVSRIPO presents the problem of how to characterize the toxicology profile of the chimeric virus. Since the in vitro methods utilized by polio vaccine manufacturers are not relevant to the HRV2 IRES sequence (i.e., MAPREC), this leaves in vivo test methods and characterization of viral genetic stability as the arbiters of product safety. Primate neurovirulence testing in vivo, including post-administration histology, was performed using cynomolgus macaques following WHO guidelines (Dobrikova et al., (2012) *J Virol* 86:2750-2759). A prior HTB-15 cell xenograft (in Balb/c mice) and plaque sequencing study demonstrated that the PVSRIPO genome was stable and non-pathogenic after serial passaging and viral expansion in vivo. Using Sanger sequencing, only two polymorphic sites were noted in the HTB-15 xenograft study as positions 97 and 1824 (Dobrikova et al., (2008) *Mol Ther* 16:1865-1872; Cello J et al., (2008) *J Med Virol* 80:352-359). Interestingly, neither of these two sites were identified as polymorphic in the Illumina deep sequencing with PVSRIPO, indicating they were the result of de novo base mutations following passaging in HTB-15 cells. Taken together, results of the two prior studies demonstrated the lack of toxicity of PVSRIPO relative to wild-type PV. These two general approaches have been used to establish that PVSRIPO does not exhibit a neuropathic phenotype in primates and, using both direct and plaque-based Sanger sequencing methods, PVSRIPO exhibits a low level of sequence heterogeneity. Other less sensitive methods that make a gross assessment of viral genetic stability and uniformity were also employed such as temperature sensitivity (i.e., RCT40) and general safety testing (e.g., in vivo adventitious agent testing and RT-qPCR). As sequencing technology has progressed, the inherent sensitivity limitation with Sanger sequencing (LoD of ~15-20% variation per base) has been overcome with 'Next Generation Sequencing' (NGS) methods that are capable of <1% theoretical sensitivity to base variants (Cabannes et al., (2014) PDA J Pharm Sci and Tech 68:631-638; Liu et al., (2012) Comparison of next-generation sequencing systems. J Biomed Biotech 2012; 2012:251364; Neverov &Chumakov (2010) PNAS USA 107:20063-20068). Most NGS deep sequencing methods are only limited in sensitivity by their intrinsic mis-incorporation or mis-call error rates which are greater than the sensitivity limits of the underlying base detection technologies.

What is needed are improved methods for detecting mutations in lots of virus-derived therapeutics, such as PVS-RIPO.

SUMMARY

Provided herein are methods of assaying a virus-derived therapeutic for the presence of a viral sequence variant. Exemplary virus-derived therapeutics that can be analyzed using the disclosed methods include, but are not limited to: a virus, a viral template plasmid, or a vaccine, such as one derived from, a polio virus (such as PVS-RIPO), measles virus, hepatitis A virus, hepatitis B virus, hepatitis C virus, adenovirus, herpes virus, mumps virus, influenza virus, rubella virus, HIV, or HTLV.

The disclosed methods include extracting (e.g., isolating) nucleic acid molecules from a viral seed bank, harvest, and/or purified drug product lots (such as a master viral bank or a working cell bank), wherein the viral seed bank, harvest, and/or purified drug product lots (such as a master viral bank or a working cell bank) includes host cells containing the virus-derived therapeutic. Due to the presence of undesired host cell genomic DNA and host cell mitochondrial DNA in the resulting sample, the extracted nucleic acid molecules are incubated (e.g., contacted) with DNase under conditions that substantially digest host cell genomic DNA and host cell mitochondrial DNA, but do not substantially digest the desired viral nucleic acid molecule (such as a viral genomic RNA or DNA, or a viral template plasmid). An examples of such a condition is 30 minutes at 37° C. The resulting enriched viral nucleic acid molecules can be DNA or RNA. If they are RNA, the method includes producing double-stranded (ds) DNA (e.g., dscDNA) from the enriched viral RNA, for example using reverse transcription and generating a second viral nucleic acid strand. Viral ds DNA (e.g., dscDNA) is amplified (e.g., using PCR), and the amplified viral ds DNA quantified. A sequencing library is then generated from at least 500 pg the amplified viral ds DNA. The sequencing library includes 5'-adaptors and 3'-adaptors attached to the viral ds DNA (e.g., the viral ds DNA fragments include 5' adaptors and 3' adaptors ligated thereto). The resulting sequencing library is sequenced using next generation sequencing (for example using parallel single-end or paired-end sequencing) to produce a raw sequence dataset that includes a plurality of sequence reads. The plurality of sequence reads are aligned with a reference sequence for the virus-derived therapeutic (such as a non-mutated sequence) to produce an aligned sequence containing a plurality of aligned sequence reads. From the aligned sequence reads, the sequence of the virus-derived therapeutic can be determined, and the presence of sequence variations (e.g., mutations), if any, identified.

In some examples, after sequencing the virus-derived therapeutic from the MVB, the method further includes introducing the virus-derived therapeutic from the MVB into a host cell, such as a mammalian cell (e.g., Vero cell), for production of the virus-derived therapeutic. The resulting virus-derived therapeutic produced in the second host call can then be sequenced, and its sequence compared to the virus-derived therapeutic obtained and sequenced from the MVB. For example, the method can further include introducing (e.g., transforming) the virus-derived therapeutic into mammalian host cells and growing the mammalian host cells under conditions that allow propagation of the virus-derived therapeutic. Viral nucleic acid molecules from the mammalian host cells are extracted (e.g., isolated). As above, the isolated viral nucleic acid molecules can be DNA or RNA. If they are RNA, the method includes producing ds DNA (e.g., dscDNA) from the isolated viral RNA, for example using reverse transcription and generating a second viral nucleic acid strand. Viral ds DNA (e.g., dscDNA) is amplified (e.g., using PCR), and the amplified viral ds DNA quantified. A sequencing library is then generated from at least 500 pg the amplified viral ds DNA, sequenced, the resulting plurality of sequence reads aligned with a reference sequence, and the sequence of the virus-derived therapeutic determined, and the presence of sequence variations (e.g., mutations), if any, identified, as described above.

The method also allows for at least two different virus-derived therapeutics (such as 2, 3, 4, or 5 different virus-derived therapeutics) to be assayed simultaneously or contemporaneously, for example by using "bar codes" or "tags" that allow one to distinguish between the different virus-derived therapeutics. In some examples, the different virus-derived therapeutics are different viruses. In other examples, the different virus-derived therapeutics are the same virus, but from a different source (such as from different MVBs). In such examples, producing the sequencing library can include producing one or more sequencing libraries for each virus-derived therapeutic, wherein the one or more sequencing libraries comprise 5' adaptors and 3' adaptors, and wherein each of the one or more sequencing libraries includes a unique barcode for identification. The one or more sequencing libraries are pooled and sequenced. The pooled raw sequence dataset can be demultiplexed using the barcodes to produce a demultiplexed raw sequence dataset for each sequencing library. Each of the demultiplexed raw sequence datasets can be aligned with its appropriate reference sequence for the virus-derived therapeutic. In some examples, when aligning each of the demultiplexed raw sequence datasets with the appropriate reference sequence for the virus-derived therapeutic, the mean read length, percentage of aligned reads, coverage, SNPs, or a combination thereof, are determined for the aligned sequence reads. When an unaligned sequence read is produced, the unaligned sequence read can be added to a pool of unaligned sequence reads for identification. From the aligned sequence reads, the sequence of each virus-derived therapeutic analyzed can be determined, and the presence of sequence variations (e.g., mutations), if any, identified.

In some examples, producing the sequencing library from the ds DNA (e.g., dscDNA) includes randomly fragmenting the double-stranded DNA to produce DNA (e.g., cDNA) fragments, ligating 5' adaptors and 3' adaptors to the DNA (e.g., cDNA) fragments to produce adaptor-ligated DNA (e.g., cDNA) fragments. In such methods the adaptor-ligated DNA (e.g., cDNA) fragments are amplified to produce the sequencing library. The sequencing library can be clonally amplified, for example using primers complementary to the 5' adaptors and the 3' adaptors (in some examples the primers are attached to solid surface or particle), thereby producing a clonally amplified sequencing library. The clonally amplified sequencing library is sequenced to produce the raw sequence dataset comprising a plurality of sequence reads. For example, sequencing the clonally amplified sequencing library can be performed using primers complementary to the 5' adaptors and the 3' adaptors.

In some examples, when an aligned sequence read is produced, the mean read length, percentage of aligned reads, coverage, SNPs, or a combination thereof, are determined for the aligned sequence reads.

In some examples, when an unaligned sequence read is produced, the unaligned sequence read is added to a pool of unaligned sequence reads for identification.

In some examples, the method includes reporting consensus homology for the virus-derived therapeutic to the reference sequence for the virus-derived therapeutic, coverage per base per position, heterogeneous bases at greater than a defined percentage of reads (e.g., heterogeneous bases at greater than 0.1% of reads), InDels, or a combination thereof.

In some examples, following analysis of the virus-derived therapeutic, the method further includes administering the sequenced virus-derived therapeutic to a subject, if the determined viral sequence variants are not contraindicated (e.g., if no mutations are detected that would lead of a toxic phenotype).

The foregoing and other objects and features of the disclosure will become more apparent from the following detailed description, which proceeds with reference to the accompanying figures.

BRIEF DESCRIPTION OF THE DRAWINGS

Figure 5F:
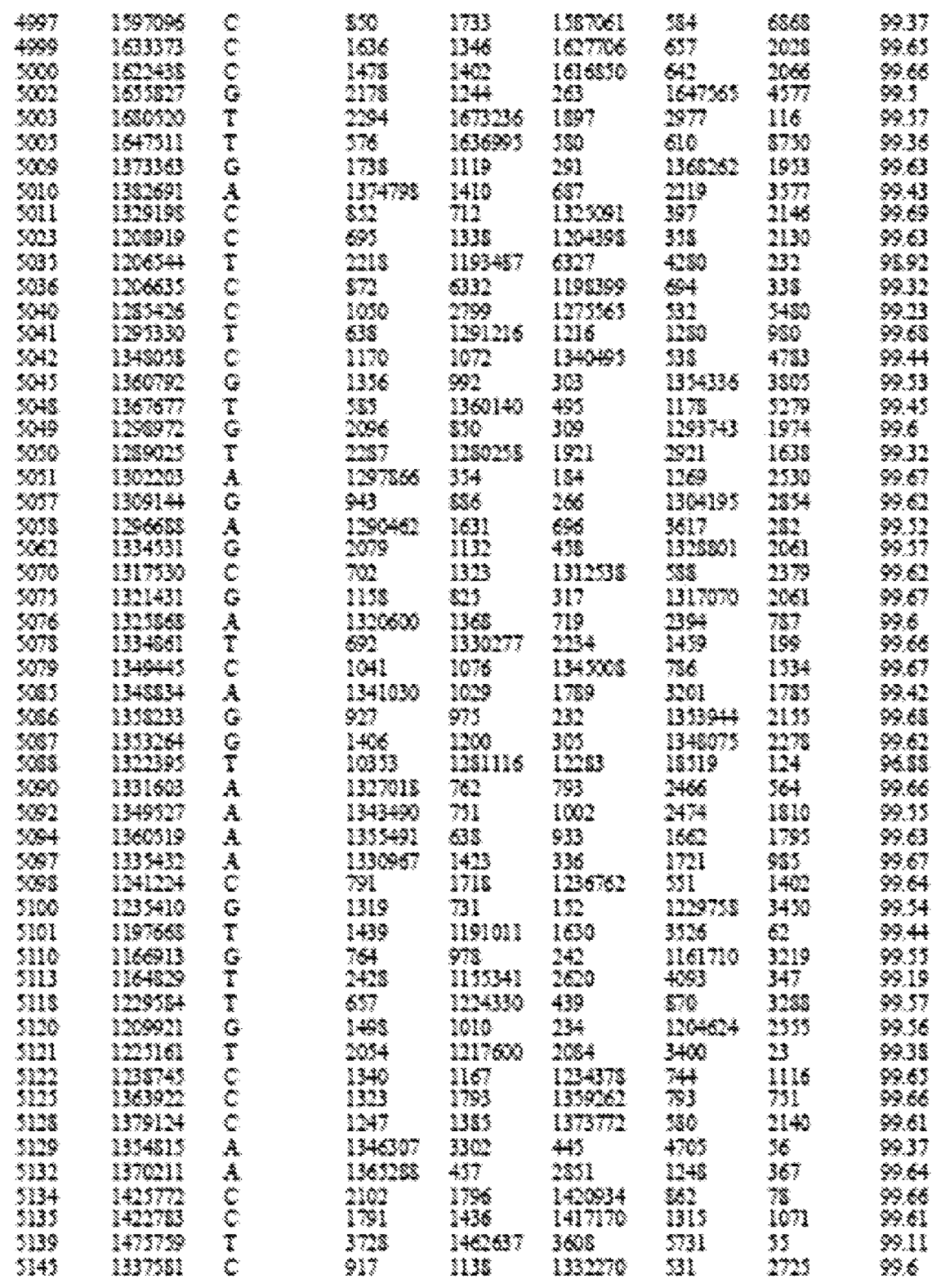
Figure 5N:
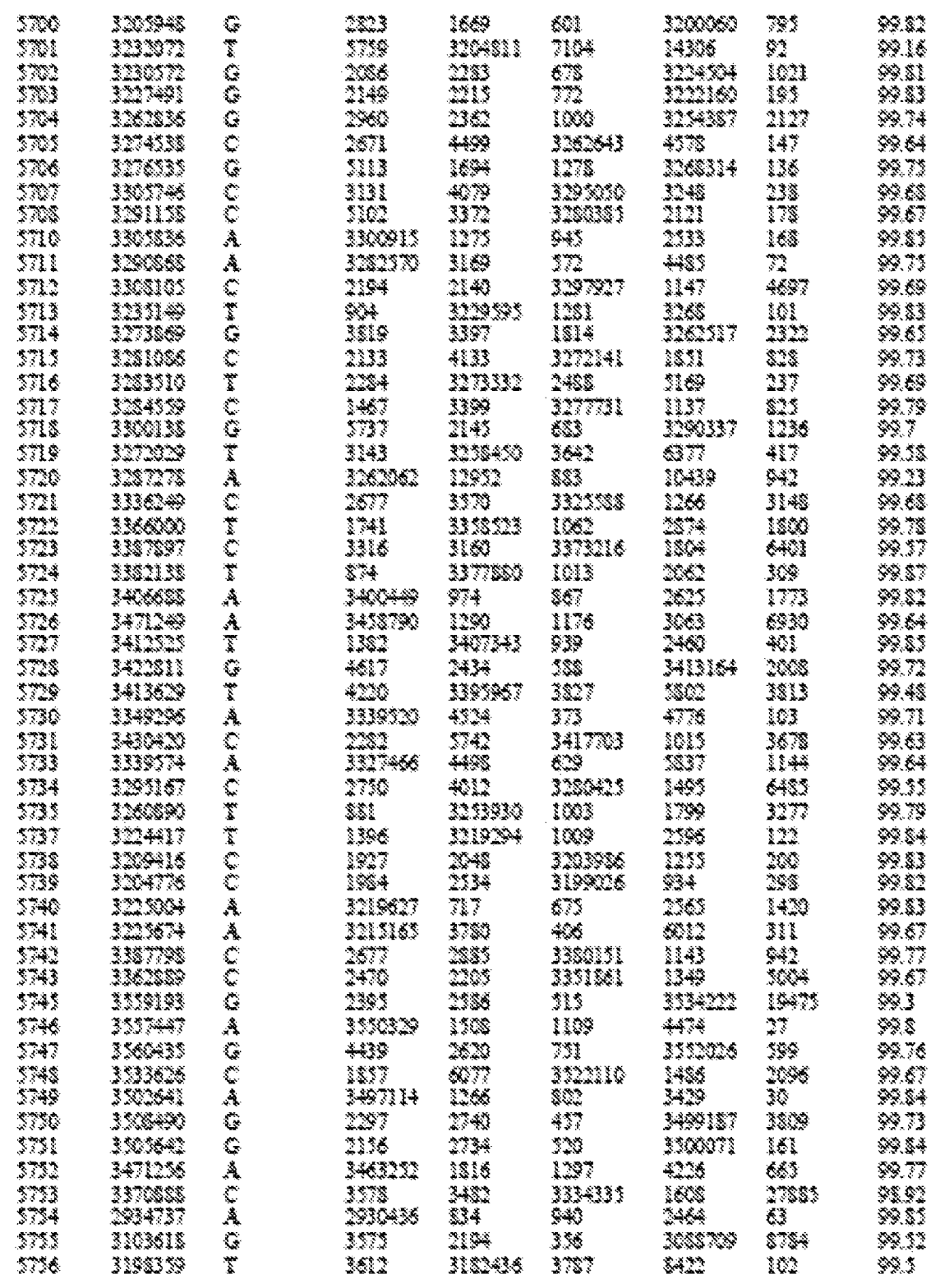

FIGS. 5A-5OO show variations of the Master Viral Seed Bank Lot (SEQ ID NO. 80).

SEQUENCE LISTING

Figure 1:
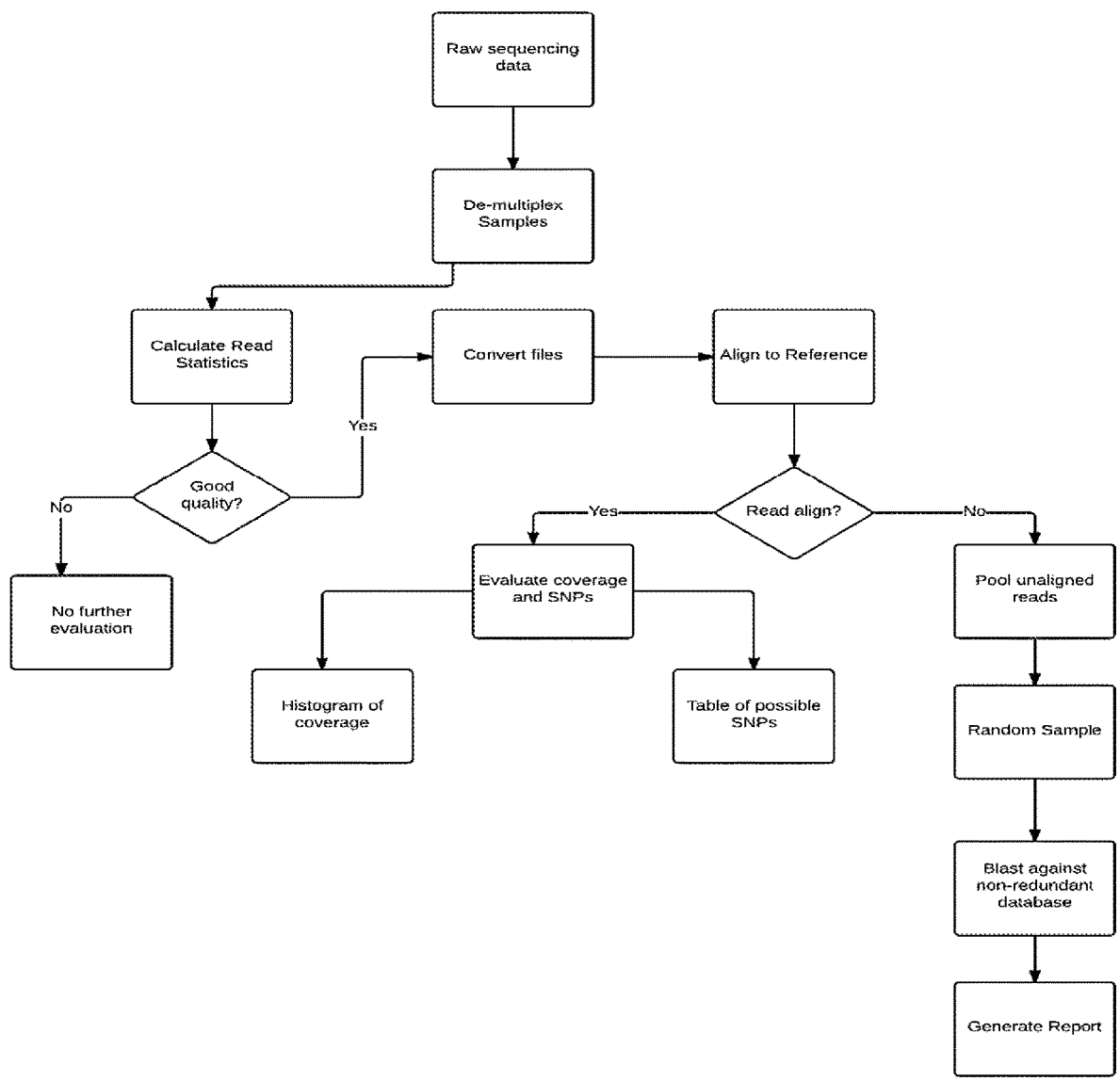
FIG. 1 is a flow diagram of one embodiment of the analysis of deep sequencing data.

The nucleic and amino acid sequences are shown using standard letter abbreviations for nucleotide bases, and three letter code for amino acids, as defined in 37 C.F.R. § 1.822. Only one strand of each nucleic acid sequence is shown, but the complementary strand is understood as included by any reference to the displayed strand. The sequence listing generated on Jul. 29, 2016 (24.3 kb) and submitted herewith is herein incorporated by reference.

SEQ ID NOS: 1-79 are nucleic acid primer sequences used in sequencing assays.

SEQ ID NO. 80 is a PVS-RIPO Master Viral Seed, lot L0403006 viral consensus sequence. The extreme 3' end bases (29) are missing and the 5'-most base (position #1) is incorrect, likely due to primer-based error.

DETAILED DESCRIPTION

Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Jul. 29, 2016) are herein incorporated by reference.

In order to facilitate review of the various embodiments of the disclosure, the following explanations of specific terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Adjuvant: A compound, composition, or substance that when used in combination with an immunogenic agent (such as a virus analyzed using the disclosed methods) augments or otherwise alters or modifies a resultant immune response. In some examples, an adjuvant increases the titer of antibodies induced in a subject by the immunogenic agent. In another example, if the antigenic agent is a multivalent antigenic agent, an adjuvant alters the particular epitopic sequences that are specifically bound by antibodies induced in a subject.

Exemplary adjuvants include, but are not limited to, Freund's Incomplete Adjuvant (IFA), Freund's complete adjuvant, B30-MDP, LA-15-PH, montanide, saponin, aluminum salts such as aluminum hydroxide (Amphogel, Wyeth Laboratories, Madison, N.J.), alum, lipids, keyhole lympet protein, hemocyanin, the MF59 microemulsion, a mycobacterial antigen, vitamin E, non-ionic block polymers, muramyl dipeptides, polyanions, amphipatic substances, ISCOMs (immune stimulating complexes, such as those disclosed in European Patent EP 109942), vegetable oil, Carbopol, aluminium oxide, oil-emulsions (such as Bayol F or Marcol 52), *E. coli* heat-labile toxin (LT), Cholera toxin (CT), and combinations thereof.

In one example, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CG oligodeoxynucleotides, as described in U.S. Pat. Nos. 6,194,388; 6,207,646; 6,214,806; 6,218,371; 6,239,116; 6,339,068; 6,406,705; and 6,429,199, and IL-2 or other immunomodulators.

Administration: To provide or give a subject an agent, such as a virus analyzed using the disclosed methods, by any effective route. Exemplary routes of administration include, but are not limited to, injection (such as subcutaneous, intramuscular, intradermal, intraperitoneal, intratumoral, and intravenous), oral, transdermal, intranasal, and inhalation routes.

Amplifying a nucleic acid molecule: To increase the number of copies of a nucleic acid molecule, such as a viral RNA or DNA. The resulting products are called amplification products or amplicons. An example of in vitro amplification is the polymerase chain reaction (PCR), in which a sample (such as a sample containing viral nucleic acid molecules) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule.

Attenuated pathogen: A pathogen with a decreased or weakened ability to produce disease while retaining the ability to stimulate an immune response like that of the natural pathogen. In another example, a pathogen is attenuated by selecting for avirulent variants under certain growth conditions (for example see Sabin and Boulger. *J. Biol. Stand.* 1:115-8; 1973; Sutter et al., 2003. Poliovirus vaccine—live, p. 651-705. In S. A. Plotkin and W. A. Orenstein (ed.), Vaccines, Fourth ed. W.B. Saunders Company, Philadelphia). An exemplary attenuated pathogen is the Sabin polio virus.

Contact: Placement in direct physical association, including a solid or a liquid form. Contacting can occur in vitro or ex vivo, for example, by adding a reagent to a sample (such as one containing bacterial cells expressing a viral template plasmid), or in vivo by administering to a subject (such as administration of a virus analyzed using the disclosed methods).

Effective amount: The amount of an agent (such as a virus analyzed using the disclosed methods) that is sufficient to effect beneficial or desired results, such as a protective immune response, such as an anti-cancer response.

A therapeutically effective amount may vary depending upon one or more of: the subject and disease condition being treated, the weight and age of the subject, the severity of the disease condition, the manner of administration and the like, which can readily be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition. In one embodiment, an "effective amount" (e.g., of virus analyzed using the disclosed methods) is an amount sufficient to reduce the volume/size of a tumor (such as a glioblastoma), the weight of a tumor, the number of metastases, reduce the volume/size of a metastasis, the weight of a metastasis, or combinations thereof, for example by at least 10%, at least 20%, at least 25%, at least 50%, at least 70%, at least 75%, at least 80%, at least 90%, at least 95%, or at least 99% (as compared to no administration of the therapeutic agent). In one embodiment, an "effective amount" (e.g., of a virus purified using the disclosed methods) is an amount sufficient to increase the immune response in vivo, for example increase production of antibodies specific for the immunogen by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the therapeutic agent).

Host cell (HC): Cell in which a vector or virus can be propagated and its nucleic acids expressed. The cell may be prokaryotic or eukaryotic. The term also includes any progeny of the subject host cell. Thus, host cells can be transgenic, in that they include nucleic acid molecules that have been introduced into the cell, such as a viral template plasmid nucleic acid molecule or a virus. In one example, the host cell is a cell (such as a mammalian cell) in which a virus (such as PVS-RIPO) proliferates. Proliferation of the virus in host cells can be used for production of the viral material (for example, Vero cells used for production of PVS-RIPO), or, in some cases, for protein expression. For example, recombinant baculoviruses can be used for recombinant protein expression in insect cells ("baculovirus expression system"). Viral proliferation can occur in vitro, for example, in cell culture, or in vivo, when viral host cells are a part of an organism.

Immune response: A response of a cell of the immune system, such as a B-cell, T-cell, macrophage, monocyte, or polymorphonucleocyte, to an immunogenic agent (such as a virus analyzed using the disclosed methods) in a subject. An immune response can include any cell of the body involved in a host defense response, such as an epithelial cell that secretes interferon or a cytokine. An immune response includes, but is not limited to, an innate immune response or inflammation.

The response can be specific for a particular antigen (an "antigen-specific response"), such as a polio virus. In a particular example, an immune response is a T cell response, such as a CD4+ response or a CD8+ response. In another example, the response is a B cell response, and results in the production of specific antibodies to the immunogenic agent.

In some examples, such an immune response provides protection for the subject from the immunogenic agent or the source of the immunogenic agent. For example, the response can protect a subject, such as a human or veterinary subject, from infection by a pathogen, or interfere with the progression of an infection by a pathogen. An immune response can be active and involve stimulation of the subject's immune system, or be a response that results from passively acquired immunity.

Increase or Decrease: A statistically significant positive or negative change, respectively, in quantity from a control value (such as a value representing no therapeutic agent). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95%, or no more than 99%.

Isolated: An "isolated" biological component (such as a virus generated and analyzed using the disclosed methods) has been substantially separated, produced apart from, or purified away from other biological components in the cell or media in which the component occurs, such as other nucleic acid molecules and proteins (e.g., host cell chromosomal and extrachromosomal DNA and RNA, and proteins). Isolated viruses analyzed using the disclosed methods in some examples are at least 50% pure, such as at least 75%, at least 80%, at least 90%, at least 95%, at least 98%, at least 99%, at least 99.9999%, or at least 100% pure, for example, as measured by residual host cell (HC) DNA. In some examples, isolated viruses purified using the disclosed methods, or viral template plasmids expanded using the disclosed methods have less purity when measured by residual HC protein (HCP), such as at least 3% pure, at least 4% pure, or at least 5% pure (such as 3-4% pure), for example when an increase in total PFU is desired. Even at ~3% protein purity the level of HCP is within acceptable limits for a therapeutic product. In some examples, isolated viruses analyzed using the disclosed methods, when measured by residual HCP, are at least 50% pure, such as at least 75%, at least 80%, at least 90%, at least 95%, at least 98%, at least 99%, or at least 99.9999% pure.

Master cell bank (MCB): A population of cells, which can be established from a single clone, which is used as a source of materials for manufacturing, such as manufacture of a vaccine (e.g., polio virus). In some examples, the cells of the MCB include a plasmid or vector, such as a viral template plasmid encoding polio virus or polio virus, or include a virus (and thus can be referred to as a master viral bank, MVB). Cells from the MCB are expanded to form a working cell bank (WCB). MCBs and WCBs provide a flexible and practical approach for creating cell stocks. For example, in the first stage, a smaller amount of cells is grown, harvested, pooled and frozen to create the MCB, for example containing ten to twenty vials. Then from this master stock, a single vial is thawed and cultured (one to two passages) until there are enough cells to produce the initial WCB, for example containing ten to twenty vials. MCBs and WCBs can be analyzed using the methods herein, for example to identify as MCB or WCB that does not contain mutations (e.g., which may result in an undesirable virulent virus).

Next generation sequencing: Also referred to as massively parallel or deep sequencing, describe a nucleic acid sequencing technology which performs sequencing of millions of small nucleic acid fragments (e.g., DNA) in parallel. Bioinformatics analyses are used to piece together these fragments by mapping the individual reads to the reference genome. NGS is unselective, and thus allows for analysis of a genome without bias. The methods generally include the use of a DNA polymerase that catalyzes the incorporation of fluorescently labeled dNTPs into a DNA template strand during sequential cycles of DNA synthesis. During each cycle, at the point of incorporation, the nucleotides are identify by fluorophore excitation. Millions of fragments are sequenced in a massively parallel fashion. Examples of such methods include, but are not limited to: those available from Illumina (e.g., sequencing by synthesis (SBS)), Ion Torrent (e.g., from ThermoFisher Scientific), Solexa® sequencing, 454® sequencing, chain termination sequencing, dye termination sequencing, or pyrosequencing. In some examples, single molecule sequencing is used.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of a virus purified using the disclosed methods.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Poliovirus (PV): An enterovirus of the Picornaviridae family that is the causative agent of poliomyelitis (polio). Poliovirus has three serotypes. Exemplary polio sequences are provided in Toyoda et al., *J. Mol. Biol.* 174:561-85, 1984 (herein incorporated by reference).

Non-natural forms of the polio virus include the recombinant oncolytic poliovirus PVS-RIPO and the attenuated Sabin oral polio vaccine (OPV), and can be analyzed using the disclosed methods. PVS-RIPO is a recombinant, live attenuated, nonpathogenic oncolytic virus containing the oral poliovirus Sabin type 1 in which the internal ribosomal entry site (IRES) is replaced with the IRES from human rhinovirus type 2 (HRV2), with potential antineoplastic activity (see for example Brown et al., *Cancer* 120:3277-86, 2014 and Goetz et al., *Cytokine Growth Factor Rev.* 2010 21(2-3):197-20). The OPV includes 57 nucleotide substitutions which distinguish the attenuated Sabin 1 strain from its virulent parent (the Mahoney serotype), two nucleotide substitutions attenuate the Sabin 2 strain, and 10 substitutions are involved in attenuating the Sabin 3 strain.

The primary attenuating factor common to all three Sabin vaccines is a mutation located in the virus's internal ribosome entry site (IRES) which alters stem-loop structures, and reduces the ability of poliovirus to translate its RNA template within the host cell. Exemplary Sabin sequences are provided in GenBank® Accession Nos. E01572.1, E01571.1 and E01570.1, as well as Nomoto et al., *Proc Natl Acad Sci USA.* 79(19): 5793-5797, 1982.

Another form of the PV is the chemically inactivated polio vaccine (IPV) developed by Dr Jonas Salk. This is based on three virulent strains Mahoney (type 1 poliovirus), MEF-1 (type 2 poliovirus), and Saukett (type 3 poliovirus). Such PV strains can be analyzed using the disclosed methods.

Purified: The term purified does not require absolute purity; rather, it is intended as a relative term. Thus, for example, a purified virus preparation is one in which the virus is more enriched than the virus is in a host cell or host cell extract. In one example, a preparation is purified such that the purified virus represents at least 50% of the total nucleic acid content of the preparation. In other examples, a virus is purified to represent at least 60%, at least 75%, at least 80%, at least 85%, at least 90%, at least 95%, at least 98%, or even at least 99%, of all macromolecular species present in a purified preparation prior to admixture with other formulation ingredients, such as a pharmaceutical carrier, excipient, buffer, absorption enhancing agent, stabilizer, preservative, adjuvant or other co-ingredient. In some examples, the purified preparation is be essentially homogeneous, wherein other macromolecular species are not detectable by conventional techniques. Such purified preparations can include materials in covalent association with the active agent, such as materials admixed or conjugated with the active agent, which may be desired to yield a modified derivative or analog of the active agent or produce a combinatorial therapeutic formulation or conjugate.

Recombinant: A recombinant nucleic acid molecule is one that has a sequence that is not naturally occurring or has a sequence that is made by an artificial combination of two otherwise separated segments of sequence. This artificial combination can be accomplished using routine methods, such as by chemical synthesis or by the artificial manipulation of isolated segments of nucleic acids, for example, by genetic engineering techniques such as those described in Sambrook et al. (ed.), Molecular Cloning: A Laboratory Manual, 2nd ed., vol. 1-3, Cold Spring Harbor Laboratory Press, Cold Spring Harbor, N.Y., 1989. The term recombinant includes nucleic acid molecules that have been altered solely by addition, substitution, or deletion of a portion of the nucleic acid molecule. Similarly, a recombinant protein is one encoded by a recombinant nucleic acid molecule. A recombinant virus includes one whose genes have been constructed and/or placed in an unnatural environment, for example for expression, for example using recombinant engineering techniques.

Subject: A vertebrate, such as a mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dog, cat, horse, or cow. In some examples, the subject has a tumor, such as a glioblastoma, that can be treated using the polio virus analyzed using the disclosed methods. In some examples, the subject is a laboratory animal/organism, such as a mouse, rabbit, or rat.

Transform or Transfect: A virus or vector "transforms" or "transduces" a host cell when it transfers nucleic acid into the host cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses (Wolff, J. A., ed, Gene Therapeutics, Birkhauser, Boston, USA 1994). In the case of infection by retroviruses, the infecting retrovirus particles are absorbed by the target cells, resulting in reverse transcription of the retroviral RNA genome and integration of the resulting provirus into the cellular DNA.

Transgene: An exogenous gene supplied by a vector. In one example, a transgene includes a viral template sequence, such as viral DNA template sequence for an RNA virus, such as polio (a natural polio virus or a non-naturally occurring polio virus).

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like. In some examples, treatment with the disclosed PV results in a decrease in the number, volume, and/or weight of a tumor (e.g., a brain tumor) and/or metastases.

Under conditions sufficient for: A phrase that is used to describe any environment that permits a desired activity. In one example the desired activity is transformation of a host cell by a viral template plasmid, or growth of such a transformed host cell. In one example the desired activity is sequencing of target viral nucleic acid molecules, for example using next generation sequencing. In one example the desired activity is treatment of a tumor and/or stimulation of an immune response in vivo, for example using a viruses purified using the disclosed methods.

Vaccine: An immunogenic composition that can be administered to an animal or a human to confer immunity, such as active immunity, to a disease or other pathological condition. Vaccines can be used prophylactically or therapeutically. Thus, vaccines can be used reduce the likelihood of infection or to reduce the severity of symptoms of a disease or condition or limit the progression of the disease or condition. In one example, a vaccine includes one or more viruses analyzed using the disclosed methods (e.g., a natural polio virus or a non-naturally occurring polio virus).

Vector: A nucleic acid molecule as introduced into a host cell, thereby producing a transformed host cell. A vector can include nucleic acid sequences that permit it to replicate in the host cell, such as an origin of replication. A vector can also include one or more therapeutic genes or selectable marker genes and other genetic elements known in the art. A vector can transduce, transform or infect a cell, thereby causing the cell to express nucleic acid molecules or proteins other than those native to the cell. A vector optionally includes materials to aid in achieving entry of the nucleic acid into the cell, such as a viral particle, liposome, protein coating or the like. In one example, a vector is a plasmid, such as a bacterial plasmid.

Overview

There is a long-felt need in the virus-derived therapeutic industry to identify methods that can replace the currently used monkey neurovirulence safety test (MNVT) procedure and the plaque-based sequencing methods (such as mutant analysis by PCR and restriction enzyme cleavage (MAPREC)). For example, the WHO Working Group discussion on revision of the WHO recommendations for production and control of poliomyelitis vaccines (oral) held in Geneva Switzerland in 2010 (see *Vaccine* 29 (2011) 6432-6436) noted that the attenuating effects of particular mutations in animal models can depend on the species, genetic background and route of inoculation, and therefore make extrapolation to humans uncertain. In addition, the MAPREC assay is a very laborious test, the required use of radio isotopes adds to its technical difficulty, and different laboratories have problems with various aspects of the assay. The neurovirulence testing assays currently used to test or validate a virus-derived therapeutic are expensive and time consuming. In addition, it is unclear in the field if the currently used assays have relevance to assessing neurovirulence potential for humans. The WHO Working Group recommended that new technologies for quality control of polio vaccine be developed. The methods described herein provide an improved validation/safety testing method for RNA virus-derived therapeutics, particularly vaccines, and thus provide a solution to a long-felt need in the industry.

The disclosed methods are currently under consideration for US-FDA approval. Once this approval is obtained, commercial success of the method will be achieved.

The accumulation of mutants with high neurovirulence during growth in vaccine recipients and also propagation in cell cultures has led to the requirement for neurovirulence testing, particularly of virus seed stocks. Currently, a monkey neurovirulence safety test (MNVT) procedure is performed. Briefly, in the MNVT procedure, a sample from a lot of vaccine product, for example, is injected into the lumbar region of the central nervous system of *Macaca* or *Cercopithecus* monkeys, an intraspinal inoculation. In general, 11-18 monkeys are used for evaluation of the vaccine preparation and also 11-18 control monkeys. The monkeys are observed for clinical signs of virus infection, e.g., poliomyelitis, over 17-24 days. All monkeys that survive the observation period are euthanized and processed for analysis including histopathological evaluation of virus-specific lesions in brain and spinal cord tissue. There is little evidence to support the relevance of the MNVT test to assessing neurovirulence potential for humans, particularly in the case of polioviruses (Rubin, "Toward replacement of the monkey neurovirulence test vaccine safety testing", Procedia in Vaccinology, 5, pp. 261-265 (2011)). In addition, the test is time-consuming, expensive, and the results can be unreliable, for example, according to Rubin, mumps vaccines that passed the MNVY test were causally associated with meningitis in vaccinated individuals.

In addition to the MNVT procedure, plaque-based sequencing methods are also used to evaluate lots of RNA virus-derived therapeutics. The mutant analysis by PCR and restriction enzyme cleavage (MAPREC) method is used to determine the proportion of a single base mutation at a given point within a viral RNA. If the calculated value of the mutation at this site is greater than acceptable values, the monovalent bulk vaccine (e.g., oral polio vaccine) will fail the MAPREC test. In type 3 poliovirus vaccine, the mutation of U to C at base position 472 in the viral RNA 5' NCR is directly related to the neurovirulence of the virus in monkeys. In Type 1 and 2 oral polio vaccine there are mutations within the 5' NCR which revert rapidly when passaged in the human gut or in cell culture. These include Type 1 base positions 480 G→A and 525 U→C and Type 2 base position 481 A→G. These mutations are believed to lead to increased neurovirulence when present in high proportions in the viral population or through interaction with other mutations within the viral genome. Interestingly, no correlation with virulence in monkeys has been established when these mutations are present at levels typically found in vaccine batches. (World Health Organization, "Standard Operating Procedure: Mutant Analysis by PCR and Restriction Enzyme Cleavage (MAPREC) for Oral Poliovirus (Sabin) Vaccine Types 1, 2, or 3", Version 5 (2012)). Therefore, the MAPREC test for Type 1 and 2 oral polio vaccines has been developed to measure the consistency of vaccine production. The MAPREC test is, however, limited to determining only a small number of genomic loci known to contain attenuation markers. (Rubin, "Toward replacement of the monkey neurovirulence test vaccine safety testing", Procedia in Vaccinology, 5, pp. 261-265 (2011)).

Seven lots of the single-stranded RNA virus PVSRIPO were analyzed using Illumina deep sequencing protocols. The lots included the original Master Viral Banks (MVB, lot # L0403006) manufactured in 2004 and viral product lots derived from the 2004 MVB, including a non-clinical toxicology lot, the phase 1 clinical lot from 2009, clinical drug substance and drug product lots manufactured in 2014, and a reference standard lot. Illumina deep sequencing was also performed on a second MVB lot (MVB, lot # L1311002) manufactured using plasmid in vitro transcription and transfection in 2013. All of the lots examined exhibited surprisingly limited sequence micro-heterogeneity across the chimeric viral genome with average read depths in excess of $2 \times 10^5$ per base. The sequence variation observed, with the exception of the extreme 5' end (a known hyper-variable region in polio), was shown to consist of <1% heterogeneous base calls relative to the canonical reference sequence; with only 5 polymorphic positions observed repeatedly in more than one lot of PVSRIPO. These five heterogeneous positions and their associated base variant patterns were observed to be consistent across all of the lots tested. This indicates that the limited variation present in the clinical lots of PVSRIPO is derived from the variation originally present in the parental MVB lot or may represent preferred modes of polymerase mis-incorporation during viral replication or cDNA sequencing. The plasmid DNA used to generate the MVB by in vitro transcription (IVT) may be a third source of the base variation pattern observed in the seven PVSRIPO lots. The deep sequencing of PVSRIPO validates prior analytical and neurotoxicity data which indicate PVSRIPO is a surprisingly stable single-stranded RNA virus. The second MVB lot of PVSRIPO (Lot L1311002) exhibits a low level of sequence micro-heterogeneity and the sequence variation pattern observed was consistent with the earlier 2004 MVB lot and its subsequent clinical lots.

The present methods differ from other methods of analyzing virus-derived therapeutics (e.g., viral seed banks, harvests, and purified drug product lots, such as master viral seed bank lots and working cell bank lots) to determine the presence and frequency of substantially all potential genetic mutations across the complete viral genome. For example, Neverov and Chumakov (*PNAS* 107:20063-8, 2010) provide a sequencing method to analyze an oral polio virus vaccine. The Chumakov laboratory developed the MAPREC method currently used to analyze polio vaccine lots. As noted in the introduction of this paper, the authors acknowledge the limitation of the MAPREC method, such as its limited ability to monitor only a few genomic loci known to contain markers of attenuation and missing mutations at other sites. As determinations of attenuation may be unknown, this limits the utility of the MAPREC method. The Neverov and Chumakov reference proposes massively parallel sequencing methods to sequence live viral vaccines. However, the reference fails to provide detail regarding the viral preparation steps, likely because large volume high-titer cultures (i.e., clarified supernatants) or 'purified' vaccine lots were used (viral RNA was obtained from HeLa or Vero cell supernatant). That is, the authors were not limited by sample volumes when generating viral RNA extracts. In contrast, the present inventors found that a DNAase step was needed to remove excess host cell nucleic acids (such as dsDNA) from the master viral bank or working cell bank samples, in order to increase the ratio of viral nucleic acids to host cell nucleic acids (which provides a more robust sequencing result). The PureLink Viral RNA kit used by Neverov and Chumakov does not include DNase.

Hall et al. (*J. Virol. Meth.* 195:194-204, 2014) disclose a method that uses centrifugation, filtration and nuclease treatment to enrich enteroviruses sequences. Hall et al. teach using the DNase prior to extracting nucleic acid molecules, which is more procedurally efficient since the DNase is removed during extraction. In contrast, the inventors found that by extracting nucleic acids prior to contacting them with DNase, the efficiency of the DNase reaction is unexpectedly and significantly improved when used after extraction and inactivated separately. In addition, the use of DNase prior to extraction as taught by Hall et al. reduces the overall efficiency of the extraction process and can negatively affect viral RNA yields since it will bind un-encapsulated 'free' RNA. For example, the inventors observed about a 2-fold increase in the amount of viral RNA obtained using DNase following RNA extraction. Hall et al. and Djikeng papers are solely rely on random hexamers for RT-priming and/or amplification priming, which leads greater loss of coverage depths at both ends of any virus sequence. The disclosed methods avoid the sole use of random hexamers (vs. in combination with oligo(dT) and/or conserved sequence 'full-length' primers) as it may lead to positional coverage bias within the genome and at the ends and it could mask some SNPs. Similar methods are provided by Djikeng et al. (BMC Genomics 9:5, 2008).

Table 1 provides a summary comparing the disclosed methods to other methods for analyzing virus-derived therapeutics.

methods and can be performed within 1-2 weeks, unlike primate neurotoxicity testing which typically requires several months to complete. In addition, the results reported herein cannot be obtained using traditional Sanger sequencing methods since the Sanger methods are limited in specificity to the primer sequences used, and in detection sensitivity to approximately 10-20% of the total signal. In other words, only a genetic variant that consisted of greater than approximately 10-20% of the entire sample could be reliably detected using Sanger sequencing methods, and generally only those high-frequency variants that did not occur at a sequencing or PCR priming site.

The sequencing methods disclosed herein do not require sequencing or PCR primers specific for the target viral nucleic acid that can bias sequencing results. Sequencing protocols utilizing the pre-amplification PCR primers and the sequencing primers that target the ligated 5'- and 3'-adaptor sequences, and do not directly target viral cDNA sequences, can be used (e.g., such as the Illumina® protocols). The methods described herein reduce primer-mediated

TABLE 1

Comparison of Disclosed Method to Other Methods

| Disclosed Method | Neverov and Chumakov | Hall et al. | Djikeng et al. |
| --- | --- | --- | --- |
| Extract nucleic acid molecules from a cells of a master viral bank or a working cell bank | Isolate RNA from HeLa or Vero cell supernatant using PurLink viral RNA/DNA mini kit | Cell culture supernatant is centrifuged, filtered, and then treated with DNase | Cell culture supernatant is centrifuged, filtered, and then treated with DNase (100 U) or RNase (10 ug/ml) at 37° C. for 1 hour |
| Contact extracted nucleic acid molecules with DNase (e.g., 30 min at 37° C.) | No DNAse | Extract RNA using PureLink Viral kit | Isolate RNA and/or DNA |
| If the enriched viral nucleic acid molecules are RNA, produce double-stranded cDNA | Reverse transcribe RNA and treat with RNAse H | | Reverse transcribe RNA into DNA |
| amplifying and quantifying viral double-stranded DNA | PCR amplify cDNA | Real-time quantitative PCR followed by reverse transcription using random hexamers and RNase H digestion | |
| Produce sequencing library from at least 500 pg of the viral double-stranded DNA (enzymatic method) | Illumina cDNA mechanical shearing method | | Generate sequencing library using random primers |
| Sequence sequencing library using NGS | Sequencing using massively parallel sequencing | Metagenomic sequencing using 1 ug DNA | Sequence library using ABI 3730 x1 sequencing system |

Methods of Analyzing a Virus-Derived Therapeutic

Described herein are methods to rapidly and directly screen lots (e.g., viral seed banks, harvests, and purified drug product lots, such as master viral seed bank lots and working cell bank lots) of virus-derived therapeutics (e.g., polio and other viral vaccine products) in vitro using next generation sequencing methods (e.g., massively parallel sequencing) to determine the presence and frequency of substantially all potential genetic mutations across the complete viral genome. This method has routinely demonstrated several orders of magnitude (typically ≥4 log) more sensitivity to sequence variants than current plaque-based sequencing bias (e.g., hiding SNPs and InDels that occur at PCR priming sites) prior to, or during, sequencing while maintaining the advantages of overlapping reads via the use of quasi-random cDNA fragmentation. In addition, the sequencing methods described herein optionally employ a minimal amount of PCR pre-amplification of the target virus-derived therapeutic, with the level of pre-amplification readily compensated for during post-sequencing analysis where the use of higher PCR cycles concomitantly decreases the signal-to-noise ratio but an increase in the sensitivity threshold can be used to minimize reporting of false positive results. The methods can detect sequence variation at any arbitrary level (e.g., <0.0001% or PPM has been achieved)

and is only limited by the depth of coverage and/or the number of target copies present in the sample.

In addition to testing purified virus, a variation of this method utilizing DNase was developed for unpurified samples (e.g., crude cell culture lysates from a MVB containing large amounts of host cell nucleic acids, with only a minimal impact on assay sensitivity and sequence read depths. The background mass and copy number of host cell RNA and DNA in a given sample volume may be several logs greater than the amount of viral RNA present, making traditional Sanger sequencing methods impossible or potentially biased due to the need for extensive pre-amplification (PCR cycling) prior to Sanger sequencing.

Provided herein are methods of assaying a virus-derived therapeutic for the presence of a viral sequence variant. These sequencing and screening methods can be used to analyze lots of virus-derived therapeutic (such as those present in a MVB or WCB) for the presence of undesirable viral sequence variations (such as one or more nucleotide deletions, insertions, or substitutions). Exemplary virus-derived therapeutics that can be analyzed using the disclosed methods include, but are not limited to: a virus, a viral template plasmid, or a vaccine. Exemplary virus-derived therapeutics that can be sequenced using the methods disclosed herein include those based on RNA viruses that exhibit high mutation rates, such as polio virus, measles virus, hepatitis A virus, hepatitis C virus, mumps virus, influenza virus, rubella virus, HIV, HTLV, and the like. Exemplary vaccines that can be analyzed with the disclosed methods include MMR (measles, mumps, rubella) and MMRV (measles, mumps, rubella, chicken pox). In one example, the RNA virus-derived therapeutic is a vaccine, specifically PVS-RIPO, the live attenuated, oral (SABIN) serotype 1 poliovirus vaccine containing a heterologous internal ribosomal entry site stemming from human rhinovirus type 2. The disclosed methods also allow for analysis of more than one virus-derived therapeutic at a time, for example by using multiplexing.

The disclosed methods include extracting (e.g., isolating) nucleic acid molecules from viral seed banks, harvests, and purified drug product lots (e.g., a master viral bank (MVB) or a working cell bank (WCB)). Isolating nucleic acid molecules including viral genomic nucleic acids (e.g., RNA) from the viral seed banks, harvests, and purified drug product lot can be performed using methods known in the art such as the commercially available QIAamp® viral RNA mini kit from Qiagen. Total RNA can be quantitated spectrophotometrically or by quantitative RT-PCR.

Viral seed banks (e.g., MVB and WCB) include host cells (such as *E. coli* or other bacterial cells and their undesired host cell genomic DNA and host cell mitochondrial DNA) containing the virus-derived therapeutic, and harvests (e.g., from Vero cells), may include undesired host cell genomic DNA and host cell mitochondrial DNA. Thus, in some examples, the virus-derived therapeutic to be analyzed is present in an unpurified sample, such as those from viral seed banks and harvests (e.g., a MVB or a WCB). In one aspect, a sample of a virus-derived therapeutic is an unpurified sample, such as one containing at least 85%, at least 90% or at least 95% of the total nucleic acid from sources other than the virus-derived therapeutic, such as host cell genomic and mitochondrial DNA. In one example, the method includes treating isolated viral genomic RNA from the unpurified sample with DNase and then inactivating the DNase prior to producing double-stranded cDNA from the isolated viral genomic RNA. The DNase treatment removes free DNA and allows for improved cDNA synthesis of the target viral RNA. In one example, the method includes treating isolated viral genomic DNA from the unpurified sample with DNase and then inactivating the DNase and recovering the viral genomic DNA. Such DNase treatment removes host cell DNA but allows for recover of viral DNA (e.g., if in a capsid). In some examples, if the virus-derived therapeutic is a DNA virus, an appropriate structure-specific nuclease can be used instead of DNase following extraction. In some examples, if the virus-derived therapeutic is a DNA virus, DNAse treatment is performed prior to nucleic acid extraction. In some examples, DNase treatment is performed before and after extraction of nucleic acids.

In other examples, the virus-derived therapeutic to be analyzed is present in a purified sample, such as those from purified drug product lots. Purified samples include, for example, clinical lots of vaccine. Purified samples typically contain greater than 70%, typically greater than 95% of their total nucleic acids from the RNA virus-derived therapeutic. In some examples, DNase treatment is not required for such purified samples. In one example, the sequence of a virus-derived therapeutic present in a purified sample is compared to the sequence of the virus-derived therapeutic previously obtained from an unpurified sample (e.g., at an earlier stage of processing). Thus, the disclosed methods can include analyzing the virus-derived therapeutic in the unpurified sample using the methods provided herein, and then subsequently analyzing the virus-derived therapeutic in the purified sample using the methods provided herein. This allows one to determine if the sequence of the virus-derived therapeutic changed during manufacturing of the virus-derived therapeutic.

Due to the presence of undesired host cell genomic DNA and host cell mitochondrial DNA in the resulting extracted sample from an unpurified sample, the extracted (e.g., isolated) nucleic acid molecules are incubated (e.g., contacted) with DNase under conditions that substantially digest host cell genomic DNA and host cell mitochondrial DNA, but do not substantially digest the desired viral nucleic acid molecule (such as a viral genomic RNA or DNA, or a viral template plasmid). An example of such as condition is at least 10 minutes (such as at least 15, at least 20, or at least 30 minutes) at 37° C. In another example, the condition is at least 10 minutes (such as at least 15 minutes, at least 20 minutes, at least 30 minutes, at least 60 minutes, at least 120 minutes, or at least 180 minutes) at 2° C. to 40° C. (with lower temperatures generally requiring longer incubation times). If a thermostable DNase is used, the sample can be incubated above 40° C. In some examples, the extracted or isolated nucleic acid molecules are incubated with the DNAse for less than 1 hour, such as less than 45 minutes, or no more than 30 minutes, such as 10-30 minutes. In some examples, the extracted or isolated nucleic acid molecules are incubated with low amounts of DNAse, such as less than 10 U at 2 U/uL, less than 5 U at 2 U/uL, for example 1 U to 10 U at 2 U/uL or 1 U to 5 U at 2 U/uL, such as 4 U at 2 U/uL. It was surprisingly found that the DNase did not significantly degrade viral RNA, even though DNase has some RNase activity. The presence of the DNase increase the signal: noise ratio of the desired virus-derived therapeutic nucleic acids to the undesired host cell nucleic acids. In some examples, the purity of the desired virus-derived therapeutic nucleic acids following DNase treatment is at least 75%, at least 80%, at least 85%, at least 90%, or at least 95%. In some examples, the amount of virus-derived therapeutic nucleic acids degraded during DNase treatment is less than 10%, less than 5%, less than 4%, less than 3%, less than 2%, less than 1%, or less that 0.5%. In some examples, the amount of host cell nucleic acids degraded during DNase treatment is at least 50%, at least 60%, at least 70%, at least 75%, at least 80%, at least 85%, at least 90%, or at least 95%.

The resulting enriched viral nucleic acid molecules can be DNA or RNA. If they are RNA, the method includes producing double-stranded (ds) DNA (e.g., dscDNA) from the enriched viral RNA, for example using reverse transcription and generating a second viral nucleic acid strand. For example, the ThermoScript™ system from Life technologies, can be used with an oligo(dT)$_x$ primer such as an oligo(dT)$_{20}$ primer and dNTPs to produce cDNA. In another example, the SMARTScribe system with SMARTer Oligo IIA and Oligo(dT)$_x$ primers from Clonetech, are used to produce cDNA from low viral copy samples. RNAseH can be added to remove RNA/DNA hybrids. cDNA can then be quantitated, for example spectrophotometrically. Second strand DNA synthesis can be performed using methods known in the art such as the NEBNext® Second Strand Synthesis Kit from New England Biolabs. The QIAquick® PCR purification kit can be used to purify the ds cDNA which can then be quantitated, for example spectrophotometrically. Viral ds DNA (e.g., dscDNA) (whether generated or extracted directly from the host cells) can be amplified (e.g., using PCR), and the amplified viral ds DNA quantified, for example spectrophotometrically.

A sequencing library is then generated from at least 500 pg ng (such as at least 1 ng, at least 2 ng, at least 5 ng, or at least 10 ng) of the amplified viral ds DNA (e.g., ds cDNA), such as 500 pg to 1 ng, 500 pg to 5 ng, 500 pg to 10 ng, or 1 ng to 5 ng of the amplified viral ds DNA. The sequencing library includes 5'-adaptors and 3'-adaptors attached to the viral ds DNA (e.g., the viral ds DNA fragments have a 5'-adaptor and a 3' adaptor ligated thereto). The sequencing library can be produced by randomly fragmenting the ds DNA (e.g., ds cDNA) to produce DNA (e.g., cDNA) fragments, ligating 5' adaptors and 3' adaptors to the DNA (e.g., cDNA) fragments, and amplifying (e.g., clonally amplifying) he adaptor-ligated DNA (e.g., cDNA) fragments. In such methods the adaptor-ligated DNA (e.g., cDNA) fragments are amplified to produce the sequencing library. In one example, the amplifying is performed using oligonucleotides complementary to the 5'-adaptors and the 3'-adaptors (wherein the primer can be attached to a solid surface or particle, e.g., are surface-bound or particle-bound) to produce a clonally amplified sequencing library. The DNA (e.g., cDNA) fragments of the sequencing library typically have a size of 200 to 400 base pairs. Fragmenting the ds DNA (e.g., ds cDNA) and ligating 5'- and 3-adaptors can be performed using Illumina® Nextera® "tagmentation". In the "tagmentation" process, fragmenting (e.g., enzymatically cutting) the ds DNA (e.g., ds cDNA) and tagging the fragments with adaptor sequences is performed in a single step. The fragmenting and ligating can also be done as discrete steps. After ligating the adaptors to the ds DNA (e.g., ds cDNA), the DNA ligase can be inactivated. A sequencing library is thus randomly fragmented double stranded DNA molecules which are ligated at their 3' and 5' end to adapter sequences. Use of the tagmentation process provides better control of fragment lengths with concomitantly improved sample yields. In turn this allows for better recoveries and greater potential read depths and sample coverage. The tagmentation method is also more reproducible than kinetic fragmentation methods.

The specific design of the 5' and 3' adapters depends on the NGS platform to be used. The adapter sequences provide a known sequence composition allowing, for example, subsequent library amplification or sequencing primer annealing. As adaptors, double-stranded or partially double-stranded nucleic acids of known sequence can be used. The adapters may have blunt ends, cohesive ends with 3' or 5' overhangs, may be provided by Y shaped adapters or by stem-loop shaped adapters. Y shaped adapters are described e.g. in U.S. Pat. No. 7,741,463 and stem-loop shaped adapters are described e.g. in US2009/0298075, herein incorporated by reference regarding the specific design of the adapters. Exemplary adaptors have a length of at least 7, at least 10, or at least 15 bases, such as 10 to 100 bases, 15 to 75 bases, or 20 to 60 bases. Either the same or different adaptors can be used at the 3'- and 5'-end of the fragments. Using the same type of adaptor for both ends, such as a Y shaped or a stem-looped shaped adapter, has the advantage that no fragments are lost during library preparation due to adapter mispairing, which is an advantage when working with low amounts of DNA.

Once the tagged fragments have been produced, an amplification step is performed. Using a minimal amount of PCR pre-amplification of the target virus can improve the signal-to-noise ratio and increase the sensitivity threshold to minimize reporting of false positive results. Changes in amplification can be readily compensated for during post-sequencing analysis. In one example, 10 to 15 cycles, such as 12 cycles, of PCR amplification are employed. Optionally, during amplification, barcodes are added to the DNA (e.g., cDNA) fragments. Barcodes are specific DNA sequences that can be used to identify the sample of origin. Barcodes can be used to demultiplex or differentiate sequence reads from different samples. The use of barcodes also allows for in-silico linkage analysis, direct intra-assay comparison of two or more lots, and the like. The use of unique barcodes can also be used to rapidly identify laboratory cross-contamination from prior or concomitant studies.

Once the sequencing library is produced and optionally barcoded, the sequencing library is clonally amplified, for example using surface-bound or particle-bound oligonucleotides complementary to the 5' adaptors and the 3' adaptors. In the Illumina® protocol, clonal amplification uses bridge amplification of oligonucleotides complementary to the 5'-adaptors and the 3'-adaptors that are bound (e.g., attached) to the surface of a flow cell. Template clusters are thus formed directly on a flow cell. In the Ion Torrent PGM™ method, library fragments are clonally amplified onto microbeads.

The resulting clonally amplified sequencing library is then sequenced using NGS technology (for example using parallel single-end or paired-end sequencing) to produce a raw sequence dataset that includes a plurality of sequence reads. That is, the clonally amplified library fragments, or fragments from multiple libraries, are sequenced by synthesis in parallel. In one aspect, parallel paired-end sequencing is used. In paired-end sequencing, both ends of the same fragment are sequenced. In the Illumina® protocol, after completion of the first read, the clonal clusters are modified in situ to regenerate the templates for the paired read. Paired reads generate greater genomic information than single reads (e.g., 2×75 bp base paired reads compared to 150 bp single reads). In one example, the parallel paired-end sequencing is 2×75 to 2×200 bp sequencing. In one example, sequencing the clonally amplified sequencing library is performed using primers complementary to the 5'-adaptors and the 3'-adaptors.

The resulting plurality of sequence reads are aligned with a reference sequence for the virus-derived therapeutic (such as a non-mutated sequence of the same virus) to produce an aligned sequence containing a plurality of aligned sequence reads. In some examples, at least 80% of the sequence reads align with the reference sequence for the virus-derived therapeutic, such as at least 85, at least 90%, or at least 95%. From the aligned sequence reads, the sequence of the virus-derived therapeutic can be determined, and the presence of sequence variations (e.g., mutations), if any, identified (e.g., reported). In some examples, the mean read length of the plurality of sequence reads is about 75 to about 150 base pairs.

In some examples, the reporting includes coverage per base per position. The term coverage refers to the number of times a particular nucleotide is read during the sequencing process. Coverage is thus the average number of reads representing a particular nucleotide in the aligned sequence, in either direction. In one example, the coverage per base is at least 4×. The method can thus include determining that the aligned sequence is acceptable for screening the lot of the virus-derived therapeutic when the coverage of each base in the aligned sequence is 4× or greater, such as at least 4×, at least 5×, at least 6×, at least 7×, at least 8×, at least 9× or at least 10×. Average coverage is based on the total number of base reads divided by the size of the reference (or observed) target genome. Average coverage, however, can thus be misleading because when sequencing a viral genome using a single RT primer, the 3' end of the cDNA will typically have much greater depth of coverage than the 5' end. In some examples, if it is determined that the coverage of each base in the aligned sequence is less than 4×, Sanger sequencing can be performed on the virus-derived therapeutic to provide coverage of 4× or greater across the entire aligned sequence. For example, at the 5' end of the PVS-RIPO sequence, the strong RNA structure in the viral IRES domain can lead to RT exhaustion, resulting in reduced coverage. For example, if the portion of the genome lacking appropriate coverage is near the 5' end of the genome, linear PCR amplification of the PVS-RIPO cDNA can be performed using only reverse primers to yield a minimum of 4× sequence coverage of the 5' end. A high-cycle number of linear (non-exponential) PCR may be employed to prevent over-writing the native PVS-RIPO viral sequence with primer sequence, especially at the under-represented (low copy dscDNA) and hyper-variable 5' end of the PVS-RIPO virus, for example. Primers are selected or designed for the regions necessitating additional coverage using target sites that have been previously demonstrated to have reduced sequence variability. Consensus homology to the PVS-RIPO reference sequence and any heterogeneous bases across the Sanger sequenced region are included in the final report.

In some examples, when aligning the raw sequence datasets with the appropriate reference sequence for the virus-derived therapeutic, the mean read length, percentage of aligned reads, coverage, SNPs, or a combination thereof, are determined for the aligned sequence reads. Thus, SNPs can be determined for the aligned sequence reads. Variants can be defined according to the following criteria (e.g., for a polio vaccine): if sequencing depth at a given base position is equal to or exceeds 4,096,000, potential variations are called at greater than 0.1%; if depth is less than 4,096,000 but greater than 4096, variants exceeding a frequency of 4096 or greater are called; if the depth of coverage at a given base position is less than 4096 reads, potential variants are called if the consist of greater than 1.0%. Based on published Polio vaccine limits for example, (where polymorphisms approximately >0.1% at key neurovirulence sites in the Polio IRES could result in the observation of a pathogenic phenotype in monkeys) a 0.1% threshold is an exemplary threshold. However, the threshold can be set at any arbitrary value limited only by the target copy number and the fidelity of the RT, pre-PCR, and sequencing reactions employed.

In some examples, the method includes reporting consensus homology for the virus-derived therapeutic to the reference sequence for the virus-derived therapeutic, coverage per base per position, heterogeneous bases at greater than a defined percentage of reads (e.g., heterogeneous bases at greater than 0.1% of reads), InDels, or a combination thereof. Consensus homology of the virus-derived therapeutic to the reference sequence can be reported as a pairwise alignment of a portion or all of the consensus sequence and the sequence dataset, a report of variations at individual positions for a portion or all of the consensus sequence and the sequence dataset, or any other suitable format. For the polio virus, elevated levels of polymorphism are expected (and observed) at the 5'-end (base positions 1-34) of each viral lot; this region of the Polio genome (VPg binding and Stem a/b) is known to exhibit high sequence variability in vivo. Reporting can also include coverage per base per position of a portion or all of the consensus sequence and the sequence dataset. Such data can be presented as a table or a graph, for example. Coverage can also include total coverage estimated by taking the total number of sequenced bases and dividing by the size of the genome. Reporting can also include heterogeneous bases at greater than 0.1% of reads which are expected to be above the signal to noise threshold. While identification of harmful markers such as markers of attenuation is particularly important, requiring that no mutations accumulate in vaccine lots will help to maintain vaccine safety. The methods described herein can thus be used to identify regions of genetic instability. Quantifying mutations in vaccine batches is important for quality control as well as to maintain manufacturing consistency of viral vaccines. In another aspect, changes in the mutational profile from source plasmid to MVB/WVB (viral seeds) to manufacturing of clinical lots can be examined. In addition, the results will provide an indication of viral bank genetic stability and whether the bank(s) remain suitable for clinical lot manufacturing.

In some examples, when an unaligned sequence read is produced, the unaligned sequence read is added to a pool of unaligned sequence reads for identification. In general, unaligned read sequences can be analyzed by NCBI BLASTn to determine their identity; it is expected that unaligned reads, especially those from unpurified viral samples, will be from host cell genomic or mitochondrial DNA sequences, although human DNA or other laboratory contaminant DNA sequences may be observed as well. The identification of unaligned sequence reads by BLASTn analysis allows for the identification of potential contaminants other than host cell (e.g., Vero) DNA. In other words, identification of unaligned reads can act as an adjunct to viral contaminant PCR and AVA safety testing as well as a means to identify potential process or laboratory contamination from human DNA. The information that can be ascertained from unaligned sequence reads includes: sample or testing laboratory contamination; manufacturing contamination (prior product, cell line contamination (e.g., HeLa contamination), human DNA, etc.); detection and identification of adventitious agents (lytic or lysogenic viruses, bacteria, *mycoplasma*, etc.) in the host cell line; potential to uniquely identify the host cell bank lot via mtDNA and/or gDNA sequences; possible identification of excessive host cell MCB/WCB age (passage number) or stress due to changes in mtDNA or gDNA sequences (or even mRNA expression levels); unaligned reads may be diagnostic for changes in the sample preparation method and/or sequencing; and unaligned reads act as a measure of sample purity, similar to residual host cell DNA testing.

In some examples, after sequencing the virus-derived therapeutic from the MVB or the WCB, the method further includes introducing the virus-derived therapeutic obtained and sequence from the MVB into a host cell, such as a mammalian cell (e.g., Vero, HEK293, HeLa, or PerC6 cell), for production of the virus-derived therapeutic (e.g., a vaccine). The resulting virus-derived therapeutic produced in the second host cell can then be sequenced using a similar protocol as used for the MVB or WCB, except that DNase is generally not required, as the virus-derived therapeutic (e.g., a vaccine) is of higher purity than the virus-derived therapeutic obtained from the MVB or WCB. The resulting sequence of the virus-derived therapeutic can be compared to a corresponding reference sequence and/or to the sequence of the virus-derived therapeutic obtained from the MVB or WCB.

For example, the method can further include introducing (e.g., transforming) the virus-derived therapeutic into mammalian or other host cells and growing the mammalian host cells under conditions that allow propagation of the virus-derived therapeutic. Viral nucleic acid molecules from the mammalian host cells are extracted (e.g., isolated) and purified, for example from the supernatant. In some examples, the purity of the desired virus-derived therapeutic nucleic acids following such extraction and isolation is at least 50%, at least 60%, at least 75%, at least 80%, 90%, at least 95%, at least 98%, at least 99%, at least 99.9%, or at least 99.99%. As above, the isolated viral nucleic acid molecules can be DNA or RNA. Optionally, the isolated viral nucleic acid molecules can be treated with DNase as described above (in some examples, the host cells or culture supernatant is treated with DNase prior to or after viral nucleic acid isolation). If they are RNA, the method includes producing ds DNA (e.g., dscDNA) from the isolated viral RNA, for example using reverse transcription and generating a second viral nucleic acid strand. Viral ds DNA (e.g., dscDNA) is amplified (e.g., using PCR), and the amplified viral ds DNA quantified. A sequencing library is then generated from at least 500 pg ng (such as at least 1 ng, at least 2 ng, at least 5 ng, or at least 10 ng) of the amplified viral ds DNA (e.g., ds cDNA), such as 500 pg to 1 ng, 500 pg to 5 ng, 500 pg to 10 ng, or 1 ng to 5 ng of the amplified viral ds DNA, sequenced, the resulting plurality of sequence reads aligned with a reference sequence, and the sequence of the virus-derived therapeutic determined, and the presence of sequence variations (e.g., mutations), if any, identified, as described above. In some examples, the resulting sequence of the virus-derived therapeutic can be compared to the sequence of the virus-derived therapeutic obtained from the MVB or WCB.

The method allows for at least two different virus-derived therapeutics (such as at least 3, at least 4, at least 5, at least 10, or at least 20, such as 2, 3, 4 or 5 different virus-derived therapeutics) to be assayed simultaneously or contemporaneously, for example by using "bar codes" or "tags" that allow one to distinguish between the different virus-derived therapeutics. In some examples, the different virus-derived therapeutics are different viruses (e.g., different polio viruses or different RNA viruses). In other examples, the different virus-derived therapeutics are the same virus (e.g., PVS-RIPO), but from a different source (such as from different MVBs or WCBs). The methods are conducted as described above, except that producing the sequencing library can include producing one or more sequencing libraries for each virus-derived therapeutic, wherein the one or more sequencing libraries include 5'-adaptors and 3'-adaptors, and wherein each of the one or more sequencing libraries includes a unique barcode for identification. The one or more sequencing libraries are pooled, sequenced as described herein using NGS, and analyzed as described above. The pooled raw sequence dataset can be demultiplexed using the barcodes to produce a demultiplexed raw sequence dataset for each sequencing library. Each of the demultiplexed raw sequence datasets can be aligned with its appropriate reference sequence for the virus-derived therapeutic. From the aligned sequence reads, the sequence of each virus-derived therapeutic analyzed can be determined, and the presence of sequence variations (e.g., mutations), if any, identified. For example, individual sequence reads can be classified as aligned sequence reads and unaligned sequence reads based on their alignment or non-alignment with the reference sequence. Aligned sequence reads can be evaluated for mean read length, percentage of aligned reads, coverage, SNPs, Insertions/Deletions (InDels) or a combination thereof. In some examples, the method includes reporting consensus homology for the virus-derived therapeutic to the reference sequence for the virus-derived therapeutic, coverage per base per position, heterogeneous bases at greater than a defined percentage of reads (e.g., heterogeneous bases at greater than 0.1% of reads), InDels, or a combination thereof.

Thus, in some examples, once the raw sequence dataset has been produced, the dataset is de-multiplexed. De-multiplexing refers to sorting of multiple samples that are sequenced together, generally using a barcode. For example, several dilutions of a lot of an RNA virus-derived therapeutic can be used to form libraries, wherein each library includes a unique barcode. Or, several individual lots of RNA virus-derived therapeutic can be used to form libraries, wherein each library includes a unique barcode. Demultiplexing is also useful when analyzing different sample preparation methods. The libraries can be pooled, and then the pooled libraries can be clonally amplified and sequenced together. Once the sequencing is completed, the barcodes are then used to demultiplex the sequences, that is, to assign the sequences to a specific library. Each de-multiplexed raw sequence can then be further analyzed. Demultiplexing allows for in silico linkage analysis using titrated (low copy) samples each with unique barcodes.

In some examples, following analysis of the virus-derived therapeutic, the method further includes administering the sequenced virus-derived therapeutic to a subject, if the determined viral sequence is not contraindicated (e.g., if no mutations are detected that would lead of a toxic phenotype). If any mutation (Indel or SNP) that would result in a non-sense mutation or otherwise change the viral ORFs/CDS was detected using the disclosed methods, the virus-derived therapeutic would not be administered. For example, if the following mutations were detected in a poliovirus, the virus-derived therapeutic would not be administered, but if the following mutations were not detected in a poliovirus, the virus-derived therapeutic could be administered: For type 3 poliovirus vaccine, the mutation of U to C at base position 472 in the viral RNA 5' NCR; for Type 1 and 2 oral polio vaccine a mutations within the 5' NCR which revert rapidly when passaged in the human gut or in cell culture (such as Type 1 base positions 480 G→A and 525 U→C and Type 2 base position 481 A→G discrete region of stem loop domain 5), and for PV Sabin vaccine strains and of PVS-RIPO a mutation in an IRES region that would lead to reversal of the neuro-attenuated phenotype. However, for PVS-RIPO, at the present time, there are no known HRV-2 IRES mutations that lead to pathogenic or neurotoxic phenotypes. Therefore, in some examples if PVS-RIPO is the virus-derived therapeutic, the entire PVSRIPO genome is reviewed, including: UTRs, IRES, and polyprotein CDS regions of the virus.

Exemplary Viruses

The virus-derived therapeutic analyzed using the methods provided herein to identify the presence of one or more sequence variants (e.g., mutations, such as a nucleotide insertion, deletion or substitution, or combinations thereof, relative to a reference sequence) can be a virus, a viral plasmid template (such as one that is part of a vector and includes a template sequence of the virus), or a vaccine containing a virus. For example, the virus-derived therapeutic can include plasmid DNA (e.g., a bacterial plasmid) containing a template sequence of the virus to be sequenced. Such a plasmid DNA template for a virus can be used for the production of native or recombinant viruses in a host cell. Examples of viruses that can be analyzed using the disclosed methods include a non-naturally occurring RNA-based virus, a naturally occurring RNA-based virus, non-naturally occurring DNA-based virus, or naturally occurring DNA-based virus, as well as a viral plasmid template encoding such or a vaccine containing such.

In some examples, the virus-derived therapeutic is a non-naturally occurring RNA-based virus (e.g., non-naturally occurring poliovirus). Non-naturally occurring viruses may differ from naturally occurring viruses in varying degrees. Non-naturally occurring viruses can be derived from naturally occurring viruses artificially produced ("engineered"), for example, by recombinant techniques, in which case the non-naturally occurring viruses can be referred to as "recombinant." One example of non-naturally occurring viruses is pathogenic viruses that are modified, by genetic manipulation or other processes, such as selection or chemical modification, to reduce or destroy their pathogenicity. This process or, respectively, the resulting modified virus can be termed "attenuation," "attenuated" or by other related terms.

Exemplary non-naturally occurring viruses include, but are not limited to, viral vectors, oncolytic viruses and attenuated or recombinant viruses used as vaccines. Oncolytic viruses are viruses that are used to selectively infect and/or destroy, cancer cells. Viral vectors are viruses that are used to deliver genetic material into cells, either in vivo or in vitro (in cell culture) for various applications. For example, viral vectors can be used for genetic modification, gene therapy, for protein expression or as viral vaccines. Viral vaccines are used to deliver genetic material into cells or organisms with the goal of triggering protective or therapeutic immune response. For example, live attenuated viruses can be used as vaccines to trigger immune response against naturally occurring pathogenic versions of the same viruses (such as poliovirus, rubella virus, measles virus, etc.). The terms oncolytic viruses, viral vectors and viral vaccines sometimes overlap in meaning, but all of them can be artificially created, for example, by genetic modification of naturally occurring viruses using recombinant engineering techniques. Oncolytic viruses can be based on, but are not limited to, enterovirus, herpes virus (such as herpes simplex virus), vesicular stomatitis virus, poliovirus, reovirus, Seneca virus or vaccinia virus. Viral vectors include, but are not limited to, retroviral vectors, such as lentiviral vectors and vectors based on Moloney murine leukemia virus, adenoviral vectors and vectors based on adeno-associated viruses. Viral vaccines, include, but are not limited to, influenza vaccines, measles vaccine strains, mumps vaccine, rubella vaccine, varicella (chicken pox) vaccine, smallpox vaccine, human papilloma virus vaccines, HIV and HTLV vaccines, hemorrhagic fever vaccines or any live, attenuated or inactivated viral vaccine.

In one example, the virus-derived therapeutic sequenced by the disclosed methods is a recombinant poliovirus, such as an oncolytic attenuated recombinant poliovirus exemplified by PVS-RIPO. PVS-RIPO is an attenuated form of the Sabin Type I poliovirus created by exchanging the cognate internal ribosomal entry site (IRES) of poliovirus with its counterpart from human rhinovirus type 2 (HRV 2) to yield a poliovirus strain that does not replicate in normal neuronal cells, but which exhibits oncolytic activity against brain tumor cells. Upon intratumoral administration of recombinant oncolytic poliovirus PVS-RIPO, the poliovirus is selectively taken up by and replicates in tumor cells expressing CD155 (poliovirus receptor, PVR or NECL5) eventually causing tumor cell lysis. CD155, an oncofetal cell adhesion molecule and tumor antigen, is ectopically expressed in certain cancers, such as glioblastoma multiforme (GMB). Due to the heterologous HRV2 IRES in this recombinant virus, PVS-RIPO only propagates in susceptible, nonneuronal cells (e.g., GBM). PVS-RIPO and its properties and applications are described, for example, in Goetz et al., *Cytokine Growth Factor Rev.* 2010 21(2-3):197-20, Yang et al., *J. Virol. Methods.* 2009 155(1):44-54, Cello et al., *J. Med. Virol.* 2008 80(2):352-9, and Dobrikova et al., *Molecular Therapy* 2008 16(11):1865-1872.

In one example, the virus-derived therapeutic sequenced by the disclosed methods is the attenuated Sabin poliovirus (e.g., type 1, type 2 and/or type 3 poliovirus with the appropriate mutations). In one example, the virus-derived therapeutic sequenced by the disclosed methods is one used in the inactivated polio vaccine (e.g., type 1, type 2 and/or type 3 poliovirus), which can be chemically inactivated (e.g., with formalin) following its analysis using the disclosed methods (e.g., prior to administration to a subject).

In one example, the virus-derived therapeutic sequenced by the disclosed methods is an encapsulated icosahedral RNA virus (e.g., one with a protein-based capsid), wherein the presence of the capsid protects the RNA from a DNase. Examples of such viruses include, but are not limited to, polio virus (such as those described above), rubella virus, alphavirus, hepatitis C virus, Parvovirus (B19 for example), other enteroviruses, etc.

In one example, the virus-derived therapeutic sequenced by the disclosed methods is a single or double stranded a encapsulated DNA virus (e.g., one with a protein-based capsid), wherein the presence of the capsid protects the DNA from a DNase or other nuclease. Examples of such viruses include, but are not limited to, adenovirus, hepatitis B virus, varicella-zoster virus, cytomegalovirus, Epstein-Barr virus, or herpes simplex virus (HSV).

In one example, the virus-derived therapeutic sequenced by the disclosed methods is or is derived from a measles virus, hepatitis A virus, hepatitis C virus, mumps virus, influenza virus, rubella virus, human immune deficiency virus (HIV), or human T-lymphotropic virus (HTLV).

In some examples, the virus-derived therapeutic is a viral template plasmid. In some examples, the viral template plasmid includes a DNA template for an RNA virus, such as a polio virus (e.g., template for PVS-RIPO, inactivated polio virus (IPV), attenuated polio virus (i.e., Sabin vaccine). In one example, the viral template plasmid includes a DNA template for a positive-strand RNA virus, such as a Picornavirus (such as Aphthoviridae [for example foot-and-mouth-disease virus (FMDV)], Hepatitis A, or polio), Cardioviridae; Enteroviridae (e.g., Coxsackie viruses, Echoviruses, Enteroviruses, and Polioviruses); Rhinoviridae (rhinoviruses, such as rhinovirus A, B or C)); Togavirus (e.g., rubella; alphaviruses (such as Western equine encephalitis virus, Eastern equine encephalitis virus, and Venezuelan equine encephalitis virus)); Flavivirus (e.g., Dengue virus, Zika virus, West Nile virus, hepatitis C virus, and Japanese encephalitis virus); and Coronavirus (e.g., SARS coronaviruses, such as the Urbani strain). In one example, the viral template plasmid includes a DNA template for a negative-strand RNA virus, such as an Orthomyxyovirus (such as influenza, such as influenza A or B), Rhabdovirus (such as Rabies), Filoviridae (such as Ebola), and Paramyxovirus (such as measles virus, respiratory syncytial virus, and parainfluenza viruses). In some examples, the viral template plasmid includes a DNA virus sequence, such as one from a Herpesvirus (such as Varicella-zoster virus, for example the Oka strain; cytomegalovirus; and Herpes simplex virus (HSV) types 1 and 2), adenovirus (such as adenovirus type 1, type 14, type 5, type 40, or type 41), Poxvirus (such as Vaccinia virus), Hepatitis B virus, and Parvovirus (such as Parvovirus B19). In some examples, the viral template plasmid includes a DNA or RNA template for a retrovirus, such as human immunodeficiency virus type 1 (HIV-1), such as subtype C, HIV-2; equine infectious anemia virus; feline immunodeficiency virus (FIV); feline leukemia viruses (FeLV); simian immunodeficiency virus (SIV); and avian sarcoma virus.

Exemplary NGS Methods

Several next-generation sequencing technologies are known. The current disclosure is not restricted to a particular NGS method. One example is pyrosequencing, which is a sequencing by synthesis technique that relies on the detection of pyrophosphate release upon nucleotide incorporation, rather than chain termination with dideoxynucleotides. Pyrosequencing methods such as those commercialized by Biotage (for low throughput sequencing) and 454® Life Sciences (for high-throughput sequencing), can be used.

In another example, the sequencing library amplicons are sequenced using an Illumina® (e.g., HiSeq), Ion Torrent®, Helicos®, PacBio®, Solid® (Applied Vioasystems) or other commercial sequencing system.

The Illumina® sequencing by synthesis technology is based on reversible dye-terminators. DNA molecules are first attached to primers on a surface and amplified so that local clonal colonies are formed (bridge amplification). Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

The Ion Torrent PGM™ system is an ion-based sequencing system that sequences nucleic acid templates by detecting hydrogen ions produced as a byproduct of nucleotide incorporation. The ion sensor comprises a field effect transistor (FET) coupled to an ion-sensitive detection layer that can sense the presence of $H^+$ ions or changes in solution pH. The ion sensor provides output signals indicative of nucleotide incorporation which can be represented as voltage changes whose magnitude correlates with the $H^+$ ion concentration in a respective well or reaction chamber. Different nucleotide types are flowed serially into the reaction chamber, and are incorporated by the polymerase into an extending primer (or polymerization site) in an order determined by the sequence of the template. Each nucleotide incorporation is accompanied by the release of $H^+$ ions in the reaction well, along with a concomitant change in the localized pH. The release of $H^+$ ions is registered by the FET of the sensor, which produces signals indicating the occurrence of the nucleotide incorporation. Nucleotides that are not incorporated during a particular nucleotide flow will not produce signals. The amplitude of the signals from the FET may also be correlated with the number of nucleotides of a particular type incorporated into the extending nucleic acid molecule thereby permitting homopolymer regions to be resolved. Further details regarding the compositions, design and operation of the Ion Torrent PGM™ sequencer can be found in U.S. Patent Publication Nos. 2009/0026082; 2010/0137143; and 2010/0282617, all of which applications are incorporated by reference herein for their disclosure of next-generation sequencing.

The ABI SOLiD™ ("Sequencing by Oligonucleotide Ligation and Detection") method (Life Technologies; WO 06/084132 A2) is based on the attachment of PCR amplified fragments of template nucleic acids via universal adapter sequences to magnetic beads and subsequent detection of the fragment sequences via ligation of labeled probes to primers hybridized to the adapter sequences. For the readout a set of four fluorescently labeled di-base probes are used. After readout, parts of the probes are cleaved and new cycles of ligation, detection and cleavage are performed. Due to the use of di-base probes, two rounds of sequencing have to be performed for each template sequence.

PacBio RS is a single molecule real time sequencing (SMRT) platform based on the properties of zero-mode waveguides. A single DNA polymerase enzyme is affixed at the bottom of a ZMW with a single molecule of DNA as a template. The ZMW is a structure that creates an illuminated observation volume that is small enough to observe only a single nucleotide of DNA being incorporated by DNA polymerase. Each of the four DNA nucleotides is attached to one of four different fluorescent dyes. When a nucleotide is incorporated by the DNA polymerase, the fluorescent tag is cleaved off and diffuses out of the observation area of the ZMW where its fluorescence is no longer observable. A detector detects the fluorescent signal of the nucleotide incorporation, and the base call is made according to the corresponding fluorescence of the dye.

In the Helicos Heliscope™ technology fragments are captured by polyT oligomers tethered to an array. At each sequencing cycle, polymerase, and single fluorescently labeled nucleotides are added and the array is imaged. The fluorescent tag is subsequently removed and the cycle is repeated.

The disclosure is further illustrated by the following non-limiting examples.

Example 1

Sequencing and Analysis of Purified Viral Samples

RNA Extraction and Reverse Transcription:

Genomic RNA is isolated from all test samples using the QIAamp® Viral RNA Mini Kit from Qiagen as per a modified version of the Qiagen protocol. Briefly, 560 µl of Buffer AVL (Viral Lysis Buffer "A"—chaotropic detergent solution) without carrier RNA is added to 140 µl of the sample. The sample is vortexed and incubated at room temperature (23°±2° C.) for 10 minutes. 560 µl of 100% ethanol is added to the sample, vortexed, and then half the sample (approximately 630 μl) is added to the QIAamp® Mini column and centrifuged for 1 minute at 6000×g. The rest of the sample is added to the column and the spin step is repeated. The column is then washed with two buffers. A double elution of 40 μl of elution buffer each is performed for a total final volume of about 80 μl. The total RNA is quantitated spectrophotometrically using a NanoDrop™ 8000 spectrophotometer. The RNA is then used to make cDNA using the ThermoScript™ RT-PCR System from Life Technologies. Briefly, 9 μl of RNA, 1 μl of oligo $(dT)_{20}$ primer, and dNTPs are incubated at 65° C. for five minutes. Following incubation, cDNA synthesis buffer, DTT, RNase-OUT™, and ThermoScript™ RT are added to the sample and the sample is incubated at 50° C. for 45 minutes, then 85° C. for five minutes to terminate the reaction. RNase H is added to the sample and incubated at 37° C. for 20 minutes. The cDNA is quantitated spectrophotometrically using a NanoDrop' 8000 spectrophotometer. A second strand reaction is then performed using the NEBNext™ Second Strand Synthesis Kit from New England BioLabs using 5 μl of the cDNA product. The cDNA is combined with second strand synthesis buffer and second strand synthesis enzyme mix and incubated at 16° C. for 2.5 hours. The product is purified using the QIAquick® PCR purification kit from Qiagen and eluted in 30 μl of nuclease-free water. The dscDNA is quantitated spectrophotometrically using a NanoDrop™ 8000 spectrophotometer and stored at −20±4° C. for short-term storage.

Library Preparation:

The prepared dscDNA is used to prepare libraries for sequencing on the Illumina® HiSeq® 2500. One library is prepared from each original sample. The libraries are prepared using the Nextera® XT library preparation kit from Illumina®. The starting total input of dscDNA is 1 ng for each library based on prior development range finding efforts using between 1 pg and 1 ng of input dscDNA. The libraries are prepared following the Illumina® Nextera® XT library preparation protocol. Briefly, each sample is fragmented enzymatically and tagged (ligated) with adapter sequences simultaneously using the Nextera® Tagmentation chemistry. The process fragments the input DNA and adds adapter sequences to the ends of the fragments for use in downstream processing. The ligation enzyme is then neutralized and a brief, 12 cycle amplification is performed to add barcodes on to each sample at the 5'- and 3'-ends. Each library can be assigned a different barcode to identify and delineate different samples during analysis. The PCR reactions are cleaned up using a double round of AMPure® XP bead washes and then eluted in TE buffer. Each of the libraries is then analyzed on the Agilent Bioanalyzer using high sensitivity DNA chips to assess for quality and quantity of the libraries. The sample libraries are stored at −20±4° C. for short-term storage.

Illumina® DNA Sequencing and Analysis:

For each sample, one Rapid flow cell is run on the Illumina® HiSeq® 2500. For each flow cell, the library is denatured and diluted for on-instrument clustering. Paired end 2×150 bp sequencing is then performed on each of the libraries using Illumina® SBS sequencing technology and reagents. The resulting data is de-multiplexed using the Illumina® HiSeq® software and then analyzed. Each flow cell is run using a single sample. FastQ files are generated for all sequenced fractions. Overall flow of data analysis process is described in FIG. 1. Samtools and mpileup software are used to convert the output files from a SAM to BAM format and index output files for viewing in the Integrated Genome Viewer. Mpileup is used with a flag to increase the depth of each position in order to examine coverages of the virus and look for potential variations.

Since 12 cycles of PCR pre-amplification are required for the Nextera® XT library preparation, the threshold for calling a viral sequence variant at a given position is established to be $2^{12}$=4096 or 0.1% of reads, whichever is greater. Variants are defined according to the following criteria: if sequencing depth at a given base position is equal to or exceeds 4,096,000, potential variations are called at greater than 0.1%; if depth is less than 4,096,000 but greater than 4096, variants exceeding a frequency of 4096 or greater are called; if the depth of coverage at a given base position is less than 4096 reads, potential variants are called if the consist of greater than 1.0%. The minimum read coverage per base position is set at 4× (regulatory minimum), before additional sequencing efforts (Illumina® or Sanger) would be required.

Reads are aligned for each sample to the PVS-RIPO reference sequence using Bowtie (short read reference aligner). The values for the total number of bases, the coverage, and the mean read length and the percent of reads aligned to the reference for each sample are calculated and compared to pre-established specifications for assay validity. The estimated coverage is found by taking the total sequenced bases and dividing by the size of the PVS-RIPO reference sequence (7303 base pairs). Plots of coverage compared to location across the reference for each sample are prepared, as well as plots of sample read length for each sample. Analysis is performed to examine variants in each sample when compared to the reference sequence. Elevated levels of polymorphism are expected (and observed) at the 5' end (base positions 1-34) of each viral lot; this region of the poliovirus genome (VPg binding and Stem a/b) exhibits high sequence variability in vivo. Non-aligned read sequences can be analyzed by NCBI BLASTn to determine their identity; it is expected that non-aligned reads, especially those from unpurified viral samples, will be from Vero host cell genomic or mitochondrial DNA sequences, although human DNA or other laboratory contaminant DNA sequences may be observed as well.

Example 2

Sequencing and Analysis of Crude and Unpurified Viral Samples

RNA Extraction and Reverse Transcription:

Viral RNA is extracted from each of the test samples using the Qiagen QIAamp® Viral RNA mini extraction kit without the addition of carrier RNA. An aliquot of each sample is used for the extraction. Since the majority (by copy number and mass) of nucleic acids in unpurified viral samples are host cell genomic and mitochondrial DNA, an additional purification step is necessary to remove these interfering molecules. A DNase digestion of free DNA in the sample is used which permits the viral RNA to be unaffected. An aliquot of the extracted RNA from the master viral bank sample is subsequently DNase treated using the Turbo DNase-Free™ kit from Life Technologies.

The sample is treated with 2 μl of the Turbo DNase, incubated at 37° C. for 30 minutes, and then inactivated with the DNase inactivation reagent. The resulting enriched viral RNA is quantitated using the Leidos/BDP-QC "PO1PR" RT-qPCR assay. The RNA is then used as the input for reverse transcription and second strand synthesis using the SMARTer® Ultra™ Low Input RNA Preparation Kit from Clontech Laboratories. A first strand synthesis is performed using the SMARTer® IIA CDS and Oligonucleotide primers at 42° C. for 90 minutes. When used with PVSRIPO, the SMARTer IIA Oligo improves the recovery of full-length poly-adenylated PVSRIPO RNA (and contaminating Vero mRNA) sequences through the use of the 5' terminal transferase activity of SMARTScribe RT with the SMARTer IIA Oligo which prevents tagging of cDNA generated from stalled RT procession events.

The resulting full-length cDNA is then amplified by long distance PCR using the oligo-dT and SMART primers introduced in the cDNA preparation. The sample is then polished to remove primers and dNTPs using AMPure beads and quantitated on a Qubit 2.0 Fluorometer or NanoDrop 8000 spectrophometer and validated for size on the Agilent 2100 Bioanalyzer using a DNA chip. Alternatively a quantitative PCR reaction targeting the HRV-2 IRES or the 5' end of the polio polyprotein CDS sequence can be used to determine the target copy number prior to sequencing.

Library Preparation:

The dscDNA from the two different preparations is used as the template for library preparation; the Nextera® XT Library Preparation Kit from Illumina® is used. One nanogram of each dscDNA sample will be used to prepare each library. The Nextera® kit uses "tagmentation" technology, where the input is fragmented and tagged with adapters in one single incubation step. The ligation enzyme is then neutralized and each sample is barcoded through a short, 12 cycle amplification, and then purified using AMPure® XP beads. Following purification, the quantity and quality of each library is assessed using Agilent 2100 Bioanalyzer High Sensitivity DNA chips.

Illumina® Sequencing:

The libraries are then be used for sequencing on the Illumina® HiSeq® 2500 instrument. The instrument is used in Rapid Run mode and each library is sequenced on one Rapid Run Flow Cell. The libraries are denatured and diluted, and then the on-board clustering capabilities of the instrument are used for cluster formation. The libraries are sequenced using 2×100 bp paired end sequencing. The resulting sequence must obtain a minimum of 4× coverage across all bases or additional Sanger sequencing will be performed to complete the coverage across those regions, this is expected to occur at the 5' of the virus where RT exhaustion occurs due to strong RNA structure in the viral IRES domains. Illumina® sequence analysis procedures follow those for purified viral samples detailed above and in FIG. 1. A report detailing consensus homology to the PVSRIPO reference sequence, coverage per base position, and heterogeneous bases at >0.1% of reads or >4096 reads as applicable is generated.

Example 3

Sanger Sequencing

If any base pair of the reference sequence has coverage <4 sequencing reads using the Illumina® methodology, Sanger Sequencing will be employed. If the portion of the genome lacking appropriate coverage is near the 5' end of the genome, several gap filling techniques may be used including alternative NGS methods such as Roche/454 FLX and/or alternative pre-amplification methods such 'linear amplification' of the PVS-RIPO cDNA using only reverse primers to prevent primer masking of the 5' sequence variability. A high-cycle number of linear (non-exponential) PCR is employed to prevent over-writing the native PVS-RIPO viral sequence with primer sequence, especially at the under-represented (low copy dscDNA) and hyper-variable 5' end of the PVS-RIPO virus. Finally, if none of these approaches are successful in covering a remaining sequence gap, traditional PCR followed by Sanger fluorescent sequencing may be performed. The sequence data obtained from these gap-filling methods, including consensus sequence homology to the PVSRIPO reference sequence and any heterogeneous bases observed, are included in the final report.

Example 4

Criteria for a Valid Test

In Examples 1 and 2, criteria for a valid test include:

1. Extracted RNA must be a minimum of 5 nanograms total per sample.
2. Resultant cDNA must be a minimum of 2 nanograms total per sample for use in the second strand reaction.
3. Libraries must be detectable using the Agilent 2100 High Sensitivity DNA chip and are the appropriate size for sequencing (approximately 300 bp).
4. Sanger sequencing will be utilized, if required, to provide a minimum of 4× coverage for the desired regions from multiple linear amplifications (if at the variable 5' end) or from multiple primer sets if elsewhere in the viral genome.

In Examples 1 and 2, sequence acceptance criteria include:

1. Total reads for one Illumina® flow cell must be >45 million.
2. The percentage of reads aligned to the reference should exceed 75%.
3. Average coverage of the reference viral sequence is >18,000×.
4. Each base must be covered at 4× or greater. This can be from Illumina® alone, or a combination of Illumina® and Sanger sequencing.

Example 5

RT-PCR and Sanger Dye-Terminator Sequencing of Purified and Crude Viral Samples RNA Extraction and Reverse Transcription:

Following an approved procedure, 250 μl of test sample is added to 1120 μl Qiagen buffer AVL/Carrier RNA, vortexed, and incubated at room temperature for 10 minutes. Half of the sample+buffer AVL (685 μl) is transferred to a second micro-centrifuge tube, and 560 μl of ethanol (96-100%) is added to each tube, mixed by pulse-vortexing for 15 seconds, and briefly centrifuged. The solution is then added to a QIAamp spin column, washed with appropriate wash buffers, and eluted in 60 μL Buffer AVE. The viral RNA is quantitated using a spectrophotometer per an approved procedure. The viral RNA is then stored at ≤−65° C. until use.

PCR Amplification and Sequencing Primer Selection:

The synthetic oligonucleotides used for PCR amplification and Sanger sequence analysis of test articles are derived from the PVSRIPO reference sequence (see Table 2). The primers are designed to anneal approximately 250 bases apart, have an approximate 50% GC content, and be between 18-24 bp in length. Primer sites are designed such that when both strands of cDNA are sequenced, four or more reads will be generated per base pair (two from each strand) based on the expected read lengths from each primer extension.

TABLE 2

Representative oligonucleotide primers used for Sanger sequencing of PVSRIPO.
Additional primer sequences lot listed have also been utilized.

| Primer name | 5' to 3' primer sequence | SEQ ID NO: |
|---|---|---|
| PVSRIPO.f2 | CAAACAATGGACAAGGTGT | 1 |
| PVSRIPO.f3 | TCCTGATAAAAACATCCC | 2 |
| PVSRIPO.f4 | ATTCGCCGTACCAGAGATG | 3 |
| PVSRIPO.f5 | TGTGAGTTCAATGGATTAAG | 4 |
| PVSRIPO.f6 | TGTTCTGTGGATCCATGATG | 5 |
| PVSRIPO.f7 | CCGTGAAACGGTGGGGGCG | 6 |
| PVSRIPO.f8 | GGGCATGCCTTAAATCAAG | 7 |
| PVSRIPO.f9 | GCCCTGGAGTGGATTACAAG | 8 |
| PVSRIPO.f11 | CAAGGTGACAGTTGGTTGAAG | 9 |
| PVSRIPO.f12 | CAGGTAAATCTGTAGCAAC | 10 |
| PVSRIPO.f13 | TGAAATGTGTAAGAACTGTC | 11 |
| PVSRIPO.f14 | GCAGTGGCTGGAGTTGTCT | 12 |
| PVSRIPO.f15 | CTGAGACAAATGATGGAGTC | 13 |
| PVSRIPO.f16 | AAACGATCCCAGGCTTAAG | 14 |
| PVSRIPO.f18 | CCTACAAGGGCATAGATTTAG | 15 |
| PVSRIPO.f19 | ATTGCTCCCAGAGTACTC | 16 |
| PVSRIPO.r33 | TGGCATTACTGGATGAATAAG | 17 |
| PVSRIPO.r34 | TCTCCGAATCCGATTTTCTC | 18 |
| PVSRIPO.r36 | TCGCTTCAGGGCCGCTGC | 19 |
| PVSRIPO.r37 | GGTGAAGCGTGGGTTGGTA | 20 |
| PVSRIPO.r38 | CAGGAGGGGGACTCGTCTTG | 21 |
| PVSRIPO.r40 | CTGACATTATTGAATAGAA | 22 |
| PVSRIPO.r41 | TCAAGTTCTTAAGTAGCTTTTC | 23 |
| PVSRIPO.r42 | CCCTGCGTTGCAATTGCAC | 24 |
| PVSRIPO.r43 | TAGAGGGAGTCACCTAGTG | 25 |
| PVSRIPO.r44 | CTGAGTTATCCACGGTTAT | 26 |
| PVSRIPO.r45 | GACGACTATTCTGGTTTGG | 27 |
| PVSRIPO.r46 | AGAGTATGGGATCGTCTG | 28 |
| PVSRIPO.r47 | TACCATACTATCTATCGAG | 29 |
| PVSRIPO.r48 | ATGTCCCGCAGTGCATCAG | 30 |
| PVSRIPO.r49 | TGGTAGAACCACCATACGC | 31 |
| PVSRIPO.r50 | CGACCAGCCAAACGATTTC | 32 |
| PVSRIPOrev1 | GAG TCC CAT GTC CCG CAG | 33 |
| pVSRIPOREV2 | CCA ACA TAC GGT ACC GAG ATC | 34 |
| pVSRIPOrev4 | TGC TTT CAC CAG GTG AAG CGT | 35 |
| pVSRIPO.altREV1 | TAC CCG TGA AAG TGC CTC CTT TCT | 36 |
| pVSRIPO.altf10 | TGC AAC TAC CAT TTG GCC ACT CAG | 37 |
| pVSRIPOaltR39 | AAT GTC CAT GTC GAA CGC AAA GCG | 38 |

TABLE 2-continued

Representative oligonucleotide primers used for Sanger sequencing of PVSRIPO. Additional primer sequences lot listed have also been utilized.

| Primer name | 5' to 3' primer sequence | SEQ ID NO: |
| --- | --- | --- |
| pVSRIPO.altender | ATT TAC CCC TAC AGC AGT ATG ACC CAA | 39 |
| pVSRIPO.altF17 | TGT ATG TTC CTG TCG GTG CTG TGA | 40 |
| pVSRIPO altF1 | TTA AAA CAG CTC TGG GGT TGT ACC C | 41 |
| RTPCR1 R51 | TTTTTATCAGGACATCCTTGATGGGC | 42 |
| RT-PCR 1 F52 | TATATTGGCACCATGGGAGCT | 43 |
| RTPCR2 F53 | GGACCAACAACTGTGCTACAC | 44 |
| RTPCR2 R54 | AAGTCAAAGGGAATCATGGTG | 45 |
| RTPCR3 R55 | GCTCTATATGTGTGGTATCTC | 46 |
| RTPCR3 R56 | TATGTGTGGTATCTCGCATCA | 47 |
| RTPCR4 R57 | TGGTGGAGAGGGGTGTAAGCG | 48 |
| RTPCR5 F58 | GGTGACCAGTACCATCACTGA | 49 |
| RTPCR5 R59 | TTTCAGCTATGGCTCTAGCAA | 50 |
| RTPCR8 F60 | CATCTTTAGTGCCTCGAACCA | 51 |
| RTPCR8 F61 | GACTATGGACTAACTATGACT | 52 |
| RTPCR8 R62 | TTACATTCTCCCATGTGACTG | 53 |
| RTPCR8 F63 | ATCACGTTCGCTCTCTGTGCC | 54 |
| PVS2RIPO PCR2R | TGT GTT CCC AAC ATC GCC TCC TTA | 55 |
| PVSRIPO8 F64 | CAG CCC TGC TTG GTT CGA GGC | 56 |
| PVSRIPO-1 REND | CTT CTA AGT TGA ATT CCT AAG | 57 |
| R35 | TCT TCT TTC CCA TTG CTA C | 58 |
| PCR7-F17b | GAG CAG GAC AGT GTG GTG GAG T | 59 |
| PCR6-14a | GCA AGG GAG AGT TCA CTA TGT T | 60 |
| PVSRIPO-1 DSnew1 | TGCGGTTAACGATCGCAGT | 61 |
| PVSRIPO-1 DSnew2 | TCATCTGCCAGGTCTACCAG | 62 |
| PVSRIPO-1 DSnew3 | CTAGTACTCCGGTATTGCGGT | 63 |
| PVSRIPO-2 DSnew1 | CATCGCCTCCTTACGCTTC | 64 |
| PVSRIPO-3 DSnew1 | GTGGCCATTATAACCGTGGA | 65 |
| PVSRIPO-3 DSnew2 | GTTTGCCATGTGTAGTCGTC | 66 |
| PVSRIPO-4 DSnew1 | GATCTCGGTACCGTATGTTG | 67 |
| PVSRIPO-4 DSnew2 | CTCTATGGTGCAGCATCTCT | 68 |
| PVSRIPO-4 DSnew3 | ACTCAGCAGATTGGAGACA | 69 |
| PVSRIPO-5 DSnew1 | GATGGTTATCCATCCAGTC | 70 |
| PVSRIPO-5 DSnew2 | GTCGAAGTGTGATGGATC | 71 |
| PVSRIPO-6 DSnew1 | CATGGCATCCCTGGAGGAG | 72 |
| PVSRIPO-6 DSnew2 | AGCCTCCATACAATTGCCA | 73 |
| PVSRIPO-6 DSnew3 | GTCCTTTAGTGTGTGGTAAG | 74 |
| PVSRIPO-6 DSnew4 | TGGCATCCAAGATCTCCA | 75 |

TABLE 2-continued

Representative oligonucleotide primers used for Sanger sequencing of PVSRIPO.
Additional primer sequences lot listed have also been utilized.

| Primer name | 5' to 3' primer sequence | SEQ ID NO: |
|---|---|---|
| PVSRIPO-7 DSnew1 | CACTGTCCTGCTCTGGTTG | 76 |
| PVSRIPO-PCR2 | TAG TAA CGC GGC TTC GAA ACA GGA | 77 |
| PVSRIPO-R51 | TTTTTATCAGGACATCCTTGATGGGC | 78 |

Following extraction, PVSRIPO RNA is reverse transcribed (RT) and PCR amplified in ~1200 base sections using a SuperScript III RT-PCR kit. Approximately 0.1 micrograms of extracted viral RNA is combined with 25 µl of 2× reaction mix, and 10 pmoles each of forward and reverse primer and brought to a 50 µl final volume with nuclease free water. Amplicons are purified using a QIAquick PCR Cleanup Column per an approved procedure. To verify that an amplicon of expected size is present following PCR, an aliquot of each PCR reaction is analyzed by agarose gel electrophoresis and stained with ethidium bromide for imaging. Successful PCR reactions are subsequently stored at −18±2° C. until further use.

Sanger Sequencing Using Fluorescent Dye-terminator Chemistry: Fluorescent dye-terminator DNA cycle sequencing of the test article samples and a pGEM3Z control plasmid is carried out using the ABI BigDye v1.1 Sequencing Kit per an approved procedure. 2.0 µl of 5× BigDye Sequencing Buffer is combined with 2.0 µl Ready Reaction Premix, 2 µl of 2 µM sequencing primer, 20 ng of purified PCR product and purified water to a final reaction volume of 10 µl. For the pGEM3Z control reactions that serve as the reaction and instrument controls, 200 ng of pGEM3Z are sequenced with 20 ng (approximately 3.2 pmol) of the M13F-20 positive control primer (5' GTAAAACGACGGCCAGT-3'; SEQ ID NO: 79). Control reactions are performed with each sequencing set-up (i.e., plate) and analyzed on the ABI3130xl per an approved procedure. Cycle sequencing reactions were performed using a PTC-225 Peltier thermal cycler per an approved procedure. Before analysis, sequencing reactions are purified from unincorporated dye terminators, salts, and low molecular weight compounds using Centriflex Gel Filtration Cartridges. Automated DNA sequence analysis is carried out using an ABI3130xl DNA sequencer following an approved procedure. During the capillary electrophoresis and detection process, fluorescent sequence data is gathered from each channel of the 3130xl by the sequencing computer and analyzed. The raw sequence run data is trimmed and aligned into a contiguous arrangement of sequences, also known as a "contig" using Sequencher software (GeneCodes, Ann Arbor, Mich.), per an approved procedure. The contig for each sample is then aligned with the PVSRIPO reference sequence and searches for base changes, indels, gaps, and ambiguities (polymorphic) sites are conducted manually with automated assistance from ABI software, Sequencher, BioEdit, CloneManager, and other sequence analysis suites.

Sequencing Acceptance Criteria for Sanger-Based Methods:

The pGEM3Z positive control sequencing reactions run on each sequencing plate must generate at least 500 base length of read (LOR) and have a quality value (QV) ≥20 for the first 500 bp of the sequence read as determined by the Applied Biosystems (ABI 3130xl) analysis report. Overall sequencing quality of the plasmid controls must be greater than 90%.

Example 6

Sequencing of a PVS-RIPO Lot

DNA Extraction and Reverse Transcription:

Genomic RNA was isolated from all test samples using the QIAamp® Viral RNA Mini Kit from Qiagen as per a modified version of AIB SOP MOLBI000050. Briefly, 560 µl of Buffer AVL without carrier RNA was added to 140 µl of the sample. The sample was vortexed and incubated at room temperature (23°±2° C.) for 10 minutes. 560 µl of 100% ethanol was added to the sample, vortexed, and then half the sample (approximately 630 µl) was added to the QIAamp® Mini column and centrifuged for 1 minute at 6000×g. The rest of the sample was added to the column and the spin step was repeated. The column was then washed with two buffers. A double elution of 40 µl of elution buffer each was performed for a total final volume of about 80 µl. The RNA was quantitated spectrophotometrically using a NanoDrop™ 8000 spectrophotometer as per AIB SOP MOLBI000077. The RNA was then used to make cDNA using the ThermoScript™ RT-PCR System from Life Technologies. Briefly, 1 µg of RNA in 7 µl, 1 µl of oligo dT primer, dNTPs, and water were incubated at 65° C. for five minutes. Following incubation, cDNA synthesis buffer, DTT, RNase Out, and ThermoScript™ RT were added to the sample and the sample was incubated at 50° C. for 45 minutes, then 85° C. for five minutes to terminate the reaction. RNase H was added to the sample and it was incubated at 37° C. for 20 minutes. The cDNA was quantitated spectrophotometrically using a NanoDrop™ 8000 spectrophotometer as per AIB SOP MOLBI000077. A second strand reaction was then performed using the NEBNext™ Second Strand Synthesis Kit from New England BioLabs using 100 total nanograms of the cDNA product. The cDNA was combined with second strand synthesis buffer and second strand synthesis enzyme mix and incubated at 16° C. for 2.5 hours. The product was purified using the QIAquick® PCR purification kit from Qiagen and eluted in 30 µl of nuclease-free water. The dscDNA was quantitated spectrophotometrically using a NanoDrop™ 8000 spectrophotometer as per AIB SOP MOLBI000077 and stored at −20±4° C. for short-term storage.

Library Preparation:

The prepared dscDNA was used to prepare libraries for sequencing on the Illumina® HiSeq® 2500. A total of eleven libraries were prepared from each original sample. The libraries were prepared using the Nextera® XT library preparation kit from Illumina®. The starting total input of dscDNA differed for each library prepared and were as follows: library 1-1000 pg, library 2-750 pg, library 3-500 pg, library 4-250 pg, library 5-100 pg, library 6-75 pg, library 7-50 pg, library 8-25 pg, library 9-10 pg, library 10-5 pg, library 11-1 pg. The dscDNA was diluted to the varying input amounts based on the quantitation from the Nano-Drop™ 8000 spectrophotometer. The libraries were prepared following the Illumina® Nextera® XT library preparation protocol. Briefly, each sample was tagged and fragmented enzymatically simultaneously using the Nextera® Tagmentation chemistry. The process fragments the input DNA and adds adapter sequences to the ends of the fragments for use in downstream processing. A brief, 12 cycle amplification was then performed to add barcodes on to each sample. Each dilution was assigned a different barcode to separate out the different samples during analysis. The PCRs were cleaned up using a double round of AMPure® XP bead washes and then eluted in TE buffer. Each of the libraries was then analyzed on the Agilent Bioanalyzer to assess for quality and quantity of the libraries. The libraries were stored at −20±4° C. for short-term storage.

Next Generation DNA Sequence Analysis:

For each original sample, two flow cells were run on the Illumina® HiSeq® 2500. The first flow cell consisted of one single library—the highest input library (library 1). The second flow cell had all 11 libraries combined at equimolar concentrations. For each flow cell, the library or library pool was denatured and diluted for on-instrument clustering. Paired end 2×150 bp sequencing was then performed on each of the libraries using Illumina® SBS sequencing technology and reagents. When applicable, resulting data was de-multiplexed using the Illumina® HiSeq® software and then analyzed. Reads were aligned to the supplied reference genome sequence PVS-RIPO (SEQ ID NO. 1). FastQ files were generated for all sequenced fractions and will be supplied on a drive and mailed. FastQ files from the two lanes were combined into a single data set and analyzed as one sample. Overall flow of data analysis process is described in FIG. 1. Samtools and mpileup were used to convert the output files from a SAM to BAM format and index output files for viewing in the Integrated Genome Viewer. Mpileup was used with a flag to increase the depth of each position in order to examine coverages of the virus and look for potential variations. Variants were defined according to the following criteria; if sequencing depth at a given position is equal to or exceeded 4,096,000 potential variations were called at greater than 0.1%; if depth is less than 4,096,000 and greater than 4096 variants exceeding a frequency of 4096 or greater are called; if depth of coverage is less than 4096, potential variants are called that are greater than 1.0%. The minimum read coverage was set at 4×. If a position had coverage less than the minimum, no data was reported for that position.

Sequencing Results of PVSRIPO Toxicology Material, Lot L0603006, QC-052548-02

Figure 2:
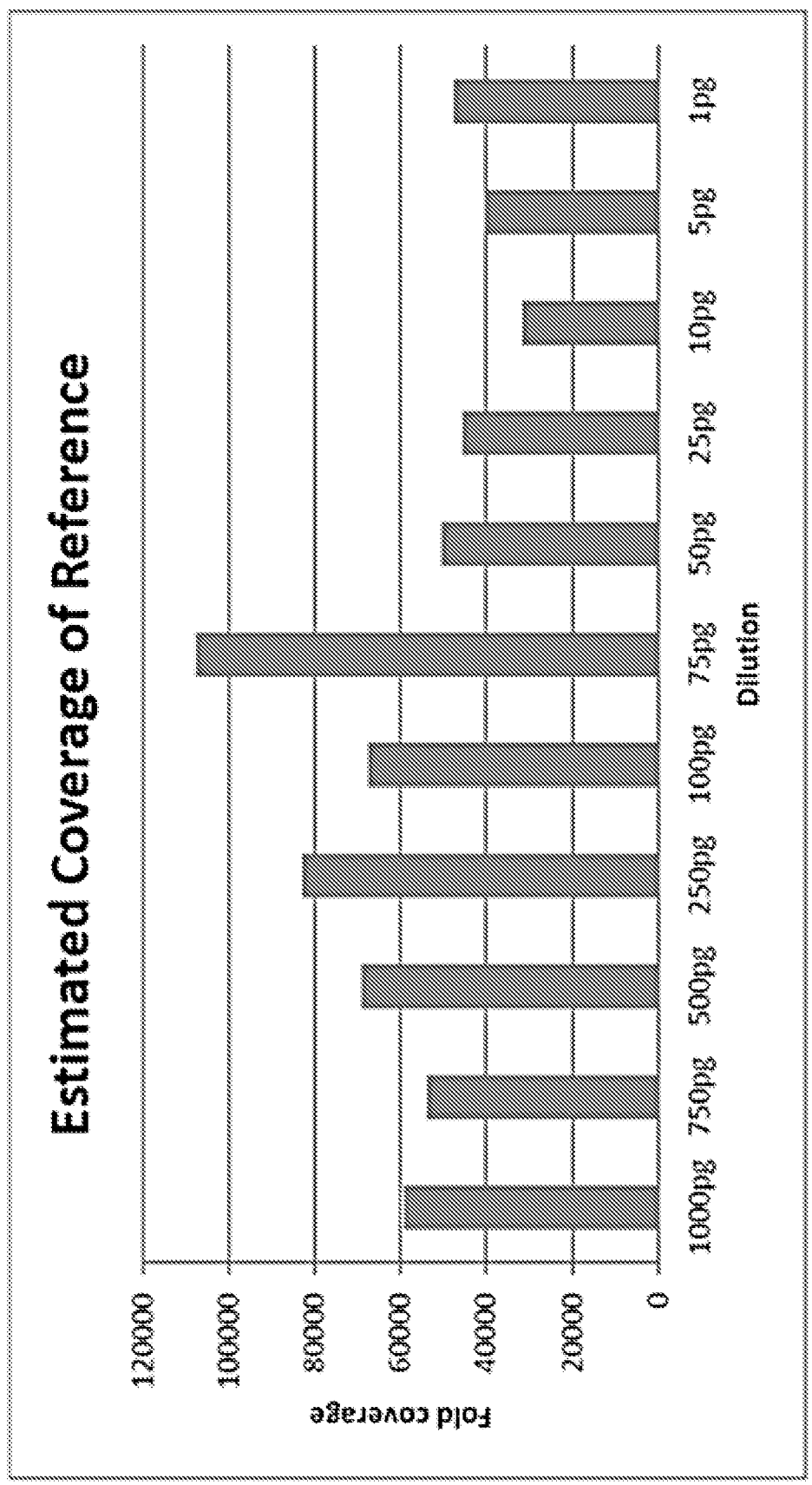
FIG. 2 shows alignment statistics for dilution libraries of a PVS-RIPO vaccine lot. Estimated coverage of the reference sequence is shown.

Dilution Series:

Reads were de-multiplexed using Illumina® HiSeq® software. After separating the barcodes, reads were aligned to the reference sequence using Bowtie (short read reference aligner). Alignment statistics are shown in Table 3 and FIG. 2. At the 1000 pg input, approximately 87% of the reads align to the reference sequence. As the input amount decreased, the proportion of reads that aligned decreased. Additional analyses were performed to identify potential contaminating sequence using the 1000 pg sample. A small number of the unmapped reads were compared to the non-redundant database and many hits came back to host cell Chlorocebus (Vero) DNA.

TABLE 3

Alignment statistics for each of the dilution libraries

| Dilution (input mass (pg)) | Number of reads | Aligned | Percentage |
|---|---|---|---|
| 1000 | 4910983 | 4267441 | 86.90% |
| 750 | 3956379 | 3367519 | 85.12% |
| 500 | 5219665 | 4335411 | 83.06% |
| 250 | 6219724 | 4863890 | 78.20% |
| 100 | 5350547 | 3042589 | 56.87% |
| 75 | 8405898 | 5265675 | 62.64% |
| 50 | 4074065 | 2095240 | 51.43% |
| 25 | 3862454 | 1341020 | 34.72% |
| 10 | 2989317 | 109897 | 3.68% |
| 5 | 3769713 | 121189 | 3.21% |
| 1 | 4355564 | 19918 | 0.46% |
| Undet* | 1457557 | 599775 | 41.15% |

*= Error in barcode prevents these sequences from being assigned to a particular sample.

All samples were analyzed to determine the minimum, maximum, and mean read lengths (Table 4).

TABLE 4

Read length statistics for each dilution library.

| Sample ID | Minimum | Maximum | Mean |
|---|---|---|---|
| 1000 pg | 35 | 151 | 88.20 |
| 750 pg | 35 | 151 | 99.54 |
| 500 pg | 35 | 151 | 96.89 |
| 250 pg | 35 | 151 | 97.43 |
| 100 pg | 35 | 151 | 92.22 |
| 75 pg | 35 | 151 | 93.58 |
| 50 pg | 35 | 151 | 90.53 |
| 25 pg | 35 | 151 | 86.30 |
| 10 pg | 35 | 151 | 77.35 |
| 5 pg | 35 | 151 | 77.10 |
| 1 pg | 35 | 151 | 79.87 |

Thus, aligned reads (i.e., reads that contain viral sequence vs. 'junk'/random and host cell DNA sequences) peak at ~500-1000 pg ds-cDNA input, and there is no apparent effect above ~25 pg input on read lengths.

Figure 3:
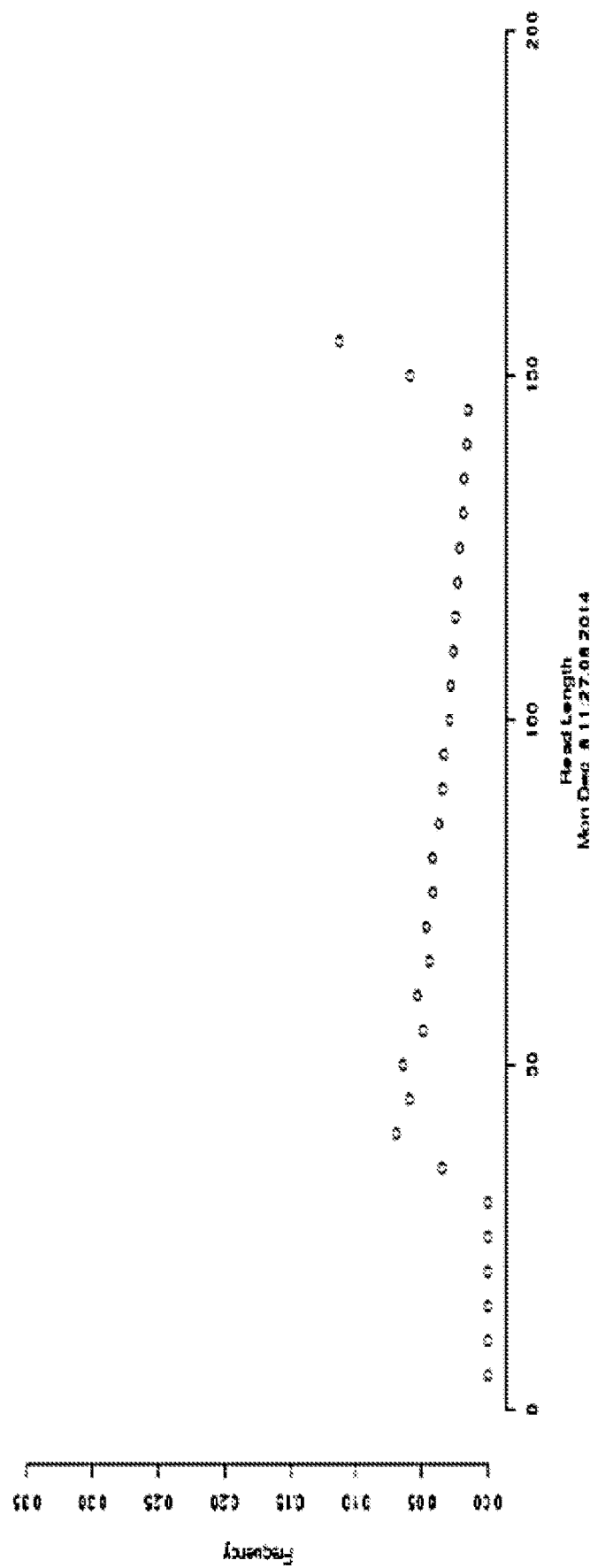
FIG. 3 is an exemplary read length plot for a 100 pg sample of a PVS-RIPO vaccine lot.

A sample read length plot is shown in FIG. 3. The average read length is approximately 100 base pairs. Approximate coverage was calculated for the entire virus using the following equation.

$$\frac{\text{Number of nucleotides sequenced}}{\text{Length of virus}}$$

Figure 4:
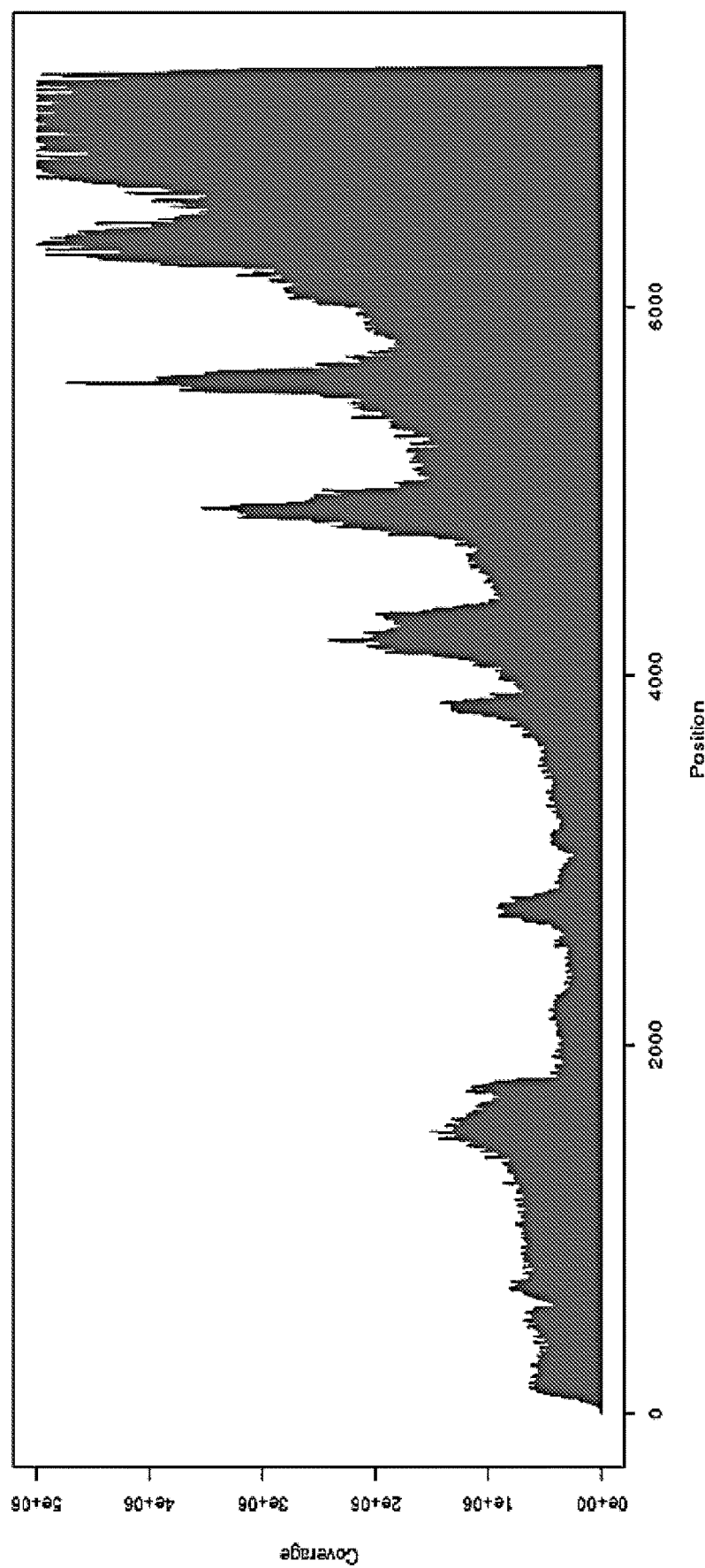
FIG. 4 is an exemplary coverage plot for a 100 pg sample of a PVS-RIPO vaccine lot Toxicology lot L0603006.
Figure 6:
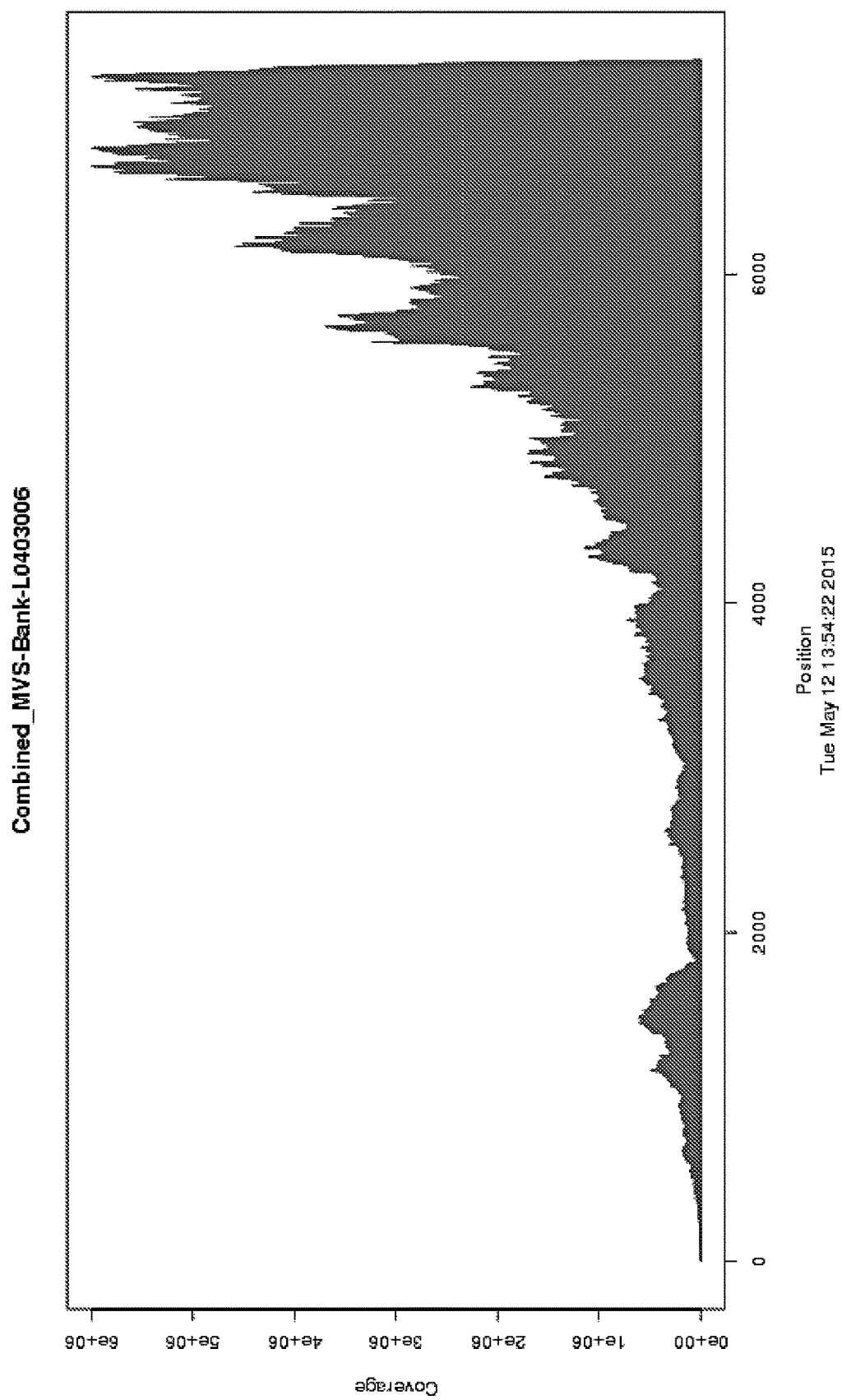
FIG. 6 shows coverage depth of PVSRIPO Master Viral Bank lot L0403006.
Figure 7:
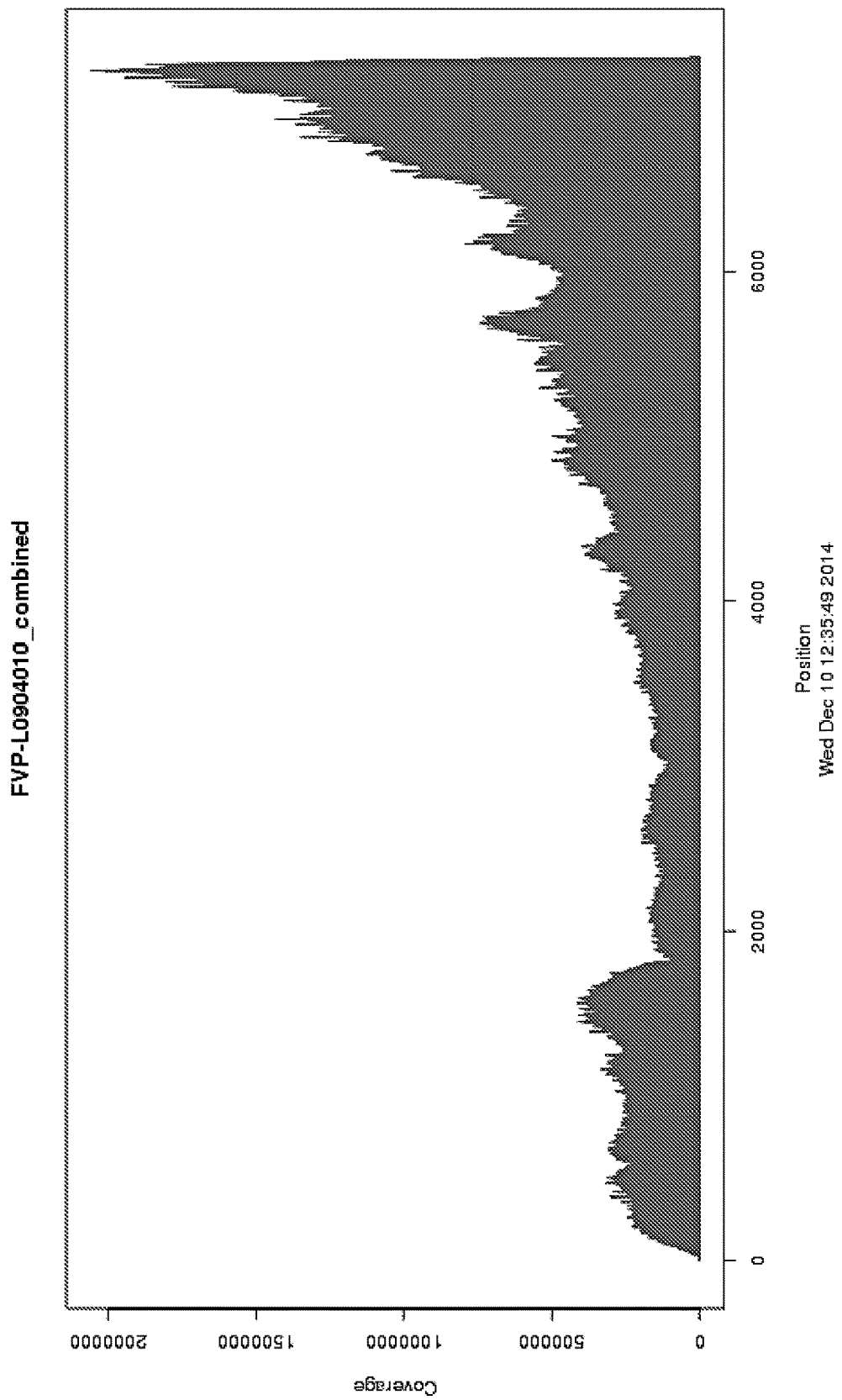
FIG. 7 shows coverage depth of PVSRIPO Final Vialed Product lot L0904010.
Figure 8:
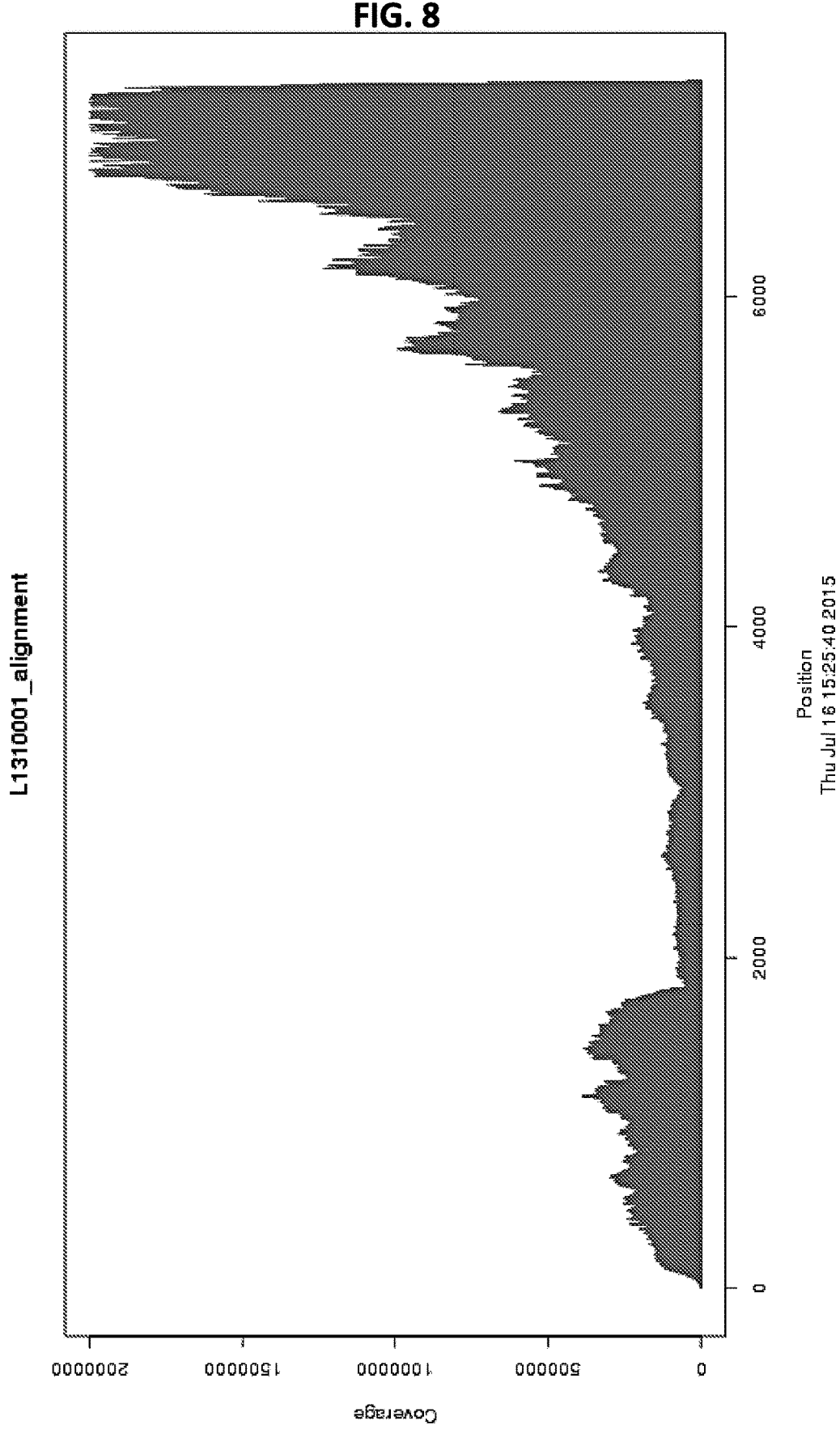
FIG. 8 shows coverage depth of PVSRIPO Reference Standard lot L1310001.
Figure 9:
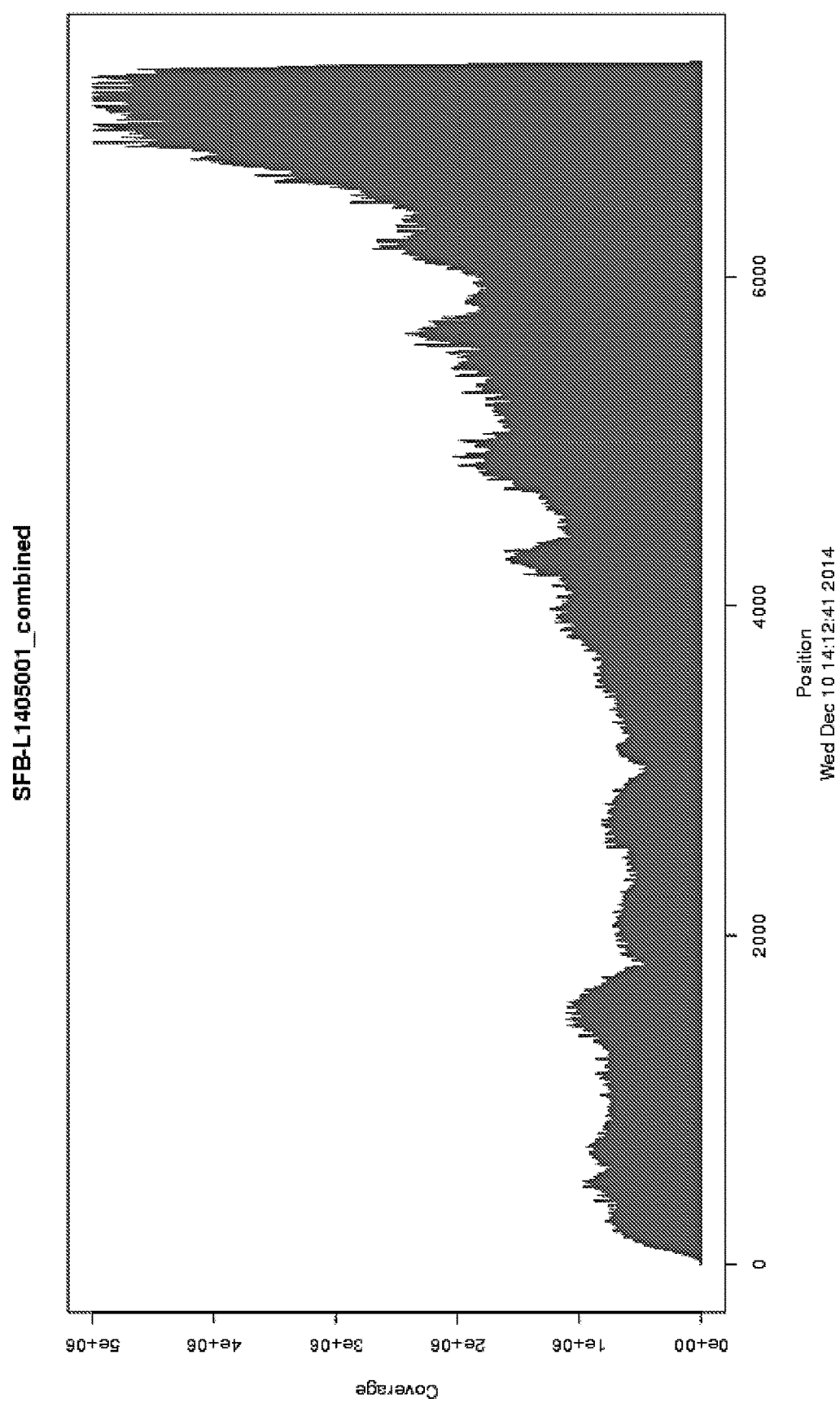
FIG. 9 shows coverage depth of PVSRIPO Purified Sterile Bulk Lot L1405001.
Figure 10:
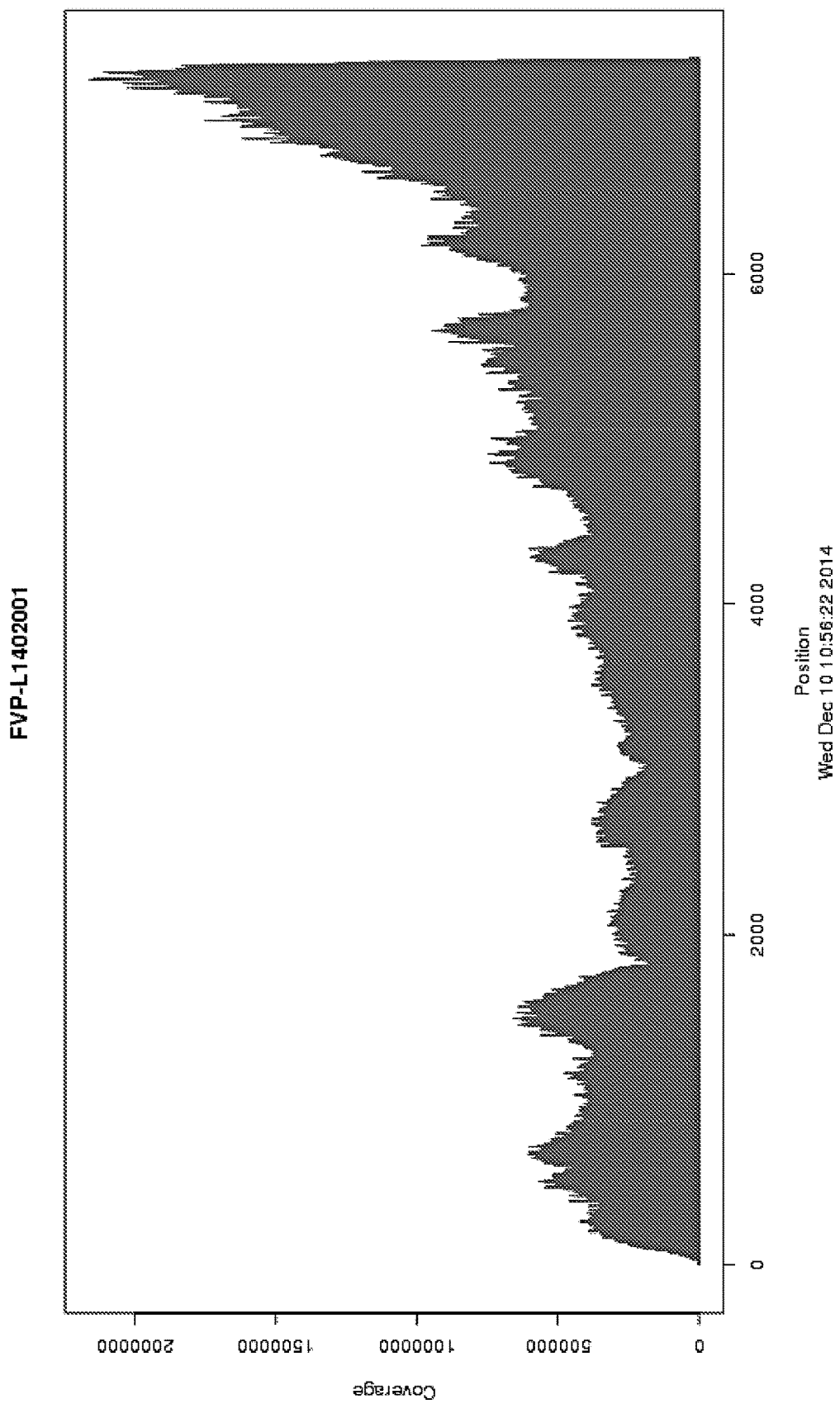
FIG. 10 shows coverage depth of PVSRIPO Final Vialed Product Lot L1402001.
Figure 11:
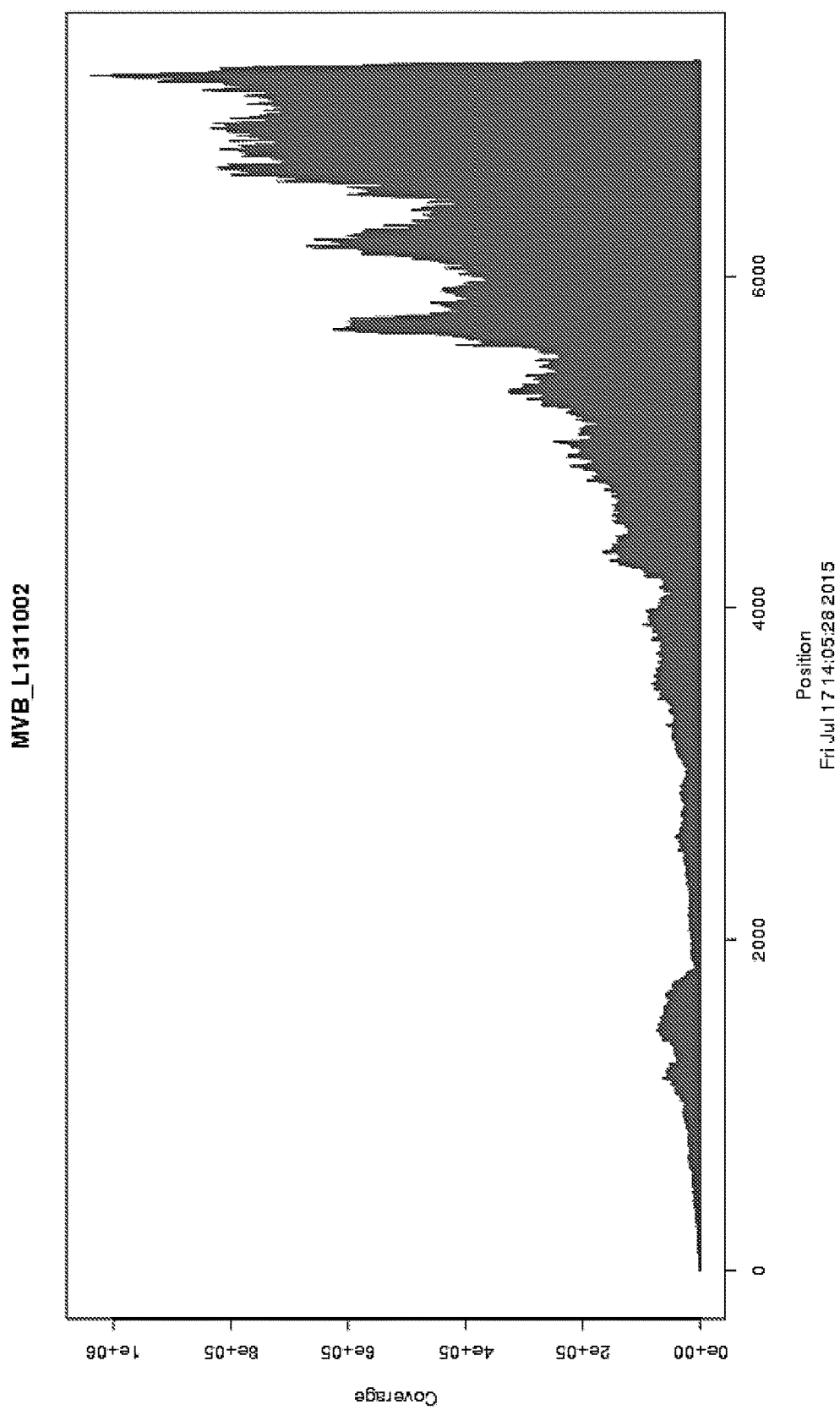
FIG. 11 shows coverage depth of PVSRIPO Master Viral Bank lot L131100.

Estimated coverage is shown in Table 5 for each fraction included in the dilution series. Coverage estimation does not reflect the true nature of a next generation sequencing experiment, as coverage varies from one base to the next, additional analyses were performed to describe the coverage across the reference sequence. An exemplary coverage plot is shown in FIG. 4. Full length coverage was achieved with the 1 ng input. The 5' end of the virus had less coverage than the other regions.

TABLE 5

Estimated coverage of the PVSRIPO genome for each dilution library based on read length and number of reads

| Dilution | Estimated Coverage |
| --- | --- |
| 10000 pg | 59307 |
| 750 pg | 53924 |
| 500 pg | 69249 |
| 250 pg | 82980 |
| 100 pg | 67564 |
| 75 pg | 107713 |
| 50 pg | 50500 |
| 25 pg | 45644 |
| 10 pg | 31662 |
| 5 pg | 39796 |
| 1 pg | 47633 |

Single Input Experiment

A second flow cell was run using a single 1000 pg sample. There were 171,001,369 reads in the sample, of which 87.2%% aligned to the reference sequence. The estimated coverage was 751,294 fold.

Example 7

Seven lots of PVSRIPO were analyzed using Illumina deep sequencing, three of which had been previously sequenced using RT-PCR (of ~1200 base sections of the viral genome) followed by Sanger fluorescent sequencing using ABI BigDye® Terminator chemistry with an ABI 3130xl sequencer. Initial NGS development efforts focused on identifying which method would provide the greatest depth of coverage while minimizing intrinsic error rates due to reverse transcription and pre-amplification prior to sequencing. A key criteria was to utilize PCR and sequencing primers that targeted sequences that were not part of the vial genome. This meant that adaptamers were used for any NGS method selected following viral cDNA fragmentation.

Prior Sanger sequencing methods utilized PCR pre-amplification and sequencing primers derived from the theoretical viral sequence and which directly targeted viral cDNA sequences. Despite the use of generously overlapping sequencing reads, the use of direct PCR and sequencing priming creates a strong bias in favor of the primer sequences used, effectively preventing recovery of any heterologous bases at the priming positions. This biasing effect is especially egregious at the extreme ends of the viral cDNA where overlapping reads are limited to a single direction. This effect leads to the inability to recover the extreme 3'-end of the viral sequence containing the polyadenylation signal, even when oligo dT priming is used for reverse transcription (RT). This inability to recover the extreme 3' sequence may be due to reduced fluorescent signal levels combined with an increase in sequence homogeneity (i.e., homopolymeric adenine) preventing accurate base calls in this region.

An NGS adaptamer approach was used to minimize any enzymatic limitations to recovering the extreme 3'-end of the virus, but it but requires a computationally intensive de novo genome assembly. Deep sequencing with the Illumina system utilized the 7303 nucleotide PVSRIPO MVB reference sequence as a guide to rapidly align and generate the viral genomic consensus sequence and to identify base variants. However, de novo alignments generated without the use of the reference sequence are expected to recover the extreme 3'-end of the virus and identify any large (>10 nt) indels present in the viral genome.

All lots of PVSRIPO since 2004 have utilized the Sanger sequence derived from the Master Viral Bank (Seed) lot L0403006 as the reference sequence. The MVB sequence was determined to be fully homologous to the source plasmid sequence (lot L0401014) using Sanger sequencing methods. The PVSRIPO samples analyzed for sequencing have fallen into four categories—purified plasmids, E. coli plasmid banks, crude Vero harvests and MVB lots, and purified virus. The extraction and preparation methods required for the four sample types differ by necessity. A summary is provided in Table 6.

TABLE 6

Summary of Sanger and NGS (Illumina) sequencing completed for PVSRIPO.

| PVSRIPO Process Stage | Lot Number | Sanger Sequencing | Illumina Sequencing | Comments |
| --- | --- | --- | --- | --- |
| Plasmid | L0401014 | QC-020658 | Not Conducted | N/A |
| MVB/Seed* (original MVB) | L0403006 | QC-022271 | QC-052548* | Acts as Ref. Seq. |
| Toxicology* | L0603006 | QC-029927 | QC-052548* | Derived from 2004 MVB lot |
| Clinical DS | L0904009 | QC-042162 | Not Conducted | Derived from 2004 MVB lot |
| Clinical DP | L0904010 | QC-042162 | QC-052908 | Derived from 2004 MVB lot |
| Reference Std. | L1310001 | Not Conducted | QC-052862 | Derived from 2004 MVB lot |
| MVB (new lot) | L1311002 | Conducted to recover extreme 5' end | QC-052647 | Second MVB lot, new manufacture from plasmid |
| Clinical DS (new lot) | L1405001 | Not Conducted | QC-053193 | Derived from 2004 MVB lot |
| Clinical DP (new lot) | L1402001 | Not Conducted | QC-053193 | Derived from 2004 MVB lot |

*Sequenced as part of the Illumina method development process (non-GLP).

Example 8

Results

To elucidate the location and extent of base heterogeneity in PVSRIPO, a deep sequencing approach was used. Previously PVSRIPO lots, including the plasmid and master viral bank materials, were analyzed by Sanger sequencing (2003-2009). As an alternative, an HTB-15 glioma cell passaging and plaque Sanger sequencing approach was conducted in 2007-2008 with six PVSRIPO isolates (Dobrikova et al. (2008) *Mol Ther* 16:1865-1872). This only identified two locations in the PVSRIPO genome (positions 97 and 1824) that exhibited polymorphic bases by Sanger sequencing (i.e., consisted of more than ~15% of the total viral population). The limited viral sequence variation observed in PVSRIPO by Sanger sequencing, including with post-passage plaque sequencing, indicated that PVSRIPO was more stable during propagation in Vero (and HTB-15 glioma cells) than would be expected of Polio wild-type or vaccine strains (Sanjuan et al. (2010) *J Virol* 84:9733-48). However, in order to clearly demonstrate the genetic stability of PVSRIPO, a deep sequencing approach capable of reporting individual (i.e., low copy) virion sequences in a given lot would be required. A review of commercial deep sequencing methods is detailed in Table 7 (Liu et al. (2012) *J Biomed Biotech* 2012:251364).

remaining lots. One of the results of optimization of the SMARTer ultra low-copy methods used with the MVB lots was to improve the RT fidelity and identify common RT error motifs later employed with the analysis of the 2013 MVB lot test. For this reason PVSRIPO lots L0403006 and L0603006 appear to have a higher volume of base positions with low-frequency polymorphisms (error rates) than other lots derived from the L0403006 MVB. Despite the higher background observed with the two lots used for method development, they both demonstrate patterns of polymorphism consistent with the other five lots tested.

A summary of the nucleic acid extractions and Nextera XT library preparation results are shown in Table 8. The two MVB banks (L0403006 and L01311002) both exhibit low extracted masses consistent with the lower copy numbers present in these samples as well as the much higher level of background host cell-derived nucleic acids. The observed averaged genome coverage depths for all seven lots ranged between $2.2 \times 10^5$ and $1.5 \times 10^6$, roughly 1-2 logs lower than the calculated theoretical maximum coverage based on the mass of recovered viral RNA.

TABLE 7

Summary of Sanger and deep sequencing methods relative to ssRNA virus preparations.

| Instrument/ Method | Advantages | Disadvantages | Notes |
|---|---|---|---|
| Sanger, Capillary with Terminator Dye (ABI 3130xl) | Robustness; Ready availability; Well understood; Long read lengths with high accuracy for non-polymorphic sequences | Requires high copy numbers for detection; Poor sensitivity to polymorphism (<20%); Typically relies on internal priming sites; Very limited depth of coverage | Used with PVSRIPO samples 2003-2009 and 5' end sequencing |
| Roche/454 FLX | Long read lengths (>700 bp) | Relatively low depth of coverage for NGS | Used with 5' end sequencing |
| Illumina HiSeq (with Nextera XT) | Highest depths of coverage (>1e9) possible; ideal for high-copy targets | Short read-lengths (~100 nt); may exhibit higher error rates than other methods | Used with PVSRIPO samples 2003-2009, except plasmid DNA |
| ABI SOLiD | Low error rate; intermediate depth of coverage | Very short read lengths makes assemblies difficult | Not used |
| ION Torrent PGM | Low cost; relatively simple to use | Highest error rates and lower coverage depths than Illumina HiSeq | Used with 5' end sequencing |

Given the short genomic length (<7400 nt) and high titer of virus (>$1 \times 10^9$ TCID$_{50}$/mL) in the purified PVSRIPO samples, an adaptamer library preparation with Illumina sequencing was selected as a methods that would generate high quality reads with concomitant high read depths from PVSRIPO samples (Neverov & Chumakov (2010) *PNAS USA* 107:20063-20068).

Initial method development activities were performed with the 2004 MVB lot (L0403006) and the 2006 non-clinical lot L0603006, several improvements to the general methods detailed above were made prior to testing the

TABLE 8

Summary of Illumina RNA extraction, observed and theoretical maximum coverage, and library construction results with PVSRIPO.

| PVSRIPO Lot Number | Total RNA Mass Extracted | Mean Library Size | Theoretical Maximum Coverage[1] | Observed Average Coverage[2] |
|---|---|---|---|---|
| L1311002 (MVB)[3] | 9.7 ng | 396 bp | ~$2 \times 10^6$ | $2.2 \times 10^5$ |
| L0403006 (MVB)[3,4] | 37.0 ng | ~300 bp | ~$1 \times 10^7$ | $1.4 \times 10^6$ |
| L0603006[4] | 228.8 ng | ~300 bp | ~$6 \times 10^7$ | $7.5 \times 10^5$ |
| L0904010 | 214.6 ng | 314 bp | ~$6 \times 10^7$ | $4.1 \times 10^5$ |
| L1310001 | 356.9 ng | 510 bp | ~$1 \times 10^8$ | $5.1 \times 10^5$ |

TABLE 8-continued

Summary of Illumina RNA extraction, observed and theoretical maximum coverage, and library construction results with PVSRIPO.

| PVSRIPO Lot Number | Total RNA Mass Extracted | Mean Library Size | Theoretical Maximum Coverage[1] | Observed Average Coverage[2] |
|---|---|---|---|---|
| L1405001 | 376.4 ng | 352 bp | ~1 × 10$^8$ | 1.5 × 10$^6$ |
| L1402001 | 348.5 ng | 315 bp | ~1 × 10$^8$ | 5.7 × 10$^5$ |

[1]Based on RNA extraction recovery and volumetric ratios of subsequent cDNA synthesis and sequencing steps, assuming 100% of the total RNA input mass consists of PVSRIPO viral RNA.
[2]Calculated average coverage of all bases from reads that align to the PVSRIPO reference sequence, assuming an equal depth of coverage across the 7303 bases of the viral reference genome.
[3]MVB lots are not column purified and have a larger percentage of host cell nucleic acids, impacting viral RNA extraction yields.
[4]Illumina method development study results. RNA extraction and cDNA synthesis methodologies are similar but not identical to those used with later GLP studies.

As detailed in Table 9, mean read lengths for the various lots ranged between 88 and 108 bp with more than one gigabase sequenced for each lot. The percentage of reads that aligned to the Sanger-derived MVB reference sequence was, in all cases, between 85% and 93%, with the vast majority of the non-aligned reads corresponding to Vero cell mtDNA, gDNA, and mRNA sequences, as determined by nBLAST using a random selection of non-aligned reads. A small fraction of the non-aligned reads represent extreme viral 3' end sequences missing from the reference and may potentially contain even rarer (and so far unobserved) viral sequences that may harbor 'large' (>10 nt) indels that do not readily align to the PVSRIPO reference sequence. Computationally intensive de novo viral genome assemblies are being pursued to identify and characterize any large indels (if present) and the 3' terminal sequence heterogeneity of PVSRIPO. Also shown in Table 9 is the number of base positions for each lot that exceed the 'called variant threshold' level—this threshold is >0.1% across the majority of the PVSRIPO genome where depths exceed 4096 reads per base.

TABLE 9

Summary of Illumina read depths, read lengths, reference sequence alignment scores, and variant position ratios for seven lots of PVSRIPO.

| PVSRIPO Lot Number | Total Bases Sequenced[1] | Mean Read Length | Percent Alignment of Reads to the Reference Sequence | Number of Called Variant Bases Positions[2] | Ratio of Variant Positions to Bases Sequenced[3] |
|---|---|---|---|---|---|
| L1311002 (MVB) | 1.61 × 10$^9$ | 88.9 bp | 88.7% | 27 | 1:5.96 × 10$^7$ |
| L0403006 (MVB)[4] | 1.07 × 10$^{10}$ | 94.3 bp | 93.1% | 2183 | 1:4.90 × 10$^6$ |
| L0603006[4] | 6.29 × 10$^9$ | 88.2 bp | 87.2% | 461 | 1:1.36 × 10$^7$ |
| L0904010 | 3.47 × 10$^9$ | 97.3 bp | 85.7% | 50 | 1:6.94 × 10$^7$ |
| L1310001 | 4.06 × 10$^9$ | 88.0 bp | 91.5% | 29 | 1:1.40 × 10$^8$ |
| L1405001 | 1.27 × 10$^{10}$ | 108.3 bp | 86.8% | 331 | 1:3.84 × 10$^7$ |
| L1402001 | 4.75 × 10$^9$ | 106.7 bp | 87.6% | 112 | 1:4.24 × 10$^7$ |

[1]Including reads that did not align to the reference sequence.
[2]For positions with read depths >4096, the polymorphism 'call' threshold is set to ≥0.1%; for read depths ≤4096, the threshold is set to ≥1.0%.
[3]A gross measure of the combined base polymorphism + method error rate.
[4]Illumina method development study results. RNA extraction and cDNA synthesis methodologies are similar but not identical to those used with later GLP studies and have attendant higher error rates.

A larger number of polymorphic base positions are observed for lots with greater read depths and especially for the two lots used with the Illumina method. Not including the two method development lots (L0403006 and L0603006), the number of called variant base positions ranges between 27 and 331 in the remaining five lots tested. The 5' end hyper-variable region of the PVSRIPO (and polio) genome lies within positions 1 through 34; as expected, and despite (or perhaps because of) the low read depths, this is the region of the viral genome that exhibits the highest frequency of base variants and polymorphisms as detailed in Table 10. Table 10 also breaks down the number of polymorphic and variant base positions in each major region of the PVSRIPO genome, with the majority occurring in the polio polyprotein coding sequence—the largest element within the viral genome.

TABLE 10

Comparison of sequence variant frequencies and locations (base positions) in seven lots of PVSRIPO using Illumina deep sequencing.

| PVSRIPO Lot Number | Number of Called Variant Bases Positions (Total) | Percent Variant Base Reads[1] | Percent of Variant Base Positions/ Genome[2] | Variant Bases Positions in 5' Terminus (1-34) | Variant Base Positions in IRES (35-622) | Variant Base Positions in IRES V/VI Domains (450-622)[3] | Variant Base Positions in Polyprotein CDS (623-7255) | Variant Base Positions in 3' UTR (7256-7303+) |
|---|---|---|---|---|---|---|---|---|
| L1311002 (MVB) | 27 | 0.007% | 0.37% | 10 | 2 | 0 | 15 | 0 |
| L0403006 (MVB)[4] | 2183 | 0.189% | 29.9% | 25 | 18 | 0 | 2109 | 31 |
| L0603006[4] | 461 | 0.080% | 6.31% | 9 | 3 | 1 | 442 | 7 |
| L0904010 | 50 | 0.013% | 0.68% | 11 | 0 | 0 | 37 | 2 |
| L1310001 | 29 | 0.007% | 0.40% | 4 | 1 | 1 | 22 | 2 |
| L1405001 | 331 | 0.033% | 4.53% | 10 | 6 | 1 | 308 | 7 |
| L1402001 | 112 | 0.025% | 1.53% | 11 | 1 | 1 | 97 | 3 |

[1]Total number of called variant base reads as a percentage of the total number of aligned bases read across the genome. An alternative gross measure of the combined base polymorphism + method error rate.
[2]Frequency of called base variants as a percentage of the reference genome length (MVB reference standard sequence of 7303 nucleotides without the 29 base 3' UTR terminal sequence.)
[3]Key IRES domains for mediating interaction between the viral genome and eIF4G-ribosome complex. Sequence polymorphisms in this region of the genome are most likely to result in potential modifications to intra-cellular tropism and viral expression.
[4]Illumina method development study results. RNA extraction and cDNA synthesis methodologies are similar but not identical to those used with later GLP studies.

The most critical region for changes in intra-cellular viral tropism and pathogenicity are the IRES domains V and VI which mediate binding and assembly of the eIF4G-rbosomal complex. In this region of PVSRIPO only a single polymorphism (at position 618) was observed in four of the seven lots analyzed (Table 11). Three of the lots were not found to be polymorphic at position 618 as the canonical guanine consisted of >99.9% of all reads; while for the remaining four lots, >97% of all reads at position 618 were guanine. The four lots exhibiting polymorphism at position 618 have the identical substitution pattern (G>>T>A>C). Polymorphism at position 618 was not observed in the parental MVB lot (L0403006) or in the L0904010 clinical lot despite the observation of polymorphism at 618 in four lots derived from the MVB. Whether this conversion represents a true sequence mutation at position 618 during viral expansion in manufacturing or is a preferential site for polymerase substitution during the sequencing process cannot be immediately determined, although the frequency is sufficiently high (up to 2.6%) to suggest the former. Interestingly, the PVSRIPO lot which exhibited the greatest substitution (2.6%) at position 618 was the non-clinical toxicology lot L0603006. This lot was used with prior in vivo animal and xenographic studies that demonstrated the non-pathogenic phenotype and stable genotype of PVSRIPO. As detailed in Table 11, only a total of 5 sequence variation sites were observed in more than one lot of PVSRIPO and only two of these are found in the MVB lots. All of the five positions are located in the 5' UTR IRES at positions: 35, 60, 80, 340, and 618. The preferred substitution patterns of the 5 sites are also conserved, most critically between the two polymorphic sites (positions 35 and 60) present in the independently generated Master Viral Banks.

TABLE 11

All five PVSRIPO IRES sequence variants that are observed in more than one lot, including a comparison of polymorphic base substitution patterns where present. Reference sequence cDNA bases are shown the column header for each position.

| PVSRIPO Lot Number | Position 35 (Ref.—G) | Position 60 (Ref.—T) | Position 80 (Ref.—C) | Position 340 (Ref.—A) | Position 618[1] (Ref.—G) |
|---|---|---|---|---|---|
| L1311002 (MVB) | G 97.5%<br>C 2.5% | T 98.4%<br>G 1.6% | C ≥99.9% | A ≥99.9% | G ≥99.9% |
| L0403006 (MVB) | G 98.5%<br>C 1.0%<br>A 0.5%<br>T N/D[2] | T 98.5%<br>G 0.7%<br>A 0.4%<br>C 0.4% | C ≥99.9% | A ≥99.9% | G ≥99.9% |
| L0603006 | G ≥99.9% | T ≥99.9% | C 97.7%<br>G 2.2%<br>T 0.1%<br>A <0.1% | A 99.0%<br>T 0.5%<br>G 0.4%<br>C <0.1% | G 97.4%<br>T 2.5%<br>A <0.1%<br>C <0.1% |
| L0904010[3] | G ≥99.9% | T ≥99.9% | C ≥99.9% | A ≥99.9% | G ≥99.9% |
| L1310001 | G ≥99.9% | T ≥99.9% | C ≥99.9% | A ≥99.9% | G 98.1%<br>T 1.8%<br>A <0.1%<br>C <0.1% |
| L1405001[4] | G 91.0%<br>C 8.9%<br>T 0.1%<br>A <0.1% | T ≥99.9% | C 97.9%<br>G 2.1%<br>T 0.3%<br>A 0.2% | A 99.1%<br>T 0.5%<br>G 0.4%<br>C <0.1% | G 98.9%<br>T 1.1%<br>A <0.1%<br>C <0.1% |

TABLE 11-continued All five PVSRIPO IRES sequence variants that are observed in more than one lot, including a comparison of polymorphic base substitution patterns where present. Reference sequence cDNA bases are shown the column header for each position.

| PVSRIPO Lot Number | Position 35 (Ref.—G) | Position 60 (Ref.—T) | Position 80 (Ref.—C) | Position 340 (Ref.—A) | Position 618[1] (Ref.—G) |
|---|---|---|---|---|---|
| L1402001[4] | G ≥99.9% | T ≥99.9% | C ≥99.9% | A ≥99.9% | G 99.0% <br> T 1.0% <br> A <0.1% <br> C <0.1% |

[1]Position 618 was the only base polymorphism observed within the key IRES Domains V and VI.
[2]N/D—None Detected.
[3]PVSRIPO Clinical DP lot L0904010 exhibited no 'above threshold' base polymorphisms within the IRES region of the viral genome (positions 35-622). Reads depths in this region increase in the 3' direction and varied for each lot with depths ranging between ~2 × 10² to ~8 × 10⁵ reads/base position. Refer to the appendixes for additional details for each lot.
[4]Lots L1405001 and L1402001 consist of the identical purified virus (bulk DS vs. vialed DP) but lot L1402001 only exhibits one of the base polymorphisms observed in L1405001. The primary difference between these two runs was the ~2-fold increase in read depth achieved with L1405001. The reason for the large discrepancy in % G at positon 35 is unknown, but may be tied to a significant G > A polymorphism present at position 34 and the end of the hyper-variable 5'UTR region.

The read depths across the 5' half of the genome containing the IRES (positions 35-622) are lower than the average due to RT exhaustion and the stronger secondary structure of the IRES domains. Despite these effects on RT efficiency, the read depths still range between $10^3$ and $10^5$ reads per base position in the IRES domains. Intriguingly, the two polymorphic positions identified in the 2010 HTB-15 xenograph study (positions 97 and 1824) were not identified as polymorphic in the Illumina deep sequencing with PVSRIPO, including lot L0603006, suggesting they were the result of de novo base mutations following passaging in the HTB-15 xenographs. Position 1824 falls within an internal homopolymeric adenine stretch prone to mutation, but which may also be partially masked by internal Oligo-dT priming during Illumina sample preparation (see below).

PVSRIPO Illumina read depths decrease rapidly when progressing from the 3' UTR (and the poly-A first strand priming site) to the 5' UTR and hyper-variable region at the 5' terminus (FIGS. 4 and 6-11). This drop in coverage occurs due to RT stalling, which can be observed as periodic spikes in the coverage depth, and by RT exhaustion when progressing from the 3' first strand priming site. Fortunately, PVSRIPO contains an 11 base internal poly-adenine stretch at positions 1822-1833 (with a single intervening guanine at position 1831) acting as an alternative internal oligo-dT priming site for first strand synthesis; albeit at a much lower extension efficiency than the 3' poly-adenine signal. The presence of the internal poly-adenine site allows for a ~3-fold increase in read depths below position 1822, including the key IRES domains.

One or more PVSRIPO-specific first strand primer sequences can be used to improve read depths and sequence coverage below positions ~4000 and ~2000 in the viral genome. Due to the rapid decay in read depths near the 5' terminus, especially in the presence of the high host-cell background in the 2013 MVB lot, several other approaches were utilized to verify the viral sequence in this region (positions 1 to ~60). Initially ION Torrent and FLX pyrosequencing NGS approaches were tried with minimal improvement in depths below position ~35 in the genome. Ultimately the extreme 5' end (below position 10) could not be recovered in depths >3 reads per base using NGS methods even with linear PCR 'amplification' using a 3' PCR priming site. While the rapid reduction 5' terminal read depths was observed with the purified lots of PVSRIPO, it most severely impacted the lower concentration and higher host cell background MVB lots.

As a fallback approach to recover the first ~20 bases at the 5' end of 2013 MVB lot L1311002, it was sequenced using Sanger methods and PVSRIPO-specific geometric PCR amplification primers. Unfortunately this approach resulted in the recovery of the PCR primer sequences rather than the true sequences present in the viral cDNA sample. This effect is typified by the sole identification of base position 1 as thymine rather than adenine. Thymine is present at position 1 in the 5' PCR primer and is incorrectly identified as the first base in the Sanger-derived reference sequence. Adenine has been verified by unbiased Illumina and other NGS methods to be the true base at position 1 in the PVSRIPO genomic cDNA. The use of PVSRIPO-specific first-strand primers targeting a base position below ~2000 will allow for improved cDNA copy numbers at the extreme 5' end and greatly improved read depths, obviating the need for supplementary Sanger sequencing approaches with unpurified low concentration viral samples such harvests, seed stocks, and banks.

Table 12 compares the published replication error rates for wild-type polio as well as the estimated incorporation error rates for the various polymerases used with the deep sequencing of PVSRIPO. The estimated error rate of native polio base incorporation is $\sim 9\times 10^{-5}$ to $\sim 9\times 10^{-6}$ while the error rate for the two RT approaches with Illumina amplification and sequencing is estimated at $\sim 5\times 10'$, equivalent to 0.05%. Therefore the rate of base incorporation error in the sequencing method is expected to be ~5 to 55 times more error prone than the native viral replication error rate in infected cells.

TABLE 12

Comparison of reported and observed error rates of polio virus, polymerases, and PVSRIPO lots.

| Organism | Used with Method Procedure | Reported Incorporation or Replication Error Rates | Notes |
|---|---|---|---|
| Wild-type Polio (Sabin)[1] | N/A - In vivo rate | A. ~$8.9 \times 10^{-6}$<br>B. ~$9.0 \times 10^{-5}$ | A. Error rate per strand replication<br>B. Error rate per cell infection |
| Polymerase:[2] | | | |
| ThermoScript AMV RT | First-Strand Synthesis | ~$1.0 \times 10^{-5}$ | Used with purified PVSRIPO lots |
| SMARTScribe RT | MVB First Strand Syn. | Est. ~$3 \times 10^{-5}$ | Used with MVB lots |
| NEBNext (high fidelity) | Second Strand Synthesis | ~$2.5 \times 10^{-6}$ | Used with purified PVSRIPO lots |
| SMARTer Titanium Taq DNA Polymerase Mix | Second Strand/ Amplification | ~$8.0 \times 10^{-5}$ | Used with MVB lots |
| Nextera XT high fidelity Polymerase | Library Amplification (12 cycles) | Est. ~$2.0 \times 10^{-6}$ per cycle (Est. ~$2 \times 10^{-5}$ per amp.) | Used with all PVSRIPO lots |
| Overall Sequencing Procedure: | | Estimated Method Error Rate: | |
| Combined Error Rate (Estimated value) | All PVSRIPO lots | Est. ~$5 \times 10^{-4}$ (1:2000 or 0.05%) | Limited by fidelity of RT Step |
| PVSRIPO Lots: | | Observed Error Rates: | |
| Lot L0403006 (MVB) | SMARTScribe RT | $1.9 \times 10^{-3}$ (0.19%) | Early development method |
| Lot L0603006 (Tox) | ThermoScript AMV RT | $8.0 \times 10^{-4}$ (0.08%) | Early development method |
| Lot L0904010 (DP) | ThermoScript AMV RT | $1.3 \times 10^{-4}$ (0.01%) | N/A |
| Lot L1310001 (Ref Std) | ThermoScript AMV RT | $6.7 \times 10^{-5}$ (0.01%) | N/A |
| Lot L1405001 (DS) | ThermoScript AMV RT | $3.3 \times 10^{-4}$ (0.03%) | N/A |
| Lot L1402001 (DP) | ThermoScript AMV RT | $2.5 \times 10^{-4}$ (0.03%) | N/A |
| Averaged Error Rate: | N/A | $5.8 \times 10^{-4}$ (0.06%) | For all lots derived from, and including, MVB L0403006 |
| Second MVB Lot: | | | |
| Lot L1311002 (MVB) | SMARTScribe RT | $7.2 \times 10^{-5}$ (0.01%) | Second plasmid derived MVB lot |

[1]Refer to Sanjuan et al. (2010) *J Virol* 84: 9733-48 for additional details.
[2]Refer to McInerney et al. Z (2014) Mol Biol Intl 2014: 287430; Das et al. (2001) Physiol Genomics 6: 57-80; and manufacturer's literature values.

The observed error rates for the aligned sequences in the seven lots of PVSRIPO analyzed range from 0.19% to 0.8% for the early method development lots and 0.01% to 0.03% for the lots using the final sequencing methodologies. No clear difference in error rates were seen between the unpurified MVB, lot L1311002, and purified virus lots. Since these rates are generally below the estimated worse-case error rate for the sequencing method at 0.05%, it cannot be discounted that many of the lower frequency variants observed are in fact the result of polymerase incorporation errors and not representative of true viral sequence variation. This appears to be especially true in the pre-optimization 2004 MVB and 2006 toxicology lots based on the high frequency of polymorphic bases observed. One interesting observation is the increase in polymorphic bases identified (i.e. >0.1% variation) as a function of increasing read depth; this is especially apparent at the 3' end of the viral genome (containing the native polio polymerase CDS and 3' UTR region). Many of the base variants in this region are likely the result of polymerase incorporation errors and not true viral polymorphisms. Additional analysis of the data is underway to further characterize these variants in an effort to identify sequence motifs that promote polymerase misincorporation events during the in vitro polymerization and amplification steps in the sequencing method.

Additional information is provided in FIGS. 5A-5NN, which shows the results from PVSRIPO MVB.

DISCUSSION

The 7 lots of PVSRIPO virus examined by Illumina deep sequencing exhibited surprisingly limited sequence microheterogeneity across the chimeric viral genome with average read depths in excess of $2\times10^5$ per base. The sequence variation observed, with the exception of the extreme 5' terminal end, was shown to consist of <1% total heterogeneous base calls relative to the canonical reference sequence and only 5 polymorphic positions were observed repeatedly in more than one lot of PVSRIPO. These five recurrent heterogeneous positions were all located within the HRV2 IRES (positions 35, 60, 80, 340, and 618) and their associated base substitution patterns were observed to be consistent across all of the lots tested. This indicates that the limited variation present in the clinical lots of PVSRIPO is derived from the variation originally present in the parental MVB lot (i.e., positions 35 and 60) or may represent preferred modes of polymerase mis-incorporation during viral replication or cDNA sequencing. The plasmid DNA used to generate the MVB via in vitro transcription and transfection may be a third source of the base variation pattern observed in the seven PVSRIPO lots.

The NGS of PVSRIPO validates prior analytical and neurotoxicity data which indicate PVSRIPO is a surprisingly stable single-stranded RNA virus. Therefore, extensive in vivo non-human primate neurotoxicity studies may not be necessary prior to the use of the second MVB lot of PVSRIPO (Lot L1311002) given the low level of micro-heterogeneity observed and the consistency of its' sequence variation pattern with the earlier clinical lots of PVSRIPO derived from the first MVB manufactured in 2004. Additional sequencing development efforts are either underway (i.e., de novo assemblies for recovery of the 3' UTR sequence) or are warranted to improve the depth of coverage at the key 5' UTR of the viral sequence. Since the unique characteristics of PVSRIPO relative to wild-type poliovirus is due to the presence of the HRV2-derived IRES, further post-administration deep sequencing studies using NHP or patient-derived samples can be used to determine the rates of mutation and the potential for HRV2 IRES recombination in clinically relevant in vivo settings.

The results provided herein provide a baseline against which future clinical studies can be compared. The lack of significant base heterogeneity in the IRES region, including in the 2013 MVB lot L1311002 and in the five lots expanded in Vero cells during manufacturing, verifies that PVSRIPO is genetically stable and that changes in viral expression, phenotype, and pathogenicity between lots are unlikely when using a well characterized MVB.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as my invention all that comes within the scope and spirit of these claims.

We claim:

1. A method of assaying a polio virus-derived therapeutic for a polio viral sequence variant, comprising:

extracting RNA from a master viral bank or a working cell bank, wherein the master viral bank or the working cell bank comprises host cells containing the polio virus-derived therapeutic;

contacting the extracted RNA with 4 U of DNase at 2 U/µl for 20-40 minutes at 37° C. under conditions that substantially digest host cell genomic DNA and host cell mitochondrial DNA, but do not substantially digest viral RNA molecules, thereby generating enriched viral RNA;

inactivating the DNase;

producing double-stranded cDNA from the enriched viral RNA using oligo(dT)x primers, thereby generating viral double-stranded cDNA;

amplifying the viral double-stranded cDNA;

quantifying the viral double-stranded cDNA;

producing a sequencing library from 500 pg to 1 ng of the viral double-stranded cDNA by randomly fragmenting the double-stranded cDNA to produce cDNA fragments, ligating 5' adaptors and 3' adaptors to the cDNA fragments to produce adaptor-ligated cDNA fragments, and amplifying the adaptor-ligated cDNA fragments to produce the sequencing library;

clonally amplifying the sequencing library using surface-bound oligonucleotides complementary to the 5' adaptors and the 3' adaptors to produce a clonally amplified sequencing library;

sequencing the clonally amplified sequencing library using parallel single-end or paired-end sequencing to produce a raw sequence dataset comprising a plurality of sequence reads;

aligning the plurality of sequence reads with a reference polio sequence for the polio virus-derived therapeutic to produce an aligned sequence containing a plurality of aligned sequence reads; and determining polio viral sequence variants from the aligned sequence.

2. The method of claim 1, wherein the method further includes determining for the plurality of aligned sequence reads, a mean read length, percentage of aligned reads, coverage, SNPs, or a combination thereof.

3. The method of claim 1, wherein when an unaligned sequence read is produced, the unaligned sequence read is added to a pool of unaligned sequence reads for identification.

4. The method of claim 1, wherein the method further comprises reporting consensus homology for the polio virus-derived therapeutic to the reference sequence for the polio virus-derived therapeutic, coverage per base per position, heterogeneous bases at greater than 0.1% of reads per base position, or a combination thereof.

5. The method of claim 1, wherein producing the sequencing library from the viral double-stranded DNA comprises:

randomly fragmenting the viral double-stranded DNA to produce DNA fragments, ligating 5' adaptors and 3' adaptors to the DNA fragments to produce adaptor-ligated DNA fragments, and amplifying the adaptor-ligated DNA fragments to produce the sequencing library; and clonally amplifying the sequencing library using surface-bound or particle-bound oligonucleotides complementary to the 5' adaptors and the 3' adaptors to produce a clonally amplified sequencing library;

wherein the clonally amplified sequencing library is sequenced to produce the raw sequence dataset comprising a plurality of sequence reads.

6. The method of claim 1, further comprising:

administering the sequenced polio virus-derived therapeutic to a subject if the determined polio viral sequence variants are not contraindicated.

7. The method of claim 1, wherein the host cells are *E. coli* cells or Vero cells.

8. The method of claim 1, wherein contacting the extracted RNA with 4U of DNase at 2 U/μl comprises incubating the extracted RNAs with the 4U DNase at 2 U/μl for 30 minutes at 37° C.

9. The method of claim 1, wherein clonally amplifying the sequencing library further comprises adding barcodes to the adaptor-ligated cDNA fragments during amplification.

10. The method of claim 7, wherein clonally amplifying the sequencing library comprises bridge amplification and the surface comprises a surface of a flow cell.

11. The method of claim 1, wherein the sequencing is parallel paired-end sequencing.

12. The method of claim 4, wherein reporting comprises coverage per base per position.

13. The method of claim 1, further comprising determining that the aligned sequence is acceptable for screening the polio virus-derived therapeutic when the coverage of each base in the aligned sequence is 4× or greater.

14. The method of claim 1, further comprising determining that the coverage of each base in the aligned sequence is less than 4× and performing Sanger Sequencing to provide coverage of 4× or greater across the entire aligned sequence.

15. The method of claim 1, wherein the polio viral sequence variant comprises a mutation in an internal ribosome entry site (IRES).

16. The method of claim 1, wherein the polio virus-derived therapeutic is or is derived from polio vaccine PVS-RIPO.

17. The method of claim 1, further comprising:

introducing the polio virus-derived therapeutic into Vero host cells;

growing the Vero host cells under conditions that allow propagation of the polio virus-derived therapeutic;

extracting polio RNA molecules from the Vero host cells;

optionally contacting the extracted polio RNA with DNase under conditions that substantially digest Vero host cell genomic DNA and Vero host cell mitochondrial DNA, but do not substantially digest polio RNA;

reverse transcribing the extracted viral polio RNA, thereby generating polio double-stranded DNA;

amplifying the polio double-stranded cDNA;

quantifying the polio double-stranded cDNA;

producing a sequencing library from 500 pg to 1 ng of the polio double-stranded cDNA by randomly fragmenting the polio double-stranded cDNA to produce polio cDNA fragments, ligating 5' adaptors and 3' adaptors to the polio cDNA fragments to produce adaptor-ligated polio cDNA fragments, and amplifying the adaptor-ligated polio cDNA fragments to produce the sequencing library;

clonally amplifying the sequencing library using surface-bound oligonucleotides complementary to the 5' adaptors and the 3' adaptors to produce a clonally amplified sequencing library;

sequencing the clonally amplified sequencing library using parallel single-end or paired-end sequencing to produce a raw sequence dataset comprising a plurality of sequence reads;

aligning the plurality of sequence reads with a reference polio sequence for the polio virus-derived therapeutic to produce an aligned sequence containing a plurality of aligned sequence reads; and determining polio viral sequence variants from the aligned sequence.

* * * * *

SEQUENCE LISTING

<160> NUMBER OF SEQ ID NOS: 80

<210> SEQ ID NO 1
<211> LENGTH: 19
<212> TYPE: DNA
<213> ORGANISM: Artificial sequence
<220> FEATURE:
<223> OTHER INFORMATION: Synthetic primer

<400> SEQUENCE: 1
caaacaatgg acaaggtgt                                                    19

<210> SEQ ID NO 2
<211> LENGTH: 18
<212> TYPE: DNA
<213> ORGANISM: Artificial sequence
<220> FEATURE:
<223> OTHER INFORMATION: Synthetic primer

<400> SEQUENCE: 2
tcctgataaa aacatccc                                                     18

<210> SEQ ID NO 3
<211> LENGTH: 19
<212> TYPE: DNA
<213> ORGANISM: Artificial sequence
<220> FEATURE:
<223> OTHER INFORMATION: Synthetic primer

<400> SEQUENCE: 3
attcgccgta ccagagatg                                                    19

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
tgtgagttca atggattaag                                               20

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
tgttctgtgg atccatgatg                                               20

<210> SEQ ID NO 6
<211> LENGTH: 19
<212> TYPE: DNA
<213> ORGANISM: Artificial sequence
<220> FEATURE:
<223> OTHER INFORMATION: Synthetic primer

<400> SEQUENCE: 6
ccgtgaaacg gtggggcg                                                 19

<210> SEQ ID NO 7
<211> LENGTH: 19
<212> TYPE: DNA
<213> ORGANISM: Artificial sequence
<220> FEATURE:
<223> OTHER INFORMATION: Synthetic primer

<400> SEQUENCE: 7
gggcatgcct taaatcaag                                                19

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
gccctggagt ggattacaag                                               20

<210> SEQ ID NO 9
<211> LENGTH: 21
<212> TYPE: DNA
<213> ORGANISM: Artificial sequence
<220> FEATURE:
<223> OTHER INFORMATION: Synthetic primer

<400> SEQUENCE: 9
caaggtgaca gttggttgaa g                                             21

<210> SEQ ID NO 10
<211> LENGTH: 19
<212> TYPE: DNA
<213> ORGANISM: Artificial sequence
<220> FEATURE:
<223> OTHER INFORMATION: Synthetic primer

<400> SEQUENCE: 10
caggtaaatc tgtagcaac                                                19

<210> SEQ ID NO 11
<211> LENGTH: 20

```
<212> TYPE: DNA
<213> ORGANISM: Artificial sequence
<220> FEATURE:
<223> OTHER INFORMATION: Synthetic primer

<400> SEQUENCE: 11
tgaaatgtgt aagaactgtc                                            20

<210> SEQ ID NO 12
<211> LENGTH: 19
<212> TYPE: DNA
<213> ORGANISM: Artificial sequence
<220> FEATURE:
<223> OTHER INFORMATION: Synthetic primer

<400> SEQUENCE: 12
gcagtggctg gagttgtct                                             19

<210> SEQ ID NO 13
<211> LENGTH: 20
<212> TYPE: DNA
<213> ORGANISM: Artificial sequence
<220> FEATURE:
<223> OTHER INFORMATION: Synthetic primer

<400> SEQUENCE: 13
ctgagacaaa tgatggagtc                                            20

<210> SEQ ID NO 14
<211> LENGTH: 19
<212> TYPE: DNA
<213> ORGANISM: Artificial sequence
<220> FEATURE:
<223> OTHER INFORMATION: Synthetic primer

<400> SEQUENCE: 14
aaacgatccc aggcttaag                                             19

<210> SEQ ID NO 15
<211> LENGTH: 21
<212> TYPE: DNA
<213> ORGANISM: Artificial sequence
<220> FEATURE:
<223> OTHER INFORMATION: Synthetic primer

<400> SEQUENCE: 15
cctacaaggg catagattta g                                          21

<210> SEQ ID NO 16
<211> LENGTH: 18
<212> TYPE: DNA
<213> ORGANISM: Artificial sequence
<220> FEATURE:
<223> OTHER INFORMATION: Synthetic primer

<400> SEQUENCE: 16
attgctccca gagtactc                                              18

<210> SEQ ID NO 17
<211> LENGTH: 21
<212> TYPE: DNA
<213> ORGANISM: Artificial sequence
<220> FEATURE:
<223> OTHER INFORMATION: Synthetic primer

<400> SEQUENCE: 17
```
tggcattact ggatgaataa g       21

<210> SEQ ID NO 18
<211> LENGTH: 20
<212> TYPE: DNA
<213> ORGANISM: Artificial sequence
<220> FEATURE:
<223> OTHER INFORMATION: Synthetic primer

<400> SEQUENCE: 18
tctccgaatc cgattttctc       20

<210> SEQ ID NO 19
<211> LENGTH: 18
<212> TYPE: DNA
<213> ORGANISM: Artificial sequence
<220> FEATURE:
<223> OTHER INFORMATION: Synthetic primer

<400> SEQUENCE: 19
tcgcttcagg gccgctgc       18

<210> SEQ ID NO 20
<211> LENGTH: 19
<212> TYPE: DNA
<213> ORGANISM: Artificial sequence
<220> FEATURE:
<223> OTHER INFORMATION: Synthetic primer

<400> SEQUENCE: 20
ggtgaagcgt gggttggta       19

<210> SEQ ID NO 21
<211> LENGTH: 20
<212> TYPE: DNA
<213> ORGANISM: Artificial sequence
<220> FEATURE:
<223> OTHER INFORMATION: Synthetic primer

<400> SEQUENCE: 21
caggaggggg actcgtcttg       20

<210> SEQ ID NO 22
<211> LENGTH: 19
<212> TYPE: DNA
<213> ORGANISM: Artificial sequence
<220> FEATURE:
<223> OTHER INFORMATION: Synthetic primer

<400> SEQUENCE: 22
ctgacattat tgaatagaa       19

<210> SEQ ID NO 23
<211> LENGTH: 22
<212> TYPE: DNA
<213> ORGANISM: Artificial sequence
<220> FEATURE:
<223> OTHER INFORMATION: Synthetic primer

<400> SEQUENCE: 23
tcaagttctt aagtagcttt tc       22

<210> SEQ ID NO 24
<211> LENGTH: 19
<212> TYPE: DNA
<213> ORGANISM: Artificial sequence

```
<220> FEATURE:
<223> OTHER INFORMATION: Synthetic primer

<400> SEQUENCE: 24
ccctgcgttg caattgcac                                                    19

<210> SEQ ID NO 25
<211> LENGTH: 19
<212> TYPE: DNA
<213> ORGANISM: Artificial sequence
<220> FEATURE:
<223> OTHER INFORMATION: Synthetic primer

<400> SEQUENCE: 25
tagagggagt cacctagtg                                                    19

<210> SEQ ID NO 26
<211> LENGTH: 19
<212> TYPE: DNA
<213> ORGANISM: Artificial sequence
<220> FEATURE:
<223> OTHER INFORMATION: Synthetic primer

<400> SEQUENCE: 26
ctgagttatc cacggttat                                                    19

<210> SEQ ID NO 27
<211> LENGTH: 19
<212> TYPE: DNA
<213> ORGANISM: Artificial sequence
<220> FEATURE:
<223> OTHER INFORMATION: Synthetic primer

<400> SEQUENCE: 27
gacgactatt ctggtttgg                                                    19

<210> SEQ ID NO 28
<211> LENGTH: 18
<212> TYPE: DNA
<213> ORGANISM: Artificial sequence
<220> FEATURE:
<223> OTHER INFORMATION: Synthetic primer

<400> SEQUENCE: 28
agagtatggg atcgtctg                                                     18

<210> SEQ ID NO 29
<211> LENGTH: 19
<212> TYPE: DNA
<213> ORGANISM: Artificial sequence
<220> FEATURE:
<223> OTHER INFORMATION: Synthetic primer

<400> SEQUENCE: 29
taccatacta tctatcgag                                                    19

<210> SEQ ID NO 30
<211> LENGTH: 19
<212> TYPE: DNA
<213> ORGANISM: Artificial sequence
<220> FEATURE:
<223> OTHER INFORMATION: Synthetic primer

<400> SEQUENCE: 30
atgtcccgca gtgcatcag                                                    19
```

```
<210> SEQ ID NO 31
<211> LENGTH: 19
<212> TYPE: DNA
<213> ORGANISM: Artificial sequence
<220> FEATURE:
<223> OTHER INFORMATION: Synthetic primer

<400> SEQUENCE: 31
tggtagaacc accatacgc                                                    19

<210> SEQ ID NO 32
<211> LENGTH: 19
<212> TYPE: DNA
<213> ORGANISM: Artificial sequence
<220> FEATURE:
<223> OTHER INFORMATION: Synthetic primer

<400> SEQUENCE: 32
cgaccagcca aacgatttc                                                    19

<210> SEQ ID NO 33
<211> LENGTH: 18
<212> TYPE: DNA
<213> ORGANISM: Artificial sequence
<220> FEATURE:
<223> OTHER INFORMATION: Synthetic primer

<400> SEQUENCE: 33
gagtcccatg tcccgcag                                                     18

<210> SEQ ID NO 34
<211> LENGTH: 21
<212> TYPE: DNA
<213> ORGANISM: Artificial sequence
<220> FEATURE:
<223> OTHER INFORMATION: Synthetic primer

<400> SEQUENCE: 34
ccaacatacg gtaccgagat c                                                 21

<210> SEQ ID NO 35
<211> LENGTH: 21
<212> TYPE: DNA
<213> ORGANISM: Artificial sequence
<220> FEATURE:
<223> OTHER INFORMATION: Synthetic primer

<400> SEQUENCE: 35
tgctttcacc aggtgaagcg t                                                 21

<210> SEQ ID NO 36
<211> LENGTH: 24
<212> TYPE: DNA
<213> ORGANISM: Artificial sequence
<220> FEATURE:
<223> OTHER INFORMATION: Synthetic primer

<400> SEQUENCE: 36
tacccgtgaa agtgcctcct ttct                                              24

<210> SEQ ID NO 37
<211> LENGTH: 24
<212> TYPE: DNA
<213> ORGANISM: Artificial sequence
<220> FEATURE:
<223> OTHER INFORMATION: Synthetic primer
```

<400> SEQUENCE: 37
tgcaactacc atttggccac tcag                                      24

<210> SEQ ID NO 38
<211> LENGTH: 24
<212> TYPE: DNA
<213> ORGANISM: Artificial sequence
<220> FEATURE:
<223> OTHER INFORMATION: Synthetic primer

<400> SEQUENCE: 38
aatgtccatg tcgaacgcaa agcg                                      24

<210> SEQ ID NO 39
<211> LENGTH: 27
<212> TYPE: DNA
<213> ORGANISM: Artificial sequence
<220> FEATURE:
<223> OTHER INFORMATION: Synthetic primer

<400> SEQUENCE: 39
atttacccct acagcagtat gacccaa                                   27

<210> SEQ ID NO 40
<211> LENGTH: 24
<212> TYPE: DNA
<213> ORGANISM: Artificial sequence
<220> FEATURE:
<223> OTHER INFORMATION: Synthetic primer

<400> SEQUENCE: 40
tgtatgttcc tgtcggtgct gtga                                      24

<210> SEQ ID NO 41
<211> LENGTH: 25
<212> TYPE: DNA
<213> ORGANISM: Artificial sequence
<220> FEATURE:
<223> OTHER INFORMATION: Synthetic primer

<400> SEQUENCE: 41
ttaaaacagc tctggggttg taccc                                     25

<210> SEQ ID NO 42
<211> LENGTH: 26
<212> TYPE: DNA
<213> ORGANISM: Artificial sequence
<220> FEATURE:
<223> OTHER INFORMATION: Synthetic primer

<400> SEQUENCE: 42
tttttatcag gacatccttg atgggc                                    26

<210> SEQ ID NO 43
<211> LENGTH: 21
<212> TYPE: DNA
<213> ORGANISM: Artificial sequence
<220> FEATURE:
<223> OTHER INFORMATION: Synthetic primer

<400> SEQUENCE: 43
tatattggca ccatgggagc t                                         21

<210> SEQ ID NO 44

```
<211> LENGTH: 21
<212> TYPE: DNA
<213> ORGANISM: Artificial sequence
<220> FEATURE:
<223> OTHER INFORMATION: Synthetic primer

<400> SEQUENCE: 44
ggaccaacaa ctgtgctaca c                                              21

<210> SEQ ID NO 45
<211> LENGTH: 21
<212> TYPE: DNA
<213> ORGANISM: Artificial sequence
<220> FEATURE:
<223> OTHER INFORMATION: Synthetic primer

<400> SEQUENCE: 45
aagtcaaagg gaatcatggt g                                              21

<210> SEQ ID NO 46
<211> LENGTH: 21
<212> TYPE: DNA
<213> ORGANISM: Artificial sequence
<220> FEATURE:
<223> OTHER INFORMATION: Synthetic primer

<400> SEQUENCE: 46
gctctatatg tgtggtatct c                                              21

<210> SEQ ID NO 47
<211> LENGTH: 21
<212> TYPE: DNA
<213> ORGANISM: Artificial sequence
<220> FEATURE:
<223> OTHER INFORMATION: Synthetic primer

<400> SEQUENCE: 47
tatgtgtggt atctcgcatc a                                              21

<210> SEQ ID NO 48
<211> LENGTH: 21
<212> TYPE: DNA
<213> ORGANISM: Artificial sequence
<220> FEATURE:
<223> OTHER INFORMATION: Synthetic primer

<400> SEQUENCE: 48
tggtggagag gggtgtaagc g                                              21

<210> SEQ ID NO 49
<211> LENGTH: 21
<212> TYPE: DNA
<213> ORGANISM: Artificial sequence
<220> FEATURE:
<223> OTHER INFORMATION: Synthetic primer

<400> SEQUENCE: 49
ggtgaccagt accatcactg a                                              21

<210> SEQ ID NO 50
<211> LENGTH: 21
<212> TYPE: DNA
<213> ORGANISM: Artificial sequence
<220> FEATURE:
<223> OTHER INFORMATION: Synthetic primer

<400> SEQUENCE: 50
```
tttcagctat ggctctagca a                                               21

<210> SEQ ID NO 51
<211> LENGTH: 21
<212> TYPE: DNA
<213> ORGANISM: Artificial sequence
<220> FEATURE:
<223> OTHER INFORMATION: Synthetic primer

<400> SEQUENCE: 51
catctttagt gcctcgaacc a                                               21

<210> SEQ ID NO 52
<211> LENGTH: 21
<212> TYPE: DNA
<213> ORGANISM: Artificial sequence
<220> FEATURE:
<223> OTHER INFORMATION: Synthetic primer

<400> SEQUENCE: 52
gactatggac taactatgac t                                               21

<210> SEQ ID NO 53
<211> LENGTH: 21
<212> TYPE: DNA
<213> ORGANISM: Artificial sequence
<220> FEATURE:
<223> OTHER INFORMATION: Synthetic primer

<400> SEQUENCE: 53
ttacattctc ccatgtgact g                                               21

<210> SEQ ID NO 54
<211> LENGTH: 21
<212> TYPE: DNA
<213> ORGANISM: Artificial sequence
<220> FEATURE:
<223> OTHER INFORMATION: Synthetic primer

<400> SEQUENCE: 54
atcacgttcg ctctctgtgc c                                               21

<210> SEQ ID NO 55
<211> LENGTH: 24
<212> TYPE: DNA
<213> ORGANISM: Artificial sequence
<220> FEATURE:
<223> OTHER INFORMATION: Synthetic primer

<400> SEQUENCE: 55
tgtgttccca acatcgcctc ctta                                            24

<210> SEQ ID NO 56
<211> LENGTH: 21
<212> TYPE: DNA
<213> ORGANISM: Artificial sequence
<220> FEATURE:
<223> OTHER INFORMATION: Synthetic primer

<400> SEQUENCE: 56
cagccctgct tggttcgagg c                                               21

<210> SEQ ID NO 57
<211> LENGTH: 21
<212> TYPE: DNA

```
<213> ORGANISM: Artificial sequence
<220> FEATURE:
<223> OTHER INFORMATION: Synthetic primer

<400> SEQUENCE: 57
cttctaagtt gaattcctaa g                                          21

<210> SEQ ID NO 58
<211> LENGTH: 19
<212> TYPE: DNA
<213> ORGANISM: Artificial sequence
<220> FEATURE:
<223> OTHER INFORMATION: Synthetic primer

<400> SEQUENCE: 58
tcttctttcc cattgctac                                             19

<210> SEQ ID NO 59
<211> LENGTH: 22
<212> TYPE: DNA
<213> ORGANISM: Artificial sequence
<220> FEATURE:
<223> OTHER INFORMATION: Synthetic primer

<400> SEQUENCE: 59
gagcaggaca gtgtggtgga gt                                         22

<210> SEQ ID NO 60
<211> LENGTH: 22
<212> TYPE: DNA
<213> ORGANISM: Artificial sequence
<220> FEATURE:
<223> OTHER INFORMATION: Synthetic primer

<400> SEQUENCE: 60
gcaagggaga gttcactatg tt                                         22

<210> SEQ ID NO 61
<211> LENGTH: 19
<212> TYPE: DNA
<213> ORGANISM: Artificial sequence
<220> FEATURE:
<223> OTHER INFORMATION: Synthetic primer

<400> SEQUENCE: 61
tgcggttaac gatcgcagt                                             19

<210> SEQ ID NO 62
<211> LENGTH: 20
<212> TYPE: DNA
<213> ORGANISM: Artificial sequence
<220> FEATURE:
<223> OTHER INFORMATION: Synthetic primer

<400> SEQUENCE: 62
tcatctgcca ggtctaccag                                            20

<210> SEQ ID NO 63
<211> LENGTH: 21
<212> TYPE: DNA
<213> ORGANISM: Artificial sequence
<220> FEATURE:
<223> OTHER INFORMATION: Synthetic primer

<400> SEQUENCE: 63
ctagtactcc ggtattgcgg t                                          21
```

<210> SEQ ID NO 64
<211> LENGTH: 19
<212> TYPE: DNA
<213> ORGANISM: Artificial sequence
<220> FEATURE:
<223> OTHER INFORMATION: Synthetic primer

<400> SEQUENCE: 64
catcgcctcc ttacgcttc                                               19

<210> SEQ ID NO 65
<211> LENGTH: 20
<212> TYPE: DNA
<213> ORGANISM: Artificial sequence
<220> FEATURE:
<223> OTHER INFORMATION: Synthetic primer

<400> SEQUENCE: 65
gtggccatta taaccgtgga                                              20

<210> SEQ ID NO 66
<211> LENGTH: 20
<212> TYPE: DNA
<213> ORGANISM: Artificial sequence
<220> FEATURE:
<223> OTHER INFORMATION: Synthetic primer

<400> SEQUENCE: 66
gtttgccatg tgtagtcgtc                                              20

<210> SEQ ID NO 67
<211> LENGTH: 20
<212> TYPE: DNA
<213> ORGANISM: Artificial sequence
<220> FEATURE:
<223> OTHER INFORMATION: Synthetic primer

<400> SEQUENCE: 67
gatctcggta ccgtatgttg                                              20

<210> SEQ ID NO 68
<211> LENGTH: 20
<212> TYPE: DNA
<213> ORGANISM: Artificial sequence
<220> FEATURE:
<223> OTHER INFORMATION: Synthetic primer

<400> SEQUENCE: 68
ctctatggtg cagcatctct                                              20

<210> SEQ ID NO 69
<211> LENGTH: 19
<212> TYPE: DNA
<213> ORGANISM: Artificial sequence
<220> FEATURE:
<223> OTHER INFORMATION: Synthetic primer

<400> SEQUENCE: 69
actcagcaga ttggagaca                                               19

<210> SEQ ID NO 70
<211> LENGTH: 19
<212> TYPE: DNA
<213> ORGANISM: Artificial sequence
<220> FEATURE:

<223> OTHER INFORMATION: Synthetic primer

<400> SEQUENCE: 70
gatggttatc catccagtc                                                  19

<210> SEQ ID NO 71
<211> LENGTH: 18
<212> TYPE: DNA
<213> ORGANISM: Artificial sequence
<220> FEATURE:
<223> OTHER INFORMATION: Synthetic primer

<400> SEQUENCE: 71
gtcgaagtgt gatggatc                                                   18

<210> SEQ ID NO 72
<211> LENGTH: 19
<212> TYPE: DNA
<213> ORGANISM: Artificial sequence
<220> FEATURE:
<223> OTHER INFORMATION: Synthetic primer

<400> SEQUENCE: 72
catggcatcc ctggaggag                                                  19

<210> SEQ ID NO 73
<211> LENGTH: 19
<212> TYPE: DNA
<213> ORGANISM: Artificial sequence
<220> FEATURE:
<223> OTHER INFORMATION: Synthetic primer

<400> SEQUENCE: 73
agcctccata caattgcca                                                  19

<210> SEQ ID NO 74
<211> LENGTH: 20
<212> TYPE: DNA
<213> ORGANISM: Artificial sequence
<220> FEATURE:
<223> OTHER INFORMATION: Synthetic primer

<400> SEQUENCE: 74
gtcctttagt gtgtggtaag                                                 20

<210> SEQ ID NO 75
<211> LENGTH: 18
<212> TYPE: DNA
<213> ORGANISM: Artificial sequence
<220> FEATURE:
<223> OTHER INFORMATION: Synthetic primer

<400> SEQUENCE: 75
tggcatccaa gatctcca                                                   18

<210> SEQ ID NO 76
<211> LENGTH: 19
<212> TYPE: DNA
<213> ORGANISM: Artificial sequence
<220> FEATURE:
<223> OTHER INFORMATION: Synthetic primer

<400> SEQUENCE: 76
cactgtcctg ctctggttg                                                  19

<210> SEQ ID NO 77
<211> LENGTH: 24
<212> TYPE: DNA
<213> ORGANISM: Artificial sequence
<220> FEATURE:
<223> OTHER INFORMATION: Synthetic primer

<400> SEQUENCE: 77
tagtaacgcg gcttcgaaac agga                                          24

<210> SEQ ID NO 78
<211> LENGTH: 26
<212> TYPE: DNA
<213> ORGANISM: Artificial sequence
<220> FEATURE:
<223> OTHER INFORMATION: Synthetic primer

<400> SEQUENCE: 78
tttttatcag gacatccttg atgggc                                        26

<210> SEQ ID NO 79
<211> LENGTH: 17
<212> TYPE: DNA
<213> ORGANISM: Artificial sequence
<220> FEATURE:
<223> OTHER INFORMATION: Synthetic primer

<400> SEQUENCE: 79
gtaaaacgac ggccagt                                                  17

<210> SEQ ID NO 80
<211> LENGTH: 7303
<212> TYPE: DNA
<213> ORGANISM: Artificial Sequence
<220> FEATURE:
<223> OTHER INFORMATION: Synthetic polynucleotide

<400> SEQUENCE: 80
ttaaaacagc tctggggttg tacccacccc agaggcccac gtggcggcta gtactccggt    60
attgcggtac ccttgtacgc ctgttttata ctcccttccc gtaacttagg aattcaactt   120
agaagttttt cacaaagacc aatagccggt aatcagccag attactgaag gtcaagcact   180
tctgtttccc cggtcaatgt tgatatgctc aacagggca aaaacaactg cgatcgttaa    240
ccgcaaagcg cctacgcaaa gcttagtagc atctttgaaa tcgtttggct ggtcgatccg   300
ccatttcccc tggtagacct ggcagatgag ctagaaata ccccactggc gacagtgttc    360
tagcctgcgt ggctgcctgc acccctatg ggtgtgaagc caaacaatgg acaaggtgtg    420
aagagccccg tgtgctcgct ttgagtcctc cggcccctga atgtggctaa ccttaaccct   480
gcagctagag cacgtaaccc aatgtgtatc tagtcgtaat gagcaattgc gggatgggac   540
caactacttt gggtgtccgt gtttcacttt ctcctttata tttgcttatg gtgacaatat   600
atacaatata tatattggca ccatgggagc tcaggtttca tcacagaaag tgggcgcaca   660
tgaaaactca atagagcgt atggtggttc taccattaat tacaccacca ttaattatta    720
tagagattca gctagtaacg cggcttcgaa acaggacttc tctcaagacc cttccaagtt   780
caccgagccc atcaaggatg tcctgataaa acatcccca atgctaaact cgccaaacat    840
agaggcttgc gggtatagcg atagagtact gcaattaaca ctgggaaact ccactataac   900
cacacaggag gcggctaatt cagtagtcgc ttatgggcgt tggcctgaat atctgaggga   960
cagcgaagcc aatccagtgg accagccgac agaaccagac gtcgctgcat gcaggtttta  1020

```
tacgctagac accgtgtctt ggacgaaaga gtcgcgaggg tggtggtgga agttgcctga   1080
tgcactgcgg gacatgggac tctttggcca aaatatgtac taccactacc taggtaggtc   1140
cgggtacacc gtgcatgtac agtgtaacgc ctccaaattc caccagggggg cactagggggt  1200
attcgccgta ccagagatgt gtctggccgg ggatagcaac accactacca tgcacaccag   1260
ctatcaaaat gccaatcctg gcgagaaagg aggcactttc acgggtacgt tcactcctga   1320
cgacaaccag acatcacctg cccgtaggtt ctgcccggtg gattacctct ttggaaatgg   1380
cacgttattg gggaatgcct ttgtgttccc gcaccagata ataaacctac ggaccaacaa   1440
ctgtgctaca ctggtactcc cttacgtgaa ctccctctcg atagatagta tggtaaagca   1500
caataattgg ggaattgcaa tattaccatt ggccccatta aattttgcta gtgagtcctc   1560
cccagagatt ccaatcacct tgaccatagc ccctatgtgc tgtgagttca atggattaag   1620
aaacattacc ctgccacgct tacagggcct gccggtcatg aacacccctg gtagcaatca   1680
atatcttact gcagacaact tccagtcacc gtgtgcgctg cctgaatttg atgtgacccc   1740
acctattgac atacccggtg aagttaagaa catgatggaa ttggcagaaa tcgacaccat   1800
gattcccttt gacttaagtg caaaaaaaaa gaacaccatg gaaatgtata gggttcggtt   1860
aagtgacaaa ccacatacag acgatcccat actctgcctg tcactctctc cagcttcaga   1920
tcctaggttg tcacatacta tgcttggaga atcctaaat tactacacac actgggcagg   1980
atccctgaag ttcacgtttc tgttctgtgg atccatgatg gcaactggca aactgttggt   2040
gtcatacgcg cctcctggag ccgacccacc aaagaagcgt aaggaggcga tgttgggaac   2100
acatgtgatc tgggacatag gactgcagtc ctcatgtact atggtagtgc catggattag   2160
caacaccacg tatcggcaaa ccatagatga tagtttcacc gaaggcggat acatcagcgt   2220
cttctaccaa accagaatag tcgtccctct ttcgacaccc agagagatgg acatccttgg   2280
ttttgtgtca gcgtgtaatg acttcagcgt gcgcttgatg cgagatacca cacatataga   2340
gcaaaaagcg ctagcacagg ggttaggtca gatgcttgaa agcatgattg acaacacagt   2400
ccgtgaaacg gtgggggcgg caacgtctag agacgctctc ccaaacactg aagccagtgg   2460
accagcacac tccaaggaaa ttccggcact caccgcagtg gaaactgggg ccacaaatcc   2520
actagtccct tctgatacag tgcaaaccag acatgttgta caacataggt caaggtcaga   2580
gtctagcata gagtctttct tcgcgcgggg tgcatgcgtg gccattataa ccgtggataa   2640
ctcagcttcc accaagaata aggataagct atttacagtg tggaagatca cttataaaga   2700
tactgtccag ttacggagga aattggagtt cttcacctat tctagatttg atatggaatt   2760
tacctttgtg gttactgcaa atttcactga gactaacaat gggcatgcct taaatcaagt   2820
gtaccaaatt atgtacgtac caccaggcgc tccagtgccc gagaaatggg acgactacac   2880
atggcaaacc tcatcaaatc catcaatctt ttacacctac ggaacagctc cagcccggat   2940
ctcggtaccg tatgttggta tttcgaacgc ctattcacac ttttacgacg ttttttccaa   3000
agtaccactg aaggaccagt cggcagcact aggtgactcc ctctatggtg cagcatctct   3060
aaatgacttc ggtatttttg ctgttagagt agtcaatgat cacaacccga ccaaggtcac   3120
ctccaaaatc agagtgtatc taaaacccaa acacatcaga gtctggtgcc cgcgtccacc   3180
gagggcagtg gcgtactacg gccctggagt ggattacaag gatggtacgc ttacaccccct  3240
ctccaccaag gatctgacca catatggatt cggacaccaa acaaagcgg tgtacactgc   3300
aggttacaaa atttgcaact accatttggc cactcaggaa gatttgcaaa acgcagtgaa   3360
cgtcatgtgg aatagagacc tcttagtcac agaatcaaga gcccagggca ccgattcaat   3420
```

```
cgcaaggtgc aattgcaacg caggggtgta ctactgcgag tctagaagga aatactaccc   3480
agtatccttc gttggcccaa cgttccagta catggaggct aataactatt acccagctag   3540
gtaccagtcc catatgctca ttggccatgg attcgcatct ccaggggatt gtggtggcat   3600
actcagatgt caccacgggg tgatagggat cattactgct ggtggagaag ggttggttgc   3660
atttacagac attagagact tgtatgccta cgaagaagaa gccatggaac aaggcatcac   3720
caattacata gagtcacttg gggccgcatt tggaagtgga tttactcagc agattggaga   3780
caaaataaca gagttgacta atatggtgac cagtaccatc actgaaaagc tacttaagaa   3840
cttgatcaag atcatatcct cactagttat tataactagg aattatgaag acaccacaac   3900
agtgctcgct accctggccc ttcttgggtg tgatgcttca ccatggcagt ggcttagaaa   3960
gaaagcatgc gatgttctgg ataccctta tgtcaccaag caaggtgaca gttggttgaa   4020
gaagtttact gaagcatgca acgcagctaa gggactggag tgggtgtcaa acaaaatctc   4080
aaaattcatt gattggctca aggagaaaat tatcccacaa gctagagata agttggaatt   4140
tgtaacaaaa cttagacaac tagaaatgct ggaaaaccaa atctcaacta caccaatc    4200 atgccctagt caggaacacc aggaaattct attcaataat gtcagatggt tatccatcca   4260
gtctaagagg tttgcccctc tttacgcagt ggaagccaaa agaatacaga aactagagca   4320
taccattaac aactcatac agttcaagag caaacaccgt attgaaccag tatgtttgct   4380
agtacatggc agccccggaa caggtaaatc tgtagcaacc aacctgattg ctagagccat   4440
agctgaaaga gaaaacacgt ccacgtactc gctaccccg gatccatcac acttcgacgg   4500
atacaaacaa cagggagtgg tgattatgga cgacctgaat caaaacccag atggtgcgga   4560
catgaagctg ttctgtcaga tggtatcaac agtggagttt ataccaccca tggcatccct   4620
ggaggagaaa ggaatcctgt ttacttcaaa ttacgttcta gcatccacga actcaagcag   4680 aatttcccc cccactgtgg cacacagtga tgcattagcc aggcgctttg cgttcgacat   4740
ggacattcag gtcatgaatg agtattctag agatgggaaa ttgaacatgg ccatggctac   4800
tgaaatgtgt aagaactgtc accaaccagc aaactttaag agatgctgtc ctttagtgtg   4860
tggtaaggca attcaattaa tggataaatc ttccagagtt agatacagta ttgaccagat   4920
cactacaatg attatcaatg agagaaacag aagatccaac attggcaatt gtatggaggc   4980
tttgttccaa ggaccactcc agtataaaga cttgaagatt gacatcaaga cgagtccccc   5040
tcctgaatgt atcaatgact tgctccaagc agttgactcc caggaggtga gagattactg   5100
tgagaagaag ggttggatag tcaacatcac cagccaggtt caaacagaaa ggaacatcaa   5160
cagggcaatg acaattctac aagcggtgac aaccttcgcc gcagtggctg agttgtcta   5220 tgtcatgtat aaactgtttg ctggacacca gggagcatac actggtttac aaacaaaaa   5280 acccaacgtg cccaccatta ggacagcaaa ggtacaaggg ccagggttcg attacgcagt   5340
ggctatggct aaaagaaaca ttgttacagc aactactagc aagggagagt tcactatgtt   5400
aggagtccac gacaacgtgg ctattttacc aacccacgct tcacctggtg aaagcattgt   5460
gatcgatggc aaagaagtgg agatcttgga tgccaaagcg ctcgaagatc aagcaggaac   5520
caatcttgaa atcactataa tcactctaaa gagaaatgaa aagttcagag acattagacc   5580 acatataccct actcaaatca ctgagacaaa tgatggagtc ttgatcgtga acactagcaa   5640
gtaccccaat atgtatgttc ctgtcggtgc tgtgactgaa cagggatatc taaatctcgg   5700
tgggcgccaa actgctcgta ctctaatgta caactttcca accagagcag gacagtgtgg   5760
```

```
tggagtcatc acatgtactg ggaaagtcat cgggatgcat gttggtggga acggttcaca    5820
cgggtttgca gcggccctga agcgatcata cttcactcag agtcaaggtg aaatccagtg    5880
gatgagacct tcgaaggaag tgggatatcc aatcataaat gccccgtcca aaaccaagct    5940
tgaacccagt gctttccact atgtgtttga aggggtgaag gaaccagcag tcctcactaa    6000
aaacgatccc aggcttaaga caaactttga ggaggcaatt ttctccaagt acgtgggtaa    6060
caaaattact gaagtggatg agcacatgaa agaggcagta gaccactatg ctggccagct    6120
catgtcacta gacatcaaca cagaacaaat gtgcttggag gatgccatgt atggcactga    6180
tggtctagaa gcacttgatt tgtccaccag tgctggctac ccttatgtag caatgggaaa    6240
gaagaagaga gatatcttga acaaacaaac cagagacact aaggaaatgc aaaaactgct    6300
cgacacatat ggaatcaacc tcccactggt gacttatgta aaggatgaac ttagatccaa    6360
aacaaaggtt gagcagggga aatccagatt aattgaagct tctagtttga atgactcagt    6420
ggcaatgaga atggcttttg ggaacctata tgctgctttt cacaaaaacc caggagtgat    6480
aacaggttca gcagtagggt gcgatccaga tttgttttgg agcaaaattc cggtattgat    6540
ggaagagaag ctgtttgcct ttgactacac agggtatgat gcatctctca gccctgcttg    6600
gttcgaggca ctaaagatgg tgcttgagaa aatcggattc ggagacagag ttgactacat    6660
cgactaccta aaccactcac accacctgta caagaataaa acatactgtg tcaagggcgg    6720
tatgccatct ggttgctcag gcacttcaat ttttaactca atgattaaca acttgattat    6780
caggacactc ttactgaaaa cctacaaggg catagattta gaccacctaa aaatgattgc    6840
ctatggtgat gatgtaattg cttcctaccc ccatgaagtt gacgctagtc tcctagccca    6900
atcaggaaaa gactatggac taactatgac tccagctgac aaatcagcta tatttgaaac    6960
agtcacatgg gagaatgtaa cattcttgaa gagattcttc agggcagacg agaaatacccc   7020 atttcttatt catccagtaa tgccaatgaa ggaaattcat gaatcaatta gatggacaaa    7080
agatccuagg aacactcagg atcacgttcg ctctctgtgc ctattagctt ggcacaatgg    7140
cgaagaagaa tataacaaat tcctagctaa aatcaggagt gtgccaattg aagagcttt    7200 attgctccca gagtactcaa cattgtaccg ccgttggctt gactcatttt agtaacccta    7260
cctcagtcga attggattgg gtcatactgc tgtaggggta aat                      7303
```